United States Patent [19]

Shekhani et al.

[11] Patent Number: 5,998,381
[45] Date of Patent: Dec. 7, 1999

[54] COMPOUNDS THAT BIND BACTERIAL PILI

[75] Inventors: Mohammed Saleh Shekhani, Madison, Wis.; Joseph R. Firca, Vernon Hills; Byron Anderson, Morton Grove, both of Ill.

[73] Assignee: Ophidian Pharmaceuticals, Inc., Madison, Wis.

[21] Appl. No.: 08/760,903

[22] Filed: Dec. 6, 1996

[51] Int. Cl.⁶ .......................... A61K 31/70; C07H 15/00; C07H 17/00
[52] U.S. Cl. ............................ 514/25; 536/4.1; 536/17.2; 536/17.9; 514/23
[58] Field of Search .................. 519/25, 23; 536/17.9, 536/4.1, 17.2

[56] References Cited

U.S. PATENT DOCUMENTS

| 4,536,572 | 8/1985 | Kim et al. ................................. 536/17.9 |
| 4,867,973 | 9/1989 | Goers et al. ........................... 424/85.91 |
| 5,198,352 | 3/1993 | Neeser et al. ............................ 435/101 |

FOREIGN PATENT DOCUMENTS

| 428486 | 5/1991 | European Pat. Off. ........ A61K 47/48 |
| WO 95/14028 | 5/1995 | WIPO ............................ C07H 15/203 |

OTHER PUBLICATIONS

N. Sharon, "Bacterial Lectins, Cell–Cell Recognition and Infectious Disease," *FEBS Letters* 217: 145–157 (1987).
H.–G. Leusch et al., "Binding of *Escherichia Coli* and Salmonella Strains to Members of the Carcinoembryonic Antigen Family: Differential Binding Inhibition by Aromatic α–Glycosides of Mannose," *Infection and Immunity* 59: 2051–2057 (1991).
B. Madison et al., "Type 1 Fimbrial Shafts of *Escherichia Coli* and *Klebsiella Pneumoniae* Influence Sugar–Binding Speificities of Their FimH Adhesins," *Infection and Immunity* 62:843–848 (1994).
N. Firon et al., "Aromatic Alpha–Glycosides of Mannose Are Powerful Inhibitors of the Adherence of Type 1 Fimbriated *Escherichia Coli* to Yeast and Intestinal Epithelial Cells," *Infection and Immunity* 55(2):472–476 (1987).
K.A. Schulman et al., "Cost–Effectiveness of HA–1A Monoclonal Antibody for Gram–Negative Sepsis: Economic Assessment of a New Therapeutic Agent," *JAMA* 266:3466–3471 (1991).
C.J. Fisher et al., "Initial Evaluation of Human Monoclonal Anti–Lipid A Antibody (HA–1A) in Patients with Sepsis Syndrome," *Clin. Care Med.*, 18:1311–1315 (1990).
C.H.J. Ford et al., "Antibody Mediated Targeting of Radioisotopes, Drugs and Toxins in Diagnosis and Treatment," *Indian J. Pediatr.*, 57:29–46 (1990).
H.F. Deutsch, "Preparation of Immunoglobulin Concentrates," in *Methods in Immunology and Immunochemistry*, (C.A. Williams and M.W. Chase, eds.), Academic Press, New York, pp. 315–321 (1967).

E.J. Cohn et al., "Preparation and Properties of Serum and Plasma Proteins. IV. A System for the Separation in Fractions of the Protein and Lipoprotein Components of Biological Tissues and Fluids," *J. Am. Chem Soc.*, 68:459–475 (1946).
G.L. Mandell and M.A. Sande, "Antimicrobial Agents: Pencillins, Cephalosporins, and Ohter Beta–Lactam Antibiotics," in *Goodman and Gilman's: The Pharmacological Basis of Therapeutics*, 8th Ed., (Gilman, Rall, Nies, and Taylor, eds.), Pergamon Press, New York, 46:1065–1097 (1990).
M.A. Sande and G.L. Mandell, "Antimicrobial Agents: Tetracyclines, Chloramphenicol, Erthromycin, and Miscellaneous Antibacterial Agents," in *Goodman and Gilman's: The Pharmacological Basis of Therapeutics*, 8th Ed., (Gilman, Rall, Nies, and Taylor, eds.), Pergamon Press, New York, 48:1117–1145 (1990).
A. Fiechter, "Biosurfactants: Moving Towards Industrial Application," *Trends in Biotech.*, 10:208–217 (1992).
G.L. Mandell and M.A. Sande, "Antimicrobial Agents: Drugs Used in the Chemotherapy of Tuberculosis and Leprosy," in *Goodman and Gilman's: The Pharmacological Basis of Therapeutics*, 8th Ed., (Gilman, Rall, Nies, and Taylor, eds.), Pergamon Press, New York, 49:1146–1164 (1990).
R.G. Douglas, "Antimicrobial Agents: Antiviral Agents," in *Goodman and Gilman's: The Pharmacological Basis of Therapeutics*, 8th Ed., (Gilman, Rall, Nies, and Taylor, eds.), Pergamon Press, New York, 51:1182–1201 (1990).
J.E. Bennett, "Antimicrobial Agents; Antifungal Agents," in *Goodman and Gilman's: The Pharmacological Basis of Therapeutics*, 8th Ed., (Gilman, Rall, Nies, and Taylor, eds.), Pergamon Press, New York, 50:1165–1181 (1990).
T. Nakamura et al., "Tachyplesin, a Class of Antimicrobial Peptide from the Hemocytes of the Horseshoe Crab (*Tachypleus tridentatus*): Isolation and Chemical Structure," *J. Biol. Chem.*, 263:16709–16713 (1988).
G. Alpert et al, "Limulus Antilipopolysaccharide Factor Protects Rabbits from Meningococcal Endotoxin Shock," Journal of Infectious Diseases 165:494–500 (1992).
R.R. Schumann et al., "Structure and Function of Lipopolysaccharide Binding Protein," *Science* 249:1429–1431 (1990).
M.N. Marra et al., "The Role of Bactericidal/Permeability–Increasing Protein as a Natural Inhibitor of Bacterial Endotoxin," *J. Immunol.*, 148:532–537 (1992).

(List continued on next page.)

*Primary Examiner*—Elli Peselev
*Attorney, Agent, or Firm*—Medlen & Carroll, LLP

[57] ABSTRACT

Diagnostics and treatments for bacterial infection are disclosed. The treatments prevent bacteria from adhering to host cells by interfering with the binding of the bacteria to cell receptors. Compounds that inhibit bacterial adherence to cells are engineered to be readily modified for best efficacy with different modes of treatment. The compounds can be readily modified for use to identify bacteria according to their cell binding specificities.

24 Claims, 25 Drawing Sheets

OTHER PUBLICATIONS

R. Berkow and A.J. Fletcher (eds), *The Merck Manual*, 16th ed., p. 46 (1992).

G.F. Brooks et al., *Jawetz, Melnick & Adelberg's Medical Microbiology*, 19th ed., pp. 172–173, (1991).

Pierce Chemical Co., (Rockford, IL), General Catalog, pp. E–10–E–39 (1992).

I.S. Snyder and R.G. Finch, "Basic Concepts of Chemotherapy," in *Modern Pharmacology*, 2d Ed., (C.R. Craig and R.E. Stitzel, eds.), Little, Brown and Company, Boston, 45:631–640 (1986).

J.E. Conte, Jr. and S.L. Barriere, "Antibiotic Susceptibilities," *Manual of Antibiotics and Infectious Diseases*, 6th Ed., Lea and Febiger, Philadelphia, Sec. IV, pp. 135–152 (1988).

L.E. Hood et al., *Immunology*, 2d Ed., The Benjamin/Cummings Publishing Company, Inc., Menlo Park, pp. 339–340 (1984).

M. Pollack et al., "Enhanced Survival in *Pseudomonas aeruginosa* Septicemia Associated with High Levels of Circulating Antibody to *Escherichia coli* Endotoxin Core," J. Clin. Invest., 72:1874–1881 (1983).

S.H. Zinner and W.R. McCabe, "Effects of IgM and IgG Antibody in Patients with Bacteremia Due to Gram–negative Bacilli," J. Infect. Dis., 133:37–45 (1976).

B.J. Stoll et al., "Antibodies to Endotoxin Core Determinants in Normal Subjects and in Immune Globulins for Intravenous Use," Serodiagnosis and Immunotherapy 1:21–31 (1987).

W. Marget et al., "Lipid A Antibody Determinations Using ELISA on Patients at a Children's Hospital: A Preliminary Report," Infection 11:84–86 (1983).

C. Stoll et al., "Serum Antibodies Against Common Antigens of Bacterial Lipopoly–saccharides in Healthy Adults and in Patients with Multiple Myeloma," Infection 13;115–119 (1985).

M. Sela, "Immunological Studies with Synthetic Polypeptides," in *Advances in Immunology*, vol. 5, (F. Dixon and J. Humphrey, eds.), pp. 29–129 (1966).

R.C. Bone, "The Pathogenesis of Sepsis," Ann. Intern. Med., 115:457–469 (1991).

E.S. Caplan and N. Hoyt, "Infection Surveillance and Control in the Severely Traumatized Patient," Am. J. Med., 70:638–640 (1981).

M. Meek et al., "The Baltimore Sepsis Scale: Measurement of Sepsis in Patients with Burns Using a New Scoring System," J. Burn Care Rehab., 12:564–568 (1991).

T.J. Zuerlein et al., "Superficial Cultures in Neonatal Sepsis Evaluations: Impact on Antibiotic Decision Making," Clin. Ped., 29:445–447 (1990).

R.L. Nichols, "Classification of Surgical Wounds and non-operative Factors Influencing Surgical Wound Infection," in *Decision Making in Surgical Sepsis*, B.C. Decker, Inc., Philadelphia, pp. 20–21 (1991).

R.L. Greenman et al., "A Controlled Clinical Trial of E5 Murine Monoclonal IgM Antibody to Endotoxin in the Treatment of Gram–Negative Sepsis," JAMA 266:1087–1102 (1991).

M.A. Awad et al., "Plasma Endotoxin and Glycolipid Antibodies in Children with Meningitis," Acta Paediatri., 81:560–561(1992).

W.K. Joklik et al. (eds), *Zinsser Microbiology*, 18th ed., p. 485, Appleton–Century–Crofts, Norwalk, CT (1984).

J.M. Slack and I.S. Snyder, *Bacteria and Human Disease*, pp. 128–133, Yearbook Medical Publishers (1978).

P.Y. Paterson, "Central Nervous System Infection: General Considerations," *Biologic and Clinical Basis of Infectious Diseases*, 3d ed., (G.P. Youmans et al., eds.), W.B. Saunders Co. pp. 552–568, (1985).

D.D. Morris et al., "Endotoxemia in Neonatal Calves Given Antiserum to a Mutant *Escherichia coli* (J–5)," Am. J. Vet. Res., 47:2554–2565 (1986).

A.M. Hoffman et al., "Prognostic Variables for Survival of Neonatal Foals Under Intensive Care," J. Vet. Int. Med., 6:89–95 (1992).

K. Hanasawa et al., "New Approach to Endotoxic and Septic Shock by Means of Polymyxin B Immobilized Fiber," Surg. Gyn. & Ob., 168:323–331 (1989).

K. W. Talmadge and C.J. Siebert, "Efficient Endotoxin Removal with a New Sanitizable Affinity Column: Affi–Prep Polymyxin," J. Chrom., 476:175–185 (1989).

T. Kitagawa et al., "Sensitive Enzyme Immunoassay of Colistin and Its Application to Detect Residual Colistin in Rainbow Trout Tissue," J. Assoc. Anal. Chem., (1985).

J.W. Goding, *Monoclonal Antibodies: Principles and Practice*, Academic Press, New York, p. 84 (1986).

S. Barandun et al., "Intravenous Administration of Human γ–Globulin," Vox Sang., 7:157–174 (1962).

A. Chonn et al., "The Role of Surface Charge in the Activation of the Classical and Alternative Pathways of Complement by Liposomes," J. Immunol., 146:4234–4241 (1991).

C. Galanos et al., "Galactosamine–Induced Sensitization to the Lethal Effects of Endotoxin," Proc. Natl. Acad. Sci. USA 76:5939–5943 (1979).

D.J. Capon et al., "Designing CD4 Immunoadhesins for AIDS Therapy," Nature 337:525–531 (1989).

A. Traunecker et al., "Highly Efficient Neutralization of HIV with Recombinant CD4–Immunoglobulin Molecules," Nature 339:68–70 (1989).

V. Lehmann et al., "Lethal Toxicity of Lipopolysaccharide and Tumor Necrosis Factor in Normal and D–Galactosamine–Treated Mice," J. Exp. Med., 165:657–663 (1987).

M.A. Freudenberg and C. Galanos, "Induction of Tolerance to Lipopolysaccharide (LPS)–D–Galactosamine Lethality by Pretreatment with LPS is Mediated by Macrophages," Infect. Immun., 56:1352–1357 (1988).

F. Mosteller et al., in *Probability with Statistical Applications*, Addison Wesley, Reading, MA (1970).

J.F. Zilva and P.R Pannall, *Clinical Chemistry in Diagnosis and Treatment*, Yearbook Medical Publishers, Chicago, IL pp. 21–23, 87–88 (1984).

Raff et al., "Comparison of Functional Activities Betweeen IgG1 and IgM Class–Switched Human Monoclonal Antibodies Reactive with Group B Streptococci or *Escherichia coli* K1," J. Infect. Dis., 163:346–354 (1991).

Rozenberg–Arska et al., "Bactericidal, Bacteriolytic and Opsonic Activity of Human Serum Against *Escherichia coli*," J. Med. Microbiol., 22:143–149 (1991).

Hill et al., "Comparative Opsonic Activity of Intravenous Gamma Globulin Preparations for Common Bacterial Pathogens," Am. J. Med., 76:61–66 (1984).

Gemmell et al., "Potentiation of Opsonization and Phagocytosis of *Streptococcus pyogenes* following Growth in the Presence of Clindamycin," J. Clin. Invest., 67:1249–1256 (1981).

Bohnsack et al., "An IgA Monoclonal Antibody Directed Against Type III Antigen on Group B Streptococci Acts as an Opsonin," J. Immunol., 143:3338–3342 (1989).

Sowter and McGee, "Evaluation of a New Technique for the Demonstration of Gonococci and Other Micro–Organisms in Host Cells," J. Clin. Pathol., 29:433–437 (1976).

S.M. Wolf, "The Treatment of Gram–Negative Bacteremia and Shock," N. Eng. J. Med., 307:1267–1268 (1982).

G.W. Counts and M. Turck, "Screening for Cross–Reacting Capsular Polysaccharide K Antigens of *Escherichia coli* Using Antiserum Agar," J. Clin. Microbiol., 5:490 (1977).

L.D. Sarff et al., "Epidemiology of *Escherichia Coli* K1 in Healthy and Diseased Newborns," Lancet 1:1099–1104 (1975).

M.P. Weinstein et al., "The Clinical Significance of Positive Blood Cultures: A Comprehensive Analysis of 500 Episodes of Bacteremia and Fungemia in Adults. 1. Laboratory and Epidemiologic Observations," Rev. Infect. Dis., 5:35–53 (1983).

G.H. McCracken et al., "When to Suspect Congenital Anaerobic Infection," Hosp. Pract., 9:57 (1974).

A.S. Cross et al., "The Importance of the K1 Capsule in Invasive Infections Caused by *Escherchia coli*," J. Infect. Dis., 149:184–193 (1984).

D. Rowley, Br. "The Virulence of Strains of *Bacterium Coli* for Mice," J. Exp. Pathol., 35:528–538 (1954).

H. Smith, "Pathogenicity and the Microbe in vivo," J. Gen. Microbiol., 136:377–383 (1990).

D.E. Schiff et al., "Estimation of Protective Levels of Anti–O–Specific Lipopolysaccharide Immunoglobulin G Antibody Against Experiment *Escherichia coli* Infection," Infect. Immun., 61:975–980 (1993).

A.S. Cross et al., "Choice of Bacteria in Animal Models of Sepsis," Infect. Immun., 61:2741–2747 (1993).

I. Orskov and F. Orskov, "*Escherichia coli* in Extra–Intestinal Infections," J. Hyg. Camp., 95:551–575 (1985).

D.E. Dietzman et al., "Neonatal *Escherichia coli* septicemia—Bacterial Counts in Blood," J. Pediatr., 85:128–131 (1974).

H.S. Warren et al., "Binding and Neutralization of Endotoxin by Limulus Antilipopolysaccharide Factor," Infect. Immun., 60:2506–2513 (1992).

Grey and Haseman, "Bactericidal Activity of Synthetic Peptides Based on the Structure of the 55–Kilodalton Bactericidal Protein from Human Neutrophils," Infect. Immun., 62:2732–2739.

Darveau, et al., "Peptides Related to the Carboxyl Terminus of Human Platelet Factor IV with Antibacterial Activity," J. Clinical Invest. 90:447–455 (1992).

Perrin, J. Phys. Rad. 1:390–401.

H.–G. Leusch et al., "The Putative Role of Members of the CEA–Gene Family (CEA, NCA and BGP) as Ligands for the Bacterial Colonization of Different Human Epithelial Tissues," *Zbl. Bakt.*(*Int. J. Med. Microbiol.*) 275:118–122 (1991).

Y. Murakami et al., "N–Acetyl–D–Galactosamine Inhibits TNF–60 Gene Expression Induced in Mouse Peritoneal Macrophages by Fimbriae of *Porphyromonas* (*Bacteroides*) *Gingivalis*, An Oral Anaerobe," *Biochem. and Biophysical Res. Comm.* 192:826–832 (1993).

F.–G. Hanisch et al., "Specificity of S Fimbriae on Recombinant *Escherichia Coli*: Preferential Binding to Gangliosides Expressing NeuGcα(2–3)Gal and NeuAcα(2–8)NeuAc," *Infection and Immunity* 61:2108–2115 (1993).

Glu-Gly-Gly-Ile-Trp-Thr-Gln-Leu-Ala-Leu-Val-Lys-Asn-Leu-Ala-Thr-Leu-Trp-Gln-Ser-Gly-Asp-Phe-Gln-Phe-Leu-Gly-His-Glu-Cys-His-Tyr-Arg-Val/Ile-Asn-Pro-Thr-Val-Lys-Arg-Leu-Lys-Trp-Lys-Gly-Lys-Phe-Trp-Cys-Pro-Ser-Trp-Thr-Ser-Ile-Thr-Gly-Arg-Ala-Thr-Lys-Ser-Ser-Arg-Ser-Gly-Ala-Val-Glu-His-Ser-Val-Arg-Asp-Phe-Val-Ser-Gln-Ala-Lys-Ser-Ser-Gly-Leu-Ile-Thr-Glu-Lys-Glu-Ala-Gln-Thr-Phe-Ile-Ser-Gln-Tyr-Gln/Glu

FIG. 13

Methyl-α-D-Mannopyranoside

4-Aminophenyl α-D-Mannopyranoside

N-(phenylalanyl)-4-aminophenyl α-D-mannopyranoside

COMPOUNDS THAT BIND BACTERIAL PILI

FIELD OF THE INVENTION

The present invention relates to diagnostics and treatments for bacterial diseases, particularly, treatments for the prevention and therapy of bacterially-promulgated illness in humans and animals.

BACKGROUND OF THE INVENTION

Evidence indicates that many localized bacterial infections are due to bacteria adhering to epithelial cells by means of bacterial fibrillar structures known as fimbriae, fibrillae or pili. (S. Hultgren et al., PCT Publication WO 9514028, published May 26, 1995). The fimbriae are filamentous assemblies of protein subunits composed of lectins that bind to specific sugar-containing receptors on the host cells. The fimbriae are classified according to the sugar-specificity exhibited when they attach to cell receptors. Type 1 fimbriae, which exhibit mannose-specific binding, are the most common type. Some other types of fimbriae and their sugar specificities are: type 2, Galβ4Glc; type P, Galα4Gal; type G, N-Acetylglucosamine; type S, NeuAcα2→3GalβGalNAc; type K99, NeuGcα2→3Galβ4Glc; as well as galactose-specific, L-fucose-specific, N-Acetylglucosamine-specific, Galβ4GlcNAc-specific, and GlcNAcβ3Gal-specific fimbriae. (N. Sharon (1987) *FEBS Letters* 217: 145–157).

Enterobacteria that express Type 1 fimbriae include *Escherichia coli*, *Klebsiella pneumoniae*, *Pseudomonas aeruginosa*, Salmonella spp., *Serratia marcescens*, *Shigella flexneri* (N. Sharon (1987) supra), and Citrobacter, Morganella and Aeromonas spp. (H.-G. Leusch et al. (1991) *Infection and Immunity* 59: 2051–2057).

Bacteria that have type 1 pili can be identified by the fact that the type 1 pili agglutinate yeast cells and the agglutination is inhibited by D-mannose and α-D-mannosides. For example, the compound, 4-methylumbelliferyl α-mannoside, inhibits binding; it is 10-fold more effective than p-nitrophenyl α-D-mannoside in inhibiting yeast aggregation caused by *E. coli* but only 4-fold more effective than p-nitrophenyl α-D-mannoside in inhibiting yeast aggregation caused by *K. pneumoniae*. (B. Madison et al. (1994) *Infection and Immunity* 62:843–848).

Aromatic α-glycosides of mannose inhibit both the bacteria-induced agglutination of mannan-containing yeasts and the adherence of the bacteria to epithelial cells. The mannosides 4-methylumbelliferyl (α-mannoside and p-nitro-o-chlorophenyl α-mannoside are strong inhibitors. (N. Firon et al. (1987) *Infection and Immunity* 55(2):472–476; N. Sharon (1987) supra).

*E. coli* and Salmonella bind to glycoproteins of the family of carcinoembryonic antigens (CEA), to nonspecific cross-reacting antigen (NCA-55) and to biliary glycoprotein (BGP-85). There is binding inhibition of *E. coli* (but not of salmonellae) to CEA and NCA-55 when the inhibitors, 4-methylumbelliferyl-α-mannoside, p-ethoxyphenyl-α-mannoside and p-methoxyphenyl-α-mannoside are introduced. (H.-G. Leusch et al. (1991) supra).

Other compositions and compounds that bind to type 1 fimbriae are oligosaccharides that are treated with enzyme to leave alpha 1-2 bonds between mannose residues. These active compounds are glycopeptides and/or oligosaccharides. U.S. Pat. No. 5,198,352 to Neeser et al.

While the above-named inhibitors are known, what is needed is more effective inhibitors that can be used clinically. Such an inhibitor should exhibit increased binding to fimbriae or compete more effectively with the receptor and should be readily synthesized.

SUMMARY OF THE INVENTION

The present invention relates to diagnostics and treatments for bacterial diseases, particularly, treatments for the prevention and therapy of bacterially-promulgated illness in humans and animals.

The invention includes a compound that inhibits binding of enterobacteria to host cells comprising: a) a mannose or mannose analog of α-anomeric configuration; b) an aromatic or heteroaromatic ring attached to said mannose or mannose analog by a glycosidic or pseudoglycosidic linkage; and c) a functional group which provides a site for chemical modification remote from said mannose or mannose analog, wherein said compound is other than 4-aminophenyl-α-D-mannopyranoside. In one embodiment, the compound inhibits binding of enterobacteria via type 1 fimbriae. In another embodiment, the glycosidic or pseudoglycosidic linkage consists of a carbon atom or hetero-atom substituted for the glycosidic oxygen atom. In an alternative embodiment, the functional group is a member of the group of functional groups consisting of, but not limited to, hydroxyl, thiol, carboxylic acid, phenol, amine, halogen, amide, mesylate, tosylate, triflate or like groups, olefinic double bonds, and an acetylenic group. One group of compounds satisfying these criteria is N-(phenylalanyl)-4-aminophenyl-α-D-mannopyranoside and its derivatives. Another group of compounds satisfying these criteria is cysteinyl-[N-(phenylalanyl)]-4-aminophenyl-α-D-mannopyranoside and its derivatives.

The present invention also includes a composition that inhibits binding of enterobacteria to host cells comprising a micellar formulation comprising: a) a mannose or mannose analog of α-anomeric configuration; b) an aromatic or heteroaromatic ring attached to said mannose by a glycosidic or pseudoglycosidic linkage; and c) a functional group which provides a site for chemical modification remote from said mannose or mannose analog. In one embodiment, the composition inhibits binding of enterobacteria via type 1 fimbriae. In another embodiment of the composition, the glycosidic or pseudoglycosidic linkage consists of a carbon atom or hetero-atom substituted for the glycosidic oxygen atom. In a further embodiment, the composition further comprises: (d) a lipophilic group (e.g., a long hydrocarbon chain) that assists in micellar presentation of the molecule. In still another embodiment of the composition, the functional group is a member of the group of functional groups consisting of but not limited to hydroxyl, thiol, carboxylic acid, phenol, amine, halogen, amide, mesylate, tosylate, triflate or like groups, olefinic double bonds, and acetylenic group. In another embodiment, the micellar formulation comprises a derivative of N-(phenylalanyl)-4-aminophenyl-α-D-mannopyranoside. In yet another embodiment, the micellar formulation comprises a derivative of cysteinyl-[N-(phenylalanyl)]-4-aminophenyl-α-D-mannopyranoside.

The present invention also includes a method of treatment of bacterial disease comprising: a) providing one or more fimbriae-binding compounds comprising a mannose or mannose analog of α-anomeric configuration, an aromatic or heteroaromatic ring attached to the mannose or mannose analog by a glycosidic or pseudoglyscosidic linkage, and a functional group, wherein the functional group provides a site for chemical modification remote from the mannose or mannose analog; and b) administering the fimbriae-binding compound to a subject.

In one embodiment of the method, the glycosidic or pseudoglycosidic linkage of the compound or compounds consists of a carbon atom or hetero-atom substituted for the glycosidic oxygen atom. In still another embodiment, the functional group is a member of the group of functional groups consisting of but not limited to hydroxyl, thiol, carboxylic acid, phenol, amine, halogen, amide, mesylate, tosylate, triflate or like groups, olefinic double bonds, and acetylenic group.

In one embodiment of the method, one or more compounds may be administered orally. In an alternative embodiment, the one or more compounds is administered as a micellar formulation. This may be administered via a cleansing applicator and, in one embodiment, may be administered prophylactically. In alternative embodiments of the method, the one or more compounds is administered as a micellar formulation in a solution or in a suspension. The solution may be administered as a wash or as an irrigant.

DESCRIPTION OF THE DRAWINGS

FIG. 3A shows a means by which the minimum concentration for bacterial growth inhibition is established. FIG. 3B shows a means by which a new antibiotic can be assessed for bactericidal activity.

FIG. 13 (SEQ ID NO:1) shows the sequence of Limulus antilipopolysaccharide factor (LALF), a single chain peptide known to bind and neutralize endotoxin.

DEFINITIONS

Figure 1A:
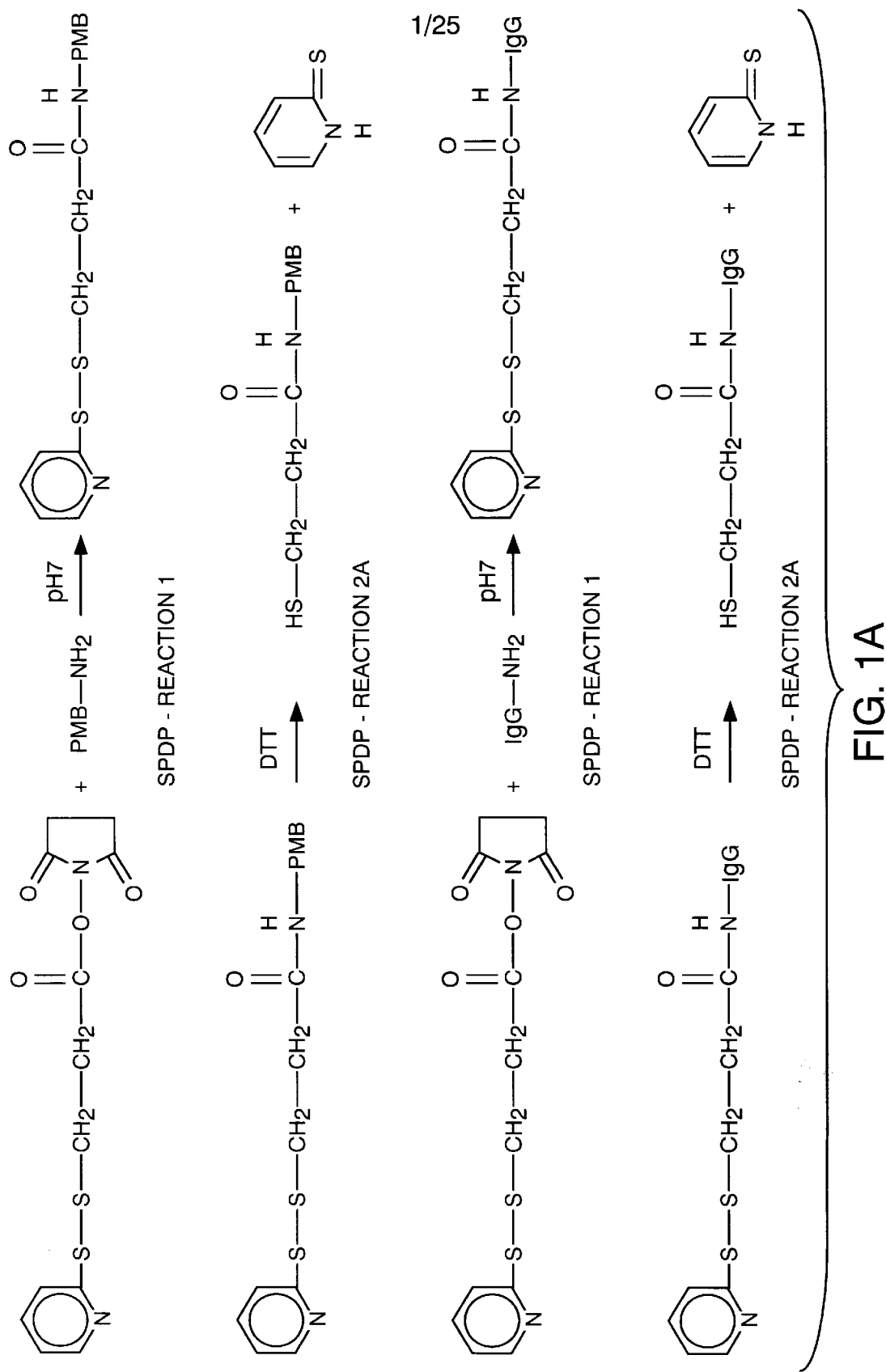
FIG. 1A schematically shows steps in the formation of intermediates in the design of an antibodiotic of the present invention.
Figure 1B:
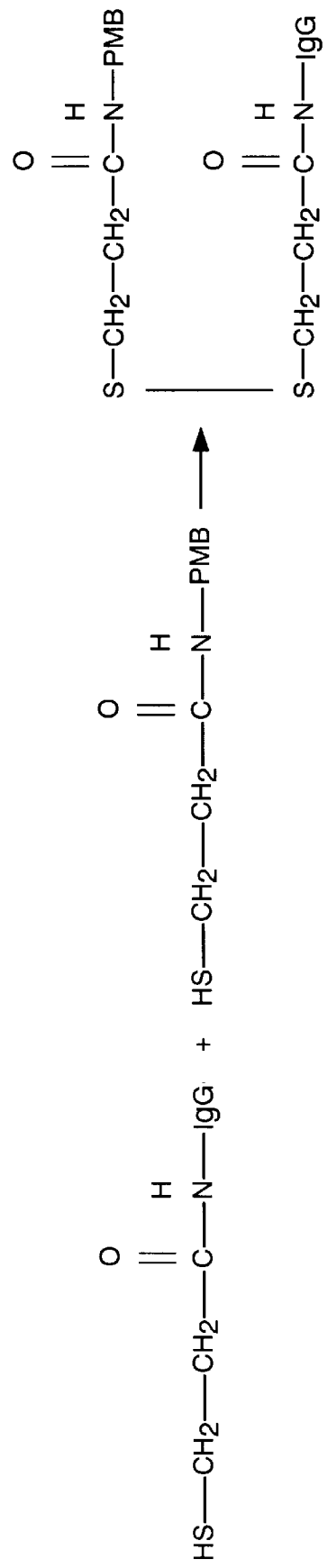
FIG. 1B schematically shows the final step in forming the antibodiotic from the intermediates of FIG. 1A.
Figure 1C:
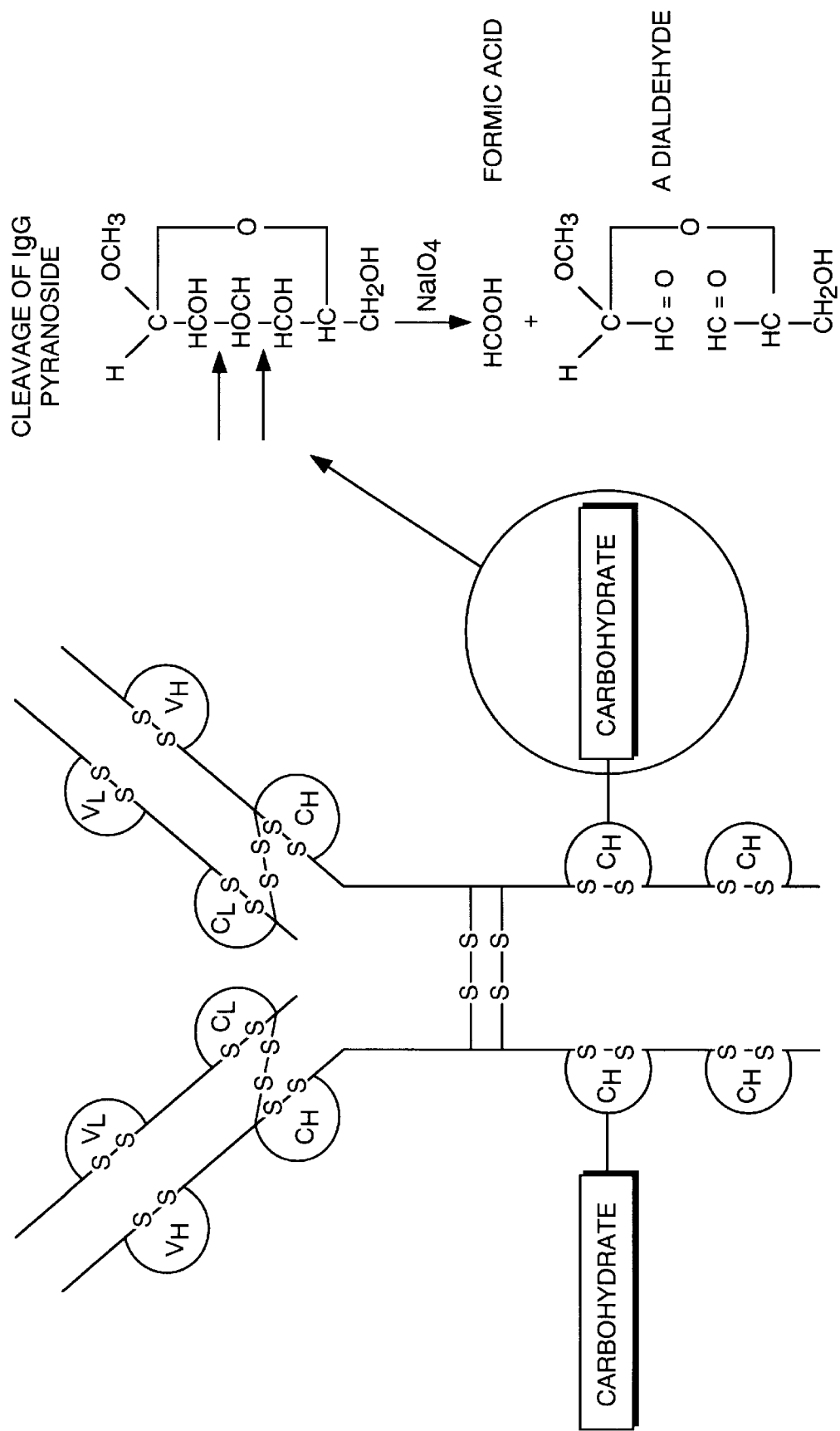
FIG. 1C schematically shows the beginning steps in the formation of intermediates in the design of another antibodiotic of the present invention.
Figure 1D:
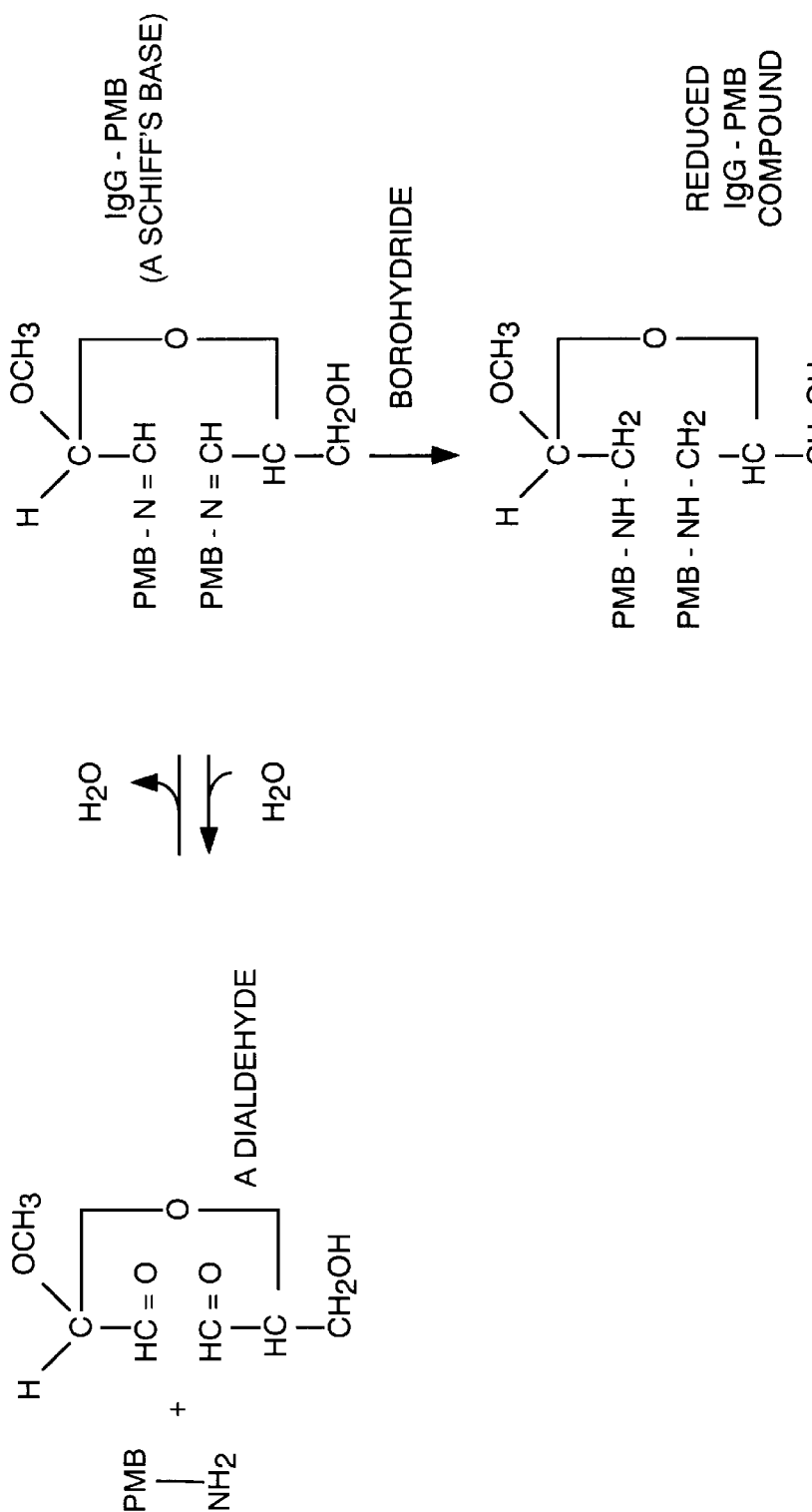
FIG. 1D shows the steps in forming the antibodiotic from the dialdehyde of FIG. 1C.

To facilitate understanding of the invention, a number of terms are defined below.

As used herein, the term "functional group" is used in reference to fimbriae-binding compounds, particularly fimbriae-binding compounds that are engineered to be conjugated to another component. In this context, the functional group is linked directly or indirectly to the aromatic or heteroaromatic ring which is in glycosidic linkage with the sugar moiety of the fimbriae-binding compound but the functional group is not on the sugar itself. By this definition, the hydroxyl groups of the sugar are not included within the definition of functional group. A functional group linked "directly" to the aromatic or heteroaromatic ring structure is covalently bonded to an atom forming the ring. A functional group linked "indirectly" to the aromatic or heteroaromatic ring structure is covalently bonded via one or more atoms to an atom forming the ring, i.e., the functional group is spaced from the ring atom by other intervening atoms or molecules. The functional group itself is an atom or group of atoms that can be chemically modified. For example, the functional group may be an amino group, a carboxylic acid moiety, a thiol, hydroxyl, phenol, amide, or other leaving group.

As used herein, the term "($\alpha$-anomeric configuration" when used in reference to fimbriae-binding compounds, refers to the configuration of the mannose or mannose analog portion of the compound which is attached by a glycosidic linkage to the aromatic or hetero-aromatic ring portion and indicates the $\alpha$-isomer. Examples of mannose analogs that are contemplated are compounds wherein the oxygen atom in the six-membered $\alpha$-mannoside is replaced by a carbon atom or other heteroatoms (e.g., a sulfur or nitrogen atom). Still other analogs are possible such as where one or more hydroxyl groups are replaced by another atom or group of atoms and where the sugar moiety is a "deoxy" derivative.

As used herein, a "micellar formulation" refers to an amphipathic compound or compounds, having both hydrophobic and polar groups which disperse in aqueous solution in such a way as to form a loose structure wherein the polar groups are exposed to the aqueous phase and the hydrophobic groups are hidden within the structure, distanced from the aqueous phase. The micellar formulation may include a lipophilic group that assists in micellar presentation of the compound.

As used herein, a "multimer," when used in reference to fimbriae-binding compounds, consists of multiple fimbriae-binding compounds attached to a backbone molecule which has one or more chains of repeating structural units. A backbone molecule refers to an organic molecule having repeating structural units (e.g., polysaccharide).

As used herein, "prophylactic treatment" refers to the management of the administration of a compound, composition or drug that protects a subject from disease.

DESCRIPTION OF THE INVENTION

The present invention relates to diagnostics and treatments for bacterial diseases, particularly, treatments for the prevention and therapy of bacterially-promulgated illness in humans and animals. The invention contemplates compounds that bind to fimbriae of bacteria of the family Enterobacteriaceae so as to inhibit adhesion of the bacteria to cells of an infected or infectable subject.

The contemplated fimbriae-binding compounds that will bind to mannose-specific (type 1) enterobacteria are α-mannosides having one or more aromatic or heteroaromatic rings and a site for chemical modification remote from the sugar. The inventors have discovered that the introduction of additional aromatic or heteroaromatic rings onto the initial aromatic mannoside provides for greater inhibition of bacterial adherence to cells. In addition to the aromatic ring(s), the fimbriae-binding compounds have a site which is readily modifiable chemically, which allows for conjugating the fimbriae-binding compound to another component, multimerizing the fimbriae-binding compound or altering physical and chemical properties such as solubility or bioavailability. The chemical modification site is provided for by a functional group other than the functional groups of the mannose. Some examples of functional groups that will achieve this purpose include hydroxyl groups, thiol groups, carboxylic acid, phenol, aldehyde, amine, halogen, amide, mesylate, tosylate, triflate or like groups, olefinic double bonds, or acetylenic group. These features allow for the design of fimbriae-binding compounds that are more potent inhibitors and more reactive than the previously known binding inhibitors.

The α-anomeric mannose is preferably (α-D-mannopyranoside. The sugar is attached to an aromatic or hetero-aromatic ring by glycosidic linkage. The glycosidic oxygen may be substituted by another heteroatom or a carbon.

The functional group that acts as a chemically modifiable site allows the fimbriae-binding compound to be converted to alternative forms. For example, the functional group allows for conjugation of the fimbriae-binding compound to another constituent that may be used for conventional drug targeting or Immunoadaptor™ technology. Alternatively the functional group can be used in producing multimers of the fimbriae-binding compound by attachment to a back-bone molecule having multiple binding sites. A few examples of these back-bone molecules are polysaccharide (such as dextran), polypeptide, and other natural or synthetic polymers. The back-bone molecule can impart special properties such as improved or altered solubility or bioavailability.

The conversion of an inhibitory fimbriae-binding compound to a multimeric form can be shown using, as an example, the inhibitory mannoside, 4-(N-phenylalanyl)-aminophenyl-α-D-mannopyranoside, represented by formula (1):

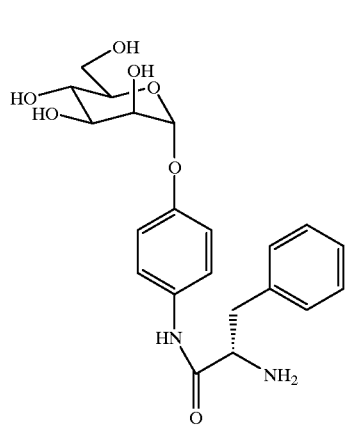

FORMULA 1

This compound inhibits the agglutination of yeast cells induced by type 1 pili-bearing bacteria. The compound of Formula (1) can be multimerized by a reductive amination of an oxidized polysaccharide, or by acylation with a compound bearing several carboxylic groups (e.g. a polypeptide containing several glutamic acids), or by attachment to a polymer. It is contemplated that one method for accomplishing the multimerization of the compound of Formula (1) can be accomplished in two steps. The first step is a condensation reaction, as shown in Scheme I:

SCHEME 1

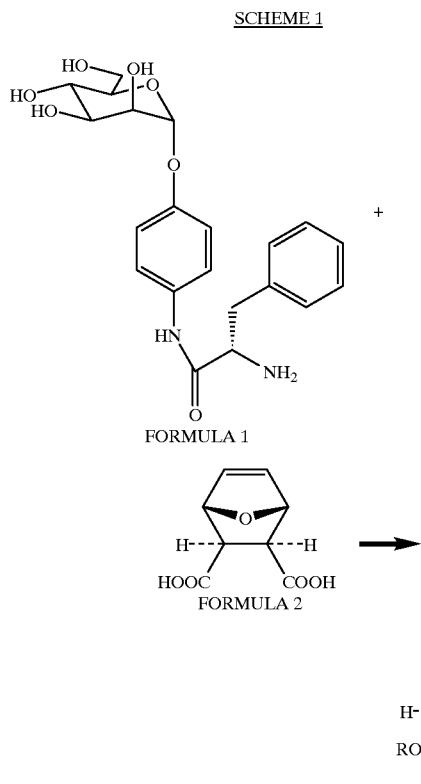

R = 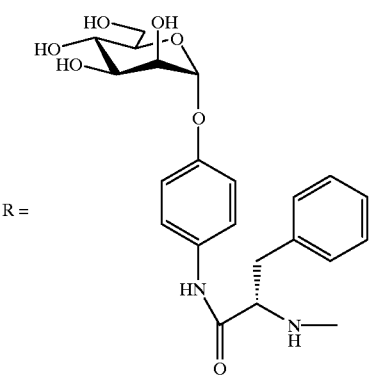

FORMULA 5

[Structure of Formula 5 shown at top right]

The second step is a ring-opening metathesis reaction which generates the multimer of Formula (4) from Formula (3 as shown in Scheme 2. In this case, the catalyst is ruthenium chloride.

SCHEME 2

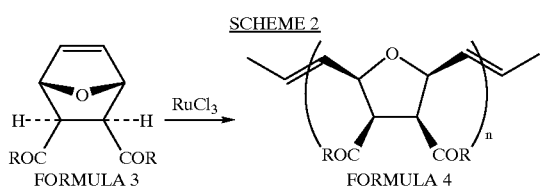

The metathesis reaction may be modified by changing the catalyst or reaction conditions, in order to control the molecular weight of the multimer. For example, the ruthenium chloride catalyst shown in Scheme 2 can be replaced with a different metal and/or a different metal-binding ligand. Alternatively, by changing the concentration of reactants, the solvent, the pH, the reaction time, or by inclusion of an accelerator or decelerator, the length of the resultant multimer is controlled.

In Scheme 1, an alternative to Formula 2 is obtained when one, rather than two sugar moieties (i.e., R) is attached to the bicyclic subunit of the structure shown in Formula 2. The position which is, thus, without a sugar moiety may be conjugated to another molecule for modification of physical and chemical properties or for drug targeting. In such a case, the corresponding analog of the structure of Formula 4 is obtained.

A different modification of the same starting fimbriae-binding compound is shown below. Acylation of the compound of Formula (1) produces the compound of Formula (5):

Additional formulations of the compounds described herein can alter and/or improve physicochemical properties. For example, a micellar formulation is contemplated to result in preparations effective in binding to pili due to multimeric presentation of the molecules, thereby preventing the bacteria from binding to its receptor. The present invention contemplates incorporating such a formulation into disposable pads or tissue in order to cleanse the external genito-urinary tissue and into a liquid formulation for use as a bladder or urethra irrigant or wash, administered, for example, in order to flush out the region or portion of the organ of interest. The former use provides for a general prophylactic routine for individuals predisposed to urinary tract infections and the latter provides for a therapeutic treatment for lower urinary tract infections. In addition, an oral small molecular weight formulation (in order to be excreted through the kidneys) would bathe the kidneys, ureters, bladder and urethra, treating both upper and lower urinary tract infections. The formulations may consist of one or more fimbriae-binding compounds to obtain synergistic effect. The formulation may consist of one or more of the fimbriae-binding compounds to obtain synergistic effect. Lastly, a major benefit arises from the fact that these compounds can be administered independently of antibiotics and, as a result, can afford a treatment for diseases caused by antibiotic-resistant bacteria. Alternatively, such compounds can be used as adjunct therapy with antibiotics. Such a treatment will also prevent antibiotic resistance from developing.

Fimbriae-binding compounds that bind to pili other than type 1 may be prepared by varying the sugar, the anomeric configuration, and the number and type of aromatic rings. For example, for type G fimbriae, the sugar moiety is contemplated as N-acetylglucosamine or for type 2 fimbriae, as Galβ4Glc.

The fimbriae-binding compounds of the present invention are contemplated for use to identify bacteria according to their cell binding specificities. Identification of bacteria in diagnostics is contemplated by means of conjugating the fimbriae-binding compound to reporter substances such as, but not limited to, dyes, luminescent or fluorescent molecules, and enzymes.

The present invention also relates to therapeutics for the prevention and treatment of blood-borne and toxin mediated diseases, and in particular the prevention and treatment of sepsis caused by various types of organisms in humans as well as other animals. The present invention is particularly suited for the in vivo neutralization of the effects of endotoxin. However, it is contemplated that the present invention will be used in the treatment of gram-negative and gram-positive sepsis. Although the invention may be used for treatment of sepsis due to one organism, it may also be used to treat sepsis caused by multiple organisms (e.g., sepsis and/or bacteremia due to gram-negative and gram-positive organisms). The present invention also contemplates treatment comprising multiple antibody-antibiotic conjugates used in combination. It is also contemplated that the present invention will be used to treat bacteremia, viremia or fungemia, by enhancing the removal of organisms by opsonization.

In accordance with the present invention, soluble antibody-antibiotic conjugates or "antibodiotics" are administered intravenously, intra-muscularly, subcutaneously, intradermally, intraperitoneally, intrapleurally, intrathecally or topically. The conjugate is water-soluble if it has a solubility in physiologic saline of at least 0.1 mg/ml, and preferably of at least 1.0 mg/ml, when measured at room temperature. The present invention contemplates the use of antibodiotics in a therapeutic preparation for both prophylactic and acute treatment.

While the benefit conveyed by treatment according to the present invention is not dependent on the understanding of the mechanism(s) by which soluble antibody-antibiotic conjugates achieve a therapeutic result, it is believed that, in the case of bacteria, success is accomplished by: (i) binding and opsonization of bacteria; (ii) bacterial killing (direct killing by the conjugate and/or complement-mediated); and (iii) neutralization and removal of free bacterial toxins (e.g., gram-negative endotoxin, thereby preventing initiation and/or escalation of the septic reaction).

It is believed that antibodiotics provide a low cost, reasonably effective and needed preventive as well as treatment. Antibodiotics can suppress fungal and viral infection. Furthermore, antibodiotics suppress bacteremia as well as endotoxin-mediated effects. Antibodiotics with long (e.g., days to weeks) duration of action are easily administered. Furthermore, since the invention encompasses antibodiotics with reactivity against gram-negative organisms as well as antibodiotics with reactivity to gram-positive organisms, a wider spectrum of protection is expected than any other known approach.

It is also contemplated that this invention will be used in diagnostic applications. These diagnostic applications include methods to detect LPS from particular organisms or the surface structures present on organisms which are recognized by antibiotics (i,e., the receptors expressed on cell surfaces which bind antibiotic).

The description of the invention involves: (I) Antibodiotic Design and Characterization; (II) Antibodiotic in vitro and in vivo Efficacy; (III) Antibodiotic Applications; and (IV) Therapeutic Preparations and Combinations. Section III describes the use of antibodiotics for: (A) Prophylactic Use in Humans; (B) Acute Therapy in Humans; and (C) Veterinary Care.

I. Antibodiotic Design and Characterization

A. Antibodies

In designing antibodiotics, all types of antibody (e.g., IgG, pentameric and monomeric IgM, secretory and monomeric IgA, IgE and IgD) are contemplated. Nonetheless, there are advantages to using a particular class of antibody. Table 1, for example, compares the characteristics of IgG and IgM. While IgM has the advantage of better opsonization and complement activation, IgG has a longer half-life in vivo and can be raised to higher titers because of the fact that it is the primary antibody raised during secondary responses to antigen. Consequently, the preferred antibody for conjugation according to the present invention is IgG.

While antigen-specific IgG can be employed (e.g., bacteria-seeking antibodies), antigen-specificity may result in a shorter half-life of the compound (and/or greater cost). Consequently, the preferred antibody is non-specific. [Contrast C. H. J. Ford et al., Indian J. Pediatr. 57:29–46 (1990).]

Goers et al. (U.S. Pat. No. 4,867,973) describe the use of antibody conjugated to antimicrobials, but with antigen-specific antibody. In contrast, the conjugates of the present invention utilize non-specific antibody. Goers et al. describe in particular the conjugation to antigen-specific monoclonal antibodies. Monoclonal antibodies have not been a step forward in the prevention and/or treatment of bacteremia and sepsis. While these preparations should possess greater potency and specificity than polyclonal sera, they are: a) prohibitively expensive; b) frequently immunogenic; and c) exhibit unusually short circulating half-lives (typically less than 24 hours).

With respect to cost, Centoxin (a commercially produced antigen-specific monoclonal antibody) serves as a real life example; the price was approximately $3,700.00 per 100 mg dose. Pharmacoeconomic analysis indicated that—even if the product was used under strict guidelines for acute cases—"its use could add $2.3 billion to the nation's health care budget." [K. A. Schulman et al., JAMA 266:3466–3471 (1991).] The expense of Centoxin is such that it simply could not be used prophylactically. The conjugates of the present invention, on the other hand, are produced from materials costing a fraction of this figure (e.g., $2.00 per 100 mg dose) because of the readily available inexpensive source of pooled donor IgG.

Also, human monoclonals while perhaps lessening the chance of immunogenicity, do not overcome the problem of short circulating half-lives. In a study using human monoclonal anti-lipid A antibody in patients with sepsis syndrome, the mean serum half-life was approximately sixteen (16) hours. [See C. J. Fisher et al., Clin. Care Med. 18:1311–1315 (1990).] To maintain a protective level of antibody, this reagent would need to be given repeatedly. Again, the cost of such an approach would be staggering.

From the above, it should now be clear why the limitation to "non-specific immunoglobulin" is a critical limitation that is unique to the present invention. Non-specific IgG is easily and cheaply obtained, requiring no immunization and eliciting no immune response in a syngeneic setting. Non-specific IgG does not have the standardization problems of antigen-specific antibody. Simply put, there is no antigen-specific titer to be concerned about (let alone variability in the titer from unit to unit). Rather, standardization comes from the conjugated ligand; conjugation of non-specific IgG results in >1000-fold increase in LPS-binding titer and by standardization of the ligand that is attached, one standardizes the activity of the therapeutic. Finally, non-specific IgG, unlike monoclonals, has a long half-life needed for a prophylactic (compare the >21 day half-life of pooled polyclonal human IgG with the mean serum half-life of 16 hours for the human monoclonal antibodies discussed above).

For purposes of expense, IgG from donors (i.e., human and animal) rather than cell lines is desirable. In this regard, typically large pools of plasma are used as starting material. Large scale fractionation techniques known in the art include ethanol precipitation and precipitation with high concentrations of salt. [See H. F. Deutsch in *Methods in Immunology and Immunochemistry*, (C. A. Williams and M. W. Chase, eds.), Academic Press, New York, pp. 315–321 (1967).] There is also the somewhat complicated procedure where the immunoglobulin is isolated from Cohn Effluent III by diafiltration and ultrafiltration. [See E. J. Cohn et al., J. Am. Chem Soc. 68:459–475 (1946).]

This latter procedure is used to make a commercially available human IgG preparation called Gammimune® N (Miles, Inc., West Haven, Conn.). Of course, each individual donor used to make the product must be tested and found nonreactive in tests to determine exposure to or the presence of pathogens. In this product, which is intended for intravenous administration, the protein (as a 4.5–5.5% solution) has not been chemically modified other than in the adjustment of the pH of the solution to 4.0–4.5. Isotonicity is achieved by the addition of (9–11%) maltose.

Each milliliter (ml) contains approximately 50 mg of protein, of which not less than 98% has the electrophoretic mobility of gamma globulin. Not less than 90% of the gamma globulin is monomeric. There are traces of IgA and IgM. The distribution of IgG subclasses is similar to that found in normal serum.

The commercial product displays a broad spectrum of opsonic and neutralizing antibody activities. When administered intravenously, essentially 100% of the infused IgG antibodies are immediately available in the recipient's circulation. The in vivo half-life equals or exceeds the three week half-life reported for IgG in the literature. It is therefore quite acceptable for use in the preparation of antibody-antibiotic conjugates of the present invention.

TABLE 1

|  | IgM | IgG |
| --- | --- | --- |
| Structure | Pentameric | Monomeric |
| C' Fixation | +++ | + |
| Opsonophagocytosis | +++ | + |
| Half-life | 5 days | 25 days |
| Biodistribution | Slow | Fast |
| Secondary Response | Minimal | Large |

Of course, the infusion of large amounts of antibody in humans is contraindicated in individuals who are known to have had previous anaphylactic or severe systemic responses to IgG. Care must also be taken to confirm that there is no sensitivity to the trace amounts of other antibody (e.g., IgA).

Before administration of the antibody-antibiotic conjugates of the present invention to humans, it may be good medical practice to have an antibodiotic sensitivity test performed. This can be done by subcutaneously injecting a small amount of the conjugate in the arm of the patient. A salt solution is injected in the other arm as a control. Normally, a positive hypersensitivity test is indicated by no more than formation of a welt on the skin surface with surrounding swelling. Some patients, however, develop anaphylactic shock (i.e., a full-blown immediate hypersensitivity reaction). It is recommended that adrenalin be available for these cases.

The usual dosage of the commercial intravenous immunoglobulin product is 100–200 mg/kg (2–4 ml/kg) of body weight administered approximately once a month by intravenous infusion. The dosage may be given more frequently or increased as high as 400 mg/kg (8 ml/kg) body weight, if the clinical response is inadequate, or the level of IgG achieved in the circulation is felt to be insufficient.

The present invention contemplates a typical dosage for antibodiotics that is much less than that given for the commercial immunoglobulin preparations. This is particularly true where the number of conjugated antibiotic molecules exceeds one (1) per immunoglobulin molecule. The present invention contemplates a conjugate dosage range of 0.1–100 mg/kg, and a preferred range of 1–20 mg/kg. The amount of PMB (assuming 3 molecules per IgG molecule) contained in a dose for this preferred range will be 0.025–0.5 mg/kg.

B. Antibiotics

Thousands of natural, synthetic, and semi-synthetic compounds have been identified that possess antibacterial, antifungal, antiviral, or antiparasitic activity.

In the design of antibody-antibiotic conjugate, a primary consideration is the mode of action of the antibiotic. Since the conjugates will be much larger molecules than the parent antibiotics, only antibiotics that bind to exposed or secreted components (e.g., toxins) of the bacteria, fungus, virus, or parasite are likely to target the antibody carrier to the pathogen or its products. For example, penicillin antibiotics disrupt bacterial cell wall synthesis and bind to surface-exposed components of certain bacteria whereas aminoglycoside antibiotics commonly bind to ribosome subunits in the cell cytoplasm. The former is a much better candidate for effective antibody-antibiotic conjugates than the latter.

Antibiotics vary greatly in the type and species of organisms upon which they are active. For example, certain antibiotics such as the polymyxins are far more effective against gram-negative bacteria, whereas other antibiotics such as vancomycin tend to be more effective against gram-positives. Some, like the cephalosporins, and broad-spectrum penicillins are comparably effective against both types. Other antibiotics, such as amphotericin are primarily antifungal agents whereas amantadine exhibits activity against certain influenza viruses. In designing antibody-antibiotic conjugates for the prevention or treatment of disease one must consider the spectrum of antibiotic activity desired and select those antibiotic(s) that are active against the target pathogen(s) and, as described above, act primarily on exposed components of the pathogen(s).

As used herein, the term "pathogen" refers to any organism which is associated with infection or disease, whether that organism is among those traditionally considered pathogens (e.g., *S. aureus, S. pyogenes, S. dysenteriae, S. flexneri*, etc.) or is an opportunistic pathogen (e.g., *P. aeruginosa, S. marcesens, S. mitis*, etc.).

Within a family of antibiotics (e.g., penicillins, cephalosporins, polymyxins) there are structural features common to all members. However, there often exists a wide variety of natural and synthetic variations on this common structure that may influence the activity spectrum, pharmacokinetics, or other properties of the antibiotic. In the design of antibody-antibiotic conjugates, these structural differences within an antibiotic family are important from two perspectives. First, the activity spectrum may influence the choice of antibiotic; and, second, the chemical differences between antibiotics will influence the range of cross-linking chemistries available to conjugate the antibiotic. For example, the variable side chain component of penicillin antibiotics is a methyl benzyl group in penicillin G but the variable side chain group is a phenolic group with a primary amine side chain in amoxicillin. The latter antibiotic presents a wider array of potential modes for cross-linking than does penicillin G.

In Table 2, several families of antibiotics are disclosed that possess surface- and/or product-reactive activities against various pathogens. This is just for illustration and by no means is intended to limit the invention to these compounds alone.

A preferred antibiotic of the present invention is polymyxin B (PMB). As noted above, this antibiotic binds to and neutralizes endotoxin. However, when used in vivo, PMB is short-lived, and furthermore, at the recommended therapeutic dose for systemic infections, there is a significant risk of nephrotoxicity.

The level of protection achieved by the present invention is best understood when compared with other known approaches (see Table 3). For example, the widely-tested and publicized monoclonal antibody Centoxin-HA-1A is capable of binding endotoxin and neutralizing its biological activity. However, when compared to an IgG-PMB conjugate of the present invention, the monoclonal antibody is costly and suffers from low affinity and short half-life. The latter characteristics may explain why the human clinical studies have yet to yield clear benefits.

TABLE 2

Antibiotics That May Be Conjugated To Antibodies

| Type | Examples | Activity | Spectrum |
|---|---|---|---|
| Penicillins[1] | penicillin G, amoxicillin, nafcillin, ampicillin, ticarcillin, carbenicillin, cloxacillin, penicillin V | antibacterial, inhibition of cell wall synthesis | antibacterial, gram-positive and gram-negative |
| Cephalosporins[2] | cefoxitin, ceforanide | antibacterial, inhibition of cell wall synthesis | antibacterial, gram-positive and gram-negative |
| Polymyxin | polymyxin B, colistin | antibacterial binds and inhibits cell wall synthesis | antibacterial, primarily gram-negative |
| Vancomycin[3] | vancomycin, teicoplanin, ristocetin | antibacterial, binds to cell wall precursor, inhibits synthesis | antibacterial, primarily gram-positive |
| Biosurfactants[4] | circulin, EM49, polypeptin, brecistin, cerexin, tridecephin, surfactin | surface-active | antibacterial |
|  | surfactin, subsporin, mycosubtilisin, bacillomycin | surface-active | fungicidal |
| Other Peptide Antibiotics[5] | viomycin, capreomycin | not known | antimycobacterial (tuberculostatic) |
|  | bacitracin, gramicidin, gramicidin S, tyrocidine | surface-active | antibacterial |
| Amantadine[6] | amantadine | blocks ion channel | antiviral (Influenza A) |
| Polyene macrolide[7] | amphotericin | surface activity on membrane sterols | antifungal |
| Endotoxin binding proteins | tachyplesin[8] | surface active | antibacterial |
|  | Limulus anti-LPS factor[9] | LPS-binding | antiendotoxin |
|  | LPS binding protein (human)[10] | LPS-binding | anti-endotoxin |
|  | bactericidal permeability increasing protein[11] | LPS-binding | anti-endotoxin |

[1]G. L. Mandell and M. A. Sande in Goodman and Gilman's: The Pharmacological Basis of Therapeutics, 8th Ed., (Gilman, Rall, Nies, and Taylor, eds.), Pergamon Press, New York, pp. 1065–1097 (1990).
[2]Id.
[3]M. A. Sande and G. L. Mandell in Goodman and Gilman's: The Pharmacological Basis of Therapeutics, 8th Ed., (Gilman, Rall, Nies, and Taylor, eds.), Pergamon Press, New York, pp. 1117–1145 (1990).
[4]A. Fiechter, Trends in Biotech. 10:208–217 (1992).
[5]G. L. Mandell and M. A. Sande in Goodman and Gilman's: The Pharmacological Basis of Therapeutics, 8th Ed., (Gilman, Rall, Nies, and Taylor, eds.), Pergamon Press, New York, pp. 1146–1164 (1990).
[6]R. G. Douglas in Goodman and Gilman's: The Pharmacological Basis of Therapeutics, 8th Ed., (Gilman, Rall, Nies, and Taylor, eds.), Pergamon Press, New York, pp. 1182–1201 (1990).
[7]J. E. Bennett in Goodman and Gilman's: The Pharmacological Basis of Therapeutics, 8th Ed., (Gilman, Rall, Nies, and Taylor, eds.), Pergamon Press, New York, pp. 1165–1181 (1990)
[8]T. Nakamura et al., J. Biol. Chem. 263:16709–16713 (1988).
[9]G. Alpert et al., J. Infect. Dis. 165:494–500 (1992).
[10]R. R. Schumann et al., Science 249:1429–1431 (1990).
[11]M. N. Marra et al., J. Immunol. 148:532–537 (1992).

TABLE 3

|  | Centoxin | IgG-PMB |
|---|---|---|
| Dosage | 100 mg | 100–500 mg |
| Raw Material Cost | $300 | $2–10 |
| Endotoxin Affinity | low | high |
| Half-life | short (<24 hr) | long (>20 days) |
| Safety | good | good |

Others have attempted to reduce the toxicity of polymyxin B by attachment to dextran. [D. A. Handley, Eur. Patent Appl. Pub. No. 428486.] However, dextran has a half-life in humans of only about a day. By use of immunoglobulin according to the present invention, a much longer half-life is achieved (see Table 4 and Examples 24 and 25). Dextran, having no Fc receptor (FcR), also has no known capacity to promote opsonization or activate complement (C').

As it important that the antibodiotics be non-toxic to the host animal, the present invention contemplates the use of conjugates which are effective against the organisms of interest, yet are non-toxic to the host. The non-toxic character of IgG-PMB is demonstrated in Example 27.

As noted previously, the present invention also contemplates antibodiotics having reactivity with gram-positive organisms and their toxins. In one embodiment, the present invention contemplates the use of bacitracin conjugated to immunoglobulin. In another embodiment, the present invention contemplates the use of vancomycin conjugated to immunoglobulin.

Bacitracin is a polypeptide produced by a strain of Bacillus subtilis (Tracy strain), which is primarily bactericidal for gram-positive organisms including Streptococcus pyogenes, other β-haemolytic streptococci, Pneumococcus pneumoniae, and certain strains of Clostridium species. Bacitracin exerts its effect by inhibiting early steps in the biosynthesis of peptidoglycan interfering with cell wall synthesis. Commercially available bacitracin is stable and poorly absorbed from the intestinal tract or wounds. Because of the proteinuria, hematuria and nitrogen retention observed upon systemic administration, its use is usually restricted to topical application. [See e.g., R. Berkow and A. J. Fletcher (eds.), *The Merck Manual*, 16th ed., 1992, p. 46; and G. F. Brooks et al., *Jawetz, Melnick & Adelberg's Medical Microbiology*, 19th ed., 1991, pp.172–173).]

Despite the unacceptable occurrence of nephrotoxicity associated with systemic administration of free bacitracin, when it is conjugated to immunoglobulin according to the present invention, the advantages of bacitracin can be achieved without this side-effect. It is not intended that the present invention be limited by the mechanism of action of any particular antimicrobial.

Vancomycin is active, principally, against gram-positive organisms including *Staphylococcus aureus* and *Clostridium difficile*. While it is not intended that the present invention be limited by the mechanisms of action, it is believed that vancomycin exerts its bactericidal action by interfering with cell-wall synthesis. This invention contemplates conjugates synthesized from vancomycin and non-specific human immunoglobulin using a variety of crosslinking agents and schemes. These conjugates, like the ones previously listed, suppress bacteremia as well as toxin-mediated effects for gram-positive organisms.

TABLE 4

|  | Dextran-PMB | Ig-PMB |
|---|---|---|
| Carrier | Polysaccharide | Protein |
| Conjugation Chemistry | Carbonyl, amide | —SH, CHO, NH$_2$ |
| Cross-linkers? | No | Yes |
| Bactericidal | ? | Yes |
| Expected Half-life | ≦24 hr | >20 days |
| Effector for C' | No | Yes |
| FcR | No | Yes |
| Additional Reactivities | No | Yes (IV Ig has additional reactivities) |

In one embodiment, the method involves conjugating the vancomycin to non-specific immunoglobulin by first treating the vancomycin and the immunoglobulin with different heterobifunctional crosslinking agents, and second reacting the derivatized species with each other to form a conjugate. In a second embodiment, the method involves conjugating the vancomycin to non-specific immunoglobulin by first reacting the same heterobifunctional crosslinking agent with both the vancomycin and the non-specific immunoglobulin, then second reacting both derivatized species with each other forming a conjugate. For both synthetic schemes a variety of crosslinker combinations have been contemplated and tested. Below is a table which lists the crosslinking compounds which have been tested to date for reaction with vancomycin. Some of the crosslinking agents, upon reaction with vancomycin, were insoluble in aqueous solution and were not further pursued. It is recognized, however, that should steps be taken to render them soluble (e.g. addition of solvents, further side group modification of the base vancomycin structure, etc.) that such crosslinking agents could prove useful.

The table describes the crosslinking approach, the group on the modified vancomycin that is reactive ("reactive group") with either immunoglobulin or the corresponding linker on immunoglobulin (if any), the solubility, and the biological

GRAM POSITIVE VANCOMYCIN CONJUGATES

| Compound | Abbreviation | Reactive Group on Modified Vancomycin | Soluble | MIC w/o IgG (μg/ml) | MIC w/ IgG (μg/ml) | Linker On IgG |
|---|---|---|---|---|---|---|
| Vancomycin | Vanco | n/a | Yes | 1.0 | No | No |
| Sulfosuccinimidyl 6-[3-(2-pyridyldichlo) proplonamide] hexanoate:Vancomycin | Vanco:sulfo-LC | -SH | No | No | No | No |
| Iminothiolane:Vancomycin | Vanco:Traut's | -SH | Yes | 2.4 | inactive | SMCC |
| S-acetyl mercapto succinic anhydride: Vancomycin | Vanco:SAMSA | -SH | Yes | 2.6 | 440 | SMCC (suspect MBS, SMPB, GMBS, SIAB |

GRAM POSITIVE VANCOMYCIN CONJUGATES

| Compound | Abbreviation | Reactive Group on Modified Vancomycin | Soluble | MIC w/o IgG (μg/ml) | MIC w/ IgG (μg/ml) | Linker On IgG |
|---|---|---|---|---|---|---|
| m-Maleimidobenzoyl-N-hydrosulfosuc-cinimide ester:Vancomycin | Vanco:sulfo-MBS | -Maleimide | No | No | No | will work)<br>No |
| Sulfosuccinimidyl 4-(p-maleimidophenyl) butyrate:Vancomycin | Vanco:sulfo-SMPB | -Malei-mide | No | No | No | No |
| Sulfosuccinimidyl 4-(N-malimidomethyl) cyclohexane-1-carbonate:Vancomycin | Vanco:sulfo-SMCC | -Malei-mide | No | No | No | No |
| Bis (sulfonsuccinimidyl) suberate: Vancomycin | Vanco:BS$^3$ | Succinimide | No | No | No | No |
| Sulfosuccinimidyl (4-iodoacetyl) aminobenzoate:Vancomycin | Vanco:sulfoSIAB | Iodoacetyl | No | No | No | No | activity of the conjugate. The following examples describe representative reactions set forth in the table.

C. Conjugates and Cross-linking

Numerous agents have been developed for the cross-linking of biological molecules. [Pierce Chemical Co., (Rockford, Ill.), General Catalog, pp. E-10–E-39 (1992).] In general, these agents possess functional groups that are reactive with the side chains of different amino acids found in proteins or peptides. As summarized in Table 5, various functional groups will react with primary amino groups, carboxyl groups, hydroxyl groups, or thiol groups of proteins or other compounds. In the design of antibody-antibiotic conjugates, the reactive groups of both the antibody and antibiotic must be considered. In general, antibodies have many reactive groups that can be used in direct conjugation schemes (amino acids containing primary amine, carboxyl, hydroxyl, thiol [after reduction]) or modified groups (glycosylated amino acids that can be oxidized to aldehyde; or primary amines that can be made thiol-reactive) for conjugation schemes. Individual antibiotics will not, in general, possess very many different reactive groups and offer fewer choices for conjugation to antibodies. The selection of an antibiotic from a family of related compounds and the selection of a cross-linking scheme must take into consideration the reactive groups on an antibiotic.

A key concern in modifying an antibiotic is the preservation of its ability to bind to the surface or secreted products of a pathogen. The modification of individual reactive groups or excessive modification of more than one reactive group with cross-linking agents, or the steric hindrance created by attachment to a large protein such as immunoglobulin may abolish antibiotic activity. Therefore, before conjugate activity is considered, conditions for preservation of antibiotic activity must be determined by examining the biological activity of the modified or cross-linked antibiotic in simple antimicrobial assays. Preferably, one chooses a cross-linker type and concentration that preserves antibiotic activity.

Different cross-linkers may influence the activity of individual antibiotics and the efficiency with which they are conjugated to antibodies. In the design of antibody-antibiotic conjugates, the discovery of more optimal cross-linkers relies on the empirical analysis of conjugates prepared using varying concentrations of different cross-linkers.

The in vivo safety and efficacy of antibody-antibiotic conjugates will depend upon their activity, toxicity and stability. The selection of the cross-linking agent may also affect these aspects of conjugate performance. For example, in addition to influencing the activity of the conjugate imparted by the antibiotic, the cross-linker employed may affect the properties of the antibody. Effector functions dependent upon the Fc region of the antibody such as opsonization or complement fixation may be influenced by which reactive groups are utilized and their location on the antibody molecule. Furthermore, some cross-linkers may cause adverse reactions by eliciting an immune response to the haptenic groups on the cross-linker. Finally, the in vivo stability of the bonds created by the cross-linking scheme may vary in important ways. Disulfide bonds linking the antibiotic and antibody may not be as stable, for example, as amide bonds created by other cross-linkers. Dissociation between antibody and antibiotic may not be tolerable in cases where long-term prophylaxis is desired.

TABLE 5

Conjugates

| Functional Groups | Reacts With: |
|---|---|
| Aldehyde | Primary amines |
| Imide | Primary amines |
| Amino | Aldehyde |
| Cyano | Hydroxyl groups |
| Halogen (e.g., Bromine) | Thiol groups |
| Carboxyl groups | Primary amines |
| Activated carboxyl groups (e.g., N-succinimidyl esters of carboxylic acids)* | Primary amines or hydroxyl groups |
| Anhydrides (e.g., succinic anhydride and maleic anhydride) | Primary amines |
| Maleimide derivatives | Thiol groups |

*e.g., N-hydroxyl succinimide ester of N-(-4-carboxycyclo-hexyl methyl) maleimide.

D. Analogues

The present invention contemplates the use of antibody analogues. Antibody analogues are those compounds which act in an analogous manner to antibodies. In one embodiment, the present invention contemplates fragments of antibodies (e.g., Fc fractions) to make antibody-antibiotic conjugates. As herein used, the terms "antibody" and "immunoglobulin" are meant to include antibody analogues.

The present invention also contemplates the use of fusion proteins containing antibody effector sites as applied to the Immunobiotic™ and Immunoadapter™ approaches. Specifically, recombinant proteins representing human antibody sequences can be employed as a framework to attach targeting ligands.

E. New Antibiotics and Conjugates

Antibiotic compounds have been isolated from many different microbial, plant, and animal sources and new promising compounds continue to be discovered. In addition, synthetic derivatives of natural compounds as well as wholly synthetic compounds such as small peptides are also being screened for antibiotic activities in many laboratories. As used herein, the term "antibiotic" refers to any chemical compound which destroys, inhibits the growth of, or binds to microorganisms (i.e., "antimicrobials"). It is not intended that the term be limited only to those compounds which are produced by microorganisms. "Antibiotic" therefore includes compounds which are produced synthetically, as indeed many of the antibiotics are now produced in the chemistry lab rather than by microorganisms. Polymyxin and other compounds discussed herein may be produced synthetically or obtained from "natural" sources (e.g. *B. polymyxa*). Therefore, the invention contemplates the design and synthesis of a variety of antibody-antibiotic conjugates utilizing antibiotics from all sources.

Figure 2:
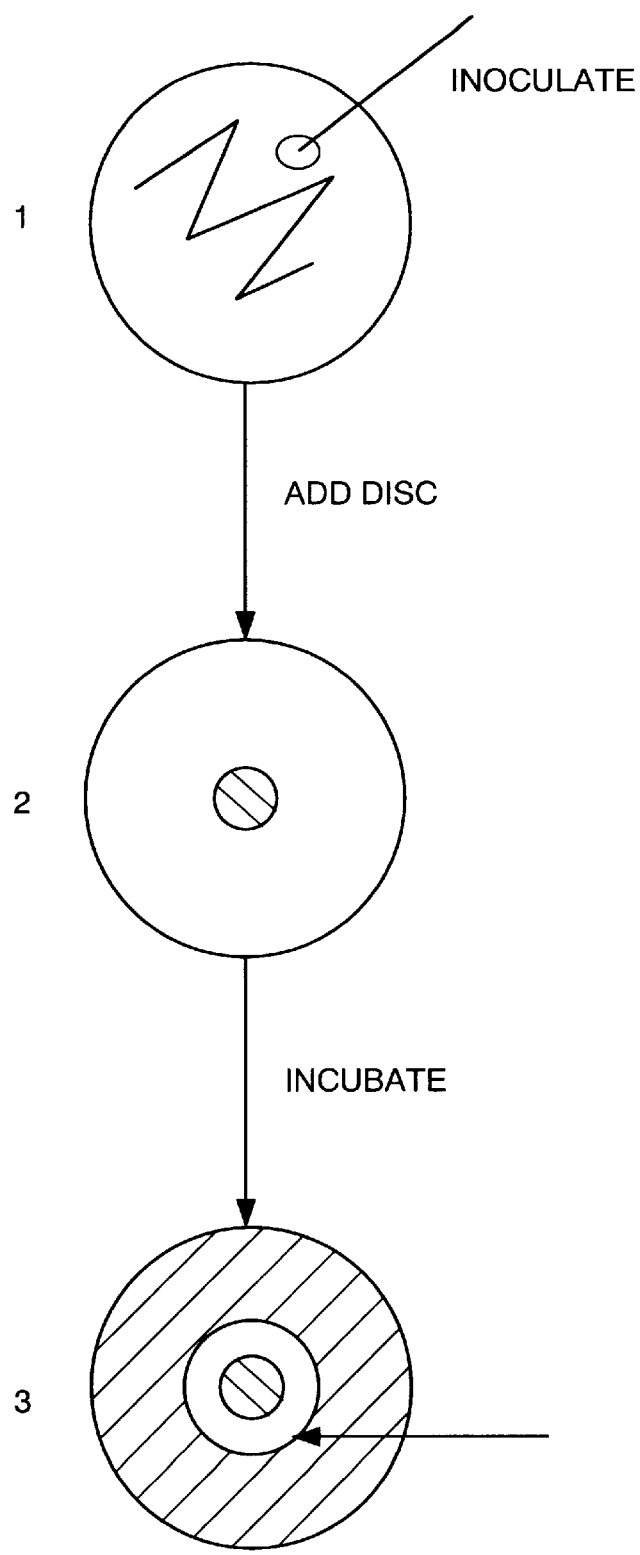
FIG. 2 schematically shows a means of screening modified antibiotics for anti-bacterial activity.
Figure 3:
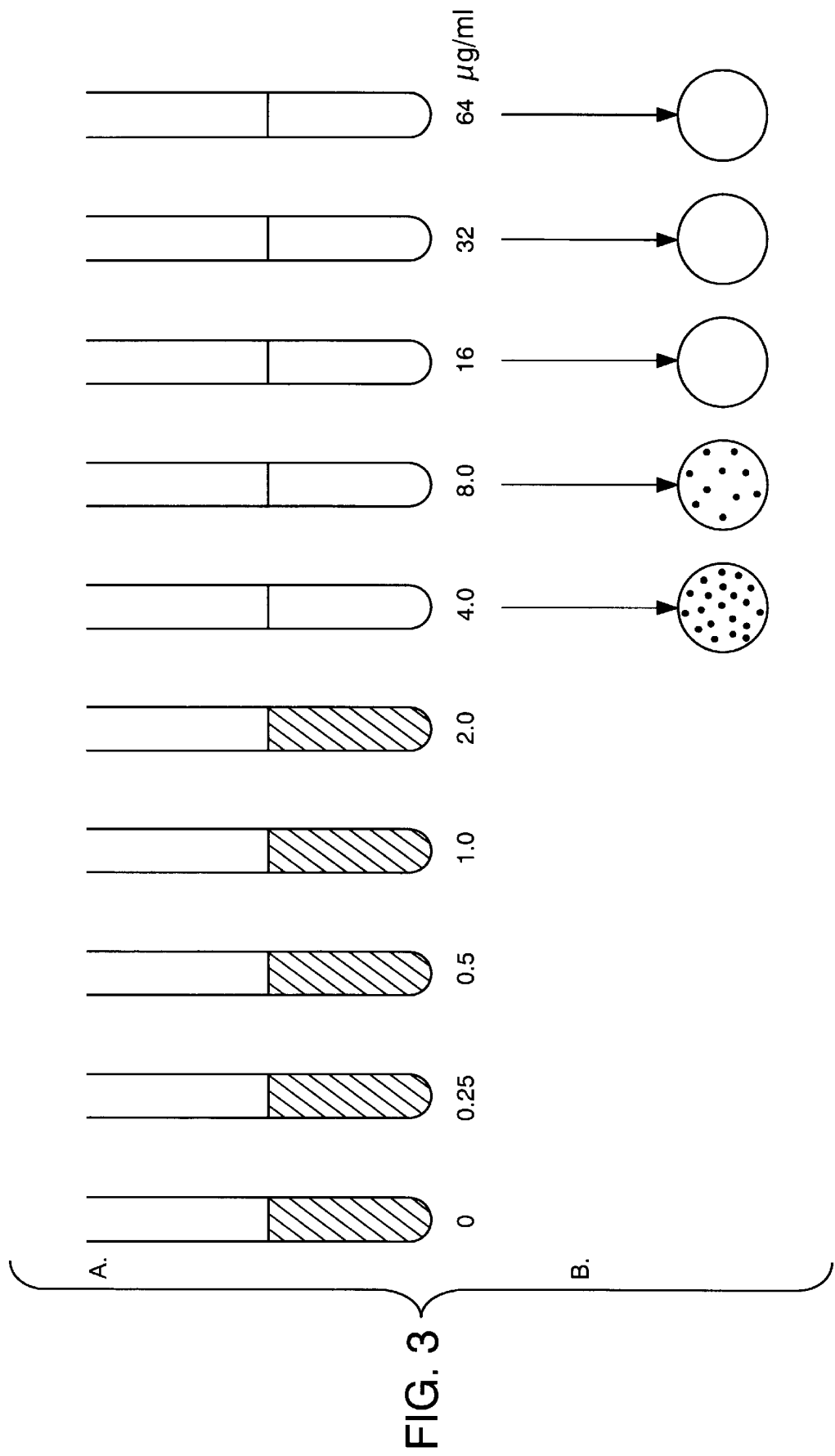
FIG. 3 outlines an alternative method by which new antibiotics can be screened for use as compounds for conjugation with immunoglobulins.
Figure 4:
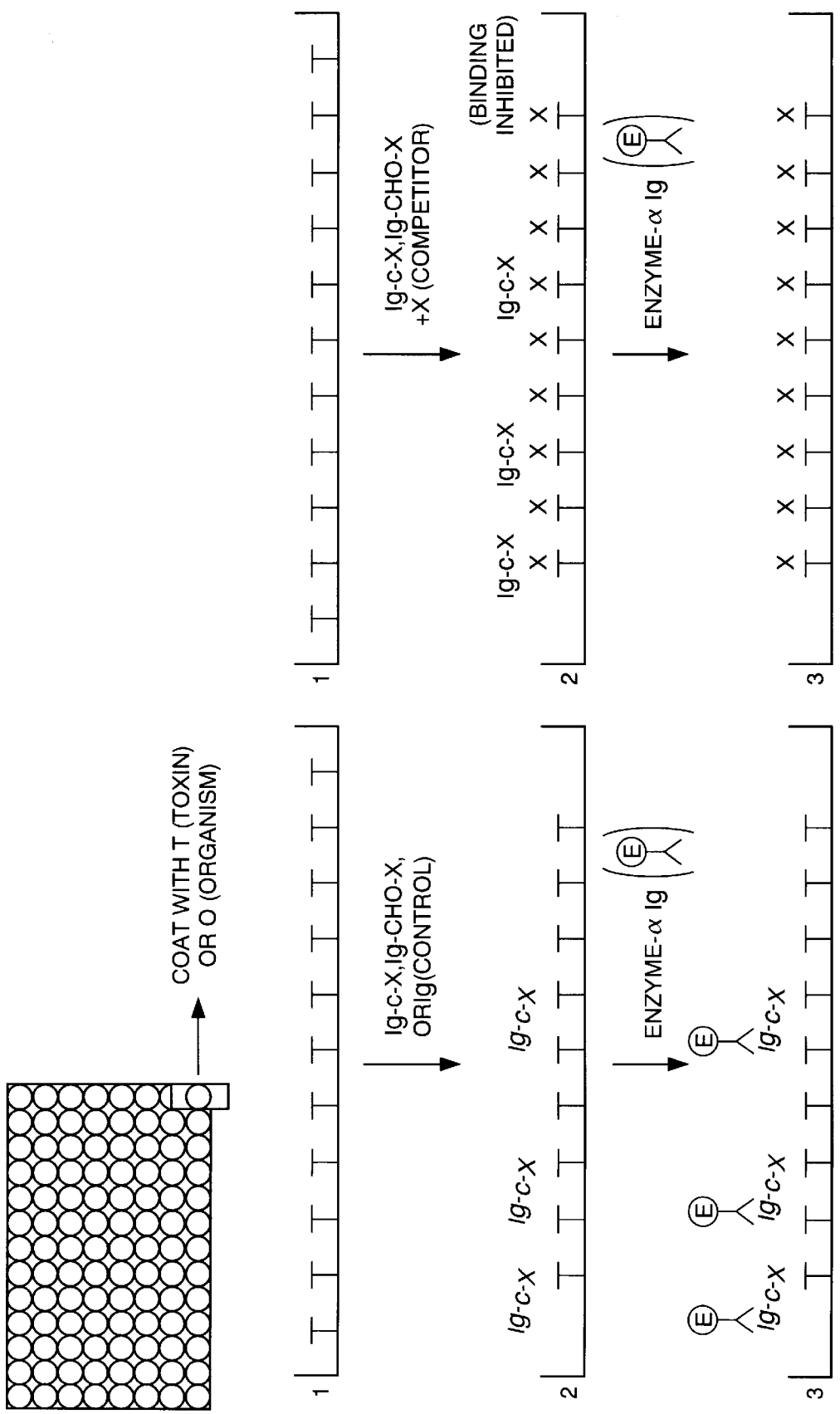
FIG. 4 describes solid phase assays for determining the level of binding of antibodiotics of the present invention. Step 1 shows toxin or organisms in a testing microwell. Step 2 schematically represents the binding of antibodiotic. Step 3 schematically shows the binding of secondary reagents.

FIGS. 2–4 outline the methods by which new antibiotics can be screened for use as compounds for conjugation with immunoglobulins. The "Screening Modes" consist of the following temporal steps:

Mode I: Conjugate the antibiotic to a cross-linker only and then assess for inhibition of organism growth in liquid culture and on a disc inhibition lawn assay (e.g., Kirby-Bauer).

Mode IIA: Conjugate the antibiotic via the cross-linker to immunoglobulin and then assess for binding to bacteria and bacterial toxin by a solid phase assay.

Mode IIB: Conjugate the antibiotic to immunoglobulin without the use of a cross-linker (e.g., periodate oxidation of the carbohydrate groups ["CHO"] of IgG) and then assess for binding to bacteria and bacterial toxin by a solid phase assay.

Mode III: Check specificity of the antibodiotic by inhibition of bacterial toxin binding with the antibiotic.

Mode IV: Assess the antibodiotic for inhibition of organisms growth in liquid culture.

By using this approach, a new antibiotic ("X") can be evaluated for use in the present invention. Although it is not required for research use, it is contemplated that in the clinical setting, the current protocols for broth dilution, disk diffusion, and other methods developed by the National Committee for Clinical Laboratory Standards (NCCLS) will be followed.

For example, antibiotic X may initially be evaluated by Mode I. In this Mode, X is only conjugated to a cross-linker "c" to create "X-c"; this compound is then added to a liquid or solid phase culture. By creating only part of antibodiotic, the question of compatibility with immunoglobulin is avoided; Mode I only addresses compatibility of "X" with the conjugation chemistry. The assay is performed and the results are compared to an identical assay of unconjugated antibiotic X.

For the lawn assay comparison in Mode I, an agar-filled petri dish is inoculated with the organism (Step 1, FIG. 2). A small filter-paper disc containing a known amount of antibiotic X or X-c is placed on the agar surface and allowed to diffuse into the medium over an 18- to 24-hr period (Step 2, FIG. 2). After this incubation, a zone of growth inhibition is apparent with X and this is compared to the zone (if any) achieved with X-c (Step 3, FIG. 2).

Alternatively for Mode I, known concentrations of X or X-c are diluted in broth in a test tube, which is then inoculated with an organism susceptible to X (FIG. 3). After incubation, the concentration that inhibits growth (i.e., no visible growth, as indicated by lack of turbidity) is determined. This value corresponds to the minimum inhibitory concentration ("MIC") (FIG. 3A). To assess bactericidal activity, an aliquot is taken from a tube showing bacteriostatic activity, and this aliquot is added to agar plates (FIG. 3B). If growth occurs, then the agent is bacteriostatic; if no growth occurs, the agent is bactericidal. The minimal bactericidal (lethal) concentration is the lowest concentration of X-c or X that produces a 99.9% reduction in organisms from the original inoculum of approximately 100,000 organisms. In this manner the minimum bactericidal concentration ("MBC") is established. [I. S. Snyder and R. G. Finch in *Modern Pharmacology*, 2d Ed. (C. R. Craig and R. E. Stitzel, eds.), Little, Brown and Company, Boston, pp. 631–640 (1986); J. E. Conte, Jr. and S. L. Barriere, *Manual of Antibiotics and Infectious Diseases*, 6th Ed., Lea and Febiger, Philadelphia, pp. 135–152 (1988).]

When comparing X-c with X, some reduction in activity is expected. However, the more potent X is, the greater the reduction in X-c activity permissible. Overall, a range of 0.01 to 50 $\mu$g/ml for both the MIC and the MBC is practical.

If the activity of X-c is good, it is further evaluated in Mode IIA. If the activity of X-c is poor, X is evaluated in Mode IIB. Both Modes IIA and IIB contemplate covalent attachment; Mode IIA uses a cross-linker to create "X-c-Ig", while Mode IIB does not use a cross-linker and generates "X-CHO-Ig." In both cases, the antibody-antibiotic conjugate, or simply the "antibodiotic", is assayed on a solid phase assay such as shown schematically in FIG. 4.

Toxin or organisms may be used in the solid phase assay to coat a microwell or other appropriate surface (Step 1, FIG. 4A). The antibodiotic is then added to test for binding (Step 2, FIG. 4A). Standard washing procedures are used to avoid non-specific binding. The antibody portion of the conjugate may thereafter serve as a target for secondary reagents (e.g., goat anti-human IgG antibody having an enzyme reporter group such as horseradish peroxidase) (see Step 3, FIG. 4A). An appropriate substrate for the enzyme may then be added (not shown) to generate a colorimetric signal.

Where toxin is used in the solid phase assay, X-c-Ig binding may be compared with that of X-CHO-Ig. Where the organism is used, care must be taken that binding is not via the Fc receptor of Ig. Unconjugated Ig can be used as a control for this purpose.

To avoid any binding due to denaturation or other artifact, conjugates showing reactivity in Mode IIA or Mode IIB should be evaluated in Mode III. As shown in FIG. 4B, this simply involves adding free antibiotic to show that it will compete specifically for binding.

The next portion of the evaluation involves testing the antibody-antibiotic conjugate for growth inhibition and/or bactericidal activity (Mode IV). This is the same assay as shown in FIG. 2, the difference being that now the complete conjugate X-c-Ig (or X-CHO-Ig) is evaluated rather than just the antibiotic (X-c).

Both X-c-Ig and X-CHO-Ig may show good toxin binding in Mode II but poor anti-bacterial activity in Mode IV. If the specificity of the binding is nonetheless confirmed in Mode III, these compounds are candidates for diagnostic reagents. Alternatively, they may be used in vivo simply to bind free toxin and thereby reduce toxin load.

Thoughtful consideration of the results of each of these steps allows any antibiotic to be analyzed for potential use in the form of an antibodiotic. Following these in vitro tests, the antibiotic can then be evaluated in vivo for reduced toxicity and pharmacokinetics."antibody" and "immunoglobulin" are meant to include antibody analogues.

F. Antibiotic Precursors and Conjugates "Antibiotic precursors" as herein defined are reactants used in the synthesis of semi-synthetic antibiotics that possess limited in vitro and in vivo anti-microbial activity. Therefore one would not typically use such compounds as anti-microbial agents. The present invention contemplates, however, that the "latent" anti-microbial potential of such compounds can be activated upon conjugation, according to the methods herein described, with immunoglobulin.

In one embodiment, the method involves, as a first step, the unlocking of the anti-microbial potential of antibiotic precursors by derivatizing them with a crosslinking agent. These derivatized antibiotic precursors by themselves possess increased anti-microbial effects compared to the free antibiotic precursors. As a second step, conjugates are made between the derivatized antibiotic precursors and human immunoglobulin. Through this latter step, a conjugate is created that possesses the benefits exhibited by the earlier described conjugates (increased half life, reduced nephrotoxicity, etc.).

G. Antibiotics and Immunoadapter™ Compounds

The present invention also links antibiotics non-covalently with the potent effector functions of antibodies. In this manner, the antibiotics serve as high affinity surface binding ligands. A hybrid molecule is created with antimicrobial properties superior to antibodies generated through natural infection or vaccination.

The Immunoadapter™ format takes advantage of ligand targeting via a non-covalent link to the antibody through the antigen combining site. This is accomplished with Immunoadapter™ compounds that consist of the surface targeting ligand (e.g. antibiotic) attached to a hapten that will bind to specific antibodies. This format has several engineering and therapeutic advantages. Small molecule targeting ligands can be engineered using synthetic organic chemistry independently of the antibody protein (thus avoiding the problem of damage to the antibody by contact with organic solvents). This flexibility in chemical synthesis allows a limitless range of small molecule and peptide ligands to be used.

This format is contemplated for both active and passive immunotherapy regimens. In the active mode, the patients circulating antibodies (either naturally-occurring or those resulting from vaccination) can be directed to microbes via the Immunoadapter™ compound. This avoids the cost, efficacy and safety concerns when using donor antibodies. Passive hapten-specific antibody may be optimal in some cases, and can be obtained from specific donor, cell culture or recombinant sources.

The design features of Immunoadapter™ compounds, include:
  microbial targeting—choice or ligands, spacial orientation, modification of ligands through chemical modification, retention of ligand activity
  linking chemistries—choice of reactive groups, efficiency of reactions, placement on antibody, length of spacer arms, novel reactive groups
  antibody compositions—retention of effector functions, solubility and serum half-life
  assay systems—in vitro and in vivo systems to analyze targeting and effector functions Importantly, Immunoadapter™ compounds can be evaluated in a similar manner as discussed above for covalently-linked antibiotics.

II. Antibodiotic In Vitro and In Vivo Efficacy

A. In Vitro Reactivity of the Fc Region

In the previous section, the key question was whether the antibiotic portion of the conjugate shows the same or similar reactivity as the native antibiotic. However, it must be emphasized that immunoglobulin is not simply an inert carrier. The Fc portion of the antibody can mediate pathogen elimination by two mechanisms that are distinct from the effects of the antibiotic. First, it is known that following binding of antibody to antigen, the Fc region can activate the classical pathway of complement, ultimately resulting in the lysis of organisms. Second, binding of the conjugate to bacteria can lead to the ingestion or opsonization of the organism by recognition of the Fc region by phagocytes (e.g., macrophages) and/or lysis by killer cells. [See L. E. Hood et al., *Immunology*, 2d Ed., The Benjamin/Cummings Publishing Company, Inc., Menlo Park, pp. 339–340 (1984).]

The present invention contemplates antibody-antibiotic conjugates with the capability of binding Fc receptors on phagocytes. It is preferred that in competition binding, the binding of the antibody-antibiotic conjugates of the present invention to such cells is substantially similar to that of normal IgG.

The present invention contemplates antibody-antibiotic conjugates which, while not activating complement systemically, are capable of binding complement to facilitate pathogen killing. Furthermore, conjugates are contemplated which bind phagocytes via the Fc region to facilitate pathogen elimination. Thus, it is contemplated that the antibody-antibiotic conjugates will mediate or enhance opsonization and removal (opsonophagocytosis) of the etiologic agent(s) of sepsis in the treated patient.

B. Efficacy of the Conjugate In Vivo

Regardless of the manner in which the conjugate is used in vivo (acute, prophylactic, etc.), the conjugate will be present in a background of the entire repertoire of host immune mediators. These immune mediators include, of course, humoral immune mediators such as endogenous antibodies directed against bacteria and their toxins.

In this regard, several studies have suggested a causal relationship between a person's humoral immune status and the susceptibility to gram-negative infections. In patients who survived *Pseudomonas aeruginosa* septicemia, both total IgG levels and the circulating titer of core antigen-specific anti-LPS levels were significantly higher than in those patients who succumbed. [M. Pollack et al., J. Clin. Invest. 72:1874–1881 (1983).] Similarly, a correlation has been found between the titer of IgG against the patient's infecting organism and the frequency of shock and death. [S. H. Zinner and W. R. McCabe, J. Infect. Dis. 133:37–45 (1976).]

These studies suggest that patients at risk of gram-negative sepsis and endotoxemia may be so because of weakened humoral immune defenses. For this reason, the present invention contemplates, in one embodiment, determining the immune status of the host prior to administration of the antibodiotic. This determination can be made by screening potential risk groups for total and endotoxin core antigen-specific IgG and IgM levels. [B. J. Stoll et al., Serodiagnosis and Immunotherapy 1:21–31 (1987).] Screening is believed to be particularly important with the elderly, full-term and pre-term neonates [W. Marget et al., Infection 11:84–86 (1983)], patients with malignancies [C. Stoll et al., Infection 13:115–119 (1985)], abdominal surgery candidates, individuals under long-term catheterization or artificial ventilation, and bum and other trauma victims.

Where the immune status is poor (e.g., low total IgG levels and low levels of anti-bacterial antibodies), the efficacy of the antibody-antibiotic conjugate is expected to be most dramatic. Where the host's immune status is good, use of the conjugate will support the endogenous anti-bacterial defenses.

For optimal in vivo treatment, the conjugate itself must be effective against clinically relevant organisms, non-toxic and non-immunogenic. Thus, it is contemplated that the conjugates of the present invention will be effective against gram-positive and gram-negative organisms which are commonly associated with sepsis (e.g., *E. coli, K. pneumoniae, P. aeruginosa, S. pyogenes, S. aureus, S. epidermidis*, etc.). It is also contemplated these conjugates will be non-toxic to the host animal. As with any chemotherapeutic, the conjugate must be effective against the infecting organisms, but not harm the host. In addition, in order to enhance the host's response to the infecting organism and to prevent such complications as serum sickness upon subsequent administration of conjugate, the conjugates themselves must be non-immunogenic. This characteristic permits the immune system of the host to focus on battling the infecting organisms, rather than attack the conjugates intended as treatment. As it is contemplated that these conjugates may be administered to the same animal multiple times (i.e., upon subsequent exposures to potentially pathogenic organisms) it is important that the host not produce antibodies against the conjugates themselves. Such antibody production would be likely to lead to rapid clearance of the conjugate upon subsequent administration or result in a serious, potentially life-threatening hypersensitivity response.

Conjugates which are non-immunogenic or poorly immunogenic due to high concentrations of D-configuration amino acids are also contemplated. Synthetic polypeptides entirely comprised of D-amino acids are generally unable to elicit an immune response. [M. Sela, in *Advances in Immunology*, Vol. 5, (F. Dixon and J. Humphrey, eds,), pp. 29–129 (1966).] Thus, conjugation of a synthetic antimicrobial comprised entirely of D-amino acids to the antibody would be beneficial in the present invention.

III. Antibodiotic Applications
A. Prophylactic Use in Humans

The diagnosis of sepsis is problematic. First, the development of sepsis does not require the persistent release of toxin(s) into, nor the presence of organisms the circulation. Thus, many patients who die of sepsis are never shown to be bacteremic. [R. C. Bone, Ann. Intern. Med. 115:457–469 (1991).] Second, even if bacteria are detected, the amount of time needed for this detection is often too great to be practical.

For these reasons and others, the present invention contemplates the use of antibodiotics in humans prior to the onset of symptoms (e.g., prophylactically). In particular, the present invention contemplates the use of antibodiotics as a prophylactic in patients at high risk for infection, as well as sepsis.

High risk patients include surgical patients (particularly the elderly), low birth weight infants, burn and trauma. Trauma patients are particularly difficult to examine because of the multitude of invasive procedures that they have undergone. Trauma patients are also typically hooked up to a number of devices, including intravascular lines, mechanical ventilators and Foley catheters. While every attempt is made to change intravascular lines, this is frequently impossible because of the extent of trauma and the lack of venous accessibility. [E. S. Caplan and N. Hoyt, Am. J. Med. 70:638–640 (1981).]

Most patients with multiple trauma have fever, as well as increased white cell counts due to the stress of the trauma itself. The classic indicators of infection, therefore, may or may not reflect an ongoing infection.

Because of this, current clinical practice involves treating patients with antibiotics only for specific indications, and for as short a period of time as possible. Generally, the average course for any documented infection is seven to ten days. Prophylactic antibiotics are used in only three instances: open fractures, penetrating abdominal injuries and penetrating facial injuries in which there is injury to the respiratory mucosa. Even in these situations, antibiotics are used for only three to five days, depending on the injury.

In contrast, the present invention contemplates treating all trauma patients prophylactically with antibodiotics. Because of the reduced toxicity of the conjugates and their longer residence time in the circulation, the present invention contemplates administering antibodiotics immediately to the trauma patient upon admission. Indeed, the antibodiotics may successfully be used at the first moment that clinical care is available (e.g., emergency mobile care).

Rather than the short (i.e., three to seven day) period of protection provided by native antibiotics, the use of the antibiotic-antibody conjugates of the present invention should protect the trauma patient during the entire period of risk.

Burn patients have many of the same problems with respect to the diagnosis and therapy for infection. Since the magnitude of thermal injury is related to the level of trauma in a burn victim, this even becomes more of a problem with acute cases.

It is reported that septicemia appears in the blood cultures of burn patients almost four days after a septic state. [M. Meek et al., J. Burn Care Rehab. 12:564–568 (1991).] Consequently, therapy with the conjugates of the present invention is particularly appropriate immediately after the burn injury as a means of preventing a septic reaction. Furthermore, in severe cases, consideration should be given to the topical administration of antibodiotics to prevent wound sepsis.

Importantly, burn victims are exposed equally to both gram negative and gram positive organisms. Burn victims are particularly good candidates for therapeutic preparations having bactericidal activity for both gram-positive and gram-negative organisms. This includes conjugates using a single antibiotic with reactivity for both groups of organisms (e.g., antibiotics such as a cephalosporin or broad-spectrum penicillin) and well as therapeutic "cocktail" preparations comprising: (i) a first conjugate consisting of a first antibiotic covalently bound to non-specific immunoglobulin; and (ii) a second conjugate consisting of a second antibiotic covalently bound to non-specific immunoglobulin (e.g., where the first antibiotic is polymyxin and the second antibiotic is bacitracin). Alternatively, two different antibiotics can be covalently bound to the same immunoglobulin molecule.

The use of blood cultures and the like has also been shown to be unreliable in the diagnosis of neonatal sepsis. Indeed, in practice cultures appear to have little or no influence on antibiotic therapy decision-making for at-risk infants. [T. J. Zuerlein et al., Clin. Ped. 29:445–447 (1990).] For this reason, the conjugates of the present invention can be applied with great advantage (i.e., antibiotics can be used without the concern of toxicity, and the longer circulating half-life allows for antibiotic therapy without necessarily prolonging hospitalization).

Finally, surgical patients also represent a risk group where the conjugates of the present invention can be used successfully. Current practice involves the prophylactic use of antibiotics in a very narrow category of cases (e.g., elective colorectal procedures, cholecystectomy, hysterectomy and Caesarean sections). [R. L. Nichols in *Decision Making in Surgical Sepsis*, B. C. Decker, Inc., Philadelphia, pp. 20–21

(1991).] One to two grams of a broad-spectrum antibiotic are administered intravenously at the induction of anesthesia. An additional dose may be given during an extensive procedure or post-operatively but prophylaxis beyond 24 hours is not indicated. Twenty-four hours of antibiotic prophylaxis is considered to be sufficient to control contamination. Continuance of antibiotic prophylaxis beyond 24 hours is an added expense, particularly when using an antibiotic with short serum and tissue half-lives. Most importantly, continuation of antibiotic prophylaxis also runs an excessive risk of drug toxicity and emergence of resistant strains.

By contrast as shown in rabbits in the accompanying Examples, the longer serum half-life of the conjugates of the present invention provide extended protection against sepsis without the expense of multiple dosing. Furthermore, since the distribution of immunoglobulin is predominantly to vascular compartments, the use of the conjugates of the present invention may reduce the risk of disruption of endogenous flora. Consequently, the conjugates of the present invention may be used liberally (e.g., in more categories of surgical procedures).

B. Acute Therapy in Humans

As noted previously, the present invention also contemplates the use of antibodiotics in a therapeutic preparation for acute treatment. In this case, treatment involves administration of the antibody-antibiotic conjugates after infection is detected and/or sepsis is suspected.

Evidence suggestive of gram-negative infection includes the following: (1) core temperature higher than 38° C. or lower than 35° C.; (2) peripheral blood leukocyte count greater than $12 \times 10^9$/L or less than $3 \times 10^9$/L (not due to chemotherapy), or at least 20% immature forms; (3) growth of gram-negative organisms from a blood culture drawn within the preceding 48 hours; or (4) documented or suspected site of gram-negative infection.

Current medical practice accepts sepsis as having no specific pharmacotherapy available. [R. L. Greenman et al., JAMA 266:1097–1102 (1991).] A systemic septic reaction is characterized by at least one of the following: arterial hypotension (systolic blood pressure <90 mm Hg or an acute drop of 30 mm Hg); metabolic acidosis (base deficit >5 mEq/L); decreased systemic vascular resistance (systemic vascular resistance <800 dynes/s·cm$^5$); tachypnea (respiratory rate >20/min or ventilation >10 L/min if mechanically ventilated); or otherwise unexplained dysfunction of the kidney (urine output <30 ml/h), or lungs.

It must be stressed that the antibodiotics of the present invention should ideally be used prior to a systemic infection, if possible. For example, the conjugates can be administered immediately after bacteremia or fungemia is detected. Similarly, conjugate(s) can be administered where there is an obvious sign of infection at a particular site (e.g., wounds, sinusitis, meningitis, respiratory, gastrointestinal, or urinary tract infections, etc.).

Primary bacteremia is typically defined as two or more blood cultures with the same bacterial organism occurring in a patient with no other obvious site of infection. Sinusitis is diagnosed in a patient who has at least two of the following: purulent nasal discharge, roentgenographic evidence of sinusitis or purulent material aspirated from the sinuses.

The lower respiratory tract is a common site of infection. Pneumonia in the intubated patient is diagnosed in a patient when there is fever, leukocytosis and a Gram stain with many polymorphonuclear leukocytes. Pneumonia may also be diagnosed in the patient with a new infiltrate that has not cleared with intensive physical therapy (this last criterion helps rule out atelectasis).

The present invention is particularly useful in treatment of acute meningitis. In this regard, one should keep in mind that the mortality and morbidity associated with meningitis has not changed over the past fifteen (15) years. [M. A. Awad et al., Acta Paediatr. 81:560–561 (1992).]

Among the bacterial causes of meningitis, two gram-negative organisms (*Neisseria meningitidis* and *Haemophilus influenzae*), and one gram-positive organism (*Streptococcus pneumoniae*), are the major culprits. *N. meningitidis* is responsible for an estimated 25–24% of meningitis in children one month of age through 15 years; for adults, the figure is 10–35%. *H. influenzae* is responsible for an estimated 40–60% of meningitis cases in children one month of age through 15 years, while *S. pneumoniae* is responsible for 10–20% of meningitis cases in the same age group, as well as 30–50% of cases in adults (over 15 years). [W. K. Joklik et al. (eds.), *Zinsser Microbiology*, 18th ed., p. 485, Appleton-Century-Crofts, Norwalk, Conn. (1984).] Other organisms such as Streptococcus spp. in groups A and B, *Staphylococcus aureus*, *Listeria monocytogenes*, and various gram-negative bacilli (e.g., enterics such as *E. coli*) are responsible for sporadic cases. Untreated, bacterial meningitis is fatal in 70–100% of patients, and infected neonates may have motor or intellectual impairment related to their infection. [J. M. Slack and I. S. Snyder, *Bacteria and Human Disease*, pp. 128–133, Yearbook Medical Publishers (1978).]

The blood-brain barrier represents a significant obstacle to treatment of meningitis, especially prophylactically. As the barrier is designed to prevent invasion of organisms and uptake of compounds (e.g., antimicrobials), intravenous antimicrobial administration is not always sufficient. For example, estimates provided in experimental studies indicate that drug concentrations in the cerebrospinal fluid and brain are approximately 1/200 to 1/500 of those in serum. [G. P. Youmans et al., *Biologic and Clinical Basis of Infectious Diseases*, 3d ed., p. 553, W. B. Saunders Co., (1985).] Even with the inflammatory changes associated with an intensity characteristic of bacterial meningitis, passage of antimicrobials is hindered by the barrier. [Id.]

Endotoxemia due to the release of endotoxins from dividing organisms and the presence of endotoxin in the cerebrospinal fluid (CSF) present serious complications during sepsis and meningitis. Endotoxin is detectable in the plasma and CSF of patients with meningitis due to gram-negative bacteria. [Awad et al, at 560.] Perhaps due to increased permeability of the bowel mucosa, endotoxin may also be found in the plasma of patients with meningitis due to gram-positive organisms (e.g., *Streptococcus pneumoniae*).

Ironically, release of endotoxin is aggravated by antimicrobial treatment. Indeed, it is believed that aggressive antibiotic treatment can be life-threatening. This is due to the increased burden of endotoxin present in the blood and CSF which results when a large number of organisms are simultaneoulsy killed by the antibiotic. This increased endotoxin burden results in the pathology associated with fatal meningitis and is a significant problem facing clinicians who must treat a seriously ill patient within the first few hours of disease.

The present invention contemplates the use of the antibody-antibiotic conjugates of the invention (e.g., antibody-polymyxin conjugates) as "endotoxin sponge(s)," i.e., compounds which bind and facilitate clearance of released endotoxin. In a preferred embodiment, it is contemplated that the conjugates will be administered prior to the administration of standard antibiotics, both in order to bind the endotoxin released during microbial growth, as well as a preparatory step which will permit aggressive antimicrobial therapy without causing adverse effects due to endotoxin release following cell death. In this manner, the conjugates will be administered in conjunction with antimicrobial treatment. Importantly, it is contemplated that the endotoxin sponge will be safely administered intrathecally or intravenously, in order to directly place the compound in the needed location.

In addition, the present invention contemplates the treatment of meningitis caused by gram-positive organisms. In this regard it is contemplated that certain conjugates will again act as an endotoxin sponge, enhancing the clearance of any endotoxin present in the blood and/or CSF due to increased bowel mucosa permeability. It is also contemplated that certain conjugates (e.g., vancomycin-antibody conjugates) will effectively remove analogous substances produced and released by gram-positive organisms. For example, a "capsular sponge" would be useful for binding and clearing the large amount of capsular material produced by Streptococcus pneumoniae. This embodiment would also enhance opsonophagocytosis, as the antiphagocytic activity of the capsule will be neutralized by the capsular sponge.

C. Veterinary Care

Septicemia and sepsis are by no means limited to human beings. Infection by gram-negative bacteria accounts for significant morbidity and mortality in neonatal livestock, such as calves. [D. D. Morris et al., Am. J. Vet. Res. 47:2554–2565 (1986).] Interestingly, humoral immune status is again related to susceptibility to sepsis and this is largely dependent on passive transfer from colostrum. For this reason, the present invention contemplates, in one embodiment, determining the immune status of the animal prior to administration of the antibodiotic. This determination can be made by screening neonatal calves for total circulating serum immunoglobulin (e.g., by ELISA).

Where the immune status is poor (e.g., low total IgG levels), the conjugate should be used prophylactically. Where the animal's immune status is good, use of the conjugate may be needed for acute therapy of gram-negative bacterial sepsis, which remains prevalent in neonatal calves even with high antibody levels.

The present invention contemplates the treatment of other animals as well. Among foals less than 10 days of age in critical distress, sepsis is the most serious problem. [A. M. Hoffman et al., J. Vet. Int. Med. 6:89–95 (1992).] Symptoms highly indicative of sepsis risk include weakness, metabolic disturbance and dehydration. In one embodiment, the invention contemplates using antibodiotics for prophylactic treatment of foals less than 10 days of age having these indicators, or those at risk of infection.

While positive blood cultures are found in less than half of the cases, those animals found positive have a very poor chance of survival. The present invention therefore contemplates using antibodiotics for acute treatment of any animal with evidence of septicemia, with or without culture-proven cases.

IV. Therapeutic Preparations and Combinations

The present invention contemplates using therapeutic compositions of soluble antibodiotics. It is not intended that the present invention be limited by the particular nature of the therapeutic preparation. For example, such compositions can be provided together with physiologically tolerable liquid, gel or solid carriers, diluents, adjuvants and excipients. In addition, antibodiotics may be used together with other therapeutic agents, including unconjugated immunoglobulin.

As noted above, these therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

With respect to the mode of administration, the antibodiotics may be employed for intravenous, intramuscular, intrathecal or topical (including topical ophthalmic) administration. Formulations for such administrations may comprise an effective amount of antibodiotic in sterile water or physiological saline.

On the other hand, formulations may contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The compositions are preferably prepared as injectables, either as liquid solutions or suspensions; solid forms suitable for solution in, or suspension in, liquid prior to injection may also be prepared.

The antibodiotics of the present invention are often mixed with diluents or excipients which are compatible and physiologically tolerable. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Where repeated administrations are required, it may be beneficial to first clear any anti-hapten antibodies by administering free antibiotic. This can then be followed by administration of the antibodiotic.

DESCRIPTION OF FURTHER EMBODIMENTS

The present invention contemplates three strategies to create anti-infectives with the effector functions and long serum half-life of immunoglobulin G and a spectrum of pathogen reactivity determined by coupling or complexing microbe-binding ligands to complete immunoglobulins or immunoglobulin fragments. The preferred embodiments employ the properties of the IgG1 subclass, i.e., a serum half-life of 21–23 days in the average patient, complement activation and opsonization mediated by the binding of immunoglobulin to receptors on phagocytes. Therefore, like natural IgG1, these novel anti-infectives will have the ability to induce both the killing of pathogens and the removal of toxic debris. The long serum half-life is desirable because a single does in then needed for extended prophylaxis. Low cumulative dosing, constant serum concentrations, and conjugation may also reduce the risk of certain toxicities associated with some ligands. The fact that IgG1 does not distribute to the GI tract is also desirable because resistance to many anti-infectives, particularly antibiotics, often arises in the flora of the GI tract.

The three strategies for the design of compounds for passive immunity contemplated in the present invention are:

The synthesis of "antibodiotics", which are formed by chemically conjugating (i.e. covalently) human immunoglobulin G (IgG) with ligands capable of binding to the surfaces of microbial pathogens.

The synthesis of Immunobiotics™ compounds by the genetic fusion of peptides that bind to microbial surfaces with fragments of IgG by methods that retain the Fc receptor-binding and complement-activating effector functions of the IgG is also contemplated. These constructs are also referred to as Artificial Antibodies.

The synthesis of Immunoadapter™ compounds to which immunoglobulin is non-covalently linked and thereby targeted to a pathogen. Immunoadapter™ compounds comprise surface targeting ligands attached to haptens that will bind to specific antibodies.

When the surface-binding ligands are antibiotics, the Immunoadapter™ compounds will have bactericidal/bacteriostatic activity that is independent of immune effector functions. The use of surface-binding ligands to target immunoglobulin effector functions will broaden the repertoire of binding specificities and affinities beyond what can be obtained with natural antibodies. With this targeting it may be possible to 1) produce a highly potent immunoglobulin formulation specific to a molecular target that is poorly immunogenic, 2) develop linkers which allow the ligand to access molecular targets in structures inaccessible to antibodies, 3) select ligands with very high target affinity and 4) select ligands with very broad target specificity. In addition, efficiencies may be gained in discovery and product development by selecting available ligands of suitable and well characterized specificity and affinity rather than by trying to isolate a natural antibody to meet specifications. One such specification is an anti-infective with immune effector functions that binds to a molecular target that is highly conserved in Gram-negative or Gram-positive bacteria or all eubacteria. Such compounds or formulations can be used for broad spectrum prophylaxis or therapy of infectious diseases and would present a high barrier to the emergence of resistant organisms.

In one embodiment, an Immunoadapter™ compound is constructed by covalently linking polymyxin B to fluoroscein. Polymyxin B serves to bind the Immunoadapter™ compound to Gram-negative organisms. The fluoroscein is a nontoxic hapten that can be bound non-covalently by the antigen recognition site of monoclonal or polyclonal anti-fluoroscein antibodies. In principle, fluoroscein can be replaced by other hapten-antibody pairs, or the same anti-fluoroscein antibody can be directed to different spectra of pathogens by altering only the ligand and linker.

It is important to stress that, in this embodiment, the immunoglobulin is not structurally modified. Consequently, retention of effector functions is assured.

In one embodiment, the Immunoadapter™ compound and immunoglobulin are mixed before administration and complexes are formed by hapten-antibody interaction (i.e. non-covalent binding). These complexes are expected to display the pharmacokinetic properties of their corresponding IgG components. After an intravenous injection, the concentrations of the complexes in serum and extravascular compartments will take more than a day to equilibrate, and the serum half-life should approach 3 weeks.

In another embodiment, the Immunoadapter™ compound may be administered alone followed by a "chasing" dose of antibody. This regimen may be appropriate when the ligand is an antibiotic and high doses with rapid distribution are needed to suppress an infection. The "chasing" antibody may be complexed with the same ligand and can be administered in a lower concentration for secondary prophylaxis. Alternatively, an uncomplexed antibody can be administered to clear ligand-bound pathogen debris.

The present invention also contemplates the creation of Immunoadapter™ compounds with ligands capable of binding to a desired target and haptens that can be recognized by antibodies endogenous to the patient. By converting the specificity of some high titer pool of hapten-specific antibodies in the patient, one can overcome the shortcomings of passive immune strategies. The cost of providing an antibody carrier is either eliminated or replaced by the cost of a vaccine to boost the titers of an endogenous antibody pool. The antibodies will already be distributed to tissues and the Immunoadapter™ compound, if relatively small, will be able to rapidly distribute to tissues.

There are at least three specifications for selecting a hapten-specific pool of antibodies. The antibodies must: possess a reasonable affinity for the hapten; not be needed for protection against any immediate threat, i.e., conversion of specificity should not put the patient at risk; be in sufficient concentrations that when complexed with Immunoadapter™ compounds they can provide protection against the target pathogens. Examples of preferred haptens include, but are not limited to, dinitrophenol, haptens recognized by antibodies to blood group antigens.

The present invention contemplates the employment of vaccination to obtain high titers of hapten-specific antibodies. The vaccine can be entirely novel, for example the antigen can be a fluoroscein hapten coupled to a carrier (e.g. a carrier such as tetanus toxoid). With this approach one can design haptens that are unlikely to interfere with the patient's humoral defenses. An alternative is to use haptens in the Immunoadapter™ compounds that are immunodominant epitopes of antigens in mandated or widely used vaccines (e.g., tetanus toxoid itself). By this approach, the patient may not need a booster vaccination or may only require only one booster vaccination just prior to entering a period of risk in which Immunoadapter™ compounds will be used for protection.

It is also notable that the vaccination can be followed by successive Immunoadapter™ compound regimens and one series of vaccinations may suffice for months or years. This further improves the cost compared to passive immune therapies.

Immunoadapter™ compounds are designed preferably using small molecules (e.g., microbial-binding peptides, PEG (polyethylene glycol), fluoroscein) that are well characterized and relatively inexpensive to manufacture. The size may also be conducive to the development of orally delivered formulations. Immunoadapter™ compounds with different ligands but the same hapten would be antagonists. Antagonism can be avoided either by developing Immunoadapter™ compounds with different haptens or by contraindicating simultaneous use of different Immunoadapter™ compounds.

The technology can be employed for the treatment, primary prophylaxis, or secondary prophylaxis of infectious diseases in many clinical or community situations. The technology is designed particularly for situations where it is known in advance that the patient will be at risk for a defined and limited duration. For example, oncology patients receiving cytotoxic chemotherapy are at high risk of infection due to a transient neutropenia that is most severe for a few days in the middle of the recovery phase of each cycle. Vaccination 2–3 weeks prior to scheduled chemotherapy should induce carrier antibody titers sufficient to provide protection during the recovery cycle. Immunoadapter™ compounds can be administered with chemotherapy, and an uncomplexed antibody pool may be replenished during the recovery phase. The replenished uncharged pool and a new dose of Immunoadapter™ compounds can be used for protection during the next cycle of chemotherapy.

Another example involving advanced notice are travelers requiring temporary protection against pathogens that are problems in certain geographical areas. Where insufficient lead time exists for conventional vaccination, an Immunoadapter™ compound may be given that is reactive with high titers of endogenous hapten-specific antibody.

Finally, rapid military deployment is a good example where the specific need may be unanticipated but there is a routine vaccination to maintain titers of anti-hapten antibodies that can be complexed with a hapten that is generic to Immunoadapter™ compounds with different target specificities.

It may be desirable to 1) determine the patient's endogenous levels of antibody prior to treatment and 2) monitor serum concentrations and clearance of complexed antibody. The following formats may be employed for this purpose when fluoroscein is used as a hapten:

a) Concentrations of uncharged antibody can be determined by adding Immunoadapter™ compound to a sample of serum and measuring the fluorescence polarization.

b) Concentrations of free Immunoadapter™ compound can be determined by one of two methods:
   fluorescence polarization after the addition of anti-target ligand antibody
   an ELISA in which the Immunoadapter™ compound is captured by an anti-ligand antibody adsorbed to the plate and detected by an anti-fluorescein antibody that is either labeled or used with a secondary anti-Fc antibody that is labeled.

c) Concentrations of complexed hapten-specific antibody can be determined by an ELISA in which the complex is captured by anti-ligand antibody adsorbed to a plate and detected by an anti-Fc antibody that is labeled.

The potential pharmaceutical applications for Immunoadapter™ technology go beyond the scope of infectious disease. For instance, antibodies could be directed to molecular targets on normal or neoplastic cells of the patient that are poor immunogens. Also, while infectious diseases are generally acute, Immunoadapter™ technology need not be restricted to acute care. For example, the present invention contemplates reagents that might be used to induce the phagocytic clearance of amyloid deposits.

EXPERIMENTAL

The following examples serve to illustrate certain preferred embodiments and aspects of the present invention and are not to be construed as limiting the scope thereof. Standard terms are employed, understandable to those skilled in the art.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); ng (nanograms); Mol. Wt. (molecular weight); L (liters); ml (milliliters); $\mu$l (microliters); cm (centimeters); mm (millimeters); $\mu$m (micrometers); nm (nanometers); ° C. (degrees Centigrade); Acm (acetamidomethyl); AcOH (acetic acid); $CH_3OH$ (methanol); $CHCl_3$ (chloroform); DMSO (dimethylsulfoxide); EDTA (ethylenediaminetetraacetic acid); $N_2$ (nitrogen gas); N-Boc (N-tertiary-Butoxycarbonyl); N-Boc-Cys-Acm-ONp (N-butoxy-carbonyl-S-acetamidomethyl-cysteine-p-nitrophenyl ester); NMR (nuclear magnetic resonance); PBS (phosphate-buffered saline); TLC (thin layer chromatography); HPTLC (high performance TLC); MHz (megaHertz); AUFS (absorption units full scale); hr (hour); sec (second); min (minutes); IV (intravenous); Ig (immunoglobulin); FCS (fetal calf serum); CFU (colony forming units); ELISA (Enzyme-Linked Immunosorbent Assay); Aldrich (Aldrich Chemical Co., Milwaukee, Wis.); Amicon (Beverly, Mass.); Bachem (Bachem Bioscience, Inc., Philadelphia, Pa.); Bio-Rad (Bio-Rad Laboratories, Richmond, Calif.); Baxter (Deerfield, Ill.); BBL (Becton Dickinson Microbiology Systems, Cockeysville, Md.); Corning (Corning, Inc., Coming, N.Y.); Falcon (Lincoln Park, N.J.); Lee (Lee Laboratories, Grayson, Ga.); Harlan Sprague-Dawley (Harlan Sprague-Dawley, Indianapolis, Ind.); ICN (ICN Biomedicals, Costa Mesa, Calif.); Mallinckrodt (Mallinckrodt, St. Louis, Mo.); Merck (Darmstadt, Germany); Pharmacia (Pharmacia, Inc., Piscataway, N.J.); Pierce (Pierce Chemical Co., Rockford, Ill.); Prochem (Prochem, Inc., Rockford, Ill.); Scientific Products or S/P (Scientific Products, McGraw Park, Ill.); S & S (Schleicher & Schuell, Inc., Keene, N.H.); Sigma (Sigma Chemical Co., St. Louis, Mo.);Spectrum (Spectrum, Houston, Tex.); Whatman (Whatman, Inc., Clifton, N.J.).

In some of the examples below, purification of products from reactants is performed using various types of chromatography. Standard terms understandable to those skilled in the art are employed to describe this purification. For example. "eluent" is a chemical solution capable of dissociating desired products bound to the column matrix (if any) that passes through the column matrix and comprises an "eluate". Products that are dissociated (if any) are freed from the column matrix and pass by elution with the "eluent" into the "eluate".

EXAMPLE 1

Attachment of an Antibiotic to Human IgG Using a Carbodiimide Cross-Linker

This example describes attempts to attach antibiotics to a carrier (i.e., in this case antibodies). In this regard, K. Hanasawa et al. describe the attachment of PMB to an immobilized fiber via carbodiimide chemistry. [Surg. Gyn. & Ob. 168:323–331 (1989).] In this example, the ability of a carbodiimide cross-linker to conjugate polymyxin B (PMB) to human IgG was analyzed.

It is known that 1-ethyl-3(3-dimethylaminopropyl) carbodiimide hydrochloride (EDC) cross-links proteins and peptides between amine and carboxylic acids. The example involved: (a) EDC-mediated cross-linking of PMB and IgG; and (b) enzyme-linked immunoassay (ELISA) of conjugate binding to LPS.

a) EDC-Mediated Cross-linking of PMB to IgG

In this and in all examples, measures were taken to make glassware, solutions, and other materials and reagents pyrogen-free because adventitious pyrogen (e.g., LPS) could inhibit conjugation reactions, absorb PMB or conjugates, or block the activity of PMB conjugates.

Human IgG (Sigma) and PMB (Sigma) were each dissolved at a concentration of 8 mg/ml in pyrogen-free MES (2-[N-Morpholino]ethanesulfonic acid) buffer (0.1M MES, 0.09 M NaCl pH 4.7). 0.5 ml of each solution were mixed together and 0.15 ml of the mixture was incubated with 0.15 ml of either 0.4 M EDC, 0.2 M EDC, 0.1 M EDC (Pierce), or control solution in MES buffer, for 2 hrs at room temperature. The reactions were stopped by the addition of 2.7 ml of TBS (50 mM Tris-HCl, 150 mM NaCl, pH 7.2). The five mixtures were dialyzed separately (molecular weight cut-off of dialysis tubing 12–14,000, Scientific Products) at 4° C. against four changes of 1500 ml of PBS over a 36 hr period. The samples containing human IgG at 0.2 mg/ml were stored at 4° C.

b) Enzyme-Linked Immunoassay of EDC-PMB Conjugate Binding to LPS

In order to determine whether the attachment of PMB facilitated the binding of IgG to LPS, a simple indirect binding assay was performed. To each well of a 96-well microtiter plate (Falcon), 100 μl of a 2.0 μg/ml solution of *E. coli* 0111:B4 LPS (Sigma) in PBS was coated, except for those control wells in which PBS but no LPS was added. After an overnight incubation at 4° C., the coating solutions were decanted and all wells were washed three times with PBS. Non-specific binding sites were blocked by the addition of 100 μl of PBS containing 5 mg/ml bovine serum albumin (BSA, Sigma) for 2 hrs at room temperature. After decanting the blocking solution, samples of the conjugates prepared in (a) above were diluted in PBS containing 1 mg/ml BSA to an initial concentration of 10 μg/ml IgG followed by five-fold dilutions. A positive control antiserum of commercially prepared rabbit anti-*E. coli* 0111:B4 antiserum (Lee Laboratories, Lot M25082) was initially diluted 1:100. One hundred (100) μl of each sample was incubated in duplicate for two hours at room temperature and the plates were washed three times with BBS-Tween 20 (0.1 M boric acid, 0.025 M Na borate, 1.0 M NaCl, 0.1% Tween 20, pH 8.3), followed by two washes with PBS-Tween 20 (0.1% Tween 20 (v/v)), and finally, two washes with PBS.

In order to detect bound antibodies, the wells incubated with the human antibody conjugates were incubated with 100 μl of a 1:500 dilution of goat anti-human IgG (whole molecule)-alkaline phosphatase conjugate (Sigma) and the wells incubated with the rabbit serum were incubated with 100 μl of a 1:500 dilution of goat anti-rabbit IgG (whole molecule)-alkaline phosphatase conjugate (Sigma) for 2 hours at room temperature. The secondary antibody solutions were discarded, the plates were washed with BBS-Tween 20, and PBS-Tween 20 as above and then twice with 50 mM $Na_2Co_3$, 10 mM $MgCl_2$, pH 9.5. After 45 minutes at room temperature, the absorbance of each well was measured at 410 nm on a Dynatech MR700 plate reader using diluent control wells as blanks. Tables 6 and 7 show the results for the rabbit control serum and EDC-conjugates.

The results in Table 6 show that the positive control serum, as expected, bound to LPS-coated wells in a specific manner. These data validate the ELISA design as being capable of detecting LPS binding antibodies.

The results in Table 7 appear to indicate that EDC cross-linking caused the IgG-PMB to bind to the LPS. However, the titration of the conjugates drops off rather abruptly between 5 and 1 μg/ml. To verify that the observed binding is specific, it must be determined that the binding is inhibitable by PMB and antigen-dependent.

TABLE 6

Binding Of Rabbit Anti-*E. coli* 0111:B4
Antiserum To *E. coli* 0111:B4 LPS ($OD_{410}$ Values)

| Serum Dilution | LPS Coated | No Antigen |
| --- | --- | --- |
| 1:1 | 1.801 | 0.032 |
| 1:5 | 1.817 | 0.028 |
| 1:25 | 1.648 | 0.024 |
| 1:175 | 0.308 | 0.026 |
| 1:625 | 0.070 | 0.027 |
| 1:3125 | 0.021 | 0.028 |
| 1:15,625 | 0.014 | 0.018 |

The ELISA described above was repeated; however, in this instance, a fixed concentration of the EDC-conjugate (10 μg/ml) that yielded the highest binding by ELISA was incubated with five-fold dilutions of polymyxin B (beginning with 10 mg/ml) and the LPS-binding activity was determined. In addition, the binding was tested in control wells containing no antigen. The results are shown in Tables 8 and 9.

TABLE 7

Binding Of EDC-Mediated Human IgG-PMB
Conjugates To *E. coli* 0111:B4 LPS ($OD_{410}$ Values)

| | EDC Conjugation Conc. (M) | | | | |
| --- | --- | --- | --- | --- | --- |
| Conjugate IgG Conc. (μg/ml) | 0.2 | 0.1 | 0.05 | 0.025 | 0 |
| 10 | 0.638 | 0.369 | 0.306 | 0.464 | 0.015 |
| /2 | 0.010 | 0.012 | 0.026 | 0.054 | 0.008 |
| 0.4 | 0.000 | 0.000 | 0.002 | 0.009 | 0.007 |
| 0.008 | 0.000 | 0.000 | 0.000 | 0.006 | 0.005 |

Since the binding of the conjugate is only inhibited at the very highest concentration of PMB tested and because the conjugate exhibited significant binding to wells that contained no antigen, it is clear that most of the binding observed is was not specific. This may reflect an inappropriate type or number of bonds between PMB and IgG and, since IgG that was not treated with a cross-linker shows very little binding to LPS, it suggests that the cross-linking of the IgG molecule is causing nonspecific binding.

TABLE 8

Specificity Of EDC-Conjugates Of IgG-PMB
Binding To LPS: PMB Inhibition Test ($OD_{410}$ Values)

| PMB Concentration (mg/ml) | 0.2 M EDC-Conjugate Binding |
| --- | --- |
| 0 | 1.757 |
| 10 | 0.755 |
| 2 | 1.775 |
| 0.4 | 1.785 |
| 0.08 | 1.770 |
| 0.016 | 1.766 |
| 0.0033 | 1.775 |

Clearly, carbodiimide chemistry does not work at a level which is practical. Indeed, it is evident that the interactions of the cross-linking reagent with the antibiotic are somewhat complex. It is to be remembered that three reactions are possible: PMB to PMB; IgG to IgG; and PMB to IgG. Only the latter reaction is productive.

TABLE 9

Antigen-Dependent Binding Of EDC-Conjugate
Of IgG-PMB To LPS ($OD_{410}$ Values)

| Conjugate Conc. (μg/ml) | LPS Coated Wells | No Antigen Wells |
| --- | --- | --- |
| 10 | 1.770 | 1.766 |
| 2 | 0.976 | 0.552 |
| 0.4 | 0.347 | 0.045 |
| 0.08 | 0.034 | 0.00 |
| 0.016 | 0.062 | 0.00 |

EXAMPLE 2

Attachment of an Antibiotic to Human IgG Using a Disuccinimide Ester

In an attempt to remedy the difficulties observed with EDC conjugates, different cross-linkers and chemistries were investigated. Talmadge and Siebert describe the attachment of PMB via a hydroxysuccinimide ester reagent. [J. Chrom. 476:175–185 (1989).] Along the lines of this approach, this example examines the ability of a homobifunctional cross-linking agent, suberic acid bis-(N-hydroxysuccinimide ester) (DSS), which cross-links peptides and proteins via their amine groups, to conjugate PMB to IgG. The example involved: (a) DSS-mediated cross-linking of PMB and IgG; and (b) ELISA of conjugate binding to LPS.

a) DSS-mediated Cross-linking of PMB to IgG

Pyrogen-free PBS was prepared in pyrogen-free water (Baxter), and stock solutions of human IgG (40 mg/ml) and PMB (40 mg/ml) were dissolved in pyrogen-free PBS. A 60 mM stock solution of DSS was prepared in 100% dimethylsulfoxide (DMSO). This solution was diluted to 6.0 mM DSS in PBS where some precipitation was noted. A stock solution of human IgG and PMB was prepared containing 20 mg/ml IgG and 20 mg/ml PMB in PBS. Five different conjugates were prepared by mixing two-fold dilutions of the stock DSS solution (0.15 ml) with a constant (0.15 ml) volume of the IgG/PMB stock solution. The five resulting DSS concentrations were 3.0 mM, 1.5 mM, 0.75 mM, 0.375 mM, and 0.0 mM DSS. After incubation for 1 hour at room temperature, the reactions were stopped by the addition of 2.7 ml of TBS. The five mixtures were dialyzed against PBS as described in Example 1 for the EDC conjugates. The resulting dialyzed conjugates contained a final concentration of 1 mg/ml IgG and were stored at 4° C.

b) ELISA of DSS Conjugated Binding to LPS

The ELISA was performed essentially as in Example 1(b) using the DSS conjugates at starting concentrations of 10 μg/ml and the same control rabbit anti-*E. coli* 0111:B4 antiserum. The results of the initial binding assay are shown in Table 10.

TABLE 10

Binding Of DSS Conjugates Of IgG-PMB To LPS ($OD_{410}$ Values)

| Conjugate IgG Conc. (μg/ml) | DSS Concentration (mM) | | | | |
|---|---|---|---|---|---|
| | 3.0 | 1.5 | 0.75 | 0.375 | 0.00 |
| 10 | 0.098 | 0.032 | 0.014 | 0.011 | 0.015 |
| 2 | 0.026 | 0.003 | 0.007 | 0.005 | 0.007 |
| 0.4 | 0.011 | 0.001 | 0.00 | 0.002 | 0.002 |
| 0.08 | 0.010 | 0.00 | 0.002 | 0.004 | 0.004 |

The results indicate a low level of binding that is correlated with the concentration of DSS utilized. The specificity of this binding was then tested by examining the ability of PMB to inhibit binding and its dependence on antigen. The assays were performed exactly as described for the EDC conjugates in Example 1(b). The results are shown in Tables 11 and 12.

These results indicate that the DSS conjugate binds somewhat non-specifically. The pattern of PMB inhibition is erratic in that the highest concentration shows no inhibition of binding but intermediate PMB concentrations do apparently inhibit.

TABLE 11

Inhibition Of IgG-PMB Binding To LPS By Free PMB ($OD_{410}$ Values)

| PMB Conc. (mg/ml) | 3.0 mM DSS Conj. of IgG-PMB (50 mg/ml) |
|---|---|
| 0 | 0.144 |
| 10 | 0.182 |
| 2 | 0.054 |
| 0.4 | 0.059 |
| 0.08 | 0.097 |

TABLE 11-continued

Inhibition Of IgG-PMB Binding To LPS By Free PMB ($OD_{410}$ Values)

| PMB Conc. (mg/ml) | 3.0 mM DSS Conj. of IgG-PMB (50 mg/ml) |
|---|---|
| 0.016 | 0.128 |
| 0.0033 | 0.213 |

TABLE 12

Antigen-Dependent Binding Of DSS Conjugate Of IgG-PMB To LPS ($OD_{410}$ Values)

| Conjugate Conc. (μg/ml) | LPS Coated Wells | No Antigen Wells |
|---|---|---|
| 50 | 0.268 | 0.096 |
| 10 | 0.168 | 0.043 |
| 2 | 0.094 | 0.007 |
| 0.4 | 0.016 | 0.010 |
| 0.08 | 0.009 | 0.00 |

These results indicate some level of specific binding above a significant amount of non-specific binding. The binding of the control rabbit antiserum at 1:500 and 1:12,500 dilution was 1.766 and 0.380, respectively and was virtually all antigen-dependent. The relatively low level of binding here suggests that hydroxysuccinimide ester reagents such as DSS are not very effective cross-linkers for PMB and IgG. This could be due to the amine-amine chemistry employed, or the properties of the DSS agent. We did note some insolubility of DSS in PBS; perhaps a more water soluble form of DSS would perform better. In addition, in both cases of the EDC and DSS conjugates, the PMB was exposed to a vast excess of cross-linker which could inhibit the ability of PMB to bind to LPS.

EXAMPLE 3

Two-Step Conjugation of PMB to IgG Using EDC and a Water Soluble Analogue of DSS In the previous two examples, cross-linkers were present in molar excess over IgG and were mixed simultaneously with both antibody and antibiotic. In this example, IgG was first modified with the cross-linker, the cross-linker removed, and then PMB added to the coupling reaction. In this way, the binding activity of PMB might be improved and the non-specific binding of the IgG reduced. In order to have an amine to amine coupling reagent that was more water soluble, $BS^3$ (Pierce), a water soluble analogue of DSS was employed. The example involved: (a) two-step conjugation of IgG-PMB with EDC; (b) two step conjugation of IgG-PMB with $BS^3$; and (c) ELISA of conjugate binding to LPS.

a) Two-step Conjugation of IgG-PMB with EDC

A 0.75 ml of a 4 mg/ml IgG solution in MES buffer was prepared as described in Example 1, and mixed with 0.75 ml of a 0.4 M EDC solution in MES buffer at room temperature for 2 hours. The unreacted cross-linker was removed by passing the 1.5 ml reaction mixture over a Sephadex G-10 (Pharmacia) column that was poured into a sterile 10 ml pipette and equilibrated with pyrogen-free MES buffer. The void volume was collected and the IgG content was determined by measuring the $OD_{280}$ of a 1:40 dilution of each fraction. The peak fraction containing 2.37 mg IgG/ml was divided into two fractions: 1.5 mg of PMB was added and dissolved in one volume; nothing was added to the other (control). After incubation at room temperature overnight, the reaction was stopped with TBS and the final IgG concentration was adjusted to 0.2 mg/ml. Both samples were dialyzed as in Example 1(a) and stored at 4° C.

b) Two-step Conjugation of IgG to PMB with $BS^3$

A 0.75 ml of a 20 mg/ml IgG solution was mixed with 0.75 ml of a 6.0 mM $BS^3$ solution, each prepared in PBS and incubated at room temperature for 1 hr. Unreacted cross-linker was removed as in Example 3(a) above and the peak IgG fractions identified and pooled. Two equal fractions of IgG at 8.35 mg/ml were made and 7.5 mg of PMB was added and dissolved in one while nothing was added to the other. After overnight incubation at room temperature, the reactions were stopped with TBS, the conjugates dialyzed and the final IgG concentration adjusted to 1.0 mg/ml.

c) ELISA of Conjugate Binding to LPS

This LPS-binding assay was performed as described in Example (1) except that the BBS-Tween 20 washes were eliminated and the Tween 20 concentration in the PBS-Tween 20 wash was lowered to 0.05% (v/v). The results are shown in Tables 13 and 14.

The 0.2 M EDC IgG-PMB conjugate exhibited a high level of binding but this was partly due to non-specific binding as evidenced by the binding to control wells containing no LPS. Further evidence of non-specific binding created by EDC cross-linking is shown by the results for the conjugate containing no PMB (which exhibited somewhat comparable levels of binding to the wells regardless of whether antigen was present or not).

TABLE 13

Binding Of Two-Step EDC Conjugates To LPS ($OD_{410}$ Values)

| Conjugate | 0–2 M EDC IgG-PMB Conj. | | 0–2 M EDC (No PMB) IgG Control | |
|---|---|---|---|---|
| IgG Conc. | LPS Coated | No Antigen | Coated | No Antigen |
| 10 | 1.790 | 1.790 | 1.784 | 1.790 |
| 2 | 1.520 | 0.886 | 0.676 | 0.522 |
| 0.4 | 0.092 | 0.146 | 0.088 | 0.079 |
| 0.08 | 0.024 | ND | 0.028 | ND |
| 0.016 | 0.046 | ND | 0.030 | ND |

TABLE 14

Binding Of Two-Step $BS^3$ Conjugate To LPS ($OD^{410}$ Values)

| Conjugate | 6.0 mM $BS^3$ IgG-PMB | | 6.0 M $BS^3$ IgG | |
|---|---|---|---|---|
| IgG Conc. (µg/ml) | LPS | No Antigen | LPS | No Antigen |
| 10 | 0.037 | 0.040 | 0.028 | 0.00 |
| 2 | 0.016 | 0.00 | 0.022 | 0.00 |
| 0.4 | 0.044 | 0.00 | 0.044 | 0.00 |
| 0.08 | 0.040 | ND | 0.076 | ND |
| 0.016 | 0.038 | ND | 0.024 | ND |

The $BS^3$ conjugates exhibited no specific binding to LPS whatsoever at the concentrations tested. However, they did not exhibit much non-specific binding either, indicating that this cross-linker may not be as problematic as EDC in causing non-specific binding of IgG.

Given the low level of $BS^3$ conjugate background binding, the ELISA was performed again using higher concentrations of the conjugates and a tenfold higher concentration of LPS coated onto the wells (2 µg LPS/well). This increased the assay sensitivity. The results shown in Table 15 indicate that the $BS^3$ conjugates do possess LPS-binding activity above background.

Together, the results of the two-step conjugations described in this example indicate that EDC creates an unacceptable level of non-specific binding, while $BS^3$, the water soluble analogue of DSS, effects a modest level of specific binding and causes very little non-specific binding in this two-step conjugation format. Additional two-step conjugation procedures using other cross-linkers were investigated to determine whether higher levels of LPS-binding activity could be achieved than those obtained with $BS^3$.

TABLE 15

More Sensitive Detection Of $BS^3$ Conjugates Of IgG-PMB Binding To LPS ($OD_{410}$ Values)

| Conjugate | 6.0 mM $BS^3$ IgG-PMB | | 6.0 M $BS^3$ IgG (Control) | |
|---|---|---|---|---|
| IgG Conc. (µg/ml) | LPS | No antigen | LPS | No antigen |
| 50 | 0.098 | 0.010 | 0.006 | 0.006 |
| 10 | 0.058 | 0.006 | 0.006 | 0.008 |
| 2 | 0.020 | 0.005 | 0.004 | 0.004 |
| 0.4 | 0.009 | 0.005 | 0.004 | 0.004 |
| 0.08 | 0.005 | ND | 0.004 | ND |

EXAMPLE 4

Three Step Conjugation of PMB to IgG Using an Amine to Sulfhydryl Coupling Chemistry with SMCC Because of the unsatisfactory results of previous examples in obtaining high specific-binding of IgG-PMB conjugates to PMB, an alternative cross-linking method was investigated using sulfosuccinimidyl 4-(N-maleimidomethyl) cyclohexane-1-carboxylate [sulfo-SMCC] in a three-step procedure similar to that of T. Kitagawa et al. [J. Assoc. Anal. Chem. (1985).] The example involved: (a) three-step conjugation of PMB to reduced IgG with sulfo-SMCC; and (b) ELISA of conjugate binding to LPS.

a) Three-step Conjugation of PMB to IgG

In the first step of this procedure, reactive thiol groups were created in the IgG by treatment with 2-mercaptoethanol. In this procedure, 4.0 mg of IgG was first dissolved in 0.45 ml of pyrogen-free 0.1M $NaPO_4$ pH 6.0. Fifty µl of 0.1 M 2-mercaptoethanol in 5 mM EDTA, 0.1 $NaPO_4$, pH 6.0 was then added and incubated at 37° C. for 1.5 hours. The free 2-mercaptoethanol was separated by applying the 0.5 ml sample to a 5 ml Sephadex G-10 column equilibrated in 0.1 M $NaPO_4$, 5 mM EDTA, pH 6.0 and the IgG containing fractions identified and pooled.

The second step of this procedure involved preparation of maleimide-activated PMB. This involved mixing 1.5 ml of a 0.16 mg/ml PMB solution in 50 mM sodium borate buffer, pH 7.6 (pyrogen-free) and 1.5 ml of a 0.46 mg/ml sulfo-SMCC (Pierce) solution in the same borate buffer (creating a final concentration of 0.053 mM of each reactant). This "SMCC-activated" PMB was incubated at 30° C. for 60 minutes.

The third step of the procedure involved incubation of 0.65 ml of the reduced IgG with 0.65 ml of the SMCC-activated PMB.

The concentrations of the two reactants were 0.0265 mM PMB and 0.013 mM IgG (a 2:1 molar ratio). After incubation at 4° C. for 20 hrs, 8.7 µl of a fresh solution of 0.1 M 2-mercaptoethanol was added and incubated at room temperature for 20 minutes. The IgG concentration was adjusted to 1.0 mg/ml with an equal volume of PBS. Samples of the conjugates were purified by dialysis against two 800 ml volumes of PBS over a 20 hour period or by gel filtration on a Sephadex G-10 column equilibrated in PBS. A control reduced human IgG fraction was prepared from the reduced IgG pool and the three preparations stored at 4° C.

b) ELISA of Conjugate-binding to LPS

The LPS binding assay procedure was the same as that described in Example 1(b) except that the LPS was coated at 2 μg/well, the BBS-Tween 20 washes were eliminated, and the Tween 20 concentration in the PBS-Tween 20 wash was lowered to 0.05%. The blocking solution and sample diluent were prepared using pyrogen-free PBS and low-endotoxin BSA (Sigma). The results are shown in Table 16.

TABLE 16

Binding Of An SMCC Conjugate Of IgG-PMB To LPS ($OD_{410}$ Values)

| Conjugate IgG Concentration (μg/ml) | SMCC IgG-PMB | | SMCC IgG Control | |
|---|---|---|---|---|
| | LPS | No Antigen | LPS | No Antigen |
| 100 | 0.084 | 0.011 | 0.038 | 0.00 |
| 20 | 0.013 | 0.00 | 0.012 | 0.00 |
| 4 | 0.00 | 0.005 | 0.00 | 0.00 |
| 0.8 | 0.00 | 0.028 | 0.00 | 0.00 |
| 0.016 | 0.00 | 0.00 | 0.00 | 0.00 |

The SMCC IgG-PMB exhibited slightly higher binding to LPS than the control but the overall level of binding was far below that of the positive control rabbit anti-*E. coli* 0111:B4 antiserum (1.097 at a 1:25,000 dilution). It is possible that reduced IgG possesses only a few thiol groups available for cross-linking and that higher concentrations of activated PMB might drive the reaction more effectively.

EXAMPLE 5

Conjugation of an Antibiotic to IgG Without Using a Bifunctional Cross-linker

In all of the previous examples, free bifunctional cross-linkers were employed in attempts to covalently attach the antibiotic polymyxin to IgG. The configurations failed to yield a conjugate with LPS-binding activity comparable to that of an immune serum. Because of the binding observed in the absence of antigen, there were probably conjugates having less than one active PMB molecule to each molecule of IgG. To investigate means of attaching antibiotics to IgG without the involvement of a bifunctional cross-linker, periodate oxidation of the carbohydrate groups of IgG [D. A. Handley, Eur. Patent Appl. Pub. No. 428486] was used to create amine-reactive aldehyde groups that could potentially react with PMB and be reduced to establish a stable covalent linkage.

The example involved: (a) periodate oxidation of IgG in pH 4.0 sodium acetate buffer; and (b) conjugation of polymyxin B to periodate oxidized IgG.

a) Periodate oxidation of IgG in pH 4.0 sodium acetate buffer was achieved by dissolving 5 mg human IgG in 1 ml of water and mixing this solution with 200 μl of sodium acetate pH 4.0 (0.3 g sodium acetate and 960 μl glacial acetic acid in 100 ml $H_2O$) and 200 μl of 0.2 M $NaIO_4$. [Modification of J. W. Goding, *Monoclonal Antibodies: Principles and Practice*, Academic Press, New York, p. 84 (1986).] After 15 minutes at room temperature in the dark, the periodate solution was removed by gel filtration on a P-10 column in 50 mM $Na_2CO_3$, pH 9.5.

b) Conjugation of periodate-oxidized IgG with PMB was carried out by adding 10 mg of PMB to the IgG prepared in (a) and incubating for 1 hour at room temperature, followed by the addition of 100 μl of $NaBH_3CN$ (4 mg/ml) and room temperature incubation for another hour and dialysis against PBS overnight at 4° C.

Inspection of the LPS binding activity (not shown) revealed that the prepared conjugate was inactive. These results suggest that the periodate-oxidation of IgG, without the use of a cross-linker, is an ineffective means of covalent conjugation of antibiotics to antibody.

EXAMPLE 6

The Derivatization of Antibiotics with Cross-Linkers: Preservation of Antibiotic Activity A significant concern with either one-step or multi-step schemes for conjugating antibiotics to antibodies is whether the conjugation scheme reduces or inactivates antibiotic function. In order to determine the best cross-linker concentration for derivatization of PMB in a multi-step conjugation scheme, the effect of the concentration of cross-linker on antibiotic activity was determined (see discussion of Mode IA above). The example involved: (a) modification of PMB with SPDP and the separation of free cross-linker; and (b) assay of derivatized PMB antibacterial activity.

a) Modification of PMB with SPDP and the separation of free cross-linker was carried out by mixing three different molar ratios of SPDP (2:1, 3:1 and 4:1) to PMB. First, 2.1 mg, 3.15 mg or 4.2 mg of SPDP (Pierce) dissolved in dimethyl sulfoxide was added to 5 mg of PMB in 0.5 ml of 50 mM sodium borate, 300 mM NaCl, pH 9.0 and incubated for 30 minutes at room temperature with occasional shaking. Free cross-linker was then removed from each sample by chromatography on a 15 ml Swift desalting column equilibrated with PBS-EDTA. The peak fractions containing the derivatized PMB were collected and pooled.

b) Assay of derivatized PMB antibacterial activity was carried out in a disc inhibition assay (see FIG. 2). *E. coli* HB101 was plated on Trypticase Soy Agar (TSA; BBL) to create a confluent lawn of bacteria. One-quarter inch blank paper discs (BBL) were then applied to the surface of the lawn and 20 μl of each test solution applied. After incubation at 37° C. overnight, zones of inhibition surrounding the disc were observed. The results (not shown) indicate that PMB derivatized at 2:1 or 3:1 molar ratios of SPDP-PMB were still active whereas antibiotic derivatized at a 4:1 molar ratio was inactive. Therefore, derivatization of PMB with SPDP should be carried out at ratios of SPDP to PMB of less than or equal to 3:1.

EXAMPLE 7

Conjugation of SPDP-PMB to IgG

Having determined an SPDP cross-linker concentration that preserved the antibiotic activity of polymyxin B in Example 6, conjugates were prepared between SPDP-PMB and IgG by reacting the derivatized antibiotic with IgG to which sulfhydryl (-SH) groups were introduced with Traut's reagent.

The example involved: (a) derivatization of PMB with SPDP; (b) derivatization of IgG with Traut's reagent; (c) conjugation of Traut-IgG with SPDP-PMB; and (d) conjugate LPS-binding activity assessment.

a) Derivatization of PMB with SPDP was carried out by adding 7 μmoles of SPDP (2.1 mg) in 50 μl of dimethylsulfoxide to 10 mg of PMB in 1 ml of 50 mM sodium borate, 300 mM NaCl, pH 9.0 and incubating at room temperature for 30 minutes on a rotating shaker. The unconjugated cross-linker was removed by applying the sample to 15 ml Swift desalting column (Pierce) equilibrated with 20 mM $NaPO_4$, 150 mM NaCl, 1 mM EDTA, pH 7.2 (PBS-EDTA). Peak fractions were pooled and stored at 4° C.

b) Derivatization of IgG with Traut's reagent was carried out by adding a five-fold molar excess (100 μl of a 0.2 mg/ml stock) of Traut's reagent (Pierce) to 5 mg of IgG dissolved in 1 ml of 50 mM triethanolamine, 0.15 M NaCl, 1 mM EDTA, pH 8.0 and incubating under nitrogen for 45 minutes at room temperature. The excess Traut's reagent was removed by gel filtration on a P-10 column equilibrated with PBS-EDTA. The peak fractions were combined.

c) Conjugation of Traut-IgG with SPDP-PMB was carried out by adding 3.5 mg Traut-IgG and 2 mg SPDP-PMB (77 fold molar excess of PMB) and incubating for 18 hours at room temperature. The conjugates were separated from free SPDP-PMB by gel filtration on a P-10 column (50 ml) equilibrated with PBS-EDTA and the peak fractions containing the IgG were collected, pooled, and stored at 4° C.

d) Conjugate LPS-binding activity assessment was carried out by evaluating the ability of each conjugate in (c) to bind LPS in an ELISA assay (see FIG. 4). The results indicated that the Traut IgG-PMB conjugate possessed limited binding activity (not shown).

EXAMPLE 8

Conjugation of SPDP-PMB to SPDP-IgG

Having determined that Traut's reagent does not generate a conjugate with preserved antibiotic activity in Example 7, conjugates were prepared between SPDP-PMB and IgG by reacting the derivatized antibiotic with IgG in which amino ($NH_2$) groups were converted to sulfhydryl (—SH) groups by activation with SPDP.

The example involved: (a) derivatization of PMB with SPDP; (b) derivatization of IgG with SPDP; (c) conjugation of SPDP-IgG with SPDP-PMB; and (d) conjugate LPS-binding activity assessment.

a) Derivatization of PMB with SPDP was carried out as in Example 7.

b) Derivatization of IgG with SPDP was carried out by adding 20 μl of 20 mM SPDP to 10 mg of IgG in 1 ml of 50 mM sodium borate, 300 mM NaCl, pH 9.0 and incubating 30 minutes at room temperature with shaking. The free cross-linker was removed by chromatography on a 15 ml Swift desalting column equilibrated in 100 mM sodium acetate, 100 mM sodium chloride pH 4.5. The peak fractions were collected and concentrated on Centriprep-30 concentrator (Amicon). To this sample, 7.7 mg of dithiothreitol in 250 μl of 100 mM sodium acetate, 100 mM sodium chloride, pH 4.5 was added and incubated at room temperature for 30 minutes. The sample was again applied to a 15 ml Swift desalting column equilibrated with PBS-EDTA and peak fractions with the highest $OD_{280}$ were collected, pooled, and concentrated on a Centriprep-30 concentrator (Amicon).

c) Conjugation of SPDP-IgG with SPDP-PMB was carried out by adding the following combinations of reactants:

5 mg SPDP-IgG and 2 mg SPDP-PMB (43 fold molar excess of PMB)

2 mg SPDP-IgG and 2 mg SPDP-PMB (107 fold molar excess of PMB) and incubating for 18 hours at room temperature. The conjugates were each separated from free SPDP-PMB by gel filtration on a P-10 column (50 ml) equilibrated with PBS-EDTA. Fractions containing PMB-IgG conjugate were collected, pooled, and stored at 4° C.

d) Conjugate LPS-binding activity assessment was carried out by evaluating the ability of each conjugate in (c) to bind LPS in an ELISA assay and comparing them with the Traut conjugate produced in Example 7. The results (FIG. 5) indicated that both SPDP-IgG-PMB conjugates possessed considerable activity—a much higher activity than that of the Traut IgG-PMB conjugate.

EXAMPLE 9

Conjugation of PMB to IgG Using a Long Chain SPDP Cross-Linker

Figure 6:
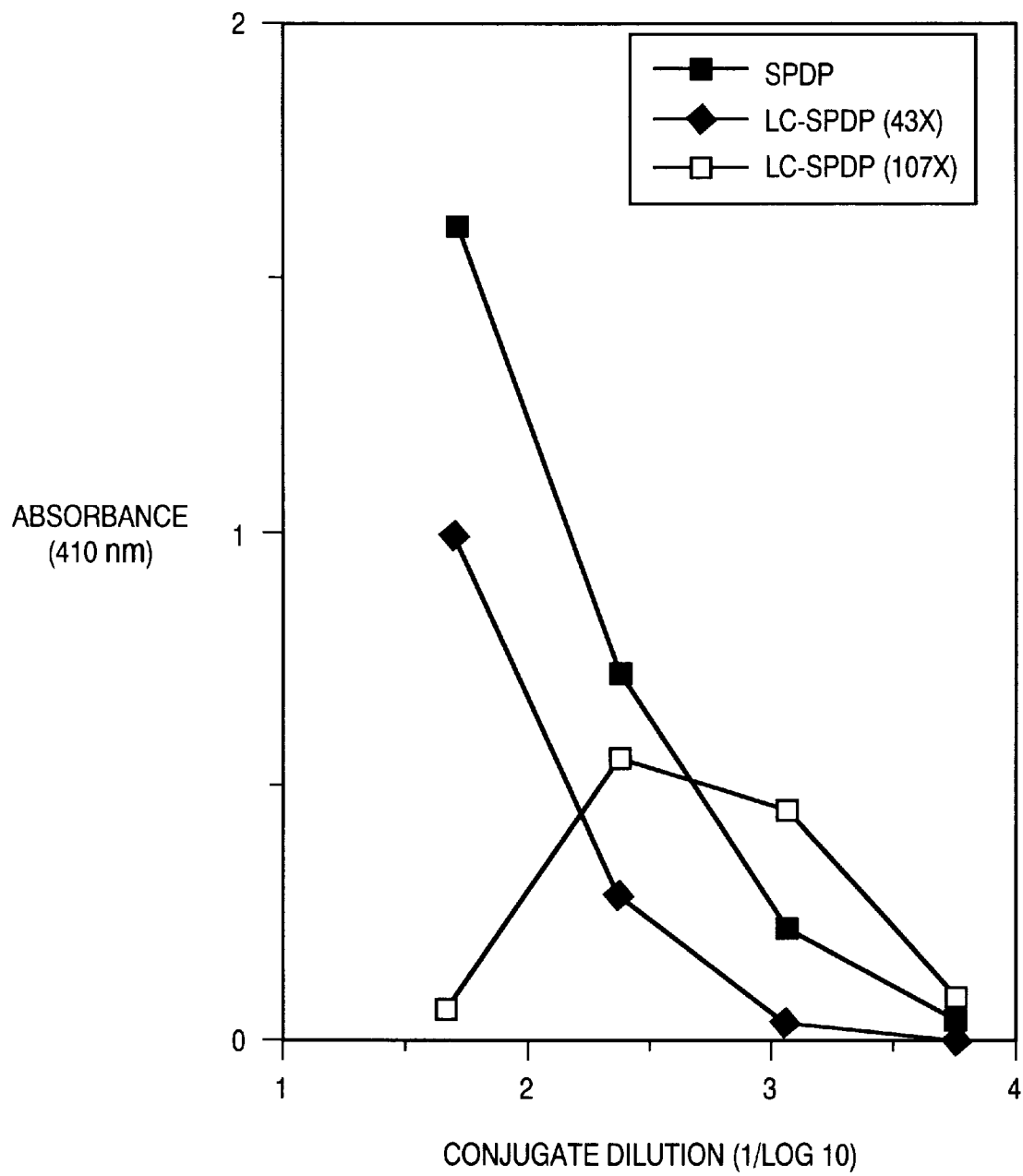
FIG. 6 shows additional conjugates of the present invention binding to LPS, as measured by ELISA.

Since SPDP proved to be an effective agent for the derivatization and cross-linking of IgG and PMB, a long chain form of SPDP (sulfo-LC-SPDP) was then examined to see if the addition of a larger spacer arm between the IgG and PMB enhanced the activity of the conjugate. This example involved: (a) derivatization of PMB with sulfo-LC-SPDP; (b) derivatization of IgG with sulfo-LC-SPDP; (c) conjugation of derivatized IgG with derivatized PMB; and (d) conjugate activity assessment by ELISA.

a) Derivatization of PMB with sulfo-LC-SPDP was carried out by adding 35 μl of a 9 mg/ml solution of sulfo-LC-SPDP to 10 mg of PMB in 1 ml of 50 mM sodium borate, 300 mM NaCl, pH 9.0 and incubating for 30 minutes at room temperature. Free cross-linker was removed by gel filtration on a 1.5×35 cm P-2 column equilibrated in PBS-EDTA. Peak fractions containing derivatized PMB were combined and stored at 4° C.

b) Derivatization of IgG with sulfo-LC-SPDP was carried out by adding 0.3 mg of sulfo-LC-SPDP to 10 mg of IgG in 50 mM sodium borate, 300 mM NaCl pH 9.0 and incubating for 30 minutes on a rotating shaker. The derivatized IgG was separated from free cross-linker on a 5 ml Swift desalting column (Pierce) equilibrated with 100 mM sodium acetate, 100 mM sodium chloride, pH 4.5 and the peak fractions collected and pooled. This sample was then reduced by adding 7.7 mg of dithiothreitol in 250 μl of the same sodium acetate buffer and incubated for 30 minutes at room temperature. Excess reducing agent was removed by gel filtration on a 10 ml P-10 column equilibrated in PBS-EDTA. The peak fractions were collected and pooled.

c) Conjugation of derivatized IgG with derivatized PMB was carried out by adding 2.5 mg of IgG to 2.5 mg of PMB (107-fold molar excess of PMB) and 3.5 mg of IgG to 1.4 mg of PMB (43-fold molar excess of PMB), and incubating for 18 hours at room temperature. The IgG-PMB conjugate was separated from the rest of the reaction mixture on a 50 ml P-10 gel filtration column equilibrated with PBS-EDTA.

d) Conjugate activity assessment by ELISA indicated that the sulfo-LC-SPDP conjugates did not possess greater activity than the shorter SPDP molecule (FIG. 6).

EXAMPLE 10

Inhibition of Specific Binding of Antibodiotic to LPS by Free Antibiotic

Figure 5:
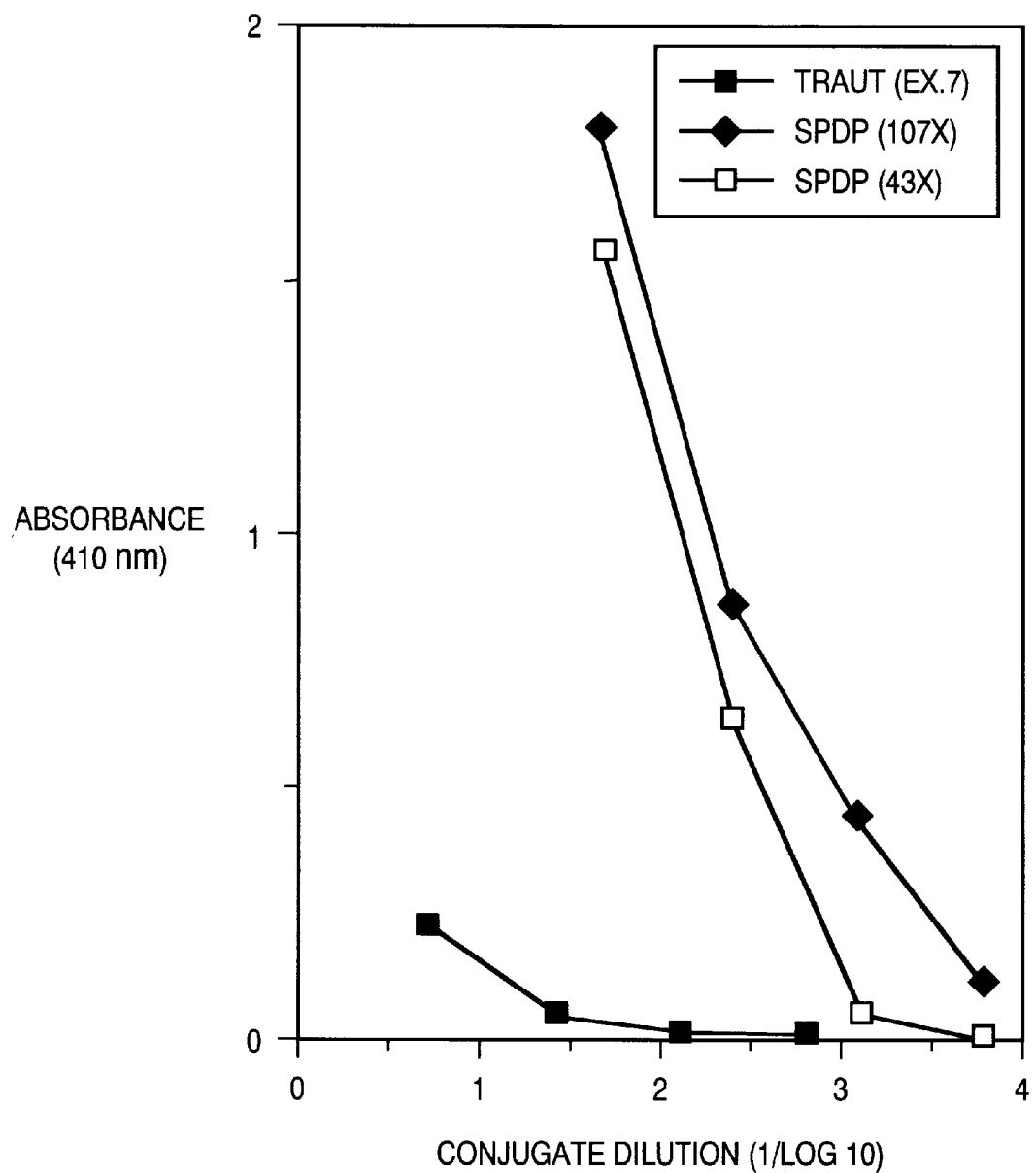
FIG. 5 shows conjugates of the present invention binding to LPS, as measured by ELISA.

In order to determine that the antibody-antibiotic conjugate binding observed in FIG. 5 is specific, free antibiotic was used to block conjugate binding (see Mode III discussion, above). This example involved: (a) mixing of the antibodiotic with free antibiotic; and (b) assaying the degree of conjugate binding to LPS in the presence of different concentrations of free antibiotic.

a) Mixing of antibodiotic with free antibiotic was performed by adding an equal volume of a 1:125 dilution (32 $\mu$g/ml) of the SPDP IgG-PMB conjugate in PBS-Tween 20 (0.05%) containing 1 mg/ml BSA with polymyxin at 0–20 $\mu$g/ml in the same buffer. Two hundred (200) $\mu$l of this mixture containing 0–2 $\mu$g of PMB and 3.2 $\mu$g of conjugate was then assayed for binding activity.

b) Assaying the degree of conjugate binding to LPS in the presence of different concentrations of free antibiotic was performed by adding 200 $\mu$l of the antibodiotic/free antibiotic mixture to wells of a 96-well microtiter plate that was coated with 2 $\mu$g of *E. coli* 0111:B4 LPS and blocked as described in Example 1. The wells were washed, goat anti-human Ig-alkaline phosphatase was added, and the binding assayed quantitatively on a MicroELISA reader exactly as described in Example 1.

Figure 7:
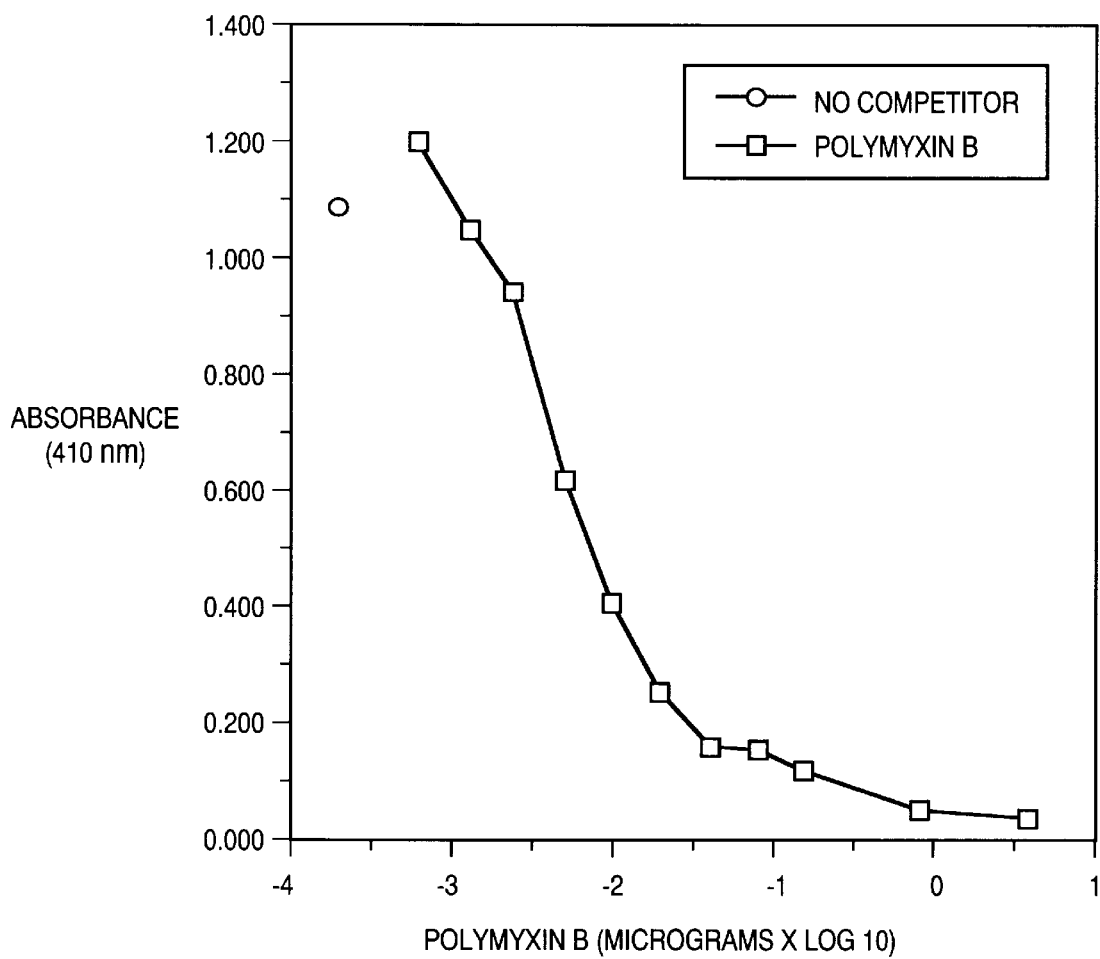
FIG. 7 shows inhibition of LPS binding of conjugates of the present invention using free polymyxin (PMB), as measured by ELISA.

The results are shown in FIG. 7 and demonstrate that free polymyxin competitively inhibits IgG-PMB binding to LPS. Clearly, the antibodiotic is binding specifically to LPS (i.e., via the conjugated PMB moieties).

Inspection of the inhibition curve gives some indication of the extent of active PMB conjugation, in that a 16 $\mu$g/ml solution of antibody ($1.1 \times 10^{-7}$ M) is 50% inhibited in its binding to LPS by a concentration of 40 ng/ml PMB ($2.6 \times 10^{-8}$ M). If one molecule of PMB was present on each PMB (making the PMB concentration on IgG equal to $1.1 \times 10^{-7}$) one would expect that an equimolar concentration of free PMB would inhibit binding by 50%. Since it requires one fourth the concentration of free PMB to inhibit this antibodiotic, one may conclude that there is at least one PMB molecule per four IgG molecules. In fact, since SPDP-modified PMB has a four-fold lower antibiotic activity than free PMB, the actual degree of IgG conjugation with PMB is probably at least four-fold higher than that calculated above (i.e., there is probably at least one PMB conjugated to each IgG molecule).

EXAMPLE 11

Conjugation Using Periodate Oxidation of IgG in NaPO$_4$

In Example 5, a means of attaching antibiotics to IgG without the involvement of a bifunctional cross-linker (i.e., periodate oxidation of the carbohydrate groups of IgG) was attempted. This involved, in part, periodate oxidation of IgG in pH 4.0 sodium acetate buffer and failed to yield a conjugate with significant activity. Because this failure may have been due to the reaction conditions, different reaction conditions were explored. This example involves: (a) periodate oxidation of IgG in phosphate buffer; and (b) conjugation of polymyxin B to periodate oxidized IgG.

a) Periodate oxidation of IgG in phosphate buffer was achieved by dissolving 10 mg of human IgG in 1 ml of 50 mM NaPO$_4$, pH 7.2 and adding 0.011 g sodium metaperiodate (final concentration 50 mM). After 30 minutes at room temperature, the periodate was removed by gel filtration on a 10 ml P-10 gel filtration column equilibrated in 50 mM NaPO$_4$, pH 7.2. The peak fractions containing antibody were pooled and concentrated to 1.5 ml.

b) Conjugation of periodate-oxidized IgG with PMB was carried out by adding 10 mg of PMB to either 5 mg or 3 mg of IgG prepared in (a) at 4° C. overnight with gentle shaking, followed by reduction with 0.1 mg/ml NaBH$_3$CN in 20 mM NaPO$_4$, pH 6.5 for 3 hours at room temperature. The IgG-PMB was separated from the rest of the reaction products by gel filtration on a 10 ml P-10 column.

Figure 8:
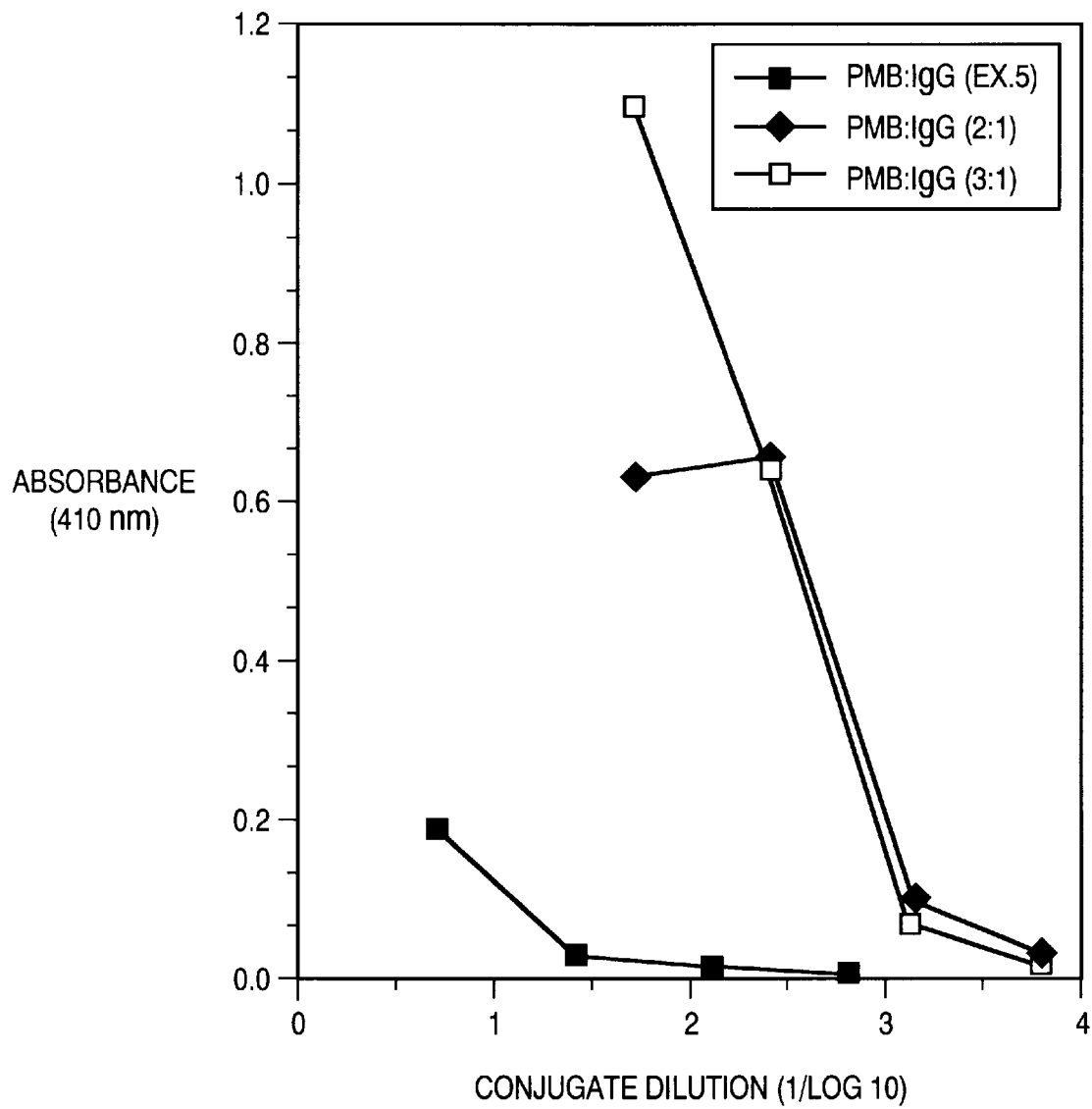
FIG. 8 shows periodate conjugates of the present invention binding to LPS, as measured by ELISA.

Inspection of the LPS binding activity (FIG. 8) revealed that the conjugates prepared were active. This is in contrast to the conjugate prepared in Example 5.

EXAMPLE 12

Antibacterial Activity of IgG-PMB Conjugates

Having determined which conjugates of IgG-PMB possessed LPS binding activity, the biological activity of the conjugates were examined (see discussion of Mode IV, above). Since polymyxin possesses direct antibiotic activity, it was possible that the conjugated polymyxin was also active. To determine whether the conjugates had any antibacterial activity, the minimum inhibitory concentration (MIC) and minimum bactericidal concentration (MBC) for the SPDP-conjugated IgG-PMB (107-fold molar excess of PMB, Example 8) and the periodate mediated IgG-PMB conjugate (3:1 ratio of PMB, Example 11) were determined. The example involved: (a) preparation of an *E. coli* bacterial inoculum; (b) determination of the MIC; and (c) determination of the MBC.

a) Preparation of an *E. coli* bacterial inoculum was initiated by first culturing *E. coli* HB101 overnight on TSA agar at 37° C. Colonies were suspended in sterile saline at $1.2 \times 10^8$ organisms/ml then diluted to $5 \times 10^5$ organisms/ml in Trypticase-Soy Broth (TSB; BBL). This concentration was confirmed by dilution plating.

b) Determination of MIC for each conjugate and a native polymyxin B control was made by mixing 0.5 ml of the $5 \times 10^5$ organisms/ml inoculum with 0.5 ml of a two-fold dilution series of each conjugate and incubating overnight in sterile 12×75 mm culture tubes at 37° C. The MIC was defined as the lowest concentration of the conjugate or PMB which resulted in complete inhibition of visible growth.

For the PMB control, the MIC was found to be 0.031 $\mu$g/ml while for the SPDP conjugate, the MIC was found to be 0.25 mg/ml. For the 3:1 (PMB:IgG) periodate conjugate, the MIC was found to be 0.031 mg/ml, which is approximately 1000-fold higher than for native PMB and eight-fold lower than for the SPDP IgG-PMB conjugate. Thus, both IgG-PMB conjugates do indeed retain antibacterial activity with the periodate conjugate exhibiting the highest degree of activity. The difference between the PMB and IgG-PMB values reflect in part, the greater size of IgG (about 100 times that of PMB) in that if PMB activity was perfectly preserved during conjugation and one PMB molecule was conjugated to each IgG molecule, the MIC would increase 100-fold due to the size of the IgG. The 1000-fold shift observed suggests that the activity of PMB is reduced by conjugation, and/or not all IgG molecules are conjugated. Nonetheless, it is surprising that a small surface-active antibiotic can still inhibit bacterial growth when conjugated to a much larger protein.

c) Determination of the MBC for each conjugate was made by plating serial dilutions of the mixtures in (b) above that exhibited no growth on TSA agar overnight at 37° C. The MBC was defined as the lowest concentration of conjugate of PMB which resulted in 99.9% or more of the viable organisms in the primary inoculum being killed. The MBC for the PMB was found to be 0.031 μg/ml, for the SPDP IgG-PMB it was 0.5 mg/ml, and for the periodate it was 0.031 mg/ml. The ability of the IgG-PMB conjugates to suppress bacterial growth and to kill bacteria on contact suggests that these compounds may be effective in preventing or treating bacteremia.

EXAMPLE 13

The Effect of IgG-PMB Conjugate on Complement and Its Activation by LPS

Both immunoglobulin and LPS have the potential to interact with complement. The interaction of LPS with complement can exacerbate the inflammatory response to endotoxemia or bacteremia. In this example, the ability of IgG-PMB conjugate to block complement activation by LPS was investigated. In addition, since immunoglobulin can also trigger adverse complement reactions [S. Barandun et al., Vox Sang. 7:157–174 (1962)], the ability of conjugate alone to activate complement was also determined. The example involved: (a) determination of the LPS concentrations sufficient to activate complement; and (b) blocking LPS-induced complement activation with IgG-PMB.

a) Determination of the LPS concentrations sufficient to activate complement was carried out by adding varying concentrations of LPS to a standard quantity of a complement source (CH50 Reference Standard; Sigma) and measuring the amount of complement consumed by titration on sensitized sheep red blood cells (SRBCs). [Modification of A. Chonn et al., *J. Immunol.* 146:4234–4241 (1991).]

To 40 μl of the Reference Standard, 40 μl of solution containing 80 μg, 8 μg, 0.8 μg, 0.0 μg of *E. coli* LPS or GVB+2 buffer (Sigma) were added, mixed, and incubated for 30 minutes at 37° C. Five or 10 μl aliquots of each mixture or a blank control were then added to CompQuick CH50 tubes (Sigma), mixed by repeated inversion and incubated for 60 minutes at room temperature with occasional mixing. The tubes were then centrifuged at 600×g for 10 minutes at 4° C. and the hemolysis present in the supernatant measured at 415 nm versus the lysis control blank solution. The $CH_{50}$ value of each mixture was calculated as follows:

$$CH_{50} \text{ of Sample} = \frac{\text{Absorbance of Sample}}{\text{Absorbance of Standard}} \times CH_{50} \text{ of Standard}$$

The results are shown in Table 17.

TABLE 17

Activation Of Complement By LPS

| Sample Tested | Abs. @ 415 nm | $CH_{50}$ Value | % Decrease |
|---|---|---|---|
| 1.0 mg/ml LPS + Ref. Std. | 0.124 | 114.7 | 51.2 |
| 0.1 mg/ml LPS + Ref. Std. | 0.170 | 157.8 | 33.1 |

TABLE 17-continued

Activation Of Complement By LPS

| Sample Tested | Abs. @ 415 nm | $CH_{50}$ Value | % Decrease |
|---|---|---|---|
| 0.01 mg/ml LPS + Ref. Std. | 0.215 | 198.9 | 15.4 |
| Reference Standard | 0.254 | 235.0 | 0.00 |

These results show that preincubation of a complement source with LPS consumes complement which is then unavailable for action on SRBCs in the second phase of the assay. The LPS effect was concentration-dependent.

b) Blocking of LPS-induced complement activation with IgG-PMB was carried out by mixing SPDP-conjugated IgG-PMB prepared as described in Example 7 with LPS and then examining the effect of pretreated LPS on complement activation. To 1.5 μg of *E. coli* 026:B6 LPS, 7.5 μg of IgG PMB or 15 μl of a buffer control was added and incubated at 37° C. for 60 minutes. Thirty (30) μl of complement (Ref-Std as in (a) above) or GVB+2 buffer was added to each sample and incubated for 60 minutes at 37° C. Twenty (20) μl of each mixture was added to CompQuick CH50 tubes (Sigma), mixed and incubated for 60 minutes at room temperature. The tubes were centrifuged as in (a) above and hemolysis quantitated at 415 nm. The results are shown in Table 18.

The results show that preincubation of IgG-PMB with LPS blocks the effect of LPS on complement activation. Furthermore, the IgG-PMB conjugate has no effect on complement activation on its own, suggesting that cross-linking with PMB has not perturbed IgG structure such that it would have a deleterious effect through

TABLE 18

Inhibition Of LPS-Mediated Complement Activation By IgG-PMB

| Sample Tested | Abs. @ 415 nm | $CH_{50}$ Value | % Δ |
|---|---|---|---|
| IgG-PMB only | 0.002 | 0.40 | — |
| IgG-PMB + Complement | 1.273 | 253.1 | +7.7 |
| LPS Only | 0.008 | 1.59 | — |
| Complement Reference Standard | 1.182 | 235 | 0.00 |
| LPS + Complement | 0.806 | 160.2 | −31.8 |
| IgG-PMB + LPS + Complement | 1.237 | 245.9 | +4.6 | spontaneous complement reactions. The ability to block LPS effects and the apparent safety of the IgG-PMB conjugate suggests that it could possess both prophylactic and therapeutic value against bacteremia and endotoxemia.

EXAMPLE 14

Improved IgG-PMB Conjugates

Methods were investigated for improving the activity of the IgG-PMB conjugates prepared by the methods of Example 7 (SPDP) and Example 11 (periodate oxidation/ Schiff base reduction). Since both families of conjugates exhibited much higher levels of LPS-binding than conjugates prepared with other chemistries, it was possible that even higher levels of binding could be achieved by increasing the degree of PMB-substitution on the IgG. The two mechanisms employed for achieving greater substitution were to increase the reactant (IgG and PMB) concentration at the conjugation step and to use more highly derivatized SPDP-PMB. The example involved: (a) preparation of a new periodate IgG-PMB conjugate; (b) preparation of new SPDP IgG-PMB conjugates; (c) ELISA of conjugate binding to LPS; (d) determination of conjugate MICs and MBCs; and (e) determination of the degree of conjugation by amino acid analysis.

a) Preparation of a new periodate IgG-PMB conjugate was carried out by oxidizing 30 mg of IgG dissolved in 1 ml of 50 mM NaPO$_4$, pH 7.2 with 10.7 mg of sodium periodate (Sigma) for 30 minutes at room temperature. The 1 ml reaction mixture was applied to a 15 ml Swift desalting column equilibrated in 50 mM NaPO$_4$, pH 7.2 and the peak IgG fractions were pooled to an IgG concentration of 7.1 mg/ml. To 1 ml of this Ig mixture containing 0.0476 μmoles of IgG, 20 mg of PMB (14.44 μmoles) was added and incubated overnight at 4° C. The reaction mixture was adjusted to pH 6.5 with 1.0 N HCl, and 10 μl of a 10 mg/ml NaBH$_3$CN solution was added and incubated at room temperature for 4 hours. The conjugate was then chromatographed on a 10 ml P-10 column and stored at 4° C.

b) Preparation of new SPDP IgG-PMB conjugates was carried out by first derivatizing PMB at 2:1 and 3:1 molar ratios of SPDP:PMB as described in Example 6. For each reaction, 5 mg of IgG in 0.5 ml was derivatized with 15 μl of 20 mM SPDP solution in DMSO by incubating for 30 minutes at room temperature with intermittent shaking. The derivatized IgG was purified on a 15 ml Swift desalting column equilibrated with acetate buffer and the peak fractions were pooled and concentrated on a Centriprep-30 concentrator (Amicon). To the 5 mg of IgG in 1.8 ml of acetate buffer, 7.7 mg of dithiothreitol in 250 μl of acetate buffer was added and incubated at room temperature for 30 minutes. Each sample was then purified on a 15 ml Swift desalting column equilibrated in PBS-EDTA. To each sample containing approximately 5 mg of SPDP derivatized IgG, 5 mg of PMB derivatized at either a 2:1 or 3:1 molar ratio of SPDP was added and incubated for 18 hours at room temperature. Each conjugate was then separated from free SPDP-PMB by gel filtration on a P-10 column (50 ml) equilibrated with PBS-EDTA, and the peak fractions were collected, pooled, and stored at 4° C.

c) ELISA analysis of conjugate binding to LPS was performed as described in Example 1 using *E. coli* 0111:B4 LPS (Sigma). The binding of different dilutions of the periodate conjugate made in (a) above, and the two SPDP conjugates made in (b) above to LPS coated and uncoated wells of a 96 well microtiter plate are shown as averages of duplicate samples in Table 19.

The results show that the 3:1 SPDP:PMB conjugate had the highest specific LPS binding activity, approximately 2–4 times the binding exhibited by the 2:1 SPDP:PMB conjugate and the periodate conjugate at concentrations of 0.8–4.0 μg/ml.

d) Determination of conjugate MICs and MBCs was carried out exactly as described in Example 12 using *E. coli* HB101 as the susceptible test strain. The results are shown in Table 20.

When compared with these determinations for the conjugates examined in Example 12, the new periodate conjugate is four times as potent, and the 3:1 SPDP-PMB conjugate is twice as potent. Surprisingly, the periodate conjugate exhibits lower LPS-binding activity by ELISA but stronger antibacterial activity than the 3:1 SPDP-PMB conjugate. Perhaps the modification of PMB and IgG with SPDP improves the conjugation efficacy but decreases the antibiotic activity compared to the conjugation of native PMB to periodate-treated IgG.

e) Determination of the degree of conjugation by amino acid analysis was carried out by examining the amino acid composition of 2:1 SPDP Ig-PMB, 3:1 SPDP Ig-PMB, and the periodate Ig-PMG conjugates above, compared with control samples of native human IgG and free polymyxin B. The novel amino acid diaminobutyric acid (DAB) which constitutes 6 of the 10 residues of PMB was the key component that was detected and quantitated.

TABLE 19

LPS-Binding Activity Of New IgG-PMB Conjugates

| Conjugate Tested | Conjugate Dilution | Absorbance at 410 nm | |
|---|---|---|---|
| | | w/Ag | w/o Ag |
| IgG-PMB (IO$_4$) | 1:10 (=0.1 mg/ml) | 1.788 | 1.694 |
| | 1:50 | 1.392 | 0.632 |
| | 1:250 | 0.440 | 0.096 |
| | 1:1250 | 0.121 | 0.039 |
| | 1:6250 | 0.035 | 0.009 |
| IgG-PMB (SPDP) 3:1 | 1:10 (=0.09 mg/ml) | 1.726 | 0.718 |
| | 1:50 | 1.650 | 0.156 |
| | 1:250 | 0.979 | 0.167 |
| | 1:1250 | 0.520 | 0.013 |
| | 1:6250 | 0.120 | 0.007 |
| IgG-PMB (SPDP) 2:1 | 1:10 (=0.1 mg/ml) | 1.592 | 0.375 |
| | 1:50 | 1.256 | 0.057 |
| | 1:250 | 0.578 | 0.015 |
| | 1:1250 | 0.151 | 0.008 |
| | 1:6250 | 0.028 | 0.010 |

TABLE 20

MIC And MBC For The New IgG-PMB Conjugates

| Conjugate | MIC | MBC |
|---|---|---|
| Periodate IgG-PMB | 7.8 μg/ml | 7.8 μg/ml |
| 2:1 SPDP IgG-PMB | 250 μg/ml | 250 μg/ml |
| 3:1 SPDP IgG-PMB | 125 μg/ml | >125 μg/ml |
| PMB Control | 0.039 μg/ml | 0.039 μg/ml |

Five samples in all were analyzed, including:
1. Free PMB (25 nmoles in 50 μl H$_2$O)
2. Periodate Ig-PMB (600 pmoles in 100 μl PBS)
3. SPDP 3:1 Ig-PMB (600 pmoles in 100 μl PBS)
4. SPDP 2:1 Ig-PMB (600 p moles in 100 μl PBS)
5. Human IgG (600 p moles in 100 μl PBS)

The samples were prepared by transferring each to a glass hydrolysis tube using three rinses of 100 μl of pure water and then concentrated to dryness in a vacuum centrifuge. To each of the sample tubes, 500 μl of distilled 6N HCl, 10 μl of 2-mercaptoethanol, and 10 μl of a 50% aqueous phenol solution were added. The tubes were then purged with nitrogen gas and capped. The samples were hydrolyzed by heating at 110° C. for 22 hours and then concentrated again to dryness. The PMB sample was suspended in 500 μl of 0.2 N sodium citrate buffer, pH 2.2 while the other four samples were suspended in 250 μl of this buffer. After thorough mixing, the sample solutions were passed through a 0.2 μm pore nylon membrane syringe filter.

A Beckman Instruments 6300 Amino Acid Analyzer was used to analyze 20 μl of each filtered hydrolysate solution. The machine was equipped with a Beckman 10 cm cationic exchange HPLC column, a Beckman sodium buffer system, a 60 minute analysis methodology, and a Beckman ninhydrin reagent detection system with absorbance measured at the 570 nm and 440 nm wavelengths. The detector sensitivity was set at 1.0 AUFS for the PMB sample and 0.5 AUFS for the other four samples.

All data collection and peak integration calculations were performed with a Gilson HPLC System Controller 712 v. 1.1 software package (Middleton, Wis.). Sample peak identification and amino acid concentrations were determined by comparison to analyses made at known concentrations of a 17 amino acid standard mixture (Beckman Standard, Lot #A108039) and (S)-(+)2,4-Diaminobutyric acid dihydrochloride (Aldrich Chemical, Lot #07301CY). The results of the amino acid analyses are shown in Table 21.

The values represent the estimated amino acid composition of each sample, determined by multiplying the percentage of each amino acid measured by the expected total number of amino acids (1320 for human IgG, for example). The moles of PMB/mole IgG were calculated by dividing the number of unique DAB residues detected by 6 (the number of DAB residues/PMB).

The results show that the 3:1 SPDP conjugate possessed the highest degree of conjugation (avg. 3.7 PMB molecules per IgG molecule). This is consistent with this conjugate possessing the highest LPS-binding activity as measured by ELISA (see (b) above). The 3:1 SPDP conjugate contained, on average, twice the number of PMB molecules than the 2:1 SPDP conjugate, which would explain the two-fold greater activity of the 3:1 SPDP conjugate in the LPS-binding ELISA. The periodate Ig-PMB is also well conjugated and it exhibited the highest degree of antibacterial activity. It appears that the SPDP linkage affords the highest degree of LPS-binding activity while the periodate linkage provides greater antibacterial activity. This may reflect steric differences in the way PMB is attached to the IgG and/or the different effects of the two conjugation chemistries on PMB activity.

TABLE 21

Amino Acid Composition Of Ig-PMB Conjugates

| Amino Acid | Letter Code | Human IgG | PMB | IgG-PMB 10₄₋ | IgG-PMB 1:2 | IgG-PMB 1:3 |
|---|---|---|---|---|---|---|
| Asp | D | 111 |   | 107 | 105 | 111 |
| Thr | S | 117 | 2 | 120 | 115 | 122 |
| Ser | S | 177 |   | 188 | 208 | 176 |
| Glu | E | 133 |   | 129 | 129 | 136 |
| Pro | P | 119 |   | 105 | 120 | 123 |
| Gly | G | 95 |   | 101 | 102 | 101 |
| Ala | A | 75 |   | 75 | 78 | 80 |
| Val | V | 116 |   | 112 | 107 | 112 |
| Met | M | 9 |   | 8 | 9 | 9 |
| Ile | I | 26 |   | 28 | 25 | 26 |
| Leu | L | 99 | 1 | 105 | 96 | 100 |
| Tyr | Y | 51 |   | 53 | 51 | 51 |
| Phe | F | 42 | 1 | 47 | 44 | 45 |
| His | H | 24 |   | 24 | 23 | 23 |
| Lys | K | 83 |   | 87 | 79 | 82 |
| Arg | R | 41 |   | 44 | 38 | 39 |
| DAB |   |   | 6 | 20 | 11 | 22 |
| TOTAL |   | 1318 | 10 | 1353 | 1340 | 1358 |
| Moles PMB/Mole IgG |   |   |   | 3.3 | 1.8 | 3.7 |

EXAMPLE 15

Figure 9:
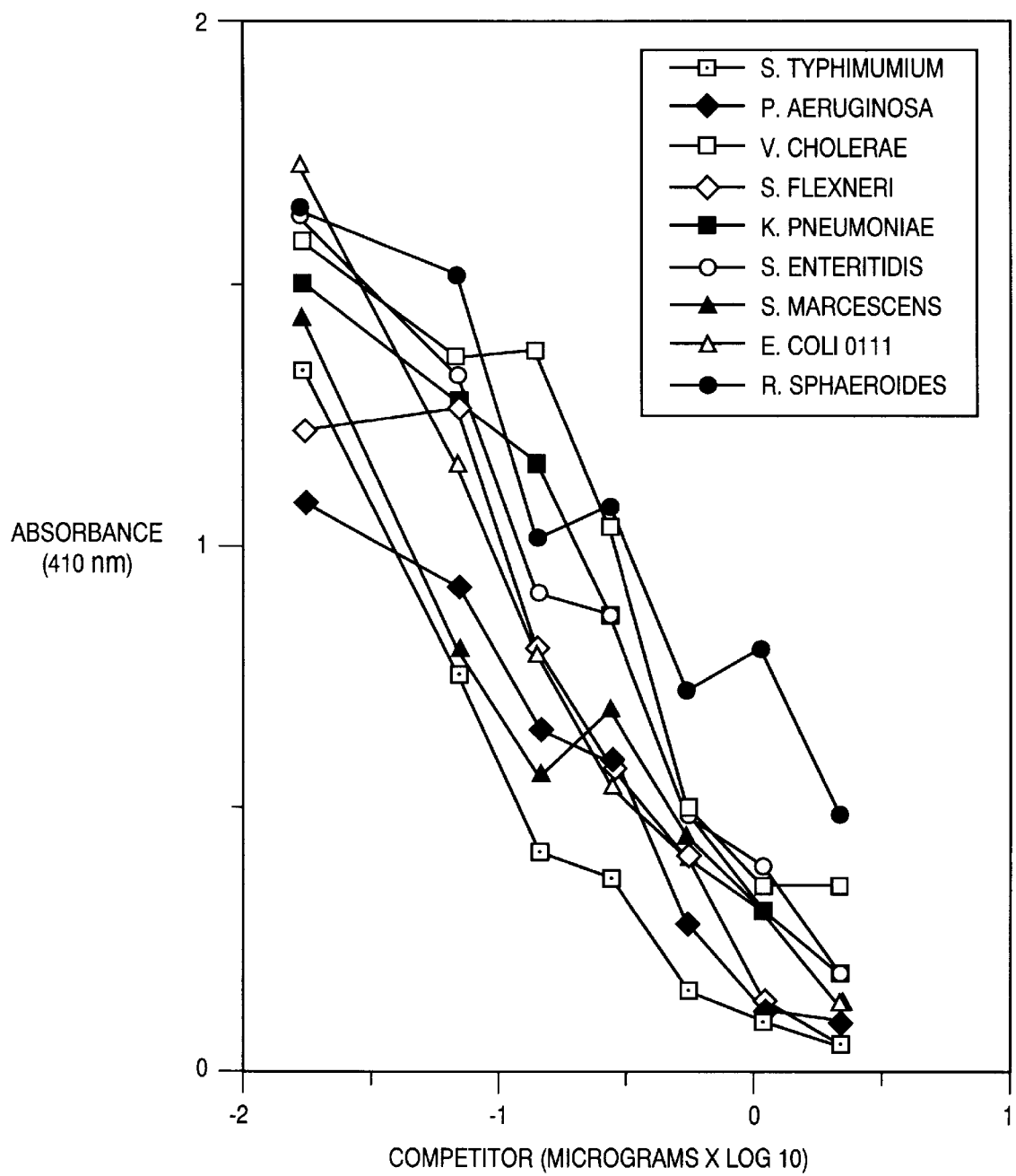
FIG. 9 shows inhibition of LPS binding of conjugates of the present invention using LPS of various bacterial species, as measured by ELISA.

The Use of IgG-PMB Conjugates as a Diagnostic: Cross-Reactivity of Different Gram-Negative LPS Antigens with IgG-PMB Since the IgG-PMB conjugates exhibited binding to *E. coli* 0111:B4 LPS, and this species is only one of many potential gram-negative agents of endotoxemia and bacteremia, it was of interest to determine whether the IgG-PMB conjugate was capable of detecting other species of LPS in a diagnostic format using a competitive ELISA. The example involved: (a) coating of *E. coli* 0111:B4 LPS to microtiter wells; (b) incubation of IgG-PMB conjugates with different concentrations of several species of LPS; and (c) assay of conjugate binding to *E. coli* 0111:B4 LPS in the presence of competitor.

a) Coating of *E. coli* 0111:B4 LPS to the wells of 96-well microtiter ELISA plates was performed as described in Example 1, (100 μl/well of pyrogen-free PBS containing 1 mM EDTA and 2 μg of LPS was coated onto the wells and allowed to incubate overnight at 4° C.). The wells were washed with PBS-0.05% Tween 20 and blocked with PBS containing 10 mg/ml endotoxin-free BSA at 37° C. for 90 minutes.

b) Incubation of IgG-PMB conjugates with different concentrations of LPS purified from *E. coli* 0111:B4 (control standard) *Salmonella typhimurium, Pseudomonas aeruginosa, Vibrio cholerae, Shigella flexneri, Klebsiella pneumoniae, Salmonella enteritidis, Serratia marcescens*, and *Rhodobacter sphaeroides* (all from Sigma, except the Rhodobacter, which was obtained from List Biologicals Laboratory, Campbell, Calif.) was carried out by adding 250 μl of a 7.2 μg/ml solution of IgG-PMB conjugate prepared with a 3:1 molar ratio of SPDP:PMB (Example 13) to 250 μl of PBS-0.05% Tween 20 containing 1 mg/ml BSA followed by incubation at 37° C.; 100 μl of these mixtures was added per well.

c) Assay of conjugate binding to *E. coli* 0111:B4 LPS in the presence of competitor was measured by incubating 100 μl of the mixtures from (b) above at 37° C. for 1 hour. The plates were then washed and the wells incubated with alkaline phosphate-conjugated goat anti-human IgG (Sigma) diluted 1:500 in PBS with 0.05% Tween 20 containing 1 mg/ml BSA, incubated 37° C. for 1 hour, washed again and incubated in p-nitrophenyl phosphate for 30 minutes and read at 410 nm, as described in Example 1. The results are shown in FIG. 9 and demonstrate that LPS antigens from all nine species representing four different orders of gram-negative bacteria compete effectively for IgG-PMB binding to *E. coli* 0111:B4 LPS. These results show that IgG-PMB conjugates can be used to detect and quantitate a LPS from a variety of bacterial species, and suggest that the IgG-PMB conjugate will be therapeutically effective against a broad spectrum of gram-negative organisms and endotoxins.

EXAMPLE 16

Neutralization of the In Vivo Effects of Endotoxin by IgG-PMB

Endotoxin (LPS) can trigger a lethal reaction in vivo. In order to determine whether IgG-PMB conjugate is capable of neutralizing the lethal effects of endotoxin, a well-characterized and accepted murine model of endotoxic shock was utilized. [C. Galanos et al., Proc. Natl. Acad. Sci. USA 76:5939–5943 (1979).] The example involved: (a) determination of a minimum lethal dose of endotoxin in galactosamine-sensitized mice; and (b) neutralization of endotoxin lethality by premixture with Ig-PMB.

a) Determination of a minimum lethal dose of endotoxin in galactosamine-sensitized mice was performed by administering different doses of *E. coli* 0111:B4 LPS to C57Bl/6 mice that were co-administered 20 mg of D-galactosamine-HCl in 400 μl of PBS. The latter compound is a specific hepatotoxic agent that increases the sensitivity of experimental animals to endotoxin several thousand-fold. [C. Galanos et al., Proc. Natl. Acad. Sci. USA 76:5939–5943 (1979).] To accomplish this determination, 1–500 ng of *E. coli* 0111:B4 LPS (List Biological Laboratories, Campbell, Calif.) in PBS was injected intraperitoneally, along with 20 mg of D-galactosamine (Sigma). It was found that 10–25 ng of endotoxin was usually sufficient to kill most or all mice within 24 hr. The variability in endotoxin lethality may be related to the different ages of the mice used. Since 10 ng was the minimal effective lethal dose, this amount of LPS was utilized in neutralization experiments.

b) Neutralization of endotoxin lethality by premixture with Ig-PMB was performed by incubating 50 ng of *E. coli* 0111:B4 LPS with 5 mg of periodate conjugated IgG-PMB (prepared as described in Example 14), or 5 mg of unconjugated control human IgG (Sigma) and 100 mg D-galactosamine in PBS and injecting a portion of each mixture intraperitoneally into C57BL/6 mice. The results are shown in Table 22. Survival was assessed 24 hours later.

TABLE 22

Neutralization Of Endotoxin Lethality By IgG-PMB (Therapeutic Prophylactic)

| Treatment | Survivors/Total |
|---|---|
| 1 mg Human IgG and 20 mg D-galactosamine | 5/5 |
| 1 mg Human IgG, 10 ng LPS and 20 mg D-galactosamine | 1/4 |
| 1 mg Periodate IgG-PMB, 10 ng LPS and 20 mg D-galactosamine | 5/5 |

Since the number of animals used in this experiment was small, the trial was repeated using: a) 12 mice in the control group treated with endotoxin, D-galactosamine, and normal human IgG and b) 12 mice in the experimental group that received endotoxin, D-galactosamine, and the periodate IgG-PMB. The per mouse dosage of each component was the same as above and the experiment was repeated exactly as above. The results are shown in Table 23.

TABLE 23

Neutralization Of Endotoxin Lethality By IgG-PMB

| Treatment | Survivors/Total |
|---|---|
| 1 mg Human IgG, 10 ng LPS and 20 mg D-galactosamine | 0/12 |
| 1 mg Periodate IgG-PMB, 10 ng LPS and 20 mg D-galactosamine | 11/12 |

The results of these two trials prove that IgG-PMB neutralizes the lethal effect of endotoxin in vivo and suggest that Ig-PMB conjugates will be useful in preventing or treating sepsis due to gram-negative bacteria.

EXAMPLE 17

Prevention of Endotoxin Lethality by Prophylactic Administration of IgG-PMB Conjugate In the previous example, the ability of IgG-PMB conjugate to neutralize endotoxin lethality in vivo was investigated by mixing conjugate or control IgG with endotoxin and administering the mixture with D-galactosamine into mice. The results showed that the conjugate neutralized the endotoxin. A more strenuous test of the ability of the conjugate to neutralize endotoxin lethality is to administer the conjugate at a separate time and via a separate route than that used to administer endotoxin. In addition, to demonstrate its prophylactic value, lower doses of conjugate were utilized. The Example involved the intravenous administration of IgG-PMB or control IgG followed 1 hr later by the intraperitoneal administration of a lethal dose of endotoxin and D-galactosamine.

Twenty (20) CS7BL/6 mice weighing twenty (20) grams each were administered 200 μg (5 mice) or 400 μg (8 mice) of IgG-PMB conjugate (periodate conjugate prepared as in Example 14) or 400 μg control human IgG (7 mice) in 100 μl of PBS through their tail vein. Ninety (90) minutes later, each mouse received 10 ng *E. coli* 0111:B4 endotoxin and 20 mg D-galactosamine in 200 μl of PBS administered intraperitoneally. After 24 hrs, the number of mice surviving in each group was recorded. The results are shown in Table 24.

TABLE 24

Prophylaxis Against Endotoxin In Challenge With IgG-PMB Conjugate

| Treatment | Survivors/Total |
|---|---|
| 400 μg Human IgG, 10 ng Endotoxin and 20 mg D-galactosamine | 0/7 |
| 200 μg IgG-PMB, 10 ng Endotoxin and 20 mg D-galactosamine | 5/5 |
| 400 μg IgG-PMB, 10 ng Endotoxin and 20 mg D-galactosamine | 8/8 |

The results show that a 10–20 mg/kg dose of IgG-PMB administered intravenously is sufficient to protect against a subsequent lethal challenge of endotoxin administered intraperitoneally. These findings suggest that the IgG-PMB conjugate given prophylactically will prevent endotoxin-mediated effects and that the conjugate is capable of neutralizing endotoxin outside of the vascular compartment.

EXAMPLE 18

Preservation of IgG Effector Functions in IgG-PMB Conjugates: Fc Receptor Binding One of the functions of IgG is to opsonize and facilitate clearance of organisms, toxins, antigens, etc. by phagocytic cells. In order to determine whether this property of IgG, which is facilitated by the Fc region of the native molecule, remains intact in IgG conjugates that have been prepared with SPDP or periodate, the binding of IgG-PMB to human monocyte/macrophage cells was examined in a competition assay. This assay is similar to that employed to examine the Fc receptor binding activity of hybrid recombinant antibody fragments fused to cell surface viral receptors. [D. J. Capon et al., Nature 337:525–531 (1989); A. Traunecker et al., Nature, 339:68–70 (1989).] The example involved: (a) preparation of a control conjugate of PMB to human albumin (a non-Fc receptor binding human protein-PMB conjugate); and (b) assay of IgG-PMB conjugate binding to Fc receptors of the human U937 monocyte/macrophage cell line.

a) In order to compare the specific properties of IgG-PMB conjugates with other protein-PMB conjugates, human albumin was conjugated with PMB using the SPDP chemistry of Example 7 (because albumin is not glycosylated, the periodate chemistry of Example 5 was not applicable to albumin). Conjugation of albumin with PMB was carried out in three steps similar to the scheme described in Example 7. The first step involved derivatization of 10 mg of PMB in 50 mM sodium borate, 300 mM NaCl, pH 9.0 with 2:1 mg of SPDP dissolved in 50 μl of dimethylsulfoxide for 30 minutes at room temperature. The free cross-linker was removed on a 15 ml Swift desalting column as described in Example 7.

Ten (10) mg of human serum albumin was derivatized with 1.2 mg of SPDP (in 25 μl DMSO), dissolved in 1 ml of 50 mM sodium borate, 300 mM NaCl, pH 9.0, and mixed for 30 minutes at room temperature. The free cross-linker was removed by gel filtration on a 15 ml Swift desalting column equilibrated with PBS-EDTA, pH 7.5 and the peak fractions containing SPDP-albumin were collected, pooled and concentrated on a Centriprep-30 concentrator. The pH of the sample was raised to 8.0 with 10 μl of 10N NaOH, and reduced with 15.4 mg dithiothreitol dissolved in 200 μl of pyrogen-free water for 30 minutes at room temperature. The reduced, derivatized albumin was purified by gel filtration on a 15 ml desalting column and concentrated on a Centriprep-30 concentrator.

The reduced, derivatized albumin was conjugated with SPDP-PMB by mixing the two solutions prepared above and incubating overnight at room temperature. The conjugate was separated from SPDP-PMB by gel filtration on a 50 ml P-10 column.

b) IgG-PMB conjugate binding to Fc receptors of the human U937 monocyte/macrophage cell line was assayed in a manner similar to that described by Capon et al. [Nature 337:525–531 (1989).] First, a saturation curve of the binding of $^{125}$I-labelled human IgG [the $^{125}$I-IgG stock concentration was 16 μg/ml=1.07×10$^{-7}$ M] (New England Nuclear, Boston, Mass.) was performed by incubating 1×10$^{-8}$ M to 1×10$^{-12}$ M $^{125}$I-IgG with 2×10$^5$ U937 cells in 0.5 ml of PBS containing 2 mg/ml BSA and 0.1% sodium azide. The cell suspensions were incubated for 60 minutes at 37° C., centrifuged for 3 minutes at 1500×g and washed three times with incubation buffer. The cell pellets were then counted for radioactivity with a Bioscan "Quick Count" benchtop radioisotope counter (Bioscan, Inc., Wash. D.C.). The binding was found to saturate at 1×10$^{-8}$ M $^{125}$I-Ig so this concentration was used for the competition assay described below.

Figure 10:
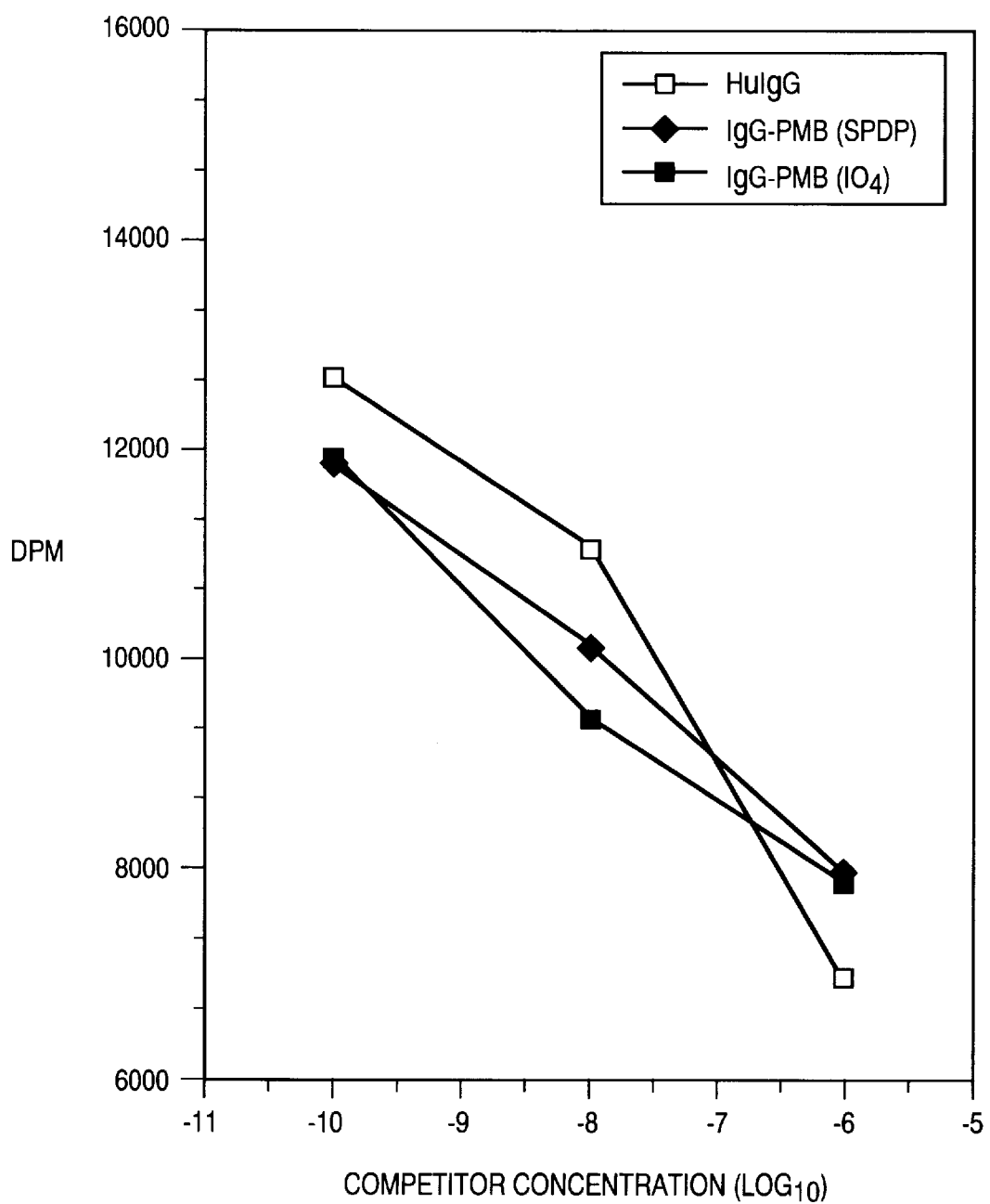
FIG. 10 shows the binding of conjugates of the present invention to phagocytic cells in a radioactive competition assay.

For the competition experiment, a constant quantity of $^{125}$I-IgG (1×10$^{-8}$ M) was incubated with 2×10$^5$ U937 cells in 0.5 ml of PBS containing 2 mg/ml BSA, 0.1% sodium azide and varying concentrations of the unlabelled competitor proteins: human IgG, IgG-PMB (SPDP), IgG-PMB (periodate), and human albumin-PMB from (a) above. The cells were incubated, washed, and the amount of bound radioactive $^{125}$I-IgG was quantitated as described above. In the absence of any of the human competitor proteins, 12,029 cpm of labelled IgG was bound to the cells. The results of the competitor assay are plotted in FIG. 10. It is clear that human IgG and both IgG-PMB conjugates have similar binding properties to the U937 cells in that all three compete comparably well at 10$^{-8}$ M and 10$^{-6}$ M. This result shows that the modification of the IgG with SPDP and PMB or by periodate oxidation of the carbohydrate side chains does not impair the ability of IgG to bind to Fc receptors. This suggests that the conjugates can facilitate Fc receptor-mediated opsonization of antigen/organisms by phagocytic cells. As expected, the human albumin-PMB exhibited no competitive binding activity at concentrations up to 10$^{-6}$ (data not shown) and is therefore unable to facilitate opsonization.

EXAMPLE 19

Preparation of an Antibody-Antibiotic Conjugate with Activity Against Gram-Positive Bacteria: IgG-Bacitracin Gram-positive organisms are responsible for approximately one-third of sepsis cases. It would be desirable to have IgG-antibiotic conjugates with activity against these organisms. To this end, conjugates were made between IgG and bacitracin and vancomycin, two surface-active gram-positive antibiotics. The example involved: (a) periodate activation of IgG; and (b) conjugation to bacitracin and vancomycin.

a) Periodate activation of IgG was carried out as described in Example 5(b), using 30 mg of human IgG and 50 mM sodium periodate in 1 ml of 50 mM NaPO$_4$, pH 7.2 for 30 minutes at room temperature. The activated IgG was purified on a 15 ml Swift desalting column (Pierce) and the peak fractions pooled.

b) Conjugation to bacitracin and vancomycin was carried out by adding 18.6 mg of bacitracin to 7.1 mg of activated IgG and 19.7 mg of vancomycin to 7.1 mg of activated IgG and each solution was incubated overnight at 4° C. The mixtures were then clarified by centrifugation to remove any precipitates formed during incubation. The reaction mixtures were adjusted to pH 6.5 with 1.0 N HCl, and 10 μl of a NaCNBH$_3$ solution (10 mg/ml) was added and incubated for 4 hours at room temperature. The conjugate was then purified on a 15 ml Swift desalting column equilibrated in PBS-EDTA, pH 7.2.

EXAMPLE 20

Antibacterial Activity of IgG-Antibiotic Conjugate on Gram-Positive Bacteria

To determine if the conjugates prepared in Example 19 possessed anti-bacterial activity, the MIC and MBC of these conjugates was assayed against *Staphylococcus epidermidis* obtained from Dr. Edward Balish, Department of Medical Microbiology, University of Wisconsin. The strain is gram-positive, DNase negative, mannitol salt negative, coagulase negative and novobiocin sensitive. The example involved: (a) preparation of an *S. epidermidis* inoculum; and (b) determination of the MIC and MBC of free and conjugated antibiotics.

a) Preparation of an *S. epidermidis* inoculum was carried out by plating organisms on TSA overnight at 37° C., and suspending bacteria at 5×10$^5$ organisms/ml in TSB.

b) Determination of the MIC and MBC of the free and conjugated antibiotics was carried out by mixing 0.5 ml of the *S. epidermidis* inoculum with 0.5 ml of solutions containing 0.3125 to 10 μg/ml of free antibiotic or 12.5 to 250 μg/ml of each conjugate. The MIC was defined as the minimum concentration of the compounds that inhibited visible growth and the MBC defined as the concentration that killed 99.9% or more of the initial organisms present in the inoculum (measured by plating those solutions that do not exhibit visible growth; see Example 10). The results are shown in Table 25.

TABLE 25

MIC And MBC Of Free And IgG-Conjugated Antibiotics
On *S. epidermidis*

| Compound | MIC (µg/ml) | MBC (µg/ml) |
|---|---|---|
| Bacitracin | 25 | 50 |
| IgG-Bacitracin | 125 | 250 |
| Vancomycin | 1.25 | 2.5 |
| IgG-Vancomycin | >50 | N.D. |

The results show that the IgG-bacitracin conjugate was indeed active against *S. epidermidis* and suggest that this compound could be useful in the prevention and treatment of gram-positive sepsis.

EXAMPLE 21

Treatment of Persons Susceptible to Gram-Negative Sepsis And Endotoxemia with an Antibody-Antibiotic Conjugate As noted earlier, studies have suggested a causal relationship between a person's humoral immune status and the susceptibility to gram-negative infections. The present invention contemplates screening for patients having a poor immune status for determining a subpopulation having the greatest need for antibodiotics. The example involves: (a) assay of patient total IgG and IgM levels; (b) assay of patient endotoxin core antigen-specific IgG and IgM levels; (c) comparison of patient immunoglobulin levels to healthy normal controls; (d) administration of immunoglobulin and/or immunoglobulin-antibiotic conjugate to patients with significant deficiencies in total or core antigen-specific immunoglobulin levels.

(a) Assay of patient total IgG and IgM levels is performed by nephelometry using the Beckman Automated immunochemistry system (Beckrman Instruments, Inc., Brea, Calif.) as described by Stoll et al., Serodiagnosis and Immunotherapy 1:21–31 (1987).

(b) Assay of endotoxin in core-antigen specific IgG and IgM levels is performed by ELISA. Plasma or sera are diluted and the level of binding of different sample dilutions to purified *E. coli* J5 endotoxin and *Salmonella minnesota* R595 endotoxin are quantitated and compared with known standards of purified anti-endotoxin antibodies. [B. J. Stoll et al., Serodiagnosis and Immunotherapy 1:21–31 (1987); and M. Pollack et al., J. Clin. Invest. 72:1874–1881 (1983).]

c) Comparison of patient immunoglobulin levels to healthy controls is performed by analyzing the total IgG and IgM levels (as mg/ml of sample) in the patient vs. the control group and the endotoxin core antigen-specific IgG and IgM levels (as µg/ml of sample) between these same two groups. Patients with ≦80% of the normal control level of total IgG and/or ≦60% of the normal control level of endotoxin core antigen-specific IgG and IgM are defined as at risk for gram-negative infection and endotoxemia.

d) Administration of immunoglobulin and/or immunoglobulin antibiotic conjugate to patients with significant deficiencies in total or core antigen-specific immunoglobulin levels is carried out to restore normal or near normal total and antigen-specific humoral defenses. To restore normal IgG levels, a 3% solution of intravenously injectable immunoglobulin (available from Sandoz Forschunginstitut, Vienna, Austria; Hyland Therapeutics, Duarte, Calif.; or Cutter Laboratories, Berkeley, Calif.) is administered twice daily until immunoglobulin levels rise to within 10% of normal levels.

Because the IgG-PMB conjugates of the present invention comprise a population of antibody molecules all of which are capable of binding to endotoxin, much less IgG-PMB conjugate is required than total IgG to restore or increase levels antigen-specific antibody. A single intravenous dose consisting of 1–20 mg of IgG-PMB conjugate per kg of body weight is administered to restore endotoxin-specific antibody levels to ≧100% of normal levels.

EXAMPLE 22

Treatment of Persons Susceptible to Gram-Negative Sepsis, Endotoxemia, and Gram-Positive Sepsis with a Cocktail of Antibody-Antibiotic Conjugates Since there is a causal relationship between a person's humoral status and their susceptibility to infection, there is also a need to restore antibody levels against gram-positive organisms as well as the levels against gram-negative organisms and endotoxin. This is achieved by administration of a cocktail of antibody-antibiotic conjugates with activity against both classes of bacteria as well as endotoxin. The example involves: (a) identification of persons at risk of infection; and (b) administration of a cocktail of antibody-antibiotic conjugates and, if necessary, total pooled human immunoglobulin to restore antigen-specific and total immunoglobulin levels.

a) Identification of persons at risk of infection is carried out by the means defined in Example 21.

b) Administration of a cocktail of antibody-antibiotic conjugates and, if necessary, total pooled human immunoglobulin to restore antigen-specific and total immunoglobulin levels is carried out by injecting a single intravenous dose of IgG-PMB (1–20 mg/kg) and a single intravenous dose of IgG-bacitracin conjugate (1–20 mg/kg) to increase the levels of gram-negative and gram-positive-reactive antibodies, respectively. If total immunoglobulin levels are also ≦80% of normal, a 3% solution of intravenously injectable immunoglobulin (available from Sandoz Forschunginstitut, Vienna, Austria; Hyland Therapeutics, Duarte, Calif.; or Cuter Laboratories, Berkeley, Calif.) is administered twice daily until immunoglobulin levels rise to within 10% of normal levels.

EXAMPLE 23

Long-Term Prophylaxis Against Endotoxin Lethality by IgG-PMB Conjugates

The long-term prophylactic effect of the IgG-PMB conjugate was examined in the D-galactosamine-sensitized mouse model. [C. Galanos et al., Proc. Natl. Acad. Sci. 76:5939–5943 (1979); V. Lehmann et al., J. Exp. Med. 165:657–663 (1987); and M. A. Freudenberg and C. Galanos, Infect. Immun. 56:1352–1357 (1988).] One mg of human IgG-PMB conjugate in PBS (prepared as described in Example 14) was given intravenously to each of 10 male C57Bl/6 mice. Ten control mice received 1 mg of unconjugated human IgG in PBS, again intravenously. Both the conjugate and control IgG solutions were at 8 mg/ml, the injection volumes were therefore 125 µl/mouse.

The in vivo experiments described in Examples 16 and 17 showed that as little as 25 µg of the IgG-PMB conjugate could provide complete protection when administered intravenously 1 hour prior to endotoxin challenge. Here, we investigated the protective window at 24 hours.

Twenty-four hours after the administration of PMB-conjugated or control IgG, both groups of mice were challenged intraperitoneally with a lethal dose of E. coli 0111:B4 endotoxin (# 201; List Biological Laboratories, Campbell, Calif.), prepared as described below. A 1 mg/ml stock solution of endotoxin was sonicated for 2 minutes in a Branson 2000 water bath sonicator and diluted 100-fold in PBS to make a 10 ng/$\mu$l working solution. Two hundred and forty mg of D-galactosamine hydrochloride (# G-1639; Sigma Chemical Co., St. Louis, Mo.) was weighed into 2 siliconized Reacti-vials (Pierce) and dissolved in 2.4 ml of PBS containing 0.1 mg/ml bovine serum albumin (BSA) as a carrier protein. Twelve $\mu$l of the 10 ng/$\mu$l endotoxin solution (120 ng) was added to each vial, and the solutions were mixed for 15 minutes at room temperature. Each vial contained enough solution for twelve 200 $\mu$l injections, consisting of 10 ng endotoxin and 20 mg galactosamine/injection. Each mouse in both groups was injected intraperitoneally with 200 $\mu$l of the mixture. The mice were given food and water ad libitum, and observed for 24 hours, using mortality as the endpoint. The results were analyzed by Fisher's exact method for estimating probabilities [F. Mosteller, et al., in *Probabilty With Statistical Applications*, Addison Wesley, Reading, Mass. (1970)]; significant protection was defined as a p value <0.05 when the experimental and control groups were compared.

The results of the prophylactic study are summarized in Table 26.

TABLE 26

| Group | # Survivors/Total | % Survival | p Value |
|---|---|---|---|
| Control | 2/10 | 20 | — |
| Experimental | 7/10 | 70 | 0.03215 |

These results show that the IgG-PMB conjugate can be given intravenously as a prophylactic, and significant protection from endotoxin lethality can be obtained for at least 24 hours after administration of the conjugate,

EXAMPLE 24

Determination of the Relative Half-Life of PMB-HIgG Conjugate and HIgG in Rabbits This example describes experiments to determine if there was any effect on the half-life of HIgG in rabbits when conjugated to PMB. The pharmacokinetic study was conducted using male New Zealand White rabbits (10 lb, 12 months old). Two rabbits each received a single dose of 3 mg of PMB-HIgG conjugate in 10 mM phosphate buffer (pH 7.1) containing 150 mM sodium chloride intravenously on day 0. At the same time, two control rabbits received intravenous injections of 3 mg of HIgG in the same buffer. Both the test samples and control samples were tested and found to be pyrogen-free. Rabbits were bled at one hour and 5 hours after the initial injection and then at days 1, 2, 3, 4, 7, 10, and 14 after the initial injection. Serum samples were collected and stored at −70° C. until tested for the presence of HIgG.

A sandwich ELISA was developed in order to detect the presence of HIgG in rabbit serum samples. Each well of a microtiter plate (Corning) was coated with 100 $\mu$l of a solution containing 25 $\mu$g/ml of goat-anti human IgG (Sigma) in 50 mM carbonate buffer, pH 9.5. After an overnight incubation at 4° C., the coating solutions were removed and all wells were washed three times with PBS-Tween-20 (.05% Tween-20 in PBS). The remaining antigen binding sites were blocked by the addition of PBS containing 10 mg/ml BSA (Sigma) for one hour at 37° C.

The test serum samples, which were stored at −70° C., were thawed just prior to assay and diluted 1:10 in PBS-Tween-20 containing 0.1% BSA. All samples were added (200 $\mu$l/well) as duplicate aliquots to wells of the microtiter plate. Negative control wells were prepared by adding 200 $\mu$l/well of 1:10 diluted normal rabbit serum in the same diluent as used with the test serum samples. As a positive control, normal HIgG was diluted in the same diluent at 20 $\mu$g/ml and subsequently underwent eight serial 1:4 dilutions up to 0.00031 $\mu$g/ml. The corresponding O.D. values were used to generate a standard curve from which corresponding HIgG levels from test serum samples were determined. Plates were incubated at 37° C. for 1 hour and washed three times in PBS-Tween-20. Alkaline phosphatase conjugated goat anti-human IgG (Sigma), diluted 1:500 in 0.1% BSA in PBS-Tween-20 was added to the wells and incubated at 37° C. for one hour. After washing the wells four times with PBS-T, 100 $\mu$l of 1 mg/ml p-nitrophenylphosphate (Sigma) in 50 mM $Na_2CO_3$, pH 9.5, and 1 mM $MgCl_2$ was added to all wells. Plates were shielded from light and allowed to develop at room temperature for 20–30 minutes. Absorbance at 410 nm was determined using a Dynatech MR 700 microplate reader.

The absorbances of duplicate wells were averaged and corrected for background by subtracting the absorbance of the blank wells, which contained only conjugate and substrate. A standard curve of absorbance versus log concentration of HIgG was plotted. Absorbances from test samples were quantified from the linear portion of the standard curve.

Figure 11:
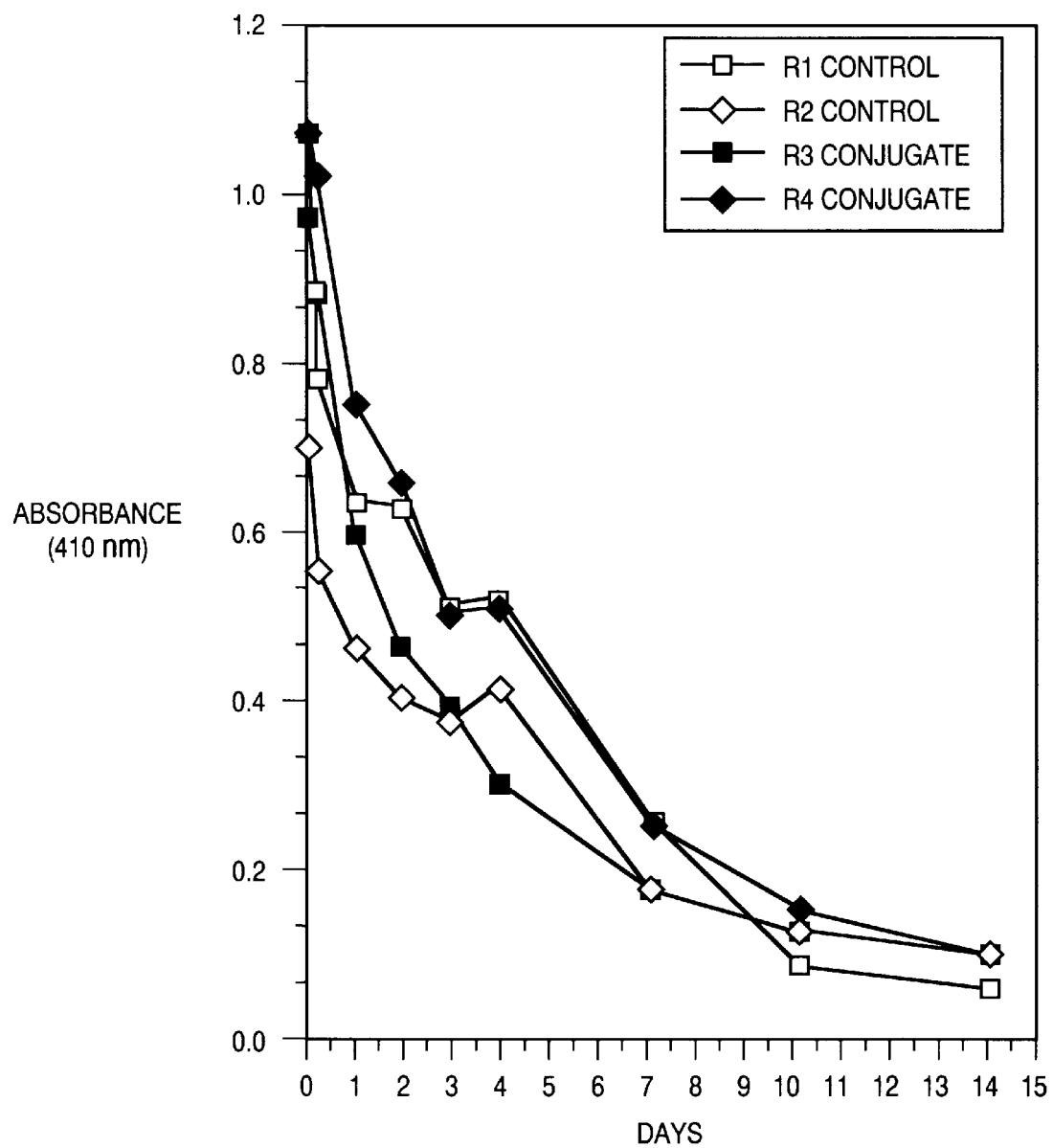
FIG. 11 shows the pharmacokinetic profile of intravenously administered PMB-HIgG and HIgG in rabbits expressed in absorbance at 410 nm.
Figure 12:
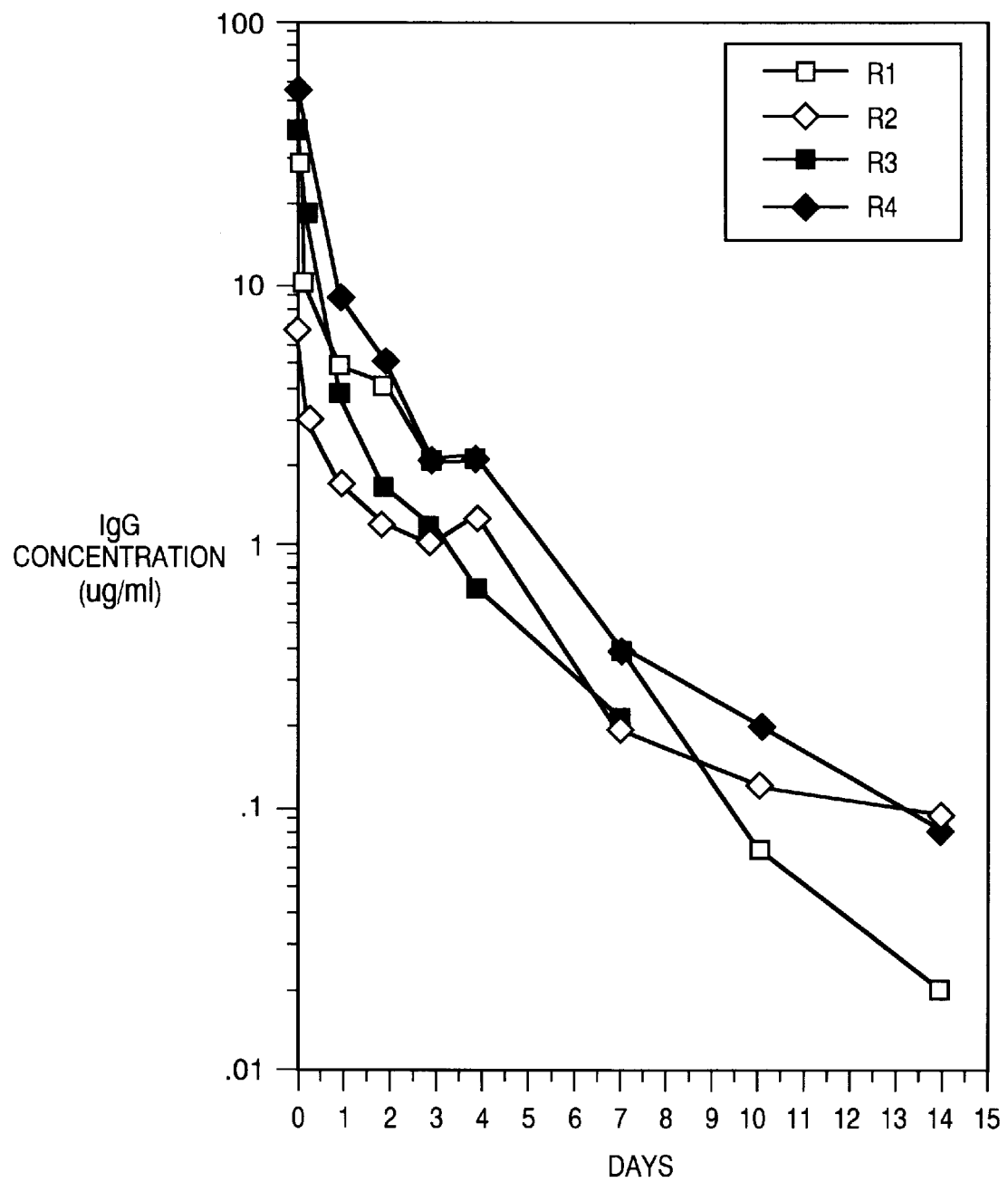
FIG. 12 shows the pharmacokinetic profile of intravenously administered PMB-HIgG and HIgG in rabbits expressed in IgG concentration.
Figures 14A, 14B:
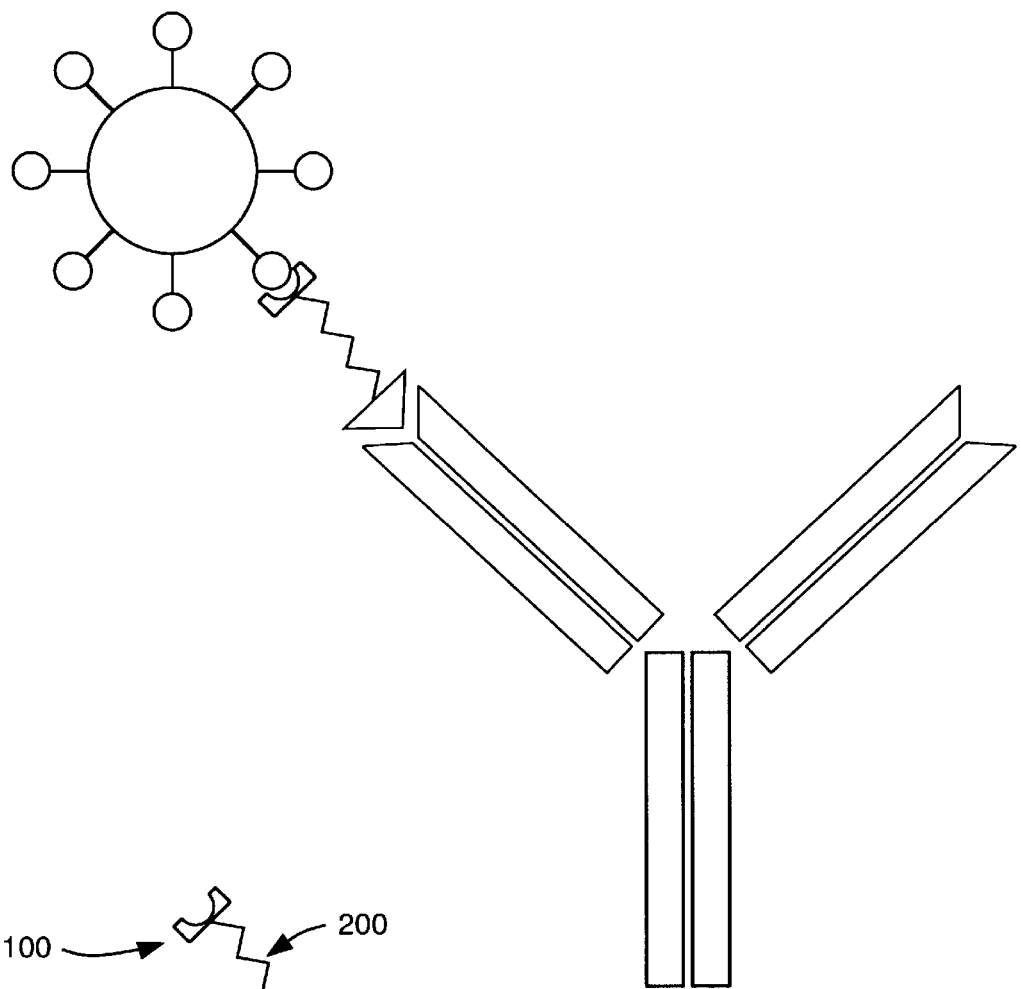
FIG. 14 shows a schematic illustrating the basic Immunoadapter™ concept.

The serum clearance curve for PMB-HIgG (R3 and R4) and HIgG (R1 and R2) are shown in FIGS. 11 and 12. The absorbance at 410 nm which directly corresponds to the concentration of HIgG is plotted against days in FIG. 11. FIG. 12 shows a graph of HIgG in $\mu$g/ml serum over time. From both FIGS. 11 and 12, it is clear that the serum half life of PMB-HIgG is similar to that of unconjugated human IgG. Since the half-life of human IgG in humans is on the order of 21 days, these experiments suggest that the conjugate half-life will be long. Therefore, in this Example, we have demonstrated that active conjugate is still detectable in rabbit sera two weeks after conjugate administration.

EXAMPLE 25

Detection of LPS-Binding of the PMB-HIgG Conjugate After Two Weeks of Circulation in Rabbits This example describes an experiment to determine if PMB-HIgG LPS-binding activity is still present after two weeks of circulation in rabbits. The study was conducted using male New Zealand White rabbits (10 lb, 12 months old). Two rabbits each received a single dose of 3 mg of PMB-HIgG conjugate in 50 mM phosphate buffer containing 150 mM sodium chloride intravenously on day 0. At the same time, two control rabbits received intravenous injections of 3 mg of HIgG in the same buffer. Both the test samples and control samples were tested and found to be pyrogen-free. Rabbits were bled at one hour and 5 hours after the initial injection and then at days 1, 2, 3, 4, 7, 10, and 14 after the initial injection. Serum samples were collected and stored at −70° C. until tested for the activity of PMB-HIgG conjugate.

In order to detect the activity of PMB-HIgG conjugate from rabbit serum (i.e., ability to bind to LPS), a simple indirect binding assay was utilized. Each well of a 96-well microtiter plate (Corning) was coated with 100 µl of a 20 µg/ml solution of LPS from *E.coli* 0111:B4 (Sigma) in PBS. Control wells were coated with PBS only (no LPS). After an overnight incubation at 4° C., the coating solutions were removed and all wells were washed 3 times with PBS-Tween-20. The remaining antigen binding sites were blocked by the addition of PBS containing 10 mg/ml BSA (Sigma, tissue culture grade) for 1 hour at 37° C. The blocking solution was removed and test rabbit serum samples diluted 1:10 in PBS-Tween-20 were added. As a positive control PMB-HIgG conjugate was also diluted in 10% normal rabbit serum and added to the wells. Samples were incubated in duplicate at 37° C. for 1 hour and the plates were washed three times with PBS-Tween-20.

In order to detect bound antibodies, the wells were incubated with 100 µl of a 1:500 dilution of goat anti-human IgG-alkaline phosphatase labeled antibody (Sigma) and incubated for 1 hour at 37° C. After removing the secondary antibody solutions, the wells were washed 4 times with PBS-Tween-20. Substrate [p-nitrophenylphosphate (Sigma)] at 1 mg/ml in 50 mM $Na_2CO_3$, and 10 mM $MgCl_2$ was added to each well. The color developed after 15–20 minutes of incubation at room temperature was measured at 410 nm using a Dynatech MR700 microplate reader.

The results of the LPS binding assay are as shown in Table 27. The conjugate from rabbit sera collected on day 14 bound to the LPS coated wells indicating that the conjugate was still active after circulating for two weeks in rabbits.

TABLE 27

Binding Of PMB-HIgG Conjugate From Rabbit Serum To LPS
Absorbance At 410 nm

| Dilution Of Anti-Serum | Sera From Control Rabbits | Sera From Experimental Group | Bleeding Date |
|---|---|---|---|
| 1:10 | 0.016 | 0.166 | Day 14 |

EXAMPLE 26

PMB-IgG Conjugates Do Not Elicit an Immune Response when Administered Intravenously into Rabbits This example describes an experiment to determine if anti-PMB antibodies are elicited in rabbits by conjugate administration. Two rabbits were each given 3 mg of PMB-HIgG conjugate intravenously on day 0. These rabbits received additional injections (boosts) at 2 weeks, 4 weeks and 7 weeks. As a control, 2 rabbits each received 3 mg of HIgG alone at the same scheduled day and time as with the experimental group. All rabbits were bled every two weeks after receiving either conjugate or IgG alone. Sera were collected and stored at −70° C. until tested for anti-PMB antibodies.

In order to detect anti-PMB antibodies in rabbit serum, a simple indirect binding assay was developed. Each well of a 96-well microtiter plate (Coming) was coated with 100 µl of a 200 µg/ml solution of PMB (Sigma) in endotoxin-free PBS. Control wells were coated with PBS only (no PMB). After an overnight incubation at 4° C., the coating solutions were removed and all wells were washed 3 times with endotoxin-free PBS-Tween-20. The remaining antigen binding sites were blocked by the addition of PBS containing 10 mg/ml BSA (Sigma, tissue culture grade) for 1 hour at 37° C. The blocking solution was removed and test rabbit serum samples diluted in 2% normal rabbit serum at dilutions of 1:10, 1:100, 1:1000 and 1:10,000 were added. A positive control antiserum (chicken anti-PMB immunoglobulin, Ophidian Pharmaceuticals Inc., Madison, Wis.) was also diluted as for the test rabbit serum samples. Samples were incubated in duplicate at 37° C. for 1 hour. Following this incubation, the plates were washed three times with PBS-Tween-20.

In order to detect bound antibodies, the wells incubated with rabbit serum were incubated with 100 µl of a 1:500 dilution of goat anti-rabbit IgG-alkaline phosphatase labeled antibody (Sigma) and the wells incubated with chicken antibody were incubated with 100 µl of 1:500 dilution of goat anti-chicken IgG (whole molecule)-alkaline phosphatase conjugate (Sigma) for 1 hour at 37° C. After removing the secondary antibody solutions, the wells were washed 4 times with PBS-Tween-20 and p-nitrophenylphosphate (Sigma) at 1 mg/ml in 50 mM $Na_2CO_3$, 10 mM $MgCl_2$ was added to each well. The color developed after 15–20 minutes of incubation at room temperature was measured at 410 nm using a Dynatech MR700 microplate reader.

The results in Table 28 show that the positive control antibody, as expected, bound to PMB. This validates that the design of ELISA is capable of detecting PMB-binding antibodies. The results in Table 29 (shown as $A_{410}$ readings of duplicate samples) indicate that none of the rabbit serum samples bound to PMB, indicating the absence of anti-PMB antibodies. These results demonstrate that PMB is not immunogenic, even on an heterologous protein carrier with repeated injections when given intravenously.

The lack of immunogenicity of this peptide may be related to its D-amino acid content, as these residues may not be recognized by the immune system.

TABLE 28

Binding Of Chicken Antibodies To PMB

| | Absorbance At 410 nm | |
|---|---|---|
| Dilution Of Antibody | Preimmune Egg Yolk Antibodies | Anti-PMB Egg Yolk Antibodies |
| 1:10 | 0.149 | 1.741 |
| 1:100 | 0.083 | 1.732 |
| 1:1,000 | 0.026 | 1.700 |
| 1:10,000 | 0.015 | 0.686 |
| 1:100,000 | 0.006 | 0.100 |

EXAMPLE 27

IgG PMB Is Not Toxic

In order to investigate the safety with which IgG-PMB conjugate can be utilized, a toxicity study was performed. Female Sprague-Dawley rats (Harlan Sprague-Dawley) weighing 250–300 g were given 2 relatively high doses of conjugate (approximately 16 mg/kg) intravenously. Serum samples, taken at various times during the study, and major organs were then analyzed for any indication of pathology.

The study consisted of 5 groups, 3 rats per group. After a 7 day acclimation period, rats in groups 1, 2, and 3 received intravenous injections of 4 mg of rat IgG conjugated to PMB (see (E) below for conjugation of PMB to rat IgG) on day 0 and again on day 2; group 4 rats received 4 mg of unconjugated rat IgG intravenously on day 0 (IgG control); and group 5 rats served as a normal control (no injection of either conjugate nor normal rat IgG). The rats were bled by cardiac puncture and sacrificed for organ pathology as indicated in Table 30.

TABLE 29

Binding Of Rabbit Antiserum To
PMB Coated Wells As Determined By ELISA

| Rabbit Identification | Dilution of Antiserum | Pre-immune | Absorbance At 410 nm Bleeding Dates | | | |
|---|---|---|---|---|---|---|
| | | | Week 2 | Week 4 | Week 7 | Week 9 |
| Rabbit #1 | 1:10 | 0.000 | 0.005 | 0.004 | 0.015 | 0.018 |
| Control | 1:100 | 0.004 | 0.008 | 0.000 | 0.001 | 0.005 |
| Group | 1:1,000 | 0.008 | 0.009 | 0.000 | 0.000 | 0.004 |
| 3 mg HIgG | 1:10,000 | 0.012 | 0.012 | 0.004 | 0.004 | 0.002 |
| Rabbit #2 | 1:10 | — | 0.000 | 0.003 | 0.013 | 0.005 |
| Control | 1:100 | — | 0.009 | 0.004 | 0.009 | 0.000 |
| Group | 1:1,000 | — | 0.014 | 0.002 | 0.005 | 0.000 |
| 3 mg HIgG | 1:10,000 | — | 0.012 | 0.000 | 0.009 | 0.001 |
| Rabbit #3 | 1:10 | 0.013 | 0.004 | 0.105 | 0.111 | 0.026 |
| Experimental | 1:100 | 0.010 | 0.006 | 0.013 | 0.012 | 0.000 |
| Group 3 mg | 1:1,000 | 0.008 | 0.006 | 0.002 | 0.007 | 0.000 |
| PMB-HIgG | 1:10,000 | 0.007 | 0.007 | 0.000 | 0.004 | 0.002 |
| Rabbit #4 | 1:10 | — | 0.000 | 0.061 | 0.039 | 0.001 |
| Experimental | 1:100 | — | 0.009 | 0.006 | 0.007 | 0.003 |
| Group 3 mg | 1:1,000 | — | 0.007 | 0.007 | 0.007 | 0.001 |
| PMB-HIgG | 1:10,000 | — | 0.000 | 0.001 | 0.007 | 0.005 |

TABLE 30

Study Design

| Group | Day 0 | Day 2 | Day 5 | Day 7 | Day 14 |
|---|---|---|---|---|---|
| 1 | 4 mg IgG-PMB, I.V. | 4 mg IgG-PMB, I.V. | Bleed; Remove Kidney, Liver, Spleen | | |
| 2 | 4 mg IgG-PMB, I.V. | 4 mg IgG-PMB, I.V. | | | Bleed; Remove Kidney, Liver, Spleen |
| 3 | 4 mg IgG-PMB, I.V. | 4 mg IgG-PMB, I.V. | | Bleed | Bleed |
| 4 | 4 mg Rat IgG, I.V. (IgG Control) | | | | Bleed; Remove Kidney, Liver, Spleen |
| 5 | Normal Control | | | | Bleed; Remove Kidney, Liver, Spleen |

Immediately following cardiac puncture, blood smears (2 slides/rat) were prepared and stained with Diff-Quik (Baxter Healthcare, McGaw Park, Ill.) for white blood cell differential counts. The remaining blood (2–7 mls) was allowed to clot at 2–8° C. The clot was pelleted by centrifugation at 2000 rpm for 10 minutes, and the serum was removed and frozen at –70° C. in 2 aliquots for blood chemistry analysis (SMAC 12) and measurement of complement activation by the $CH_{50\ EZ}$ Complement assay (Diamedix Corporation; Miami, Fla.). The organs of interest (kidney, liver, and spleen) were removed from each rat as indicated in Table 30, and fixed immediately in phosphate buffered formalin (50 mM sodium phosphate, 10% formaldehyde) until sections were made for histopathology slides.

A. Biochemical Serum Analysis for Liver and Kidney Function

All rat serum samples (18 total: 3 from groups 1, 2, 4, and 5; and 6 from group 3) were analyzed on the DuPont Dimension AR (DuPont Co., Wilmington, Del.) for the following 12 tests (SMAC 12): glucose, blood urea nitrogen (BUN), creatinine, uric acid, calcium, albumin, total protein, cholesterol, total bilirubin, alkaline phosphatase, aspartate transferase (SGOT/AST), and lactate dehydrogenase (LDH). The values for each group were averaged (Table 31) and the experimental groups (1, 2, and 3) were compared with the control groups (4 and 5) to detect any significant differences. The laboratory results were also compared to the normal ranges for each assay, determined by analyzing laboratory data for 20 female Sprague-Dawley rats (data provided by Harlan Sprague-Dawley).

The standard laboratory tests for liver disease include measurement of serum levels of bilirubin, AST, alkaline phosphatase, LDH, albumin, and, to a lesser extent, glucose. Kidney function can be assessed by measuring plasma levels of urea, creatinine, and calcium. [J. F. Zilva, P. R. Pannall, *Clinical Chemistry in Diagnosis and Treatment*, Yearbook Medical Publishers, Chicago, Ill. (1984).] With the exception of the lactate dehydrogenase value (LDH), which will be discussed below, Table 31 shows no significant differences when the values for the experimental groups 1, 2, and 3 are compared with the control groups 4 and 5. Furthermore, all the values are within or close to the normal ranges for each assay for this strain of rat.

TABLE 31

Blood Chemistry Analysis*

| Test | Group 1 Day 5 | Group 2 Day 14 | Group 3 Day 7 | Group 3 Day 14 | Group 4 Day 14 | Group 5 Day 14 |
|---|---|---|---|---|---|---|
| Glucose (mg/dl) | 121 | 111 | 135 | 92 | 100 | 85 |
| BUN (mg/dl) | 16 | 19 | 15 | 16 | 19 | 21 |
| Creatinine (mg/dl) | 0.2 | 0.1 | 0.2 | 0.1 | 0.1 | 0.1 |
| Uric Acid (mg/dl) | 2.4 | 3.0 | 2.2 | 3.4 | 2.8 | 2.8 |
| Calcium (mg/dl) | 10.2 | 9.9 | 9.9 | 9.7 | 9.6 | 9.8 |
| Albumin (g/dl) | 1.3 | 1.4 | 1.5 | 1.4 | 1.4 | 1.4 |
| Total Protein (mg/dl) | 5.6 | 5.8 | 5.9 | 6.0 | 5.8 | 6.0 |
| Cholesterol (mg/dl) | 79 | 81 | 81 | 82 | 83 | 80 |
| Total Bilirubin (mg/dl) | 0.1 | 0.2 | 0.1 | 0.1 | 0.1 | 0.1 |
| Alkaline Phosphate (U/L) | 112 | 100 | 99 | 112 | 101 | 111 |
| SGOT/AST (U/L) | 194 | 203 | 180 | 215 | 362 | 207 |
| LDH (U/L) | 880 | 3083 | 939 | 3333 | 2830 | 2660 |

*The Value For Each Measurement Represents The Average For All 3 Rats In Each Group.

The values for LDH vary considerably from group to group, and most of the values also exceed the normal range for rat serum LDH (data from Harlan Sprague-Dawley). Lactate dehydrogenase is found in high concentrations in the liver, heart, skeletal muscle, brain, kidney and in erythrocytes. Elevated values of particular isozymes can indicate liver or cardiac muscle damage, however in this study the control rats also show elevated LDH values, suggesting the elevated LDH values are not associated with the IgG-PMB conjugate. Hemolysis, which may have occurred in vitro (as the blood samples were being drawn, or if the serum was not separated from the blood cells soon enough), also increases serum LDH values (J. F. Zilva and P. R. Pannall, *Clinical Chemistry in Diagnosis and Treatment, supra*) and may explain the elevated values in this study.

It is also worth noting that the measurements for serum samples drawn on day 5 (3 days after the second injection), day 7 (5 days after the second injection) and day 14 (12 days after the second injection) show no significant differences that can be attributed to the administration of the IgG-PMB conjugate. In other words, the day 5, 7 and 14 values for all of the serum components measured are within or close to their respective normal ranges (except LDH) and show little or no significant change over time, as would be expected if the conjugate brought about any acute changes in the condition of the test rats.

B. White Blood Cell Differential

Blood smears from each rat were examined under oil immersion (1000×) to determine the white blood cell differential. At least one hundred white blood cells were counted on each slide, and the percentages of each cell type (lymphocyte, monocyte, neutrophil, eosinophil, and basophil) were calculated to determine the white blood cell differential for each rat. The differentials for rats in each group were averaged and differentials from groups 1, 2, and 3 were compared with the differentials from groups 4 and 5, to detect any significant differences in white blood cell populations. In addition, the red blood cells on each slide were examined for morphology, and a crude estimate of the number of platelets present was made. The results of the differential cell counts are summarized in Table 32.

TABLE 32

White Blood Cell Differentials*

| Cell Type | Group 1 Day 5 | Group 2 Day 14 | Group 3 Day 7 | Group 3 Day 14 | Group 4 Day 14 | Group 5 Day 14 |
|---|---|---|---|---|---|---|
| Lymphocytes | 80 | 84 | 81 | 86 | 89 | 84 |
| Monocytes | 4 | 7 | 11 | 8 | 5 | 7 |
| Neutrophils | 16 | 8 | 6 | 4 | 3 | 6 |
| Eosinophils | — | 1 | 2 | 2 | 3 | 2 |
| Basophils | — | — | — | — | — | 1 |

*Numbers Given Represent The Pecentage For Each Cell Type (Mean Values for Each Group).

Table 32 shows no significant differences in the percentages of each cell type from group to group. The differentials do show some variation from the normal reference values for rats obtained from Harlan Sprague-Dawley (about 5–10% more lymphocytes and 5–10% fewer neutrophils than expected), however this is found in both the normal control and experimental groups, suggesting this finding is not related to the administration of the IgG-PMB conjugate. The red blood cell morphology appeared normal, and platelets were abundant on all slides examined.

C. Organ Histopathology

The organs of interest were removed and fixed in phosphate buffered formaldehyde. Sections were made as described below and stained with hematoxylin and eosin.

Kidney: Full length mid-longitudinal section through center

Liver: Transverse section through hepatic lobule

Spleen: Transverse section

The slides were examined for organ pathology and no abnormalities were found.

D. Analysis of Serum Complement Activity

Immunoglobulin and immunoglobulin complexes have the potential to activate the complement system. Complement activation of this type, mediated by IgG-PMB conjugates, would exacerbate the inflammatory response to endotoxemia or bacteremia. In addition, inhibition of normal complement function would impair complement-mediated host defense mechanisms. In this example, the in vivo effect of IgG-PMB conjugate on serum complement activity was investigated.

Rat serum samples were analyzed for total hemolytic complement activity ($CH_{50}$) using the EZ Complement $CH_{50}$ Assay (Diamedix Corp., Miami, Fla.). In order to determine the effect of the conjugate on complement activity, the resulting $CH_{50}$ values obtained from untreated control rats were compared to the $CH_{50}$ values obtained from the IgG and IgG-PMB conjugate-treated rats.

TABLE 33

Analysis Of Serum Complement Activity*

| Group | Treatment (I.V.) | Day 5 | Day 7 | Day 14 |
|---|---|---|---|---|
| 1 | 4 mg Conj. on Days 0,2 | 303.8 | — | — |
| 2 | 4 mg Conj. on Days 0,2 | — | — | 312.2 |
| 3 | 4 mg Conj. on Days 0,2 | — | 290.4 | 299.8 |
| 4 | 4 mg Rat IgG on Day 0 | — | — | 338.6 |
| 5 | Untreated Control | — | — | 298.2 |

*Each Measurement Represents The Mean $CH_{50}$ Value Determined For The 3 Rats In Each Group.

Referring to Table 33 above, there were no significant differences in the $CH_{50}$ values between any of the groups tested. If IgG-PMB conjugate-mediated complement activation was occurring in vivo, this effect would have been reflected as a decrease in the $CH_{50}$ values of the conjugate-treated rats (groups 1, 2, and 3), as compared against the untreated control rats (group 5), due to depletion of complement components in the treated animals. Similarly, inhibition of normal complement function would have been indicated by a decrease in $CH_{50}$ values in the conjugate-treated groups as compared with the untreated control group. Unconjugated IgG was also found to have no effect on serum complement activity (group 4). Therefore, these results show that intravenous administration of IgG-PMB conjugate has no adverse effect on serum complement activity.

E. Conjugation of PMB Rat IgG Using Periodate Oxidation of IgG in $NaPO_4$

PMB was conjugated to rat IgG using periodate oxidation of IgG. This involved a) periodate oxidation of IgG in phosphate buffer followed by conjugation of PMB to the periodate-oxidized IgG.

a) Periodate oxidation of IgG in phosphate buffer was achieved by dissolving 25 mg rat IgG (Sigma) in 1 ml of 50 mM $NaPO_4$, pH 7.2 buffer and adding 10.7 mg of sodium metaperiodate (final concentration 50 mM). After 30 minutes of incubation at room temperature with gentle vortexing every 5 minutes, the periodate was removed by gel filtration on a 15 ml Swift desalting column (Pierce) equilibrated with 50 mM $NaPO_4$, pH 7.2 buffer. The peak fractions containing highest amount of antibody as monitored by $A_{280}$ absorbance were pooled.

b) Conjugation of periodate-oxidized IgG with PMB was carried out by adding 75 mg PMB to oxidized IgG at 4° C. overnight with gentle shaking followed by reduction with 0.1 mg/ml of NaBH$_3$CN in 20 mM NaPO$_4$, pH 6.5 for 2–3 hours at room temperature. The PMB-IgG was separated from the rest of the reaction products by gel filtration on a 15 ml Swift desalting column equilibrated with 50 mM phosphate containing 150 mM NaCl, pH 7.5 (PBS).

The activity of PMB-rat IgG conjugate was determined by LPS binding assay as described previously. Results in Table 34 indicate that PMB-rat IgG conjugate had excellent LPS binding activity.

TABLE 34

LPS Binding Activity Of PMB-Rat IgG Conjugate As Determined By ELISA (A$_{280}$)

| Conjugate IgG Concentration | LPS-Coated Wells | No Antigen Wells |
|---|---|---|
| 100 µg/ml | 1.756 | 0.110 |
| 20 µg/ml | 1.756 | 0.079 |
| 4 µg/ml | 1.737 | 0.017 |
| 0.8 µg/ml | 1.521 | 0.036 |
| 0.16 µg/ml | 0.998 | 0.021 |
| 0.032 µg/ml | 0.506 | 0.016 |

EXAMPLE 28

Demonstration of Opsonophagocytic Activity of IgG-PMB Conjugates

Opsonic IgG class antibodies mediate an important immune effector function by enhancing the phagocytic clearance of extracellular bacteria [Raff, et al., J. Infect. Dis. 163:346–354 (1991).] In this way, opsonic IgG plays a critical role in host defense mechanisms against bacterial pathogens. [Rozenberg-Arska, et al. J. Med. Microbiol. 22:143–149 (1991).] The purpose of this example was to investigate whether the IgG component of IgG-PMB conjugates retains this important effector function. This was done by assessing whether the pre-treatment of E. coli organisms with IgG-PMB conjugate potentiates phagocytic uptake (opsonophagocytosis) by the human monocytic cell line U937. Opsonophagocytosis assays provide a useful means by which the potential therapeutic efficacy of immunoglobulin preparations, used for the treatment of bacterial infection, can be assessed. [Hill, et al. Am. J. Med. 61–66 (1984).] This example involved (a) Assay for opsonophagocytic activity of IgG-PMB conjugate, and (b) Determination of the minimum effective concentration of IgG-PMB conjugate.

A. Assay for Opsonophagocytic Activity of IgG-PMB Conjugate

Opsonophagocytic activity of IgG-PMB conjugates was measured using an assay procedure which was modified from published methods. [Gemmell, et al., J. Clin. Invest. 67:1249–1256 (1981) and Bohnsack, et al., J. Immunol. 143(10):3338–3342 (1989).] E. coli strain HB101 was grown for approximately 20 hours at 37° C. on TSA (BBL). The organisms were then suspended in PBS, pH 7.2, at a concentration of 1×10$^8$ CFU./ml. Aliquots of 1.0 ml volumes of this suspension were placed into separate microfuge tubes and the tubes centrifuged at approximately 14,000×g for 5 min. at 4° C. Each of the resulting pellets was then resuspended in a 1.0 ml volume of one of the following opsonin or control solutions:

1. IgG-PMB Conjugate (prepared by periodate oxidation, as described in Example 14(a)) at the MIC for E. coli HB101 (0.062 mg/ml) (The MIC was determined as described in Example 12).

2. IgG-PMB Conjugate (same as above) at 2× the MBC for E. coli HB101 (0.25 mg/ml) (The MBC was determined as described in Example 12).

3. IgG Control (unconjugated) at 0.062 mg/ml (control for #1 above; this was the same IgG as that used for production of the conjugate).

4. IgG Control (unconjugated) at 0.25 mg/ml (control for #2 above).

5. PBS Control (no IgG or conjugate). PBS, pH 7.2 only.

The five suspensions were opsonized by incubation at 37° C. for 60 min. with periodic mixing. Following opsonization, the suspensions were centrifuged as above, and the resulting pellets were each resuspended in 0.5 ml of RPMI 1640 medium which was supplemented with 10% FCS (this will be referred to as "medium" for the remainder of this example). Into each of 5 separate polypropylene culture tubes (S/P) was placed 1.0 ml of a U937 cell suspension, which was prepared in medium, and contained 1×10$^6$ U937 cells/ml. To each tube, 0.1 ml of one of the opsonized E. coli suspensions prepared above was also added. A sixth control group was also prepared which contained 1.0 ml of the U937 cell suspension and 0.1 ml of PBS (PBS control). At this point, each tube contained 1×10$^6$ U937 cells, and 2×10$^7$ E. coli organisms, thus providing an E. coli to U937 cell ratio of 20:1. The 6 tubes were then incubated at 37° C. for 60 min. with constant shaking, in order to allow phagocytosis to occur. Following incubation, the tubes were placed on ice for several minutes to prevent further phagocytosis. The 6 tubes were then centrifuged for 10 min. at 500×g at 4° C. The resulting pellets were washed three times (centrifuging as in the previous step) with chilled PBS, to remove extracellular E. coli organisms. The final pellets were each resuspended in 0.2 ml of chilled PBS, and smears were prepared by applying 40 µl volumes of the suspensions to glass microscope slides. The smears were allowed to air-dry, and were then fixed by immersion in 100% methanol for 5 sec. and again allowed to air-dry.

The smears were stained using a modified version of the Sowter-McGee staining procedure [Sowter and McGee. J. Clin. Pathol. 29:433–437 (1976)], which chromatically differentiates between intracellular bacteria and the surrounding cytoplasm of the host cells. The slides were hydrated by immersion in water for approximately 60 sec., and were then placed in a methyl green-pyronin (MGP) solution (Sigma) for 5 min. The slides were washed in water for 15–20 sec. and then immersed in light green counterstain (0.25% Sigma Light Green SF Yellowish in distilled H$_2$O) for 3–5 sec. Following a 15–20 sec. rinse in water, the slides were dipped in 100% ethanol for 5 sec., and then in xylene for 5 sec. The slides were allowed to air-dry, and were then mounted with glass coverslips.

Scoring of opsonophagocytosis was performed in a blind manner, by light microscopy. For each experimental group, a total of 100 U937 cells were randomly counted to determine the percentage of those cells which contained one or more intracellular E. coli organisms. The results of this study are presented in Table 35.

TABLE 35

| Opsonization Treatment | U937 Cells Which Contained One Or More E. coli |
|---|---|
| IgG-PMB @ MIC (0.062 mg/ml) | 65% |
| IgG-PMB @ 2 × MIC (0.25 mg/ml) | 56% |
| IgG @ 0.062 mg/ml | 0% |
| IgG @ 0.25 mg/ml | 3% |

TABLE 35-continued

| Opsonization Treatment | U937 Cells Which Contained One Or More E. coli |
|---|---|
| PBS Control | 0% |
| U937 Cells Only (No E. coli) | 0% |

Treatment of E. coli organisms with IgG-PMB conjugates at concentrations that were equivalent to the MIC and 2× the MBC for that organism resulted in the phagocytic uptake of the organisms by greater than 50% of the U937 cells. Treatment of the organisms with comparable concentrations of the unconjugated form of the same IgG resulted in minimal to no uptake. In the absence of IgG-PMB conjugate or IgG, no phagocytic uptake of the E. coli organisms occurred (PBS control group). These results demonstrate that the IgG portion of the IgG-PMB conjugate retains opsonic effector function, and that IgG-PMB conjugates potentiate the phagocytic clearance of bacterial organisms.

B. Determination of the Minimum Effective Concentration of IgG-PMB Conjugate

The minimum concentration of IgG-PMB required to mediate opsonophagocytosis was determined by testing the conjugate at the MIC and at fractional concentrations of the MIC (sub-MIC). As an additional control, a parallel series of albumin-PMB (Alb-PMB) conjugate solutions were also tested at concentrations comparable to the IgG-PMB conjugate. The following conjugate and control solutions were assayed for opsonophagocytic activity by the procedure described in part (a) of this example:

1. IgG-PMB Conjugate (same as that used in part (a) of this Example) at the MIC for E. coli HB101 (0.062 mg/ml).
2. IgG-PMB Conjugate (same as above) at ½ the MIC for E. coli HB101 (0.031 mg/ml).
3. IgG-PMB Conjugate (same as above) at ¼ the MIC for E. coli HB101 (0.0155 mg/ml).
4. IgG-PMB Conjugate (same as above) at ⅛ the MIC for E. coli HB101 (7.75 µg/ml).
5. Alb-PMB Conjugate (prepared as described in Example 18(a)) at 0.062 mg/ml (this group served as a control for #1 above).
6. Alb-PMB Conjugate (same as above) at 0.031 mg/ml (this group served as a control for #2 above).
7. Alb-PMB Conjugate (same as above) at 0.0155 mg/ml (this group served as a control for #3 above).
8. Alb-PMB Conjugate (same as above) at 7.75 µg/ml (this group served as a control for #4 above).
9. IgG Control (unconjugated) at 0.062 mg/ml.
10. PBS Control (no IgG or conjugate). PBS, pH 7.2 only.

The results of this study are presented in Table 36.

TABLE 36

| Opsonization Treatment | U937 Cells Which Contained One Or More E. coli |
|---|---|
| IgG-PMB @ MIC (0.062 mg/ml) | 38% |
| IgG-PMB @ 1/2 MIC (0.031 mg/ml) | 41% |
| IgG-PMB @ 1/4 MIC (0.0155 mg/ml) | 14% |
| IgG-PMB @ 1/8 MIC (7.75 µg/ml) | 10% |
| Alb-PMB @ 0.062 mg/ml | 2% |
| Alb-PMB @ 0.031 mg/ml | 0% |
| Alb-PMB @ 0.0155 mg/ml | 2% |
| Alb-PMB @ 7.75 µg/ml | 5% |

TABLE 36-continued

| Opsonization Treatment | U937 Cells Which Contained One Or More E. coli |
|---|---|
| IgG @ 0.062 mg/ml | 2% |
| PBS Control | 0% |

Treatment of E. coli organisms with IgG-PMB conjugates, using concentrations at or below the MIC for the conjugate, resulted in the increased phagocytic uptake of the organisms by the U937 cells at all IgG-PMB concentrations tested. The parallel series of Alb-PMB conjugate concentrations tested did not demonstrate significant levels of opsonophagocytic activity, nor did the unconjugated IgG control. These results demonstrate that IgG-PMB conjugates possess significant levels of opsonophagocytic activity at clinically-relevant, sub-MIC concentrations, and that both the functional PMB and IgG portions of the conjugate are required simultaneously in order for the conjugate to be capable of mediating opsonophagocytosis.

EXAMPLE 29

Antimicrobial Activity of IgG-PMB Conjugates Against Clinically-Relevant Bacterial Strains MIC and MBC values were determined for IgG-PMB conjugate and native PMB control against bacterial strains which are known to be human pathogens (see Example 29 below). This example involved (a) Preparation of the Conjugate, (b) Preparation of the Bacterial Inocula, and (c) Determination of the MIC and MBC.

A. Preparation of the Conjugate

The IgG-PMB conjugate was prepared by periodate oxidation as described in Example 14(a) with the following modification, which was performed in order to more effectively remove free (unconjugated) PMB from the final conjugate preparation. The final conjugate solution was adjusted to contain 1.0% Tween-20, and then was chromatographed on a P-10 column using PBS containing 0.1% Tween-20 as the eluent. The material in the void volume was concentrated and then further purified by column chromatography as described in the previous sentence.

B. Preparation of the Bacterial Inocula

Organisms were grown, and separate inocula were prepared for the following test organisms, as described in Example 12(a): E. coli strain EC 5; Pseudomonas aeruginosa strain ATCC 27312; Pseudomonas aeruginosa strain Strong; and Pseudomonas aeruginosa strain 3.

C. Determination of the MIC and MBC

The MIC and MBC of IgG-PMB conjugate and native PMB control were determined for each of the test organisms, as described in Examples 12(b) and 12(c).

The results of the MIC determination are shown in Table 37.

TABLE 37

| Test Organism | Conjugate MIC | PMB Control MIC |
|---|---|---|
| E. coli, EC 5 | 0.03125 mg/ml | 0.156 µg/ml |
| P. aeruginosa, ATCC 27312 | 0.25 mg/ml | not done |
| P. aeruginosa, Strong | 0.25 mg/ml | not done |
| P. aeruginosa, Strain 3 | 0.25 mg/ml | 1.0 µg/ml |

The results of the MBC determinations are shown Table 38.

TABLE 38

| Test Organism | Conjugate MBC | PMB Control MBC |
|---|---|---|
| E. coli, EC 5 | 0.0625 mg/ml | 0.156 µg/ml |
| P. aeruginosa, ATCC 27312 | >0.5 mg/ml | not done |
| P. aeruginosa, Strong | 0.25 mg/ml | not done |
| P. aeruginosa, strain 3 | 0.25 mg/ml | 1.0 µg/ml |

The bacteriostatic and bactericidal activity of IgG-PMB conjugates against pathogenic bacterial strains demonstrate that these compounds may be effective for the prophylaxis and/or treatment of bacteremia.

EXAMPLE 30

Prophylactic Administration of IgG-PMB Conjugate Protects Rats against an *Escherichia coli* Bacteremia Gram negative bacteremia and endotoxic shock can trigger a lethal reaction in vivo. Indeed, overwhelming gram negative bacteremia has become a leading cause of death from infection in the hospital. [S. M. Wolf, N. Eng. J. Med. 307;1267–1268 (1982).] In particular, *E. coli* sepsis continues to be associated with an unacceptably high mortality rate, despite the availability of potent antibiotics. *E. coli* strains with the K1 capsular type have been identified as the etiologic agent in up to 24% of blood culture isolates [G. W. Count and M. Turck, J. Clin. Microbiol. 5:490 (1977)], 80% of the cases of neonatal meningitis. [L. D. Sarff et al, Lancet 1:1099 (1975).] It is the most frequent cause of nosocomial gram negative bacteremia in adults [M. P. Weinstein et al., Rev. Infect. Dis. 5:35–53 (1983)] and pyelonephritis in children. [G. H. McCracken et al., Hosp. Pract. 9:57 (1974).] In addition to the K1 type, human blood *E. coli* isolates also possess an O antigen serotype, with O18 lipopolysaccharide being most frequently associated with bacteremia. [A. S. Cross et al., J. Infect. Dis. 149:184–193 (1984).] *E. coli* serotype O18:K1 is a very virulent human pathogen, as defined by either D. Rowley, Br. J. Exp. Pathol. 35:528–538 (1954) or H. Smith, J. Gen. Microbiol. 136:377–383 (1990), they can grow in vivo from a small inoculum, evade host defenses and cause extraintestinal infections.

To test the IgG-PMB conjugate for in vivo efficacy against bacteremia caused by a virulent bacterium such as *E. coli* O18:K1, the established animal infection model described by D. E. Schiff et al., Infect. Immun. 61:975–980 (1993) was utilized. This model fulfills many criteria important in evaluating the toxicity, efficacy and safety of immunotherapeutics, some of which have been outlined by A. S. Cross et al., Infect. Immun. 61:2741–2747 (1993). Specifically, the model is an infection rather than an intoxication model in which rats are challenged with low doses of a virulent bacteria instead of using large doses of an avirulent strain. Experimental evidence indicates that models of infection, in contrast to intoxication models, more accurately reflect the course of human sepsis. Infection models: a) use bacteria that cause human sepsis possessing an invasive phenotype with virulent factors (i.e., a particular K antigen or smooth LPS antigen) [I. Orskov and F. Orskov, J. Hyg. Camp. 95:551–575 (1985)]; b) mimic the normal progression of sepsis from a focal site to colonization; c) generate levels of circulating bacteria consistent with clinical bacteremia [D. E. Dietzman et al., J. Pediatr. 85:128–131 (1974)]; and d) produce endotoxin levels and induce physiological cytokine responses such as triggering TNF kinetics similar to the clinical experience. [Reviewed by A. S. Cross et al., Infect. Immun. 61:2741–2747 (1993).]

In this Example, we tested whether the prophylactic treatment of neonatal rats with IgG-PMB could protect against bacteremia and death caused by *E. coli* O18:K1. This example involved: (a) determination of the lethal dosage of *E. coli* O18:K1 in rat pups; and (b) in vivo protection against *E. coli* O18:K1 using IgG-PMB.

A. Determination of Lethal Dosage of *E. coli* O18:K1 In Newborn Rats

Five day old pathogen-free Sprague-Dawley rats (Charles River Laboratories, Wilmington, Mass.) were inoculated subcutaneously with different doses of *E. coli* O18:K1. The *E. coli* (strain designation C5) obtained from K. S. Kim, Children's Hospital (Los Angeles, Calif.), was isolated from the cerebrospinal fluid of a child. An overnight culture of *E. coli* C5 in brain heart infusion (BHI) medium was diluted 1:40 in fresh medium and grown to early log phase to an $OD_{620}$ of 0.25 which represents approximately $1 \times 10^8$ bacteria/ml. The cells were washed twice by centrifugation with sterile saline (0.9% NaCl) and diluted to different cell densities in saline. Each dilution was streaked onto a BHI agar plate and incubated at 37° C. to determine actual cell number.

Approximately 370 to 2620 bacteria in 100 µl of sterile saline were inoculated subcutaneously into the rats. A typical lethal infection with *E. coli* O18:K1 produced a bacteremia within 18 hours, and death within 24–72 hours post-infection. We found that about 300 bacteria represented an $LD_{50}$ and killed about 50% of the pups, whereas, 1500 bacteria was usually sufficient to kill most or all rats. Since between 1500–2500 bacteria represent the minimal effective lethal dose, this concentration of *E. coli* was utilized in the in vivo bacteremia protection studies using IgG-PMB.

B. In vivo Protection against *E. coli* O18:K1 (C5) Using IgG-PMB Conjugate

To determine if the administration of IgG-PMB conjugate can protect in vivo, rat pups were pretreated with IgG-PMB or control IgG followed by an administration of a lethal dose of *E. coli* C5. The IgG used as the carrier in the conjugate and as the control was a human myeloma protein which was shown to be unreactive to the *E. coli* C5 by ELISA. The myeloma IgG was used as the carrier to produce the PMB-conjugate, in order to ensure the reactivity between the *E. coli* and IgG-PMB conjugate was exclusively due to binding between PMB and lipopolysaccharide.

Eleven to twelve 4–5 day-old Sprague-Dawley rats (weighing 10 gm) in each group were given 30 µg, 100 µg or 300 µg of an IgG-PMB conjugate or control IgG in 100 µl of endotoxin-free PBS intraperitoneally. An untreated group was given only PBS (conjugate diluent). Two hours later, each rat received approximately 2560 *E. coli* C5 bacteria in 100 µl of PBS subcutaneously behind the head. After 24 hours post-infection, the number of survivors, survivors with focal lesions and dead were recorded. The results are shown in Table 39. The focal lesions appeared very hemorrhagic and were located at or near the site of inoculation. All pups displaying focal lesions were found to be bacteremic and subsequently died within 24–48 hours of appearance of the lesion. Bacteremia was detected by collecting blood from the tail vein, diluted 20-fold in BHI broth and 20 µl aliquots were plated onto (5% sheep red cells) blood agar plates.

The results show that 30 µg of IgG-PMB conjugate/pup or a 300 µg/Kg dose was sufficient to completely protect all the animals against the generation of a focal lesion or death by *E. coli* for 24 hours post-infection. In contrast, no protection was afforded by doses of 30 or 100 µg of IgG/pup compared to the untreated group. Pups treated with IgG at the highest dose (300 μg) were protected (probably representing a nonspecific phenomenon).

These findings demonstrate that IgG-PMB conjugate given prophylactically can prevent the progression of sepsis due to *E. coli*. This was shown by the prevention of death in the pups and also the protection against focal lesions. These results imply that the conjugate is capable of systemic distribution throughout the body to regions outside the vascular compartment and inhibiting infection.

EXAMPLE 31

Derivatization of 7-Aminocephalosporanic Acid with Sulfo-MBS

This example describes the attachment of a heterobifunctional crosslinking agent to an antibiotic precursor. This example outlines the derivatization of 7-aminocephalosporanic acid, an antibiotic precursor exhibiting no significant anti-microbial properties, with m-Malcimidobenzoyl-N-hydroxysulfosuccinimide ester ("sulfo-MBS").

For the derivatization of 7-aminocephalosporanic acid, 2.9 mg of 7-aminocephalosporanic acid (Sigma) were dissolved in 1.0 ml of 50 mM phosphate buffer (pH 6.65) and 10.7 μl of 1.0 N NaOH were added during mixing to return the pH to 6.65. Then 4.6 mg of sulfo-MBS (Pierce) were added and dissolved with mixing. The mixture was incubated at ambient temperature with agitation for 4.5 hours. 10 mg of ethanolamine were added and the incubation was continued for 17 additional minutes.

The reaction mixture (0.5 ml) was applied to a 1.5×20 cm column of Bio-Rad P2 resin. The eluent was 50 mM phosphate buffer (pH 6.65) flowing at 0.5 ml/minute. The eluate (i.e. the liquid collected at the bottom of the column) was monitored for absorbance at 280 nm. 0.5 ml fractions were collected. Two major absorbance peaks were evident—one centered at 42 minutes and the other at 47.5 minutes (aminocephalosporanic acid and reaction products, respectively). Fractions corresponding to the leading edge of the first peak were pooled (2.0 ml, 3.42 A 280). 1.4 μl of 100% beta-mercaptoethanol was added to the mixture which was then filtered using a sterile Whatman 0.45 micron Puradisc. The MIC of the putative

TABLE 39

Protection Against A Lethal *E. coli* O18:K1
Bacteremia Using IgG-PMB Conjugate Treatment

| Treatment | Number of Focal Lesions | Number Dead | Number Alive |
|---|---|---|---|
| Untreated (PBS) | 4 | 3 | 4 |
| IgG (30 μg/100 μl) | 4 | 4 | 4 |
| IgG (100 μg/100 μl) | 1 | 9 | 2 |
| IgG (300 μg/100 μl) | 1 | 2 | 9 |
| IgG-PMB (30 μg/100 μl) | 0 | 0 | 12 |
| IgG-PMB (100 μg/100 μl) | 1 | 0 | 11 |
| IgG-PMB (300 μg/100 μl) | 0 | 0 | 12 |

S-hydroxyethylthio-maleimidobenzoyl-N-aminocephalosporanic acid ester was determined to be 0.86 $A_{280}$ with *Staph. aureus* compared to 3.7 $A_{280}$ for 7-aminocephalosporanic acid.

Controls were also tested for the above derivatizated precursor. Sulfo-MBS, beta-mercaptoethanol and ethanolamine were prepared at concentrations used above and assessed for activity against *S. aureus*. The compounds were inactive.

EXAMPLE 32

Derivatization of 6-Aminopenicillanic Acid with Sulfo-MBS

This example describes the attachment of the heterobifunctional crosslinking agent of Example 31 to a different antibiotic precursor. This example outlines the derivatization of 6-aminopenicillanic acid, an antibiotic precursor exhibiting no significant anti-microbial properties, with sulfo-MBS.

For the derivatization of 6-aminopenicillanic acid, 12.1 mg of 6-aminopenicillanic acid (ICN) was dissolved in 2.5 ml of 50 mM phosphate buffer (pH 6.65). The solution was continuously mixed with a stir bar and magnetic stirrer and the pH was monitored. Sulfo-MBS (24.1 mg, Prochem, Inc.) was added and the pH was adjusted to 6.85 with a 1.0 N sodium hydroxide solution. The mixture was incubated at ambient temperature for 2.5 hours.

The reaction mixture was applied to a 1.5×20 cm column of Whatman LRP-2 resin (C18 reverse phase), equilibrated with 10% methanol in water. The column was developed at 1.0 ml/min. with 10% methanol for 5 min., followed by a linear, 30 min. gradient of 10 to 90% methanol in water. The eluate containing the last peak of material absorbing at 280 nm (eluted at 26 min.) was collected and concentrated to dryness under reduced pressure using a Labconco Centravap concentrator. The derivatized aminopenicillanic acid was dissolved in 1.0 ml of 50 mM phosphate buffer plus 1.0 mM EDTA, pH 6.65. The MIC of the derivatized aminopenicillanic acid was determined to be 8 μg/ml against *S. aureus*, compared to 250 μg/ml for the native aminopenicillanic acid.

Purified human IgG (40 mg, Sigma) was dissolved in 2.5 ml of 50 mM triethanolamine, 1.0 mM EDTA, pH 8.0 and continuously stirred with a magnetic stir bar and stirrer. 100 μl of 13 mg/ml iminothiolane (Traut's Reagent, Prochem) in water was added. The pH was monitored and adjusted to 8.0 with 1.0 N. sodium hydroxide. The mixture was incubated at ambient temperature for 2 hours. The mixture was then applied to a 2.5×20 cm column of Spectra/Gel ACA 202 (Spectrum). The column was eluted at 2.0 ml/min with 50 mM sodium phosphate buffer, 1.0 mM EDTA, pH 6.5. The absorbance at 280 nm was monitored. The material in the void volume, containing iminothiolated IgG, was collected and pooled. The concentration of the iminothiolated IgG was 5.0 mg/ml.

The derivatized aminopenicillanic acid (0.5 ml, 9.0 mg/ml) was mixed with 1.75 ml of iminothiolated IgG and incubated at ambient temperature for 10 min with mixing and then at 2–8° C. overnight. The mixture was transferred to ambient temperature and incubated with agitation. After 20 minutes, 146 μl of 10 mM N-ethylmaleimide (Pierce) was added and the incubation was continued for 4 hours. The reaction mixture was passed through a Uniflo-Plus filter (S&S) and applied to a 2.5×20 cm column of Spectra/Gel ACA 202 (Spectrum). The column was eluted at 2.0 ml/min with 50 mM sodium phosphate buffer, pH 6.5. The absorbance at 280 nm was monitored. The material in the void volume, containing MBS aminopenicillanic acid:IgG was collected, pooled, concentrated using a Centricon concentrator (Amicon) and passed through a Uniflo-Plus filter (S&S). The MBS aminopenicillanic acid:IgG was found to be inactive at 0.65 mg/ml against *S. aureus*.

Controls were also tested for the above derivatized precursor. Sulfo-MBS, beta-mercaptoethanol and ethanolamine were prepared at concentrations used above and assessed for activity against *S. aureus*. The compounds were inactive.

EXAMPLE 33

Derivatization of Amoxicillin with Sulfo SMCC

This example outlines the derivatization of amoxicillin, an antibiotic exhibiting significant anti-microbial properties, with sulfo-SMCC. For the derivatization of amoxicillin, 23 mg of amoxicillin trihydrate (ICN) was added to 2.5 ml of 50 mM phosphate buffer (pH 6.65). The suspension was continuously mixed with a stir bar and magnetic stirrer and the pH was monitored. Sulfo SMCC (23 mg, Prochem, Inc.) was added and the pH was adjusted to 7.0 (and periodically readjusted to 7.0) with 1.0 N sodium hydroxide. The mixture was incubated at ambient temperature for 4 hours. (The reaction mixture was initially turbid due to suspended amoxicillin, but the mixture became clear with time.)

The reaction mixture was applied to a 1.5×20 cm column of Whatman LRP-2 resin (C18 reverse phase), equilibrated with 10% methanol in water. The column was developed at 1.0 ml/min. with 10% methanol for 5 min., followed by a linear, 30 min. gradient of 10 to 90% methanol in water. The eluate containing the last peak of material absorbing at 280 nm (eluted at 27.5 min.) was collected and concentrated to dryness under reduced pressure in a Labconco Centravap concentrator. This derivatized amoxicillin was dissolved in 1.0 ml of 50 mM phosphate buffer plus 1.0 mM EDTA, pH 6.65. The MIC of the derivatized amoxicillin was determined to be 8 µg/ml against *S. aureus*, compared to 250 µg/ml for native amoxicillin

EXAMPLE 34

Derivatization of Cefadroxil with Sulfo-SMCC

In the following example, cefadroxil, an antibiotic active against gram-positive bacteria, was reacted with the crosslinking agent sulfosuccinimidyl 4-(N-maleimidomethyl)cyclohexane-1-carboxylate ("sulfo-SMCC").

Cefadroxil (Sigma) was dissolved at 3.0 mg/ml in 50 mM phosphate (pH 6.65). sulfo-SMCC was added and dissolved at 2.6 mg/ml. After a 1 hour and 55 minute incubation at ambient temperature with agitation, ethanolamine was added at 3.4 mg/ml and the incubation was continued for an additional 42 minutes.

The reaction mixture (0.5 ml) was applied to a 1.5×13 cm column of Sephadex G10 resin (Pharmacia). The eluent was 50 mM phosphate buffer, pH 6.65, flowing at 0.5 ml/minute. The eluate was monitored for absorbance at 280 nm. 1.0 ml fractions were collected. Two major absorbance peaks were evident—one centered at 22 minutes and the other at 36 minutes (reaction products and cefadroxil, respectively). Fractions corresponding to the leading edge of the first peak were pooled (3.0 ml, 3.5 A 280). 300 µl of 100 mM beta-mercaptoethanol was added to the mixture which was then filtered using a sterile Whatman 0.45 micron Puradisc. The MIC of the putative S-hydroxyethylthio maleimidomethyl cyclohexane carboxyl-N-cefadroxil ester was determined to be 1.6 $A_{280}$ against *Staph. aureus* compared to a MIC of 0.028 $A_{280}$ for native cefadroxil. Thus, the derivatized cefadroxil was relatively inactive.

EXAMPLE 35

Derivatization of Vancomycin with Sulfo-LC-SPDP, Sulfo-MBS, Sulfo SIAB, and Sulfo-SMPB In the following example vancomycin, an antibiotic active against gram-positive bacteria, was reacted with four different heterobifunctional crosslinking agents.

Vancomycin in phosphate buffer was reacted with each of the following compounds: sulfosuccinimidyl 6-[3-(2-pyridyldithio) propionamide] hexanoate ("sulfo-LC-SPDP"), m-maleimidobenzoyl-N-hydroxysulfosuccinimide ester ("sulfo-MBS"), sulfosuccinimidyl (4-iodoacetyl) aminobenzoate ("sulfo-SIAB"), and sulfosuccinimidyl 4-(p-maleimidophenyl) butyrate ("sulfo-SMPB"). All four crosslinking agents react with a primary amino group on the vancomycin molecule, resulting in the formation of an amide bond. Vancomycin derivatized by sulfo-LC-SPDP possesses a sulfhydryl group which can be exposed under the proper conditions and can be reacted with a maleimide on derivatized IgG. Vancomycin derivatized by sulfo-MBS possesses a maleimide group which can react with a sulfhydryl group on either reduced IgG or derivatized IgG, by addition to the maleimide's carbon-carbon double bond. Finally, vancomycin derivatized by sulfo-SIAB possesses an iodo group, which can also react with a sulfhydryl group on either reduced IgG or derivatized IgG, by nucleophilic substitution for the iodo group. Sulfo MBS, sulfo SIAB, sulfo SMPB or sulfo SMCC (Pierce) were dissolved with mixing at a concentration of 20 mM in a solution of 10 mM vancomycin (ICN) in 50 mM sodium phosphate buffer, pH 7.15. The mixtures were incubated with agitation at ambient temperature. Precipitates formed in all four mixtures and the products of the reaction were not further pursued.

EXAMPLE 36

Conjugation of Vancomycin to IgG with Iminothiolane and Sulfosuccinimidyl 4-(N-maleimidomethyl)cyclohexane-1-carboxylate Because of the unsatisfactory results of the previous example in obtaining a soluble derivatized vancomycin suitable for further conjugation to immunoglobulin, an alternative crosslinking method was investigated using iminothiolane ("Traut's Reagent") to derivatize the vancomycin and sulfosuccinimidyl 4-(N-maleimidomethyl)cyclohexane-1-carboxylate ("sulfo-SMCC") to derivatize the IgG. The reaction proceeds in three steps which are outlined below. First, vancomycin is derivatized with Traut's Reagent. Second, non-specific immunoglobulin is derivatized with sulfo-SMCC. Third, the derivatized vancomycin and the derivatized IgG are reacted with each other forming a conjugate.

a) Reaction of Vancomycin with Iminothiolane 33.4 mg of vancomycin (ICN) was dissolved in 2.0 ml of freshly degassed 50 mM triethanolamine, 1.0 mM EDTA, pH 8.0 buffer. 34.5 mg of Traut's Reagent (Pierce) was dissolved, and $N_2$ gas was blown into the vial which was then tightly capped. The vial was incubated with agitation for 1 hour and 15 minutes.

The mixture (0.5 ml) was applied to a 1.5×13 cm column of Sephadex G10 (Pharmacia). The eluent was freshly degassed 50 mM phosphate, 1.0 mM EDTA, pH 6.65 buffer flowing at 0.5 ml/min. 1.0 ml fractions were collected and the fractions in the first peak (void volume of column) were pooled (3.0 ml).

The pool from the G10 column was applied to a 4 ml, 1.0 cm diameter column of Bio-Rad Affi-Gel 501, an organomercury resin. The 501 resin had been previously washed with 25 ml 50 mM sodium acetate, pH 5.0 (acetate buffer), 25 ml of 4.0 mM mercuric acetate in acetate buffer, 25 ml of acetate buffer and the equilibrated to 50 mM phosphate, 1.0 mM EDTA, 0.5% Tween 20, pH 6.65. The pool was applied at 0.2 ml/min using 50 mM phosphate, 1.0 mM EDTA, 0.5% Tween 20, pH 6.65 to wash the column. The flow was increased to 1.0 ml/min after 13 minutes. Washing continued for a total time of 85 minutes to remove native, nonthiolated vancomycin. Thiolated vancomycin was eluted from the Affi-Gel 501 resin at 1.0 ml/min using freshly prepared 10 mM beta-mercaptoethanol in 50 mM phosphate, 1.0 mM EDTA, 0.5% Tween 20, pH 6.65. The first 5 fractions, 1.0 ml each, had $A_{280}$ significantly greater than baseline and were pooled (0.116 $A_{280}$ or 29 µg/ml, 5.0 ml). The MIC for the putative iminothiolated vancomycin was determined to be 2.4 µg/ml with *S. aureus*. The MIC of vancomycin is 1–2 µg/ml.

The derivatized vancomycin was concentrated on a Labconco Centravap, 1.0 ml of water was added, and the material was applied to a 1.5×13 cm column of Sephadex G10 (Pharmacia). The column was eluted with 50 mM sodium phosphate buffer, 1.0 mM EDTA, 0.5% TWEEN 20, pH 6.65. The material in the void volume was collected and pooled.

b) Reaction of IgG with Sulfo-SMCC

In general, 15 moles of sulfo-SMCC were used per mole of IgG. Higher molar ratios of crosslinker than this resulted in precipitation of IgG. 40 mg human IgG (Sigma, Cat #I4506, Lot #063H-8875I) was dissolved in 2 ml of 50 mM phosphate pH 7.1 buffer and 1.6 mg sulfo-SMCC (Prochem, Cat #CL207, Lot #03092) was added with mixing. The mixture was incubated at room temperature for 45 min and excess crosslinker was removed by chromatography on an AcA 202 gel filtration column. A 2 ml sample was applied to a 2.5×20 cm ACA 202 gel filtration column (Spectrum) equilibrated and eluted with 50 mM MES, 0.5% Tween-20, pH 6.5 buffer. The first peak corresponding to the activated IgG was collected and absorbance at 280 nm was monitored.

c) Conjugation of Derivatized Vancomycin and Derivatized IgG

For the final conjugation of the derivatized vancomycin and the derivatized IgG, 2.95 ml of 4.4 mg/ml SMCC:IgG (from step b above) was added to 14 ml of 0.74 mg/ml iminothiolated vancomycin (from step a above). The solution was incubated at ambient temperature on a rotary shaker at 200 rpm. After one hour and five minutes, 100 µl of 3.5 mg/ml 2-mercaptoethanol was added and the incubation was continued for an additional 25 minutes. The solution was concentrated to approximately 2 ml using an Amicon Centricon 30.

The sample was loaded onto a 2.5×20 cm column of Spectra Gel ACA 202 resin (Spectrum) and eluted, at 1.0 ml/min, with PBS plus 0.1% Tween 20. 1.5 ml fractions were collected. The fractions in the void volume were pooled and sterile filtered. The activity of the conjugate was determined by standard MIC testing against *S. aureus*. The conjugate against *S. aureus* was found to be inactive at 1.1 mg/ml.

EXAMPLE 37

Conjugation of Vancomycin to IgG With S-Acetyl Mercapto Succinic Anhydride ("SAMSA") and Sulfosuccinimidyl 4-(N-Maleimidomethyl) cyclohexane-1-Carboxylate ("Sulfo-SMCC")

Because of the unsatisfactory results of the previous example in obtaining a vancomycin-IgG conjugate with antibacterial activity, an alternative crosslinking method was investigated using S-acetyl mercapto succinic anhydride ("SAMSA") to derivative the vancomycin and sulfosuccinimidyl 4-(N-maleimidomethyl)cyclohexane-1-carboxylate ("sulfo-SMCC") to derivatize the IgG. The reaction proceeds in five steps which are outlined below. First, vancomycin is derivatized with SAMSA. Second, both derivatized vancomycin and free unreacted vancomycin are separated from any unreacted crosslinking agent. Third, the derivatized vancomycin is separated from the free unreacted vancomycin. Fourth, non-specific immunoglobulin is derivatized with sulfo-SMCC. Fifth, the purified derivatized vanco mycin and the derivatized IgG are reacted with each other forming a conjugate.

a) Reaction of Vancomycin with SAMSA 20.4 mg vancomycin (Sigma, Cat #V2002, Lot #43H1090) [14 µmoles] was dissolved in 200 µl of water. 1.2 ml of saturated sodium succinate was added slowly with stirring and this mixture was cooled to 4° C. by placing the reaction mixture on ice. The mixture appeared slightly cloudy. To this mixture was added 121.8 mg of SAMSA (Sigma, Cat #A1251, Lot 3 #120H5017) dissolved in 200 µl of dimethyl sulfoxide (DMSO, Mallinckrodt, Cat #5507, Lot #5507 KLDL). The pH was monitored. The beginning pH was 8.1, and after addition of the SAMSA, it was 6.8. The reaction mixture was incubated at 4° C. for one hour followed by another one hour incubation at room temperature, while stirring constantly.

b) Separation of Excess Crosslinker

To remove excess crosslinker from modified and unmodified vancomycin, the mixture was applied to a G-10 column (2.5×20 cm, Pharmacia) equilibrated with 50 mM sodium phosphate, pH 7.1. The first peak which contained both modified and unmodified vancomycin was collected and stored at 4° C.

c) Purification of Modified Vancomycin from Unmodified Vancomycin by Affinity Chromatography on Organomercurial Column A 5ml Affi Gel 501 Organomercurial agarose column (Bio-Rad) was prepared according to the manufacturer's instructions. The column was equilibrated with 50 mM phosphate, pH 7.1. SAMSA modified vancomycin contains protected sulfhydryl groups which were deprotected with hydroxylamine hydrochloride before applying to the column. Hydroxylamine hydrochloride was added to the modified vancomycin solution to a final concentration of 0.2 M and the mixture was incubated at room temperature for five minutes. The sample was applied to the Affi Gel 501 column at a flow rate of 0.5 ml/min and the column was then washed with 10 mM 2-(N-Morpholino) ethane sulfonic acid, 1 mM EDTA, 0.5% Tween-20, pH 6.5 buffer until the baseline $A_{280}$ was obtained. The bound modified vancomycin was eluted with the same wash buffer containing 20 mM 2-mercaptoethanol. The activity of the modified vancomycin was determined to be 2.6 µg/ml by MIC testing against *S. aureus*.

d) Reaction of IgG with Sulfo-SMCC

This reaction was carried out as described in example 35, step b (above).

e) Conjugation of Derivatized Vancomycin and Derivatized IgG

Modified vancomycin was in a buffer containing 20 mM 2-mercaptoethanol which was removed by dialysis, using benzoylated dialysis tubing (Sigma Cat #D7884, Lot #43H7085). 750 µg vancomycin (~0.5 µmole) and 7.5 mg (0.05 µmole) maleimide activated IgG was used. The mixture was incubated at room temperature for one hour. Unreacted maleimide sites were blocked by adding 30 moles of 2-mercapto ethyl amine per mole of IgG and incubating the mixture at room temperature for 20 min. The conjugate was purified from excess 2-mercapto ethyl amine and unreacted vancomycin by gel filtration chromatography. The sample was applied to a AcA 202 gel filtration column (2.5×20 cm, Spectrum) equilibrated with 0.01 M phosphate buffered saline, pH 7.2 with 0.1% Tween-20. Absorbance at 280 nm was monitored. The first peak containing vancomycin-IgG conjugate was collected. The activity of the conjugate was determined by MIC testing against *S. aureus*. MIC of this conjugate against *S. aureus* was found to be 0.438 mg/ml. This example demonstrates that conjugation of vancomycin derivatized by SAMSA with IgG derivatized by sulfo-SMCC results in an active conjugate. This conjugate was found to be an effective anti-microbial agent when tested against *S. aureus*.

EXAMPLE 38

Conjugation of Limulus Antilipopolysaccharide Factor to IgG By Periodate Oxidation of IgG This example describes the conjugation of Limulus anti-lipopolysaccharide factor (LALF) to human immunoglobulin by periodate oxidation of the IgG. LALF is a single chain peptide known to bind and neutralize endotoxin. See H. S. Waver et al. Infection and Immunity 60:2506 (1992). The sequence of the peptide is shown in FIG. 13 (SEQ ID NO:1). After conjugation of the LALF to the IgG was accomplished, the conjugate was tested for binding to both *E.coli* 0111:B4 lipopolysaccharide (LPS) and *E. coli* HB101. The binding of LALF and PMB conjugates to LPS was also compared.

a) Preparation of LALF-IgG Conjugate

Purification is achieved by using a spectrophotometric LAL assay to monitor inhibition of LPS-induced lysate activation. Briefly, amoebocytes from *L. polyphemus* are collected under endotoxin-free conditions, lysed by the addition of distilled water, and centrifuged at 5,000×g for 30 min. The pellet is extracted with 3 M urea. The extract is filtered through a membrane with a 30,000-Da cutoff and concentrated by a membrane with a 8,000-Da cutoff. The retentate is applied to a cation exchange column (CM Sepharose) equilibrated with 3 M urea-10 mM ammonium acetate (pH 5.5) and step eluted with NaCl at 0.15, 0.25, 0.5 M. The 0.5 M NaCl peak is directly applied to a C-4 reversed-phase column (Vydac, Hesperia, Calif.) equilibrated with water-0.2% trifluoroacetic acid. The column is step eluted with 25, 35, and 50% isopropanol containing 0.2% trifluoroacetic acid. The 50% isopropanol peak is lyophilized and reconstituted immediately before use. The final product is typically found to be >95% pure by reversed-phase high-performance liquid chromatography and SDS-PAGE.

In this case, purified LALF was obtained from Associates of Cape Cod. Lyophilized LALF was dissolved at 15 mg/ml in 50 mM sodium acetate, pH 5.0. The MIC of this native LALF against *E. coli* HB101was found to be 16 µg/ml.

10 mg of purified, human IgG (Sigma) was dissolved in 1.0 ml of 50 mM sodium phosphate, pH 7.1. 10.7 mg of sodium meta-periodate was added to the IgG solution and dissolved with mixing. The mixture was incubated at ambient temperature on a rotary shaker at 180 rpm for 30 minutes.

The mixture was applied to a 2.5×20 cm column of Spectra-Gel ACA 202 (Spectrum) resin and eluted at 2.0 ml/min with 50 mM sodium phosphate, pH 6.7. The absorbance at 280 nm was monitored and 2.0 ml fractions were collected. The fractions corresponding to the void volume of the column (oxidized IgG) were collected.

0.66 ml of the above 15 mg/ml LALF solution was added dropwise with mixing to 1.3 ml of the oxidized IgG (2.1 mg/ml). The mixture was incubated on a rotary shaker at 180 rpm for approximately 18 hours. 39 µl of 1.0 N HCl was added with mixing. The mixture was incubated at 180 rpm for 3.0 hours at ambient temperature.

The mixture was applied to a 1.5×20 cm column of Spectra-Gel ACA 202 resin and was eluted at 1.0 ml/min. with PBS plus 0.1% Tween 20. The eluent corresponding to the void volume, containing the LALF:IgG conjugate, was collected. The MIC of the LALF:IgG conjugate against *E. coli* HB101 was determined to be 300 mg/ml.

b) Assay of LPS and *E. coli* HB101 Binding of LALF-IgG Conjugate

E. coli 0111:B4 lipopolysaccharide (LPS) was obtained from Sigma and was dissolved at 0.02 mg/ml in PBS plus 0.005% thymerosol. *E. coli* HB101 was diluted to 10,000,000 CFU/ml in PBS. 100 µl aliquots of LPS solution, *E. coli* HB101 suspension or PBS were added to wells of Falcon Pro-Bind 96 well microtiter plates. The plates were incubated for 18 hours at 2–8° C. The wells were washed 3 times with PBS. 100 µl of PBS plus 5 mg/ml BSA (Sigma Chemical Co.) was added to each well of the plates and the plates were incubated for 2.0 hours at room temperature. The plates were decanted and 100 µl of sample (e.g. conjugate, antibody, etc.) was added per well and the plates were incubated at ambient temperature for 2.0 hours. The wells were washed 6 times with BBS (0.125 sodium borate, 1.0 M NaCl, pH 8.3) plus 0.5% Tween 20, 3 times with 50 mM sodium carbonate, pH 9.5.Three Sigma 104 phosphatase substrate tablets were dissolved in 15 ml of 50 mM sodium carbonate buffer plus 10 mM $MgCl_2$ and added at 100 ml per well. After approximately 20 minutes at ambient temperature, the absorbance at 410 nm of each well was determined.

| Concentration of LALF:IgG, µg/ml | $A_{410}$ LPS PLATES | *E. coli* HB101 Plates |
|---|---|---|
| 20 | 1.52 | 0.57 |
| 4.0 | 1.40 | 0.32 |
| 0.8 | 0.08 | 0.06 |

* Net $A_{410}$ = $A_{410}$ Sample − $A_{410}$ of PBS Coated Plate

Another LALF:IgG and a PMB:IgG conjugate were prepared as described above. Binding data for PMB:IgG, LALF:IgG and control IgG to LPS-coated and uncoated (PBS) plates is given in the table below. The binding of both conjugates to the LPS-coated plates is significant, with greater binding of the LALF:IgG to LPS at 4 and 0.8 µg/ml. The LALF:IgG and PMB:IgG conjugates bind LPS in a specific manner, since binding of control unconjugated IgG to LPS-coated plates and binding of both conjugates to PBS-coated plates are low. Thus, binding is mediated by the LALF and PMB portions of the conjugates.

Binding of Conjugates to LPS Conjugate

| | $A_{410}$ | | | | | |
|---|---|---|---|---|---|---|
| Conjugate | PMB: IgG | | LALF: IgG | | Control IgG | |
| Concentration µg/ml | LPS Plates | PBS Plates | LPS Plates | PBS Plates | LPS Plates | PBS Plates |
| 20 | 1.56 | 0.13 | 1.72 | 0.25 | 0.03 | 0.02 |
| 4 | 0.18 | 0.23 | 0.95 | 0.04 | 0.01 | 0.02 |
| 0.8 | 0.02 | 0.04 | 0.12 | 0.02 | 0.01 | 0.02 |
| 0.16 | 0.01 | 0.02 | 0.02 | 0.01 | | |

EXAMPLE 39

Synthesis of Immunoadaptor™ Compounds

This example describes the synthesis of numerous Immunoadapter™ compounds.

I. Polymyxin B Conjugates
a) Preparation of PMB-Traut's (Imminothiolated PMB)

It was desired to convert a primary amine on the side chain of a diaminobutyric acid residue (DAB) on PMB to a thiol for subsequent linkage to other substances. A method that would retain the biological activity of PMB would be ideal. Since retention of positive charge is generally required for retention of biological activity, it was thought that conversion of a primary amine to an imine, using Traut's Reagent or iminothiolane, might yield a thiolated PMB with no loss of biological activity.

Traut's reagent (Prochem), 12 mg, was added with vortexing to 2.5 ml of 10 mM PMB (Sigma Chem. Co.) in 50 mM triethanolamine, 1.0 mM EDTA, pH 8.0 buffer. After 1 hour, the reaction mixture was loaded onto a 1 by 3 cm column of CM52 resin. The column was washed at 1 ml/min. with 10 mM sodium phosphate buffer, pH 6.8 containing 1.0 mM EDTA and 0.1% Tween 20 for 15 minutes. The column was developed at 1 ml/min. with a 55 minute linear gradient from 0 to 0.8 M sodium chloride in 10 mM sodium phosphate buffer, pH 6.8 containing 1.0 mM EDTA and 0.1% Tween 20.

Thiolated PMB was detected by reaction of the effluent with Ellman's reagent and trinitrobenzene sulfonic acid (TNBS). Fractions of 1.5 ml were collected. The first fraction containing both thiol (Ellman's) and amine (TNBS) was taken for MIC determination (PMB-Traut's).

b) Preparation of S-Acetylmercaptosuccinyl PMB (PMB-SAMSA)

Polymyxin B Sulfate (377.7 mg, Sigma, 6000 USP units/mg) was dissolved in a mixture of water (4.5 mL) and pyridine (4.5 mL) and the mixture was cooled to 0° C. A solution of S-Acetylmercaptosuccinic anhydride (134.1 mg) in anhydrous DMF (ca 600 µL) was then added. After stirring at 0° C. for 30 min the mixture was stirred at room temperature for 70 min. The solvent was evaporated in vacuo and the residue was taken up in water. A small amount of water-insoluble material was removed by decanting and the aqueous solution was lyophilized. The residue was chromatographed on a CM52 column (1.5 cm×6.2 cm). The column was first washed with 10 mM phosphate, I mM EDTA buffer pH 6.67 for 75 min at 1.5 mL/min. It was then eluted with 0–48% NaCl in the same buffer over a period of 80 min at 1.5 mL/min. The PMB-SAMSA elutes after 35 min of the gradient and the unreacted PMB elutes after 65 min. (Baseline separation was obtained between all peaks). The fractions corresponding to mono PMB-SAMSA were combined. The concentration was determined using a TNBSA assay.

c) Preparation of PMB-SAMSA-Mal-FL (PMB-S-mercaptosuccinyl-succinimidyl-fluorescein)

PMB (Sigma), 382 mg, was dissolved in 9 ml of 1:1 (v/v) pyridine:water and stirred in a ice/water bath. SAMSA (Sigma), 149 mg dissolved in 0.6 ml DMF, was added dropwise. After 45 minutes, the material was warmed to ambient temperature and stirred for another two hours. The solvent was removed at reduced pressure, 20 ml of water was added and the solvent was again removed under reduced pressure. 35 ml of water was added and the solution was adjusted to 0.2 M hydroxylamine HCl. After 50 minutes, the solution was adjusted to 20 mM beta mercaptoethanol and was filtered with a Gelman Acrodisc 4523 filter.

The filtrate was loaded onto a 1.5×14.5 cm column of Whatman CM52 resin at 2 ml/min. The column was washed with 10 mM sodium phosphate buffer, pH 6.8, containing 1.0 mM EDTA (Buffer A) at 1.75 ml/minute until the absorbance at 254 nm returned to baseline. The material of interest was eluted at 1.0 ml/min. by a linear gradient, over 70 minutes, from Buffer A to 350 mM sodium phosphate, pH 6.8 containing 1.0 mM EDTA. The first major peak was PMB-SAMSA and the second peak was unreacted PMB.

FL-Mal (Fluorescein-maleimide, Pierce 46130), 23 µmole in 0.6 ml DMF, was added dropwise with stirring to 3.0 ml of the above eluate containing 7.6 µmole PMB-SAMSA. The solution was stirred for one hour at room temperature. The solution was diluted to 90 ml with water and was filtered with a Gelman Acrodisc 4523 filter.

The solution was loaded at 2.0 ml/minute, onto a 1 by 5 cm column of CM52 resin. The column was washed with Buffer A at 2.0 ml/minute until the absorbance at 254 nm returned to baseline. The column was developed at 0.75 ml/minute with a 50 minute linear gradient from Buffer A to the same buffer containing 480 mM sodium chloride. The material in the one major peak was pooled (PMB-SAMSA-MAL-FL).

d) Preparation of PMB-Cys-Mal-FL

Figure 18:
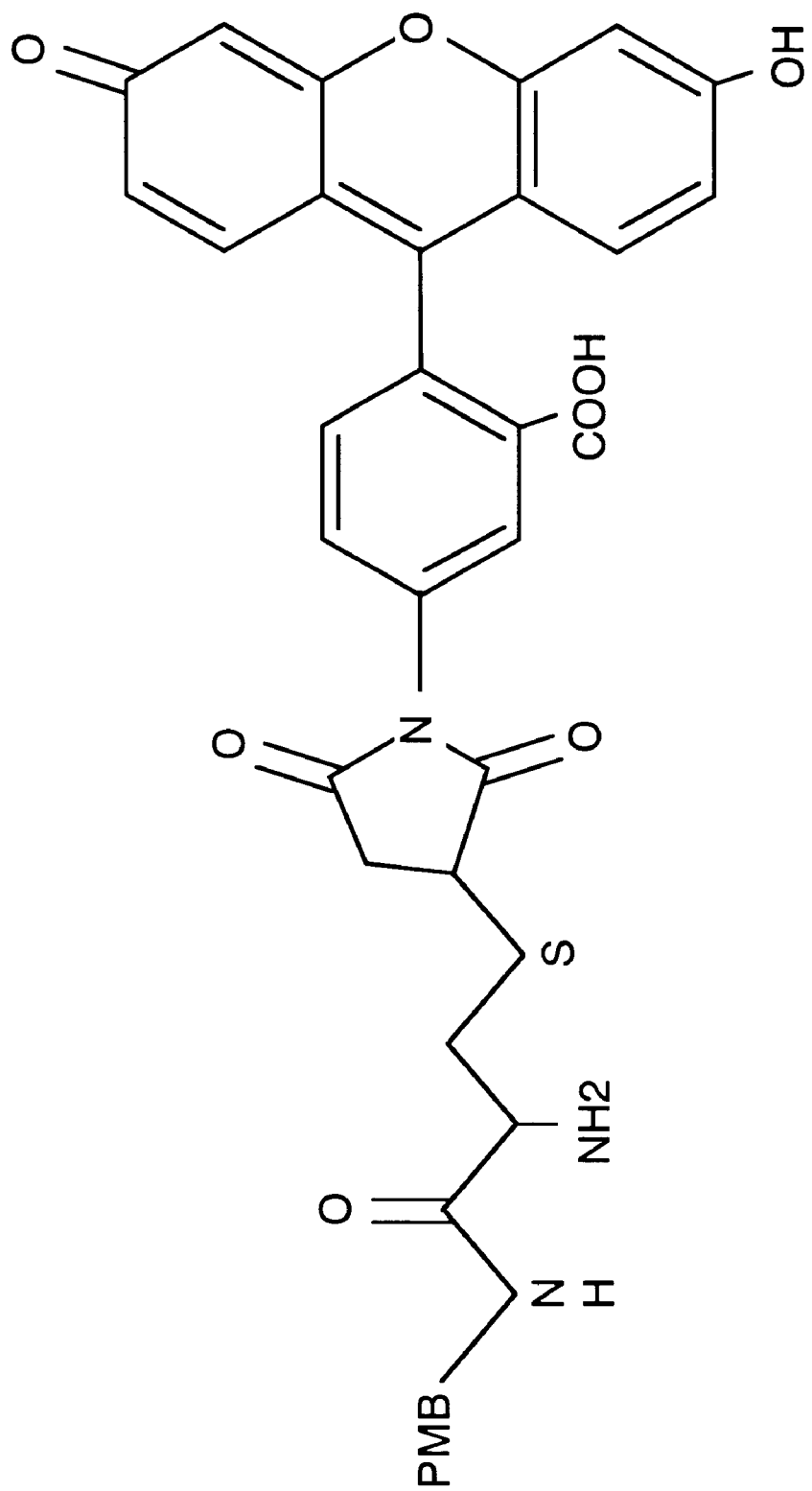
FIG. 18 shows a structure of a preferred Immunoadapter™ compound, polymyxin B-cysteine-Maleimide-fluorescein (PMB-Cys-Mal-FL).
Figure 19A:
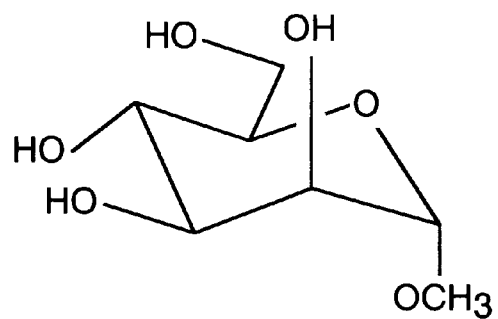
FIG. 19 shows fimbriae-binding compounds A–D from Table 62.
Figure 19B:
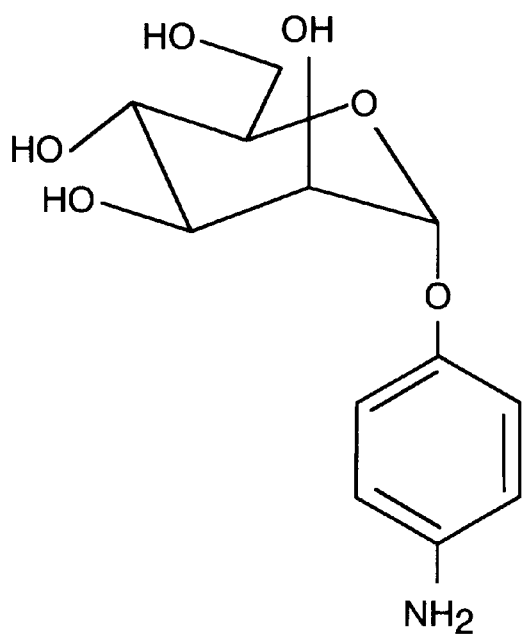
Figure 19C:
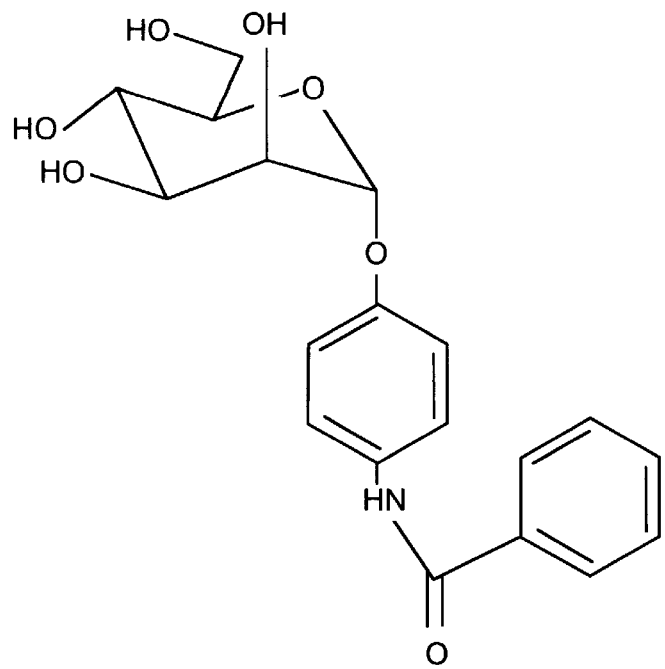
Figure 19D:
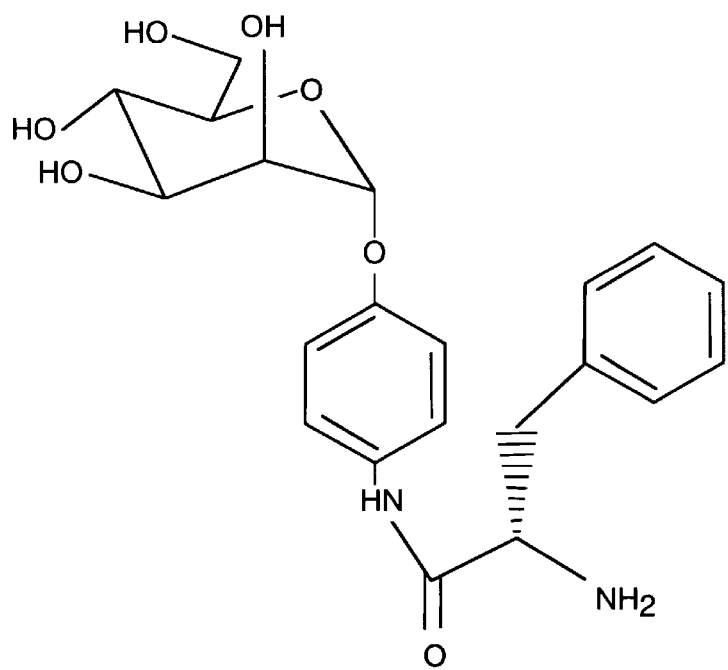

FL-Mal (Pierce), 5.4 mg dissolved in 0.8 ml DMF, was added dropwise with stirring to 1.7 µmole of PMB-Cys (cysteinyl PMB) in 8 ml of 10 mM sodium phosphate buffer, pH 6.8 containing 5 mM EDTA. After 2 hours at room temperature, the mixture was diluted to 90 ml with water, filtered with a Gelman Acrodisc 4523 filter, and applied to a 1 by 5 cm column of Whatman CM52 resin at 2.0 ml/minute. The rest of the procedure was equivalent to the last paragraph under d) above. The PMB-Cys-Mal-FL eluted in a single major peak. The structure of this conjugate is shown in FIG. 18.

e) Preparation of PMB-FITC (PMB-5-thiocarbamoyl-fluorescein)

FITC (Pierce 46110), 8.1 mg, was added with vortexing to 18 mg of PMB dissolved in 7.0 ml of 50 mM triethanolamine buffer, pH 8.2. After 2 hours, the suspension was filtered with a Gelman Acrodisc 4523 filter. The rest of the procedure was equivalent to the last paragraph under d) above. The PMB-FITC taken for MIC determination was the first fraction with significant fluorescence as there was not baseline separation between the PMB-FITC, which eluted first, and the unreacted PMB which elute last.

f) Preparation of PMB-NHS-FL (polymyxin B-fluoroscein)

NHS-FL (Pierce 46100), 5.7 mg in 125 µl DMSO, was added with vortexing to 9.4 mg PMB (Sigma) dissolved in 2.5 ml 50 mM sodium phosphate, pH 6.8. The reaction was allowed to proceed for 1 hour, 20 minutes and was then filtered and applied to a Whatman CM52 column. The rest of the procedure was equivalent to the last paragraph under a. above. During the linear gradient, two peaks at an absorbance of 254 nm were eluted. The first and smaller peak is presumably PMB-(NHS-FL)2 and the second major peak PMB-NHS-FL.

g) Preparation of Monoalanyl PMB (PMB-Ala) (Polymyxin B-Alanine)

Polymyxin B Sulfate (100 mg, Sigma, 6000 USP units/mg) was dissolved in a mixture of water (2.5 mL) and pyridine (2.5 mL) and the mixture was cooled to 0° C. A solution of t-butoxycarbonyl-Alanine p-nitrophenyl ester (Boc-Ala-ONp, 41.3 mg) in anhydrous DMF (300 µL) was then added. After stirring at 0° C. for 30 min the mixture was stirred at room temperature overnight. The solvent was evaporated in vacuo and the residue was taken up in water. A small amount or water insoluble material was removed by decanting and the aqueous solution was lyophilized. the residue was chromatographed on a CM52 column (1.5 cm×8 cm). The column was first washed with 10 mM phosphate buffer pH 6.67 for 90 min at 1.5 mL/min. It was then eluted with 0–48% NaCl in the same buffer over a period of 80 min at 1.5 mL/min. The Boc-Ala-PMB (t-butoxycarbonyl-alanine-polymyxin B) elutes after 55 min of the gradient and the unreacted PMB elutes after 70 min. (Baseline separation was obtained between all peaks).

The fractions corresponding to Boc-Ala-PMB were combined and lyophilized. The resulting powder was taken up in 20 mL of TFA containing 5% anisole at 0° C. and stirred at 0° C. for 90 min. The solution was filtered through Celite (Celite Corp.) and the solvent was evaporated in vacuo. the residue was partitioned between water and ether. the aqueous layer was washed three times with ether and lyophilized to afford a white powder. A small amount of the powder was dissolved in water and the concentration was determined using a quantitative ninhydrin assay.

h) Preparation of α,ε-di-t-butoxycarbonyl-lysyl-PMB (PMB-BocLys(Boc))

Polymyxin B Sulfate (200 mg, Sigma,6000 USP units/mg) was dissolved in a mixture of water (2.5 mL) and pyridine (2.5 mL) and the mixture was cooled to 0° C. A solution of α,ε-di-t-BocLysine NHS ester (118.3 mg) in anhydrous dioxane (ca 200 μL) was then added. After stirring at 0° C. for 30 min the mixture was stirred at room temperature overnight. The solvent was evaporated in vacuo and the residue was taken up in water. A small amount of water-insoluble material was removed by decanting and the aqueous solution was lyophilized. The residue was chromatographed on a CM52 column (1.5 cm×8.0 cm). The column was first washed with 10 mM phosphate buffer pH 6.67 for 90 min at 1.5 mL/min. It was then eluted with 0–48% NaCl in the same buffer over a period of 90 min at 1.5 mL/min. The PMB-BocLys(Boc) elutes after 60 min of the gradient and the unreacted PMB elutes after 80 min. (Baseline separation was obtained between all peaks). The fractions corresponding to mono PMB-BocLys(Boc) were combined and concentration was determined using a quantitative ninhydrin assay.

i) Preparation of Lysyl-PMB (PMB-Lys)

PMB-BocLys(Boc) was taken up in 20 mL of TFA containing 5% anisole at 0° C. and stirred at 0° C. for 60 min. The solution was filtered through Celite and the solvent was evaporated in vacuo. The residue was partitioned between water and ether. the aqueous layer was washed three times with ether and lyophilized to afford a white powder. A small amount of the powder was dissolved in $H_2O$ and the concentration was determined using a quantitative ninhydrin assay.

j) Preparation of S-(acetamidomethyl)-t-butoxycarbonylcysteinyl PMB (PMB-BocCys(Acm)

Polymyxin B Sulfate (2.0g, Sigma,6000 USP units/mg) was dissolved in a mixture of water (15 mL) and pyridine (15 mL) and the mixture was cooled to 0° C. A solution of t-butoxycarbonyl-S-(acetamidomethyl)-cysteine p-nitrophenyl ester BocCys(Acm)ONp (Bachem, 286.0 mg) in anhydrous dioxane (ca 2.0 mL) was then added. After stirring at 0° C. for 30 min the mixture was stirred at room temperature overnight. The solvent was evaporated in vacuo and the residue was taken up in water. A small amount of water-insoluble material was removed by decanting and the aqueous solution was lyophilized. The residue was chromatographed on a CM52 column (2.5 cm×17.0 cm). The column was first washed with 10 mM phosphate buffer pH 6.67 for 90 min at 1.75 mL/min. It was then eluted with 0–0.8 M NaCl in the same buffer over a period of 140 min at 1.75 mL/min. The PMB-BocCys(Acm) elutes after 85 min of the gradient and the unreacted PMB elutes after 105 min. (Baseline separation was obtained between all peaks).

The fractions corresponding to PMB-BocCys(Acm) were combined and the concentration was determined using a quantitative ninhydrin assay. The material was the lyophilized.

k) Preparation of S-(acetamidomethyl) cysteinyl PMB [PMB-Cys(Acm)]

PMB-BocCys(ACM) was taken up in 50 mL of TFA containing 5% anisole at 0° C. and stirred at 0° C. for 90 min. The solution was filtered through Celite and the solvent was evaporated in vacuo. The residue was partitioned between water and ether. the aqueous layer was washed three times with ether and lyophilized to afford a white powder. A small amount of the powder was dissolved in $H_2O$ and the concentration was determined using a quantitative ninhydrin assay.

I) Preparation of Cysteinyl-PMB (PMB-Cys)

PMB-Cys(Acm) was dissolved in 25 ml of 50% Acetic acid and the concentration was determined with a qualitative ninhydrin assay. 10 equivalents of mercuric acetate was added as a solid and the reaction was allowed to proceed for 1 hr at room temperature under nitrogen. 20 equivalents of 2-mercaptoethanol was added and the reaction was allowed to proceed for 15 min at room temperature under nitrogen. The mixture was then filtered through Celite on a sintered glass funnel and lyophilized to afford a white powder. A small amount of the powder was dissolved in $H_2O$ and the concentration was determined using a quantitative ninhydrin assay.

m) Preparation of Biotinylated Cysteinyl PMB (PMB-Cys-Biotin)

PMB-Cys (25.0 mg) was taken up in Acetate Buffer pH 6.5 (5 mL). A solution of 1-biotinamido-4-{4'-(maleimidomethyl)-cyclohexane} carboxamide (Pierce, 25 mg) in DMSO (ca 200 μL) was added at room temperature under nitrogen. The reaction was allowed to stir overnight at room temperature under nitrogen. The solution was lyophilized. The residue was chromatographed on a CM52 column (1.5 cm×15.0 cm). The column was first washed with 10 mM phosphate buffer pH 6.67 for 90 min at 1.0 mL/min. It was then eluted with 0–48% NaCl in the same buffer over a period of 90 min at 1.0 mL/min. The PMB-Cys-Biotin elutes after 50 min of the gradient. (Baseline separation was obtained between all peaks). The fractions corresponding to PMB-Cys-Biotin were combined and the concentration was determined using a quantitative ninhydrin assay.

n) Lysyl S-succinamidyl (fluorescein) PMB (PMB-Lys-FL)

2-chlorotrityl chloride resin (300 mg, Bachem) was taken up in methylene chloride (3 mL). A solution of Boc-Lys (Fmoc) (280 mg) and diisopropyl ethyl amine (260 μL) in methylene chloride (2 mL) was added dropwise over a period of 5 minutes at room temperature. The mixture was shaken for 20 min at room temperature. Methanol (2 mL) was added and the reaction was allowed to shake for 10 min. The mixture was filtered over a sintered glass funnel and washed 3 times with methylene chloride, 2 times with DMF, 2 times with 2-propanol, 2 times with DMF, 2 times with 2-propanol, 2 times with methanol, and 2 times with ethyl ether. The material was then dried under high vacuum.

The resin was taken up in 8 mL of 20% piperidine in DMF and shaken for 30 min at room temperature. The reaction was then was filtered over a sintered glass funnel and washed 3 times with methylene chloride, 2 times with DMF, 2 times with 2-propanol, 2 times with DMF, 2 times with 2-propanol, 2 times with methanol, and 2 times with ethyl ether. The material was then resuspended in 8 mL of 20% piperidine in DMF and shaken for 30 min at room temperature. The reaction was then was filtered over a sintered glass funnel and washed 3 times with methylene chloride, 2 times with DMF, 2 times with 2-propanol, 2 times with DMF, 2 times with 2-propanol, 2 times with methanol, and 2 times with ethyl ether. The material was then dried in vacuo overnight. The material was taken up in DMF (2 mL). A solution of fluorescein isothiocyanate (344 mg) in DMF (2 mL) was added at room temperature. The reaction was shaken for an additional period of 60 min. Diisopropyl ethyl amine (120 μL) was added and the reaction was shaken for 60 min. The reaction was then was filtered over a sintered glass funnel and washed 3 times with methylene chloride, 2 times with DMF, 2 times with 2-propanol, 2 times with DMF, 2 times with 2-propanol, 2 times with methanol, and 2 times with ethyl ether. The material was dried in vacuo over night. The resin was taken up in a 1:2:7 solution of acetic acid, trifluoroethanol, and dichloromethane (4.5 mL). The reaction was shaken for 45 min at which time it was filtered over a sintered glass funnel and washed twice with a 1:2:7 solution of Acetic Acid, trifluoroethanol, and dichloromethane. The filtrate was dried in vacuo to afford an orange powder. The material was dissolved in a solution of N-hydroxysuccinimide (17.2 mg) in dioxane (1 mL). A solution of dicyclohexylcarbodiimide (32.7 mg) in dioxane (1 mL) was added at room temperature under nitrogen. The reaction was allowed to proceed overnight at room temperature under nitrogen. The solution was then filtered through Celite in vacuo. The material was taken up in anhydrous DMF (ca 200 μL) and was then added to a solution of Polymyxin B Sulfate (100 mg, Sigma,6000 USP units/mg) in a mixture of water (2.5 mL) and pyridine (2.5 mL) at 0° C. After stirring at 0° C. for 30 min the mixture was stirred at room temperature overnight. The solvent was evaporated in vacuo and the residue was taken up in water. The aqueous solution was lyophilized. The residue was chromatographed on a CM52 column (2.5 cm×17 cm). The column was first washed with 10 mM phosphate buffer pH 6.67 for 145 min at 1.5 mL/min. It was then eluted with 0–48% NaCl in the same buffer over a period of 130 min at 1.5 mL/min. The PMB-Lys-Fl elutes after 90 min of the gradient and the unreacted PMB elutes after 110 min.

The fractions corresponding to mono PMB-Lys-Fl were combined and lyophilized. The resulting powder was taken up in 5 mL of TFA (trifluoroacetic acid) containing 5% anisole at 0° C. and stirred at 0° C. for 90 min. The solution was filtered through Celite and the solvent was evaporated in vacuo. The residue was partitioned between water and ether. the aqueous layer was washed three times with ether and lyophilized to afford an orange powder. A small amount of the powder was dissolved in $H_2O$ and the concentration was determined using a quantitative ninhydrin assay.

o) Preparation of 3-maleimidobenzoyl Tentagel

Tentagel-S-$NH_2$ (100 mg) (Rapp Polymere) was swelled in a solution of diisopropylethylamine (52.3 μL) in methylene chloride (3.0 mL) for 30 min under nitrogen. 3-maleimidobenzoic acid N-hydroxysuccinimide ester (94.3 mg)in methylene chloride (1 mL) was added at room temperature under nitrogen. The reaction was shaken overnight at room temperature. The reaction was filtered over sintered glass and 2×washed with methylene chloride (50 mL).

p) Preparation of PMB-Cys-Tentagel

PMB-Cys (90 mg) was dissolved in 2 mL of a 10 mM phosphate buffer at pH 6.5. 3-maleimidobenzoyl tentagel (50.0 mg) was added at room temperature under nitrogen. The reaction was nutated at room temperature overnight and then washed twice with 100 mL of water.

q) Preparation of PMB-cys-PEG-Mal and PMB-cys-PEG-Mal-BME

PMB-Cys was added to 161 mg of bis (maleimidophenyl) PEG 2000 (Prochem, Inc., Rockford, Ill.) dissolved in 7.0 ml of 10 mM sodium phosphate, pH 7.0. After 4 hours, the solution was lyophilized. The residue was dissolved in 200 ml of water and loaded onto a 2.5 by 15 cm CM52 column. The rest of the procedure was equivalent to that given above under the last paragraph of a. above, except the eluents contained 10% dioxane. The peak fractions were combined. A sample was taken and reacted with 2 equivalents of beta mercaptoethanol; (BME) to produce PMB-Cys-PEG-Mal-BME.

r) Preparation of PMB-Cys-PEG-Mal-FL

SAMSA fluorescein (Molecular Probes Inc., A-685), 10 mg, was dissolved in 1.0 ml of degassed 0.1 N NaOH. After 15 min. under nitrogen, the solution was neutralized with HCl and 0.2 ml of 0.5 M sodium phosphate, pH 6.7 was added. The solution was mixed with the pooled peak fractions from h. above (PMB-Cys-PEG-Mal). After the incubation at room temperature for two hours, the mixture was chromatographed on a 2.5 by 17.5 cm column of Sephadex G25 (Pharmacia). The material in the void volume was pooled (PMB-Cys-Mal-FL).

s) Preparation of PMB-SATA

PMB sulfate (Sigma Chemical Co.), 52 mg, was dissolved in 1.5 ml of water. Pyridine was added with mixing until the pH was about 7.5. SATA, 12 mg dissolved in 0.2 ml of DMF, was added with stirring. The reaction mixture was stirred at room temperature for 16 hours was diluted to 25 ml with water and lyophilized. The residue was dissolved in 2 ml of water and was applied to a 1 by 6 cm column of CM52 resin (Whatman). The rest of the procedure was equivalent to that given in a) above. PMB-(SATA)3 eluted first, followed by PMB-(SATA)$_2$ and PMB-(SATA)$_3$ last.

t) Preparation of PMB-sulfo-GMBS

Sulfo-GMBS (Pierce Chemical Co., 22324), 3.9 mg, was added with vortexing to 7.6 mg of PMB dissolved in 1.0 ml of 50 mM sodium phosphate buffer, pH 6.7. After 30 min., the material was chromatographed on a Biogel P2 column (Biorad) to remove excess sulfo-GMBS. The material in the void volume was pooled and applied to a 52 column as described in a) above. There were three peaks of material that absorbed at 254 nm. The first peak was presumably PMB-(sulfo-GMBS)$_2$, the second PMB-sulfo-GMBS and the third PMB.

II. Non-Polymyxin B Conjugates a) Preparation of C19G

C18G is an antibacterial peptide developed by Bristol-Myers-Squibb with the structure, ala-leu-tyr-lys-lys-leu-leu-lys-lys-leu-leu-lys-ser-ala-lys-lys-leu-gly (SEQ ID NO:2). A peptide, designated C19G, was designed by Ophidian having an additional cysteine-amide at the carboxy-terminus, allowing modification and cross linking by reaction with maleimide containing compounds. C19G was prepared to our specifications by Quality Control Biochemicals, Hopkinton, Mass. The structure of the C19G peptide is ala-leu-tyr-lys-lys-leu-leu-lys-lys-leu-leu-lys-ser-ala-lys-lys-leu-gly-cys-amide (SEQ ID NO:3). C19G was reacted in 10 mM sodium phosphate buffer, pH 6.8 with a two-fold molar excess of N-ethyl-maleimide (NEM, Sigma) for one hour (C19G-NEM).

b) Preparation of C19G-Mal-FL

C19G, 10 mg, was dissolved in 1.0 ml of degassed 10 mM sodium phosphate buffer, pH 7.0. Fluorescein-5-maleimide (FL-Mal, Molecular Probes), 18 mg, was dissolved in 0.5 ml of freshly distilled and degassed DMF. The solution of FL-Mal was added dropwise with stirring, to the solution of C19G, on ice. After 18 hours, the solvents were removed by lyophilization and the residue was dissolved in 20 ml of distilled water and filtered with an S&S Uniflo Plus 0.45 micron filter.

The filtrate was loaded onto a 1.5 by 8 cm column of CM52 (Whatman) resin. The column was washed for 230 min. at 1.5 ml/min. with 10 mM sodium phosphate, pH 6.7. The C19G-Mal-FL was eluted by a linear gradient of sodium chloride, 0 to 0.8 mM, in 10 mM sodium phosphate buffer, pH 6.7 at 1.5 ml/min. The eluent was monitored for absorbance at 254 nm and fractions of 1.5 ml were collected. Fractions number 4–12 were pooled and designated C19G-Mal-FL.

c) Preparation of C90-99-Biotin 10 mg of the C90-99 peptide, cys-lys-trp-lys-ala-gln-lys-arg-phe-leu-lys (SEQ ID NO:4), (Grey and Haseman, 1994, Infect. Immun. 62, 2732–2739) was dissolved in degassed water (2 ml) and a solution of Biotin-BMCC (1-biotinamido-4-4'-(maleimidomethyl)-cyclohexane, Pierce) (4.1 mg) in DMSO (200 mL) was added. The mixture was stirred under nitrogen for 1 day and then lyophilized. The residue was chromatographed on a CM52 column (1.0 cm×15 cm). The column was first washed with 10 mM phosphate buffer pH 6.67 for 30 min at 0.4 mL/min. It was then eluted with 0–0.8 M NaCl in the same buffer over a period of 170 min at 0.4 mL/min. The C90-99-Biotin elutes after 110 min of the gradient and the unreacted C90-99 elutes after 150 min. Concentration was determined by a quantitative ninhydrin assay.

d) Preparation of C18G-SAMSA

Cl8G, 7.3 mg, was dissolved in 2.0 ml of 50 mM sodium phosphate buffer, pH 6.8 and placed in an ice bath and stirred. The pH was adjusted to 8.0 with 0.1 N NaOH. An aliquot of 125 µl DMF containing 1.27 mg of SAMSA (Sigma), was slowly added. The pH was adjusted to 7.8 after 10 minutes. After 1.5 hours, the pH was adjusted to 5.1 with 0.1 N HCl.

The solution was loaded onto a column of CM52 resin and chromatographed as described under I. a) above. There was one broad peak of material absorbing at 254 nm which was pooled and designated C18G-SAMSA.

e) Preparation of C19G-PEG-Mal and C19G-PEG-Mal-BME

C19G, 27 mg, was dissolved in 0.63 ml of 50 mM sodium phosphate buffer, pH 6.8, and added dropwise with stirring to 1.25 ml of 20% dioxane in water containing 460 mg of bismaleimidophenyl PEG 2000 (BioAffinity Systems). The solution was incubated for two hours. The remainder of the procedure was identical to that given under I. q) for PMB-Cys-PEG-Mal.

f) Preparation of C19G-PEG-Mal-SAMSA-FL

The procedure for preparation of C19G-PEG-Mal-SAMSA-FL was identical to that given for PMB-cys-PEG-Mal-FL under I. r) above, except that C19G-PEG-Mal was used in place of PMB-cys-PEG-Mal.

EXAMPLE 40

Evaluation of Biological Activity of Immunoadapter™ Compounds

This example describes the evaluation of the biological activity of the Immunoadapter ™ compounds described in Example 39.

To function as Immunoadapter™ compounds, PMB or other conjugates that contain bacterial binding ligands must retain bacterial binding activity. In the case of anti-microbial ligands, the simplest assessment of bacterial binding is to determine whether the conjugate has a minimal inhibitory concentration (MIC) at which bacterial growth is inhibited, since to inhibit growth, a conjugate must retain the ability to interact with its bacterial target. The example involved MIC determinations utilizing PMB or C90-99 containing conjugates described in Example 39.

The MIC assays were performed as follows. Bacteria were grown overnight on TSB (Trypticase Soy Broth) plates at 37 degrees, and bacteria resuspended in sterile PBS to equal a #1 McFarland suspension. The suspension is diluted in TSB to a concentration of $5 \times 10^5$ organisms/ml. This diluted sample is the inoculum. Serial 2 fold dilutions of the conjugate to be tested are made in TSB (0.5 ml final volume of each dilution) in polystyrene tubes. 0.5 ml bacterial inoculum was added to each dilution tube. The conjugate concentrations are thus 2× the final concentration to be tested. Control tubes containing TSB alone, antimicrobial agent alone, and inoculum alone are also set. The tubes are vortexed and grown overnight in 37 degree incubator. The tubes are examined for growth the next morning, the lowest concentration of conjugate which shows no visible bacterial growth is considered the MIC value. A number of different *E. Coli* strains were used including: 1) *E. coli* J5 [ATCC 437451; Elbein, A. D., and E. C. Heath, 1965. The biosynthesis of cell wall lipopolysaccharide in *Escherichia coli*. I. The biochemical properties of a uridine diphosphate galactose 4-epimeraseless mutant. J. Biol. Chem. 240: 1919–1925] is a derivative of *E. coli* 0111:B4 and 2) HB101 is the ATCC 33694 strain. Where two numbers are shown, the second number is the MIC of free PMB determined in the same experiment.

I. Chemically Modified Derivatives of PMB

Polymyxin B (PMB) which binds to gram negative bacteria was selected as one of the ligands. A functional group was sought for introduction into the structure of PMB that did not influence its activity and was amenable to a flexible conjugation chemistry. One such group would be a thiol (SH) group. There is some literature evidence that acylation of the amino function of the diaminobutyric acid moieties of PMB results in less active derivatives. This fact was also borne out in the following experiment.

PMB was acylated with S-acetylmercaptsuccinic anhydride (SAMSA) affording a mixture of acylated products and unreacted PMB. The mono succinylated product could be easily separated from the unreacted PMB on a carboxymethyl cellulose (CM52) column using a NaCl gradient in a phosphate buffer of pH 6.67. At this pH all amino groups are protonated and thus charged and each successive succinylation removes one additional positive charge. The successively higher acylated derivatives, thus, elute at lower ionic strength and the unreacted PMB elutes last (at the highest ionic concentration).

As shown in Table 40, the mono-succinylated PMB (PMB SAMSA) was significantly less active than the parent molecules evidenced by MIC. Deacylation of the s-acetyl group using hydroxylamine afforded a thiolated derivative of PMB which was suitable for conjugation.

Realizing the importance of the primary amino groups, we decided to prepare such derivatives of PMB which would restore the same group and at the same time introduce a second functional group that could be conjugated without affecting the antibiotic activity of the molecule. An additional constraint was that the desired compound(s) should be easily separable from the other reaction products and the starting material. Thirdly, the synthetic methodology should be simple and broadly applicable. With this in mind, we reacted p-nitrophenyl ester of Boc-alanine with PMB affording a mixture containing unreacted PMB and mono and poly alanyl derivatives. Once again the monoalanyl derivative could be separated from the rest of the mixture using ion exchange chromatography based on the same principles that is explained above for succinylated derivatives.

Deblocking of the Boc-protected amino group (TFA/anisole) afforded monoalanyl PMB (PMB-ALA) which has the same number of amino groups as PMB. As hoped (Table 40) this derivative was nearly as active as the parent molecule on the basis of MIC.

In order to establish whether additional amino groups remote from the cyclic peptide structure of PMB could play any role in its antibiotic activity, the lysine derivative was prepared. Interestingly, although this molecule has an additional amino group (and charge) compared to PMB, its antibiotic activity is about the same as the parent molecule (Table 40). As expected by this model, α,ε-di-t-butoxycarbonyl lysyl derivative was significantly less active. These results suggested to us that any conjugation through the ε-amino group of a lysyl PMB derivative would also be a possible approach towards obtention of active conjugates. These conjugates are referred to as PMB-Lys-FITC; PMB-Boc-Lys-FITC.

Encouraged by these results, we reacted PMB with Boc-Cys(Acm)ONp (S-(acetamidomethyl) N-t-butoxycarbonyl cysteine p-nitrophenol ester). The monoacylated product could be conveniently separated from the other products and from unreacted PMB on an ion exchange column (CM52) using a NaCl gradient in a phosphate buffer.

Deblocking of protective groups under standard conditions afforded cysteinyl PMB. The concentration of an aqueous solution of cysteinyl PMB could be determined by a ninhydrin assay as well as by Elman's reagent which gave consistent results.

As expected the monocysteinyl PMB (PMB-CYS) had an antibiotic activity similar to that of PMB (Table 41), while the cysteinylated molecule where the amine and the thiol were protected was ten times less active. Reaction of monocysteinyl PMB with 5-maleimidofluorescein afforded a fluoresceinated cysteinyl PMB. The thiol group of the cysteinyl PMB (PMB-CYS) did not contribute to the antibiotic activity as evidenced by the fact that the fluorescein derivative was just as active as PMB itself (Table 40).

The monocysteinyl PMB also reacted cleanly with 1-biotinamido-4-{4'-(maleimidomethyl)-cyclohexane carboxamide (biotin-BMCC) to afford a biotinylated derivative (PMB-Cys-Biotin).

Another fluoresceinated derivative of PMB in which lysine was used as a spacer between PMB and fluorescein was also prepared. Thus, Boc-Lys(Fmoc) was attached to a 2-chlorotrityl chloride resin. The ε-amino group was liberated and reacted with fluorescein-5-isothiocyanate (FITC). after washing the resin, the fluoresceinated lysine was liberated and converted to an N-hydroxysuccinimidyl ester. The reaction of this activated ester with PMB and purification afforded α-Boc-ε{fluorescein) thiocarbamoyl}-lysyl PMB (PMB-Boc-Lys-FITC). As shown in Table 40, the α-Boc derivative was significantly less active than the PMB but deblocking created a derivative (PMB-Lys-FITC) with activity close to the parent molecule (Note that in table 40: 1=bacterial strains, and 2=where utilized, the first number is MIC of the test compound and the second number is the PMB control run in the same experiment). The PMB containing conjugates PMB-Cys-Mal-FL, PMB-Cys-Biotin all retain high MIC values. This demonstrates that these PMB containing conjugates bind bacteria. The C90-99 peptide is not antimicrobial in this assay, so binding to bacteria of this peptide, or conjugates containing this peptide, is not measurable in this assay. However, as shown in Table 41, there was a 40–80 fold loss of anti-bacterial activity against $E.$ $coli$ HB101 when PMB was thiolated using Traut's reagent (e.g., the PMB-Traut's conjugate). PMB was acylated with the protected thiol containing, anhydride, SAMSA with concurrent loss of positive charge at one or more DAB in PMB. As given in Table 41, the monoacylated PMB (PMB-SAMSA) was 10–30 fold less active than PMB. PMB was acylated with N-succinimidyl-S-acetylthioacetate (PMB-SATA, which contains an NHS ester and protected thiol) with losses of activity of about 10 fold and with sulfo GMBS (maleimidobutyryl oxysulfo-succinimide ester, which contains NHS ester and maleimide) with a loss of anti-bacterial activity of about 10 to 20 fold. Due to major losses of activity with the above approaches, it was reasoned that acylation of a primary amino group on PMB might be tolerated if

TABLE 40

MIC values of peptide conjugates

| Conjugate tested | Organism[1] | MIC $(\mu g/ml)$[2] |
|---|---|---|
| PMB-Cys-Mal-FL | E. coli J5 | 0.8 |
| PMB | E. coli J5 | 0.1 |
| PMB | E. coli 0111:B4 | 0.5–1.0 |
| C90-99 | E. coli 0111:B4 | >75 |
| C90-99-Cys-Biotin | E. coli 0111:B4 | >108 |
| PMB | E. coli HB101 | 0.1 |
| C90-99 | E. coli HB101 | >75 |
| C90-99-Cys-Biotin | E. coli HB101 | >540 |
| PMB-SAMSA | E. coli 0111:B4 | 3.1/0.3 |
| PMB-Ala | E. coli 0111:B4 | 0.7/1.0 |
| PMB-Lys | E. coli 0111:B4 | 2.0/1.0 |
| PMB-Boc-Cys (ACM) | E. coli 0111:B4 | 6.0/0.6 |
| PMB[Boc-Cys(Acm)]2 | E. coli 0111:B4 | 83/0.6 |
| PMB-Cys (ACM) | E. coli 0111:B4 | 1.2/1.0 |
| PMB-Cys | E. coli 0111:B4 | 0.7/0.5 |
| PMB-Cys-Mal-FL | E. coli 0111:B4 | 0.9/0.5 |
| PMB-Cys-Biotin | E. coli 0111:B4 | 1.0/0.5 |
| PMB-Boc-Lys-FL | E. coli 0111:B4 | 12.5/0.25 |
| PMB-Lys-FL | E. coli 0111:B4 | 1/0.5 |
| PMB-FITC | E. coli HB101 | 0.2/0.1 |
| PMB-SAMSA-Mal-FL | E. coli 0111:B4 | 10/0.5 | another primary amino group was added nearby to maintain the net charge on the PMB. Therefore, cysteine was coupled via the carboxyl group to a primary amino group on PMB. As shown in Table 41, there was no significant loss of activity when PMB was modified with cysteine to PMB-cys or the blocked thiol derivative PMB-cys-NEM.

TABLE 41

Minimum Inhibitory Concentration (MIC) of Chemically Modified PMB

| | MIC $\mu g/ml$ E. coli | |
|---|---|---|
| LIGAND | 0111:B4 | HB101 |
| PMB | 0.5–1 | 0.05–0.1 |
| PMB-Traut's | | 4 |
| PMB-SAMSA | 3 | 0.5–3 |
| PMB-(SAMSA)$_2$ | | 9 |
| PMB-Ala | 0.8–2 | |
| PMB-BOC-Ala | 2 | |
| PMB-Cys | 0.8–1 | |
| PMB-Cys-NEM | 0.5 | |
| PMB-Cys-Acm | 5 | |

TABLE 41-continued

Minimum Inhibitory Concentration (MIC) of Chemically Modified PMB

|  | MIC μg/ml E. coli | |
| --- | --- | --- |
| LIGAND | 0111:B4 | HB101 |
| PMB-BOC-Cys-Acm | 5 | |
| PMB-(BOC-Cys-Acm)$_2$ | 80 | |
| PMB-Cys-PEG-Mal | 64 | |
| PMB-Cys-PEG-Mal-BME | 16 | |
| PMB-Lys | 2 | |
| PMB-SATA |  | [00ff]0.6 |
| PMB-(SATA)$_2$ |  | 3 |
| PMB-(SATA)$_3$ |  | >20 |
| PMB-sulfo GMBS |  | 1 |

PMB was modified in a similar fashion with alanine, which lacks the thiol group of cysteine. As with PMB-cys, there was little or no loss of activity with PMB-ala. PMB was modified with lysine to produce PMB-lys with apparently some loss of activity perhaps due to the additional positive charge. PMB-lys is of interest for building di- and tri-peptide linkers.

The structures of select modified PMB's are given below in the summary table.

SUMMARY TABLE

| PMB | PMB-NH$_2$ | Active |
| --- | --- | --- |
| PMB-SATA | PMB-NHCOCH$_2$SCOCH$_3$ | Less Active |
| PMB-Ala | PMB-NHCOCH(NH$_2$)CH$_3$ | Active |
| PMB-Cys | PMB-NHCOCH(NH$_2$)CH$_2$SH | Active |
| PMB-Lys | PMB-NHCOCH(NH$_2$)CH$_2$CH$_2$CH$_2$CH$_2$NH$_2$ | Active |

PMB was chemically modified to PMB-cys with no loss of biological activity. Since PMB-cys contains a free thiol (SH), it can easily be further modified or linked to other substances. Also, the atoms between the thiol and the side chain amino group on PMB serve as a spacial linker. PMB-cys, and structurally related compounds, can serve as a base to build modified PMB's with variable physical properties (e.g. length and hydrophilicity/hydrophobicity).

II. Chemically Modified C18G

C18G is a cationic 18-mer antibacterial peptide (Darveau et al., 1992, J. Clinical Invest. 90, 447–455) developed by Bristol-Meyers-Squibb (BMS). C18G contains several lysine residues with potential for chemical modification, if biological activity could be retained. C18G was modified with SAMSA to produce the thiol containing material, C18G-SAMSA.

The C18G and C18G-SAMSA were assayed by utilizing a serum Bactericidal Assay as shown in Table 42. Greater than 8 fold activity was lost.

A peptide containing a C terminal cysteine amide, i.e. C18G-cys-NH$_2$ (C19G) was synthesized. The amide derivative of cysteine was chosen to avoid chemical interference by a free carboxyl group in subsequent reactions. As shown in Table 42, the C19G had about 5 fold lower activity than C18G. However, when the free thiol was blocked by reaction with N ethyl-maleimide (NEM), the activity was restored (see C19G-NEM in Table 42).

TABLE 42

Bacterial Destruction Assay (BDA) of Chemically Modified C18G

|  | BDA μg/ml E. coli | |
| --- | --- | --- |
| LIGAND | 25922 | H16 |
| C18G | 1 | 5–10 |
| C18G-SAMSA (NP 6/7/94) | >8 | |
| C19G (C18G-cys-NH$_2$) |  | 25–50 |
| C19G-NEM (94.47) |  | 2.5–5 |

Table 43 shows the MIC's of C18G and modified derivatives. Again, C18G-SAMSA demonstrated a significant loss of activity as measured by MIC. C19G-NEM retained the activity of C18G. C19G was coupled to Mal-PEG 2000-Mal and the free maleimide (Mal) was blocked with beta mercaptoethanol (BME) to produce C19G-PEG-Mal-BME. C19G-PEG-Mal-BME was three fold more active against E. coli H16 but less active against Salmonella than C19G-NEM or C18G. The C terminal cysteine amide derivative of C18G, i.e. C19G, is as active as C18G. Moreover, C19G can be coupled to a long PEG cross linker and anti microbial activity is retained.

TABLE 43

Minimum Inhibitory Concentrations (MIC) of Chemically Modified C18G

|  | MIC μg/ml | | | |
| --- | --- | --- | --- | --- |
|  | E. coli | | | Salmonella |
| LIGAND | 25922 | 0111:B4 | H16 | 34576 |
| C18G | 2–4 | 10 | 30 | 5–10 |
| C18G-SAMSA | >20 | | | |
| C19G-NEM |  | 6 | 10 | 6 |
| C19G-PEG-Mal-BME (103:18b) |  |  | 10 | 30 |

III. Fluorescent Derivatives of PMB

PMB was acylated using FITC. PMB-FITC was 2–fold less active than PMB. PMB was also acylated with NHS-FL with a loss of activity of 10–20 fold. Two of the modified PMB's from Table 41 were fluoresceinated. PMB-cys was reacted with fluorescein maleimide (FL-Mal) with no loss of acitivity compared to PMB or PMB-cys. PMB-SAMSA was deprotected and reacted with fluorescein maleimide to produce PMB-SAMSA-Mal-FL, which retained the activity of PMB-SAMSA but was significantly less active than PMB. PMB-cys-PEG-Mal was reacted with a thiolated fluorescein derivative to produce PMB-cys-PEG-Mal-S-FL. Surprisingly, the activity of this compound was identical to PMB and much more active than PMB-cys-PEG-Mal-NEM. The results are summarized in Table 44.

TABLE 44

Minimum Inhibitory Concentrations (MIC) of Fluoresceinated PMB

|  | MIC μg/ml E. coli | |
| --- | --- | --- |
| LIGAND | 0111:B4 | HB101 |
| PMB | 0.2–1 | 0.05–0.1 |
| PMB-Cys-Mal-FL (74:99a) | 1 | |
| PMB-Cys-PEG-Mal-FL | 0.5 | |

TABLE 44-continued

Minimum Inhibitory Concentrations (MIC) of Fluoresceinated PMB

| LIGAND | MIC µg/ml E. coli | |
|---|---|---|
| | 0111:B4 | HB101 |
| PMB-FITC (62:71) | | 0.2 |
| PMB-NHS-FL (55:42,55:57)) | | 0.8–1 |
| PMB-SAMSA-Mal-FL(74:83,90) | 4–20 | |

IV. Fluorescent Derivatives of C18G

The thiol on C19G was reacted with FL-Mal to produce C19G-MAL-FL which was more active against *E. coli* than C18G and equivalent to C19G-NEM. C19G-Mal-FL was less active against Salmonella than C19G-NEM or C18G. C19G-PEG-Mal was reacted with a thiolated derivative of fluorescein to produce C19G-PEG-Mal-S-FL. The antibacterial activity of this compound was equivalent to PMB and PMB-PEG-Mal. The results are summarized in Table 45.

TABLE 45

Minimum Inhibitory Concentrations (MIC) of Fluoresceinated C18G

| | MIC µg/ml | |
|---|---|---|
| LIGAND | E. coli H16 | Salmonella 34576 |
| C18G | 30 | 5–10 |
| C19G-NEM | 10 | 6 |
| C19G-Mal-FL (94:59) | 10 | 40 |
| C19G-PEG-Mal-SAMSA-FL | 10 | |

EXAMPLE 41

Figure 15:
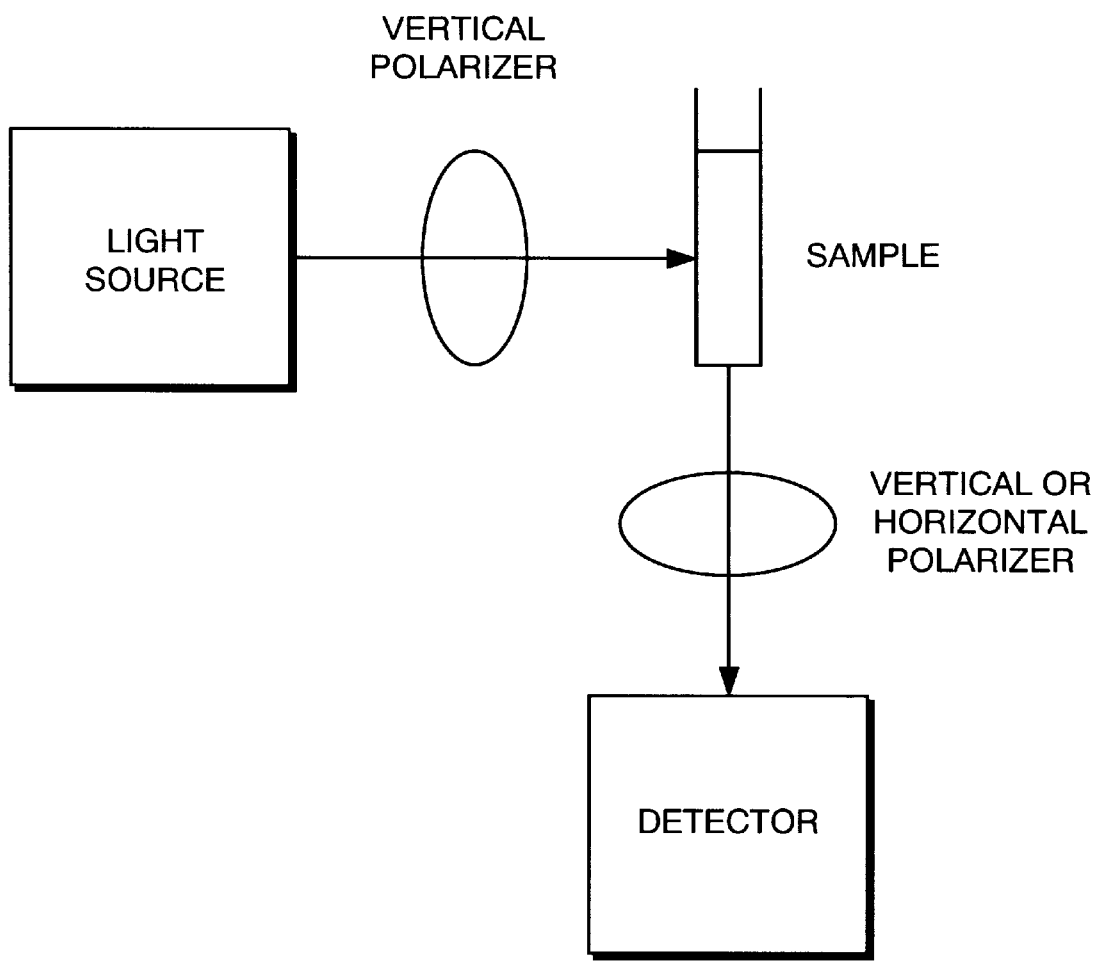
FIG. 15 shows a schematic illustrating the experimental overview of fluorescence polarization.

Demonstration of Immunoadapter™ Compound Binding to Anti-hapten and LPS Using Fluorescence Polarization Fluorescence polarization was utilized to determine if Immunoadapter™ compounds containing the hapten FL and the LPS binding ligand PMB bind both anti-fluorescein antibody and LPS respectively. Fluorescence polarization was first described in 1926 (Perrin, J. Phys. Rad 1:390:401) and has since been used to study many facets of molecular interactions. When fluorescent molecules are excited with plane polarized light, they emit in the same polarized plane provided that the molecules remain stationary throughout the excited state. However, if the excited molecule rotates or tumbles during the excited state, then the emitted light is in a different plane from the excitation light. When vertically polarized light is used to excite molecules, the emission light intensity can be monitored in both vertical and horizontal planes to detect movement of the molecule during excitation. If fluorescent molecules are very large, they move very little during excitation and the light from excitation to emission remains highly polarized. If fluorescent molecules are small, they rotate or tumble faster and the resulting emitted light is depolarized relative to the incident exciting light. In practice, small molecules (MW<1000) with fluorescent lifetimes of around 10 nanoseconds lose all their fluorescence polarization when they tumble and rotate freely. However, these molecules retain polarization when they are bound to larger molecules. A schematic diagram of a basic fluorescence polarization instrument is shown in FIG. 15.

The data for this example were generated on a fluorescence polarimeter (FPM-1, provided by Jolley Consulting and Research, Inc.) based on this optical configuration. The instrument and software generates output which includes vertical intensity (IV), horizontal intensity (IH), total intensity (IT) after correction of horizontal intensity by a constant (g), fluorescence polarization in millipolarization unit (mP) and lamp feed-back, a correction for lamp and photomultiplier tube variations.

$$\text{Fluorescence polarization} = P = IV - (g)IH$$
$$mP = P \times 1000$$
$$g = IV / IH$$
$$IT = IV + 2(IH \times g)IV + (g)IH$$

The example involved a) Fluorescence polarization studies and b) Binding of anti-fluorescein antibody to fluoresceinated PMB-coated bacteria

I. Fluorescence Polarization Studies

Fluoresceinated polymyxin B (PMB-FITC), made as described in Example 39, was purified by chromatography on a Bio-Gel P-2 resin and only the ascending portion of the first peak was collected to limit contamination with free PMB. Dilutions were made of the PMB-FITC by making 1 to 15 serial dilutions in phosphate buffered saline, pH 7.0. The following data (Table 46) addresses the intensity in arbitrary fluorescence units (AFU) and milli-polarization values (mP).

TABLE 46

Fluorescence Units and Milli-polarization Values with PMB-FITC

| DILUTION | INTENSITY (AFU) | mP |
|---|---|---|
| 1 to 15 | 2,366,955 | −33.3 |
| 1 to 150 | 195,980 | 49.9 |
| 1 to 225 | 131,556 | 55.8 |
| 1 to 3,375 | 6,884 | 46.3 |
| 1 to 50,625 | 456 | 65.0 |

From the above table one can observe that a 1 to 15 dilution is too concentrated and the fluorescence polarimeter calculates a negative value, which is meaningless. A 1 to 225 dilution is more acceptable with respect to an intensity level, but a slightly more concentrated solution would be optimal, thus the 1 to 150 dilution.

Since PMB is known to bind very tightly to lipopolysaccharide from gram negative bacteria, an experiment was designed to measure the binding of PMB-FITC. Each of ten different lipopolysaccharide (LPS) were dissolved in distilled water at a concentration of 1 mg/ml. The assay was configured by measuring the polarization of a mixture containing 50 µl of an LPS solution, 450 µl of a low intensity buffer (0.1 M phosphate and 0.1% bovine gamma globulin, pH 7.4) and 1.0 ml of a 1 to 150 dilution of PMB-FITC. Table 47 is a summary of the ability of ten LPSs to polarize PMB-FITC.

TABLE 47

Polarization of PMB-FITC by LPS

| LPS SOURCE | INTENSITY (AFU) | mP |
| --- | --- | --- |
| Control (no endotoxin) | 111,065 | 58.5 |
| E. coli 011B4 | 130,913 | 254.6 |
| E. coli 026B6 | 100,625 | 70.3 |
| K. pneumoniae | 128,485 | 258.5 |
| P. aeruginosa | 126,369 | 236.4 |
| R. sphaeroides | 174,048 | 224.7 |
| S. marsecens | 133,522 | 262.6 |
| S. enteriditis | 129,031 | 255.9 |
| S. typhimurium | 143,405 | 266.8 |
| S. flexneri | 99,982 | 246.3 |
| V. cholera | 105,606 | 174.8 |

From the above table, one can observe the polarization of PMB-FITC by all of the endotoxins. This demonstrates that the PMB in the PMB-FITC conjugate is available for ligand binding.

An experiment was performed on an Ophidian fluorescence polarimeter (re-engineered fluorometer) using a more active fluoresceinated cysteine polymyxin B (PMB-Cys-Mal-FL conjugate). Millipolarization data was hand calculated using the above equations as described for the fully automated instrument. Total intensity is not represented in the following tables. Table 48 illustrates the reactivity of PMB-Cys-Fl when reacted with mouse monoclonal anti-fluorescein antibody (#4-4-20) obtained from Edward M. Voss at the University of Illinois Urbana.

TABLE 48

Reactivity of PMB-Cys-Mal-FL with anti-Fluorescein Antibody

| SAMPLE | IV | IH | mP |
| --- | --- | --- | --- |
| Phosphate buffer (no intensity) | 3 | 1 | 474.2 |
| PMB-Cys-Mal-FL $10^{-7}$ M | 845 | 740 | 32.5 |
| antibody $5 \times 10^{-8}$ M (no intensity) | 3 | 1 | 474.2 |
| antibody $5 \times 10^{-8}$ M & PMB-Cys-Mal-FL 10-7 M | 61 | 25 | 390.3 |

From Table 48 it is clear that anti-fluorescein antibody strongly polarizes PMB-Cys-Mal-FL and while not represented here, quenches 95% of the intensity signal. This demonstrates that PMB-Cys-Fl can bind anti-fluorescein antibody.

Table 49 presents the data generated from the reaction of E. coli 0111:B4 bacteria with PMB-Cys-Fl.

TABLE 49

Binding of PMB-Cys-Fl to E. coli 0111:B4 bacteria

| SAMPLE | $V_{em}$ | $H_{em}$ | mP |
| --- | --- | --- | --- |
| E. coli 0111B4 ($2.7 \times 10^8$ bacteria) | 7 | 3 | 371.2 |
| PMB-Cys-Mal-Fl ($10^{-8}$ M) | 60 | 50 | 57.3 |
| E. coli & PMB-Cys-Mal-Fl | 26 | 12 | 256.8 |

A significant polarization can be observed from the data of Table 49. This demonstrates that PMB-Cys-Fl binds to bacteria.

II. Binding of Anti-fluorescein Antibody to Fluoresceinated PMB-coated Bacteria Results in Quenching of Fluorescence Staph. aureus and E. coli 0111:B4 were cultured in TSB media at 37 degrees C. with shaking. Cells were collected by centrifugation and suspended in 50 mM sodium phosphate buffer, pH 6.8. The cells were again collected by centrifugation and suspended in 50 mM sodium phosphate buffer containing 0.025% sodium azide (buffer).

The bacteria were diluted with buffer to an absorbance of 1.0 at 620 nm. PMB-Cys-Mal-FL was added to 2.5 ml of each diluted bacterial suspension, to a final concentration of 5.0 µg/ml. The suspensions were incubated at ambient temperature for 5 minutes. The bacteria were collected by centrifugation and suspended in buffer, repeated for a total of three times. The bacteria were then suspended in buffer and Tween 20 detergent was added to a final concentration of 0.1%. The bacteria were again collected by centrifugation and suspended in 1.5 ml buffer without Tween 20.

The bacteria were diluted 10 fold with buffer and fluorescence was measured in a Sequoia-Turner model 450 Fluorometer using NB490 and SC515 filters with the gain at 5. Mouse monoclonal anti-fluorescein antibody 4-4-20 was added with mixing to the bacterial suspensions. Table 50 summarizes the experimental results.

TABLE 50

Quenching of Fluorescence on PMB-Cys-Mal-FL Coated Bacteria

| | FLUORESCENCE (AFU) |
| --- | --- |
| S. aureus | 5 |
| E. coli | 40 |
| E. coli + 1 µg/ml anti-fluorescein antibody | 16 |
| E. coli + 2 µg/ml anti-fluorescein antibody | 15 |
| E. coli + 22 µg/ml anti-fluorescein antibody | 15 |

As shown in Table 50, PMB-Cys-Mal-FL bound more extensively to E. coli than S. aureus. (note: fluorescence is in arbitrary units). This is expected since PMB binds primarily to LPS which is present on Gram negative bacteria such as E. coli and lacking on S. aureus., a Gram positive organism.

When anti-fluorescein antibody binds to fluorescein, the fluorescence is reduced or quenched about 95%. If the fluorescein on fluoresceinated PMB coated E. coli is available on the exterior surface of the bacteria and anti-fluorescein antibody can bind then a reduction of signal is expected. If fluorescein is buried under the surface of the bacteria and anti-fluorescein antibody can not access it, no quenching of the fluorescence by anti-fluorescein antibody would be possible. The fluorescence of the Fluoresceinated PMB labeled E. coli is quenched to about ⅓ by 1 µg/ml and higher concentrations of anti-fluorescein antibody. Thus, about ⅔ of the fluorescein on the coated E. coli is freely available to interact and bind to anti-fluorescein antibody. This demonstrates that PMB-Cys-Mal-FL can simultaneously bind both anti-fluorescein antibody and the bacterial surface.

EXAMPLE 42

Characterization of the PMB-Cys-Biotin

It is desired that the PMB-Cys-Biotin conjugate (Example 39) bind to avidin or anti-biotin through the biotin hapten, in a manner that allows PMB to simultaneously bind its target. An ELISA assay was designed, to assess whether PMB-Cys-Biotin can simultaneously bind avidin and anti-PMB antibody. This example involved testing the PMB-Cys-Biotin conjugate in a capture ELISA.

The capture ELISA was preformed as described below. 96-well microtiter plates (Falcon, Pro-Bind Assay Plates)

were coated 1 hr at room temperature with 100 μl 2.5 μg/ml avidin (Sigma)well or 100 μl PBS/well. The coating suspensions were decanted, and all wells were washed three times using PBS+0.5% Tween 20 (PBST). In order to block non-specific binding sites, 100 μl of 1% BSA (Sigma, St. Louis, Mo.) in PBS (blocking solution) was then added to each well, and the plates were incubated for 1 hr. at 37° C.

The blocking solution was decanted, and duplicate samples of 150 μl of either PMB-Cys-Biotin or PMB-Cys-Fl added to the first well of a dilution series. The initial testing concentration of the premixed conjugate was 10 ng/ml in blocking buffer (see above), followed by 5 fold dilutions in blocking buffer. This was accomplished by serially transferring 30 μl aliquots to 120 μl buffer, mixing, and repeating the dilution into a fresh well. After the final dilution, 30 μl was removed from the well such that all wells contained 120 μl final volume. A total of 2 such dilutions were performed. The plates were incubated 1.5 hr at 37° C. Following this incubation, the serially diluted samples were decanted, and the wells were washed six times using PBST (Phosphate-Buffered Saline with Tween). To each well, 100 μl of 1/1000 diluted chicken anti-PMB antibody or chicken preimmune, diluted in blocking buffer was added, and the plate incubated 1 hr at 37° C. The antibody solutions were decanted and the plates were washed as described above. To each well, 100 μl of 1/1000 diluted rabbit anti-chicken IgG alkaline phosphatase (Sigma) diluted in blocking buffer was added, and the plate incubated 1 hr at 37° C. The antibody solutions were decanted and the plates were washed as described above, substituting 50 mM $Na_2CO_3$, pH 9.5 for the PBST in the final wash. The plates were developed by the addition of 100 μl of a solution containing 1 mg/ml para-nitro phenyl phosphate (Sigma, St. Louis, Mo.) dissolved in 50 mM $Na_2CO_3$, 10 mM $MgCl_2$, pH 9.5 to each well, and incubating the plates at room temperature in the dark overnight. The absorbency of each well was measured at 410 nm using a Dynatech MR 700 plate reader. The results are summarized in Table 51, and represent mean reactivities of duplicate wells. Only the ELISA readings from the maximally diluted samples in each dilution series are shown.

TABLE 51

PMB-Cys-Biotin binds avidin and anti-PMB antibody simultaneously

| Test Conjugate | Test antibody | Avidin coated wells | PBS coated wells |
| --- | --- | --- | --- |
| PMB-Cys-Biotin | Anti-PMB | 1.252 | 0.016 |
| PMB-Cys-Biotin | Preimmune | 0.014 | 0.019 |
| PMB-Cys-FL | Anti-PMB | 0.033 | 0.016 |
| PMB-Cys-FL | Preimmune | 0.010 | 0.020 |

The ELISA clearly demonstrates that the PMB-Cys-Biotin conjugate can simultaneously bind avidin and anti-PMB antibody. This indicates that the Cys linker separates the hapten and the ligand in a manner that allows binding to both sites, as was demonstrated for PMB-Cys-Mal-FL in Example 41.

EXAMPLE 43

Bead Agglutination of *E. coli* cells utilizing PMB-Cys-Biotin Immunoadapter™ Compounds The MIC determinations shown in Example 40 demonstrated that the PMB-Cys-Biotin compound binds bacteria. For an Immunoadapter™ compound to target hapten specific antibodies to the bacteria, binding must be to the bacterial surface, and not an internal target (e.g., the inner cytoplasmic membrane). To determine if PMB-Cys-Biotin stably binds to an accessible surface exposed target, bead agglutination assays were performed. The example involved a) generation of avidin coated polystyrene beads b) binding of PMB-Cys-Biotin to avidin beads and c) bacterial agglutination assays.

I. Generation of Avidin Coated Polystyrene Beads

100 μl polystyrene beads (Spherotech 0.81 μM, 5% w/v) were aliquoted to two 1.5 mL microcentrifuge tubes, centrifuged 1 min at 12,000 g in microcentrifuge and washed 2× with 1 ml PBS (vortexed and recentrifuged 1–2 min after each wash). The beads were resuspended in 900 μl PBS, and 100 μl of 1 mg/ml solution of avidin (Sigma) added, and the tubes rotated overnight at room temperature. The beads were pelleted, and washed sequentially as described above with 1 ml PBS, PBS+0.5% tween 20 (PBST), and PBS, and each sample resuspended in 200 μl PBS. The samples were pooled and stored at 4 degrees.

II. Binding of PMB-Cys-Biotin to Avidin Beads

20 μl avidin coated beads were aliquoted into 2×1.5 ml microcentrifuge tubes, and non-specifically binding sites blocked by rotating with 1 ml PBS+1% BSA for 1 hr at room temperature. 10 μg aliquots of either PMB-Cys-Biotin or PMB-Cys-Mal-Fl (negative control) were added, and the beads rotated 1 hr at room temperature. The samples were pelleted, and washed with 1 ml PBS, repelleted and resuspended with 20 μl PBS.

III. Bacterial Agglutination Assays

5 μl of each resin was added to 20 μl bacteria (1/10 dilution of a saturated overnight culture) in independent depression wells (2 wells/bacteria tested). The samples were incubated 30 min at 37 degrees, swirled, and agglutination scored. The experimental results are summarized below in Table 52. (Note that –=no agglutination, +=microagglutination and +++=macroagglutination)

TABLE 52

Bead Agglutination of Bacterial Strains Agglutination

| Bacterial strain | (PMB-Cy-Fl loaded beads) | (PMB -Cy-Biotin loaded beads) |
| --- | --- | --- |
| *E. coli* 0111:B4 | – | – |
| *E. coli* HB101 | – | + |
| Salmonella 34576 | – | + |
| *E. coli* J5 | – | +++ |

The results demonstrate specific agglutination of 3 or the 4 test bacteria using Immunoadapter™ compound loaded beads. The lack of agglutination in the control sample demonstrates that agglutination requires bead bound Immunoadapter™ compound. This demonstrates that the Immunoadapter™ compound can bind surface exposed structure on the HB101, Salmonella 34576 and J5 strains.

To determine if free Immunoadaptor™ compounds can also stably bind surface exposed bacterial structures, agglutination assays were performed using bacteria prebound to Immunoadaptor™ compounds. The assay was performed with J5 bacteria, since the agglutination signal (see table above) was the strongest with this strain. 40 μl avidin coated resin was blocked for 1 hr at room temperature with 1 ml PBS+1% BSA, pelleted as described above, and resuspended in 40 μl PBS. Stocks of 4 μg/ml PMB-Cys-Mal-FL and PMB-Cys-Biotin were made in PBS. The following assays were performed:

a) Premix: 10 μl of 4 μg/ml PMB-Cys-Mal-FL or PMB-Cys-Biotin stocks+10 μl of 1/10 diluted J5 bacteria+5 μl avidin coated beads. Incubated 1 hr at 37 degrees in depression well, swirled and agglutination scored.

b) Chase: 10 μl of 4 μg/ml PMB-Cys-Mal-FL or PMB-Cys-Biotin stocks+10 μl of 1/10 diluted J5 bacteria. Incubated 10 min at 37 degrees then added 5 μl avidin coated beads. Incubated 1 hr at 37 degrees in depression well, swirled and agglutination scored.

c) Wash+Chase: 40 μl of 4 μg/ml PMB-Cys-Mal-FL or PMB-Cys-Biotin stocks+40 μl of 1/10 diluted J5 bacteria were mixed in 1.5 ml microcentrifuge tube. Incubated 15 min at 37 degrees, pelleted cells by centrifugation, washed with 100 μl PBS (resuspended cells with micropipetter) and repelleted. Cells were resuspended in 80 μl PBS, 20 μl aliquots distributed to depression well, 5 μl avidin coated beads added, and, incubated 1 hr at 37 degrees, swirled and agglutination scored.

The results are shown in Table 53 below.

TABLE 53

Agglutination of J5 Bacteria by Avidin Beads in Premix, Chase or Wash Formats

| Format | PMB-Cys-Mal-FL | PMB-Cys-Biotin |
|---|---|---|
| Premix | − | + |
| Chase | − | + |
| Wash + Chase | − | + |

The results demonstrate that PMB-Cys-Biotin, when prebound to J5 cells, can bind to bead associated avidin. This binding is stable, since aggregation is observed when free compound is removed in the wash and chase format. This indicates that at least some of PMB-Cys-Biotin binds stably to the surface of this bacteria.

EXAMPLE 44

Immunoadaptor™ Compound Mediated Opsonization of J5 Cells

The agglutination studies of Example 43 demonstrated binding of PMB-Cys-Biotin to bacterial cells. A bacterial binding assay (BBA) was performed, to determine if this conjugate could also opsonize bacteria by targeting antibodies to bacteria. The J5 bacterial strain was selected for this study, since this strain had the strongest positive agglutination signal in example 43. A PMB-Cys-Biotin/extravidin premixed conjugate was utilized, since the increased avidity of this tetrameric complex may increase bacterial binding relative to monomeric PMB-Cys-Biotin. The example involved performing a BBA (Bacterial Binding Assay) using a ELISA Format.

Premixed conjugates of PMB-Cys-Biotin, or PMB-Cys-Mal-FL (control), with extravidin (extravidin rather than avidin was utilized, since extravidin has lower background binding to bacteria than avidin) were prepared. For 1 ml final volume, 2 μl PMB-Cys-Biotin or 8.3 μl PMB-Cys-Mal-FL (1 μg each), 100 μl PBS and 7 μl extravidin (Sigma; stock at 1 mg/ml) was incubated 1 hr at room temp, then overnight at 4 degrees. The samples were made up to 1 ml with PBS+0.5% tween 20 (PBST)+1% gelatin (blocking buffer).

The BBA assay was performed as described below. J5 bacteria were grown overnight in a standing culture. Cells were pelleted by centrifugation 5 min at 3000 rpm in Beckman GS-6 centrifuge, and bacteria resuspended (vortexing) to density of 2×10⁸ cells/ml (0.2 $OD_{600}$) in PBS. Cells were diluted to 2×10⁷ cells/ml with PBS, and 96-well microtiter plates (Falcon, Pro-Bind Assay Plates) were coated 2 hrs at room temperature with 100 μl cells/well. The coating suspensions were decanted, and all wells were washed three times using PBS. In order to block non-specific binding sites, 100 μl of 1% gelatin (Sigma, St. Louis, Mo.) in PBS (blocking solution) was then added to each well, and the plates were incubated for 1.5 hr. at 37° C.

The blocking solution was decanted, and duplicate samples of 150 μl of each premixed conjugate added to the first well of a dilution series. The initial testing concentration of the premixed conjugate was 1 μg/ml in blocking buffer (see above), followed by 5 fold dilutions into this buffer. This was accomplished by serially transferring 30 μl aliquots to 120 μl buffer, mixing, and repeating the dilution into a fresh well. After the final dilution, 30 μl was removed from the well such that all wells contained 120 μl final volume. A total of 2 such dilutions were performed (3 wells total). The plates were incubated 40 min at 37° C. Following this incubation, the serially diluted samples were decanted, and the wells were washed six times using PBST. To each well, 100 μl of 1/5000 diluted rabbit anti-avidin antibody (Sigma) diluted in blocking buffer was added, and the plate incubated 1 hr at 37° C. The conjugate solutions were decanted and the plates were washed as described above. To each well, 100 μl of 1/1000 diluted goat anti-rabbit IgG alkaline phosphatase (Sigma) diluted in blocking buffer was added, and the plate incubated 1 hr at 37° C. The conjugate solutions were decanted and the plates were washed as described above, substituting 50 mM $Na_2CO_3$, pH 9.5 for the PBST in the final wash. The plates were developed by the addition of 100 μl of a solution containing 1 mg/ml para-nitro phenyl phosphate (Sigma, St. Louis, Mo.) dissolved in 50 mM $Na_2CO_3$, 10 mM $MgCl_2$, pH 9.5 to each well, and incubating the plates at room temperature in the dark overnight The absorbency of each well was measured at 410 nm using a Dynatech MR 700 plate reader. The results are summarized in Table 54, and represent mean reactivities of duplicate wells.

TABLE 54

PMB-Cys-Biotin Directs Anti-Avidin Mediated Opsonization of J5 Bacteria

| Test Conjugate 1 μg/ml | J5 coated wells | PBS coated wells |
|---|---|---|
| PMB-Cys-Biotin/extravidin premixed congugate 200 ng/ml | 1.591 | 0.95 |
| PMB-Cys-Biotin/extravidin premixed congugate 40 ng/ml | 1.557 | 0.25 |
| PMB-Cys-Biotin/extravidin premixed congugate 1 μg/ml PMB-Cys-Mal-FL/extravidin premixed conjugate | 1.449 | 0.043 |
| 200 ng/ml PMB-Cys-Mal-FL/extravidin premixed congugate | 0.387 | 0.186 |
| 40 ng/ml PMB-Cys-Mal-FL/extravidin premixed conjugate | 0.176 | 0.061 |
| | 0.089 | 0.02 |

Although some background binding of the control PMB-Cys-Mal-FL premixed conjugate is observed, much stronger binding was observed (even at 40 ng/ml concentration) in J5 wells (but not PBS wells) incubated with PMB-Cys-Biotin but not PMB-Cys-Mal-FL (control) premixed conjugates. The low signal in the PMB-Cys-Mal-FL control lane indicates that extravidin needs linkage to PMB (through biotin in PMB-Cys-Biotin) for effective J5 bacterial binding. The detected background may be due to non-specific 'stickiness' of PMB containing conjugates, which may be elevated in the tetrameric PMB-Cys-Biotin/extravidin conjugate. These results clearly show that the PMB-Cys-Biotin premixed conjugate stably binds J5 cells (i.e., is not removed by washing 6 times with PBST) and can subsequently recruit anti-avidin. This demonstrates that the PMB-Cys-Biotin premixed conjugate can opsonize J5 cells by recruiting anti-avidin.

EXAMPLE 45

Immunoadaptor™ Compound Mediated Opsonization of a Pathogenic Bacteria

In Example 44, it was demonstrated that the PMB-Cys-Biotin/Extravidin premixed conjugate could direct anti-avidin opsonization of J5 bacteria. To determine if bacterial binding and opsonization can also be demonstrated to a encapsulated pathogenic bacteria, a modified bacteria binding assay was developed.

10 μg ml stocks of conjugates were made by diluting 10 μg conjugate [either 80 μl (PMB-Cys-Mal-FL), 20 μl (PMB-Cys-Biotin) or 10 μl (C90-99-Cys-Biotin)] to 1 ml with PBS. Premixed conjugates of PMB-Cys-Biotin, C90-99-Cys-Biotin or PMB-Cys-Mal-FL (control), with extravidin were prepared. 20 μl PMB-Cys-Biotin (10 μg) or 10 1 C90-99-Cys-Biotin (10 μg) were mixed with 20 μl extravidin (Sigma, stock at 1 mg/ml), incubated 2.5 hr at room temp, a second aliquot of 20 μl extravidin was added and incubated for 3.5 hr at room temp, PBS was added to 1 ml and the sample was stored at 4 degrees. The final concentration of conjugate in these stocks is 10 g/ml. A 10 μg/ml PMB-Cys-Mal-FL/extravidin control stock was made by mixing 16 μl PMB-Cys-Mal-FL (2 μg each), 12.5 μl extravidin (Sigma; stock at 1 mg/ml) to 0.2 ml with PBS. The H16 bacterial strain was selected for testing. This is a K1 encapsulated, serum resistant pathogenic bacteria. A fresh TSA plate was streaked with the H16 strain, grown overnight at 37 degrees and used to inoculate a 5 ml 2XYT (16 g Bacto-tryptone, 10 g yeast extract, 5 g NaCl per 1000 ml) culture. The cells were grown to mid-log ($OD_{600}$=0.5) and cells pelleted by centrifugation 5 min at 1500×g. The cells were resuspended in PBS to 0.2 $OD_{600}$/ml (estimated to be $2\times10^8$ cells/ml). 0.1 ml cells were added to 900 μl PBS in 10 siliconized microfuge tubes. Test conjugates were added, to the indicated final concentration, to each tube as follows:

1) 1 μg/ml PMB-Cys-Mal-FL (100 μl of stock solution)
2) 1 μg/ml PMB-Cys-Biotin (100 μl of stock solution)
3) 100 ng/ml PMB-Cys-Biotin (10 μl of stock solution)
4) 10 ng/ml PMB-Cys-Biotin (1 μl of stock solution)
5) 1 μg/ml C90-99-Cys-Biotin (100 μl of stock solution)
6) 100 ng/ml C90-99-Cys-Biotin (10 μl of stock solution)
7) 10 ng/ml C90-99-Cys-Biotin (1 μl of stock solution)
8) 1 μg/ml PMB-Cys-Biotin/extravidin premixed conjugate (added 100 μl of premixed conjugate)
9) 1 μg/ml C90-99-Cys-Biotin/extravidin premised pre-conjugate (added 100 μl of premixed conjugate)
10) 1 g/ml PMB-Cys-Mal-FL/extravidin premixed conjugate (added 100 μl of premixed conjugate)

Tubes 1–7 were incubated 15 min at room temp, cells pelleted by centrifugation 5 min at 500 rpm in microcentrifuge, then resuspended in 1 ml Extravidin solution (2 μg/ml in PBS). The samples were incubated 30 min at room temp, then all 10 samples were centrifuged as described above. The pellets were washed X with PBS (resuspended pellets in 1 ml PBS and recentrifuged for each wash). The pellets were resuspended in 1 ml PBS, and 100 μl of a 1/10 dilution ($2\times10^6$ cells/ml) or a 1/100 dilution ($2\times10^5$ cells/ml) were pipetted into duplicate wells of a 96-well microtiter plates (Falcon, Pro-Bind Assay Plates). The wells were coated 2 hrs at room temperature. The bacterial suspensions were decanted, and all wells were washed three times using PBS. In order to block non-specific binding sites, 100 μl of 1% gelatin (Sigma, St. Louis, Mo.) in PBS (blocking solution) was then added to each well, and the plates were incubated for 1 hr. at 37° C. The blocking solution was decanted, and 100 μl of 1/5000 diluted rabbit anti-avidin antibody (Sigma) in blocking buffer with 0.5% Tween 20 was added to each well, and the plate stored overnight at 4 degrees, then incubated 1 hr at 37° C. The antibody solutions were decanted and the plates were washed as described above. To each well, 100 μl of 1/1000 diluted goat anti-rabbit IgG alkaline phosphatase (Sigma) in blocking buffer with 0.5% Tween 20 was added, and the plate incubated 1 hr at 37° C. The antibody solutions were decanted and the plates were washed as described above, substituting 50 mM $Na_2CO_3$, pH 9.5 for the PBST in the final wash. The plates were developed by the addition of 100 μl of a solution containing 1 mg/ml para-nitro phenyl phosphate (Sigma, St. Louis, Mo.) dissolved in 50 mM $Na_2CO_3$, 10 mM $MgCl_2$, pH 9.5 to each well, and incubating the plates at room temperature in the dark overnight. The absorbency of each well was measured at 410 nm using a Dynatech MR 700 plate reader. The results are summarized in Table 55, and represent mean reactivities of duplicate wells.

TABLE 55

Anti-Avidin Antibody Opsonization [Coated H16 Bacteria]

| Sample (conjugate) | Format | ELISA titer ($2\times10^6$ bacteria) | ELISA titer ($2\times10^5$ bacteria) |
|---|---|---|---|
| 1) 1 μg/ml PMB-Cys-Mal-FL | Extravidin and anti-avidin chase | 0.162 | 0.005 |
| 2) 1 μg/ml PMB-Cys-Biotin | Extravidin and anti-avidin chase | 1.389 | 0.776 |
| 3) 100 ng/ml PMB-Cys-Biotin | Extravidin and anti-avidin chase | 1.037 | 0.050 |
| 4) 10 ng/ml PMB-Cys-Biotin | Extravidin and anti-avidin chase | 0.398 | 0.000 |
| 5) 1 μg/ml C90-99-Cys-Biotin | Extravidin and anti-avidin chase | 0.238 | 0.033 |
| 6) 100 ng/ml C90-99-Cys-Biotin | Extravidin and anti-avidin chase | 0.101 | 0.035 |
| 7) 10 ng/ml C90-99-Cys-Biotin | Extravidin and anti-avidin chase | 0.002 | 0.000 |
| 8) 1 μg/ml PMB-Cys-Biotin/ Extravidin | Premixed conjugate with anti-avidin chase | 1.455 | 1.426 |
| 9) 1 μg/ml C90-99-Cys-Biotin/ Extravidin | Premixed conjugate with anti-avidin chase | 1.416 | 1.258 |
| 10) 1 μg/ml PMB-Cys-Mal-FL/ Extravidin | Premixed conjugate with anti-avidin chase | 0.813 | 0.349 |

The results clearly demonstrate that:

1) PMB-Cys-Biotin binds stably to H16 bacteria, and is available for subsequent binding to extravidin.

2) Extravidin binding to prebound PMB-Cys-Biotin or single step PMB-Cys-Biotin/extravidin premixed conjugate binding to bacteria is stable (the bacteria were coated 3 hr at room temperature, washed, and blocked 1 hr before anti-avidin antibody was added.

3) Bacterially bound PMB-Cys-Biotin/extravidin complexes, assembled using premix or chase format, can recruit anti-avidin antibody to H16 bacteria. The relative signal is clearly higher than the control PMB-Cys-Mal-FL chase or premix with extravidin. This clearly indicates PMB containing Immunoadapter™ compound mediated anti-avidin opsonization of the pathogenic encapsulated H16 strain.

4) Single step C90-99-Cys-Biotin/extravidin premixed conjugate binding to bacteria is stable (the bacteria were coated 3 hr at room temperature, washed, and blocked 1 hr before anti-avidin antibody was added).

5) Bacterially bound C90-99-Cys-Biotin/extravidin complexes, assembled using premix (but not chase format), can recruit anti-avidin antibody to H16 bacteria. The relative signal is clearly higher than the control PMB-Cys-Mal-FL chase or premix with extravidin. This clearly indicates C90-99 containing Immunoadapter™ compound mediated anti-avidin opsonization of the pathogenic encapsulated H16 strain.

6) The use of PMB as a ligand results in higher ELISA signals than C90-99; this probably reflects the higher affinity of PMB for LPS.

EXAMPLE 46

Phagocytosis of PMB-Cy-Biotin/Extravidin Anti-Avidin Opsonized J5 cells: Chase Format As outlined in Example 45, the chase format utilizing a PMB-Cys-Biotin/extravidin premixed conjugate with an anti-avidin antibody chase maximally opsonized H16 bacteria. This format was selected for initial determination if Immunoadapter™ compounds can be utilized to stimulate immune effector functions. The example involved I) development of a phagocytosis assay and II) assessment of phagocytosis of PMB-Cys-Biotin/extravidin/anti-avidin opsonized J5 bacteria relative to that of J5 cells opsonized with control reagents.

I. Development of a Phagocytosis Assay

A phagocytosis assay was developed utilizing the J774A.1 mouse macrophage cell line. The cell line (ATCC# TIB-67) was grown in Dulbecco's modified eagle medium (D-MEM)+glutamine, with 10% heat killed fetal calf serum and 100 units ml penicillin plus 100 μg/ml streptomycin (Gibco/BRL). The cell line is adherent, and was serially passaged after 3–4 days growth at 37 degrees in $CO_2$ controlled incubator. For phagocytosis, a flask of cells (after 3–4 days growth) was rinsed with 40 mls Hanks balanced salt solution (HBSS; Gibco/BRL) and cells resuspended in 40 mls HBSS. The cells were transferred to a Falcon 2098 tube (50 ml) and centrifuged 5 min at 250 g in Beckman GS-6. Pelleted cells were resuspended in 1–2 ml HBSS, and cell density quantified on a hemocytometer. Cells were stored on ice until used. Cell viability was not diminished after 2 hrs storage.

Opsonized bacteria were prepared as follows. A 5 ml 2XYT media bacterial culture was set, and bacteria grown at 37° C. until mid-log phase (0.5–1.0 $OD_{600}$). Cells were pelleted by centrifugation 5 min at 3000 rpm in Beckman GS-6 centrifuge, and bacteria resuspended (vortexing) to density of $1>10^9$ cells/ml (1.0 $OD_{600}$) in HBSS. Cells were diluted 1/10 in HBSS in 1.5 ml siliconized microcentrifuge tubes, vortexed, and test opsonins added. The samples were incubated 15–20 min at room temperature, then stored on ice until use. Samples were vortexed immediately before adding to macrophages. Vortexing is important to prevent bacterial clumping, which would result in macrophage adherent clumps of bacteria.

1–2.5×$10^6$ J774 cells were diluted to 0.9 ml with HBSS in Falcon 2063 tubes, and 1×$10^7$ opsonized bacteria (0.1 ml of opsonized bacteria from above) immediately added, the tube capped, and rotated (end over end) at 37 degrees for 20 minutes to allow phagocytosis of opsonized bacteria. Samples were centrifuged 5 min at 250 g in a Beckman GS-6 centrifuge at 4 degrees. This pellets macrophages and associated bacteria but not free bacteria. The supernatant was decanted (macrophages visible as white pellet), 2 ml HBSS added, and the macrophage pellet carefully resuspended with a P-1000 pipette. The sample was repelleted and rewashed a total of 3×. The pellet was resuspended in 1 ml HBSS, underlayed with 1 ml 30% sucrose and recentrifuged as above for 8 minutes. The supernatant was carefully removed with a P-1000, and the pellet resuspended in 1 ml HBSS. Samples were maintained on ice throughout the experiment to limit killing of internalized bacteria.

Phagocytosed bacteria were quantified utilizing two methodologies. Internalized viable cells were released from the macrophages by diluting 3 μl cells into 3 ml $dH_2O$. The sample was vortexed, incubated 10 min at room temperature (to lyse macrophage cells by osmotic shock), revortexed, and 10 and 100 μl aliquots plated on TSA plates. Plates were incubated overnight at 37 degrees, and viable bacteria quantified. As well, internalized bacteria were directly identified cytologically. Coverslips were overlayed with 100 μl cells and incubated 15–20 min at 37 degrees in a moist chamber (on PBS saturated Whatman 3 MM chromatography paper in a covered chamber). The coverslips were rinsed with HBSS (Hanks Buffered Salt Solution (Gibco/BRL)) (prewarmed to 37 degrees) and air dried. Adhered macrophages were cytostained utilizing the Diff-Quick staining kit (Baxter) exactly as described by manufacturer. After drying, a drop of SP Accu-mount 60 (Baxter) was added to the coverslip, and the preparation mounted on a slide. Macrophage were observed at 1000× magnification under oil immersion. Phagocytosed bacteria were easily identified as dark blue rods in the light blue cytoplasm. Phagocytotic activity was determined by quantification of the % macrophage that had internalized at least 1 bacteria (100 macrophage counted for each sample). Both quantification methods yield similar values for relative phagocytosis values.

II. Assessment of Phagocytosis of PMB-Cys-Biotin/Extravidin/Anti-Avidin Opsonized J5 Bacteria Relative to that of J5 Cells Opsonized With Control Reagents Six opsonized bacterial samples were assayed for macrophage phagocytosis. The samples were prepared as outlined below.

A PMB-Cys-Biotin/Extravidin premixed conjugate (extravidin rather than avidin was utilized, since extravidin has lower background binding to bacteria than avidin) was prepared as follows. In a 1.5 ml microfuge tube, 100 μl Extravidin (Sigma; at 1 mg/ml) and 80 μl PMB-Cys-Biotin (40 μg) and 20 μl PBS were mixed and incubated >1 hr at room temperature, then stored at 4 degrees. The final concentration of PMB-Cys-Biotin in the sample was 200 μg/ml, extravidin concentration was 500 μg/ml. The extravidin solution can bind approximately 18 μg biotin/mg extravidin.

Biotin comprises approximately 10% of the PMB-Cys-Biotin molecule. Thus the reaction contains approximately 20 µg/ml biotin and 9 µg/ml biotin binding capacity (extravidin). Thus, the extravidin should be saturated with PMB-Cys-Biotin, and thus be tetrameric for PMB. Control stocks of extravidin (100 µl extravidin+100 µl PBS) and PMB-Cys-Biotin (80 µl PMB-Cys-Biotin+120 µl PBS) were made and stored at 4 degrees.

A stock of 1/10 diluted, J5 absorbed anti-avidin antibody was prepared as follows. Approximately $1\times10^9$ J5 cells from an overnight TSA plate were added to 1 ml HBSS in a 1.5 ml microfuge tube. The cells were pelleted by centrifugation 1 min at 12,000×g in microfuge, resuspended in 0.9 ml HBSS and 100 µl anti-avidin (rabbit polyclonal serum; Sigma) added. The tube was rotated 90 min at 4 degrees, the bacteria pelleted as described above. The sample was filter sterilized and stored at 4 degrees.

To $1\times10^8$ J5 bacteria in HBSS in microfuge tubes (prepared as described above), the following test solutions (from above were added:

1) 2.5 µl PMB-Cys-Biotin premixed conjugate (0.5 µg/ml PMB-Cys-Biotin final concentration)
2) 2.5 µl PMB-Cys-Biotin premixed conjugate (0.5 µg/ml PMB-Cys-Biotin final concentration)+10 µl J5 absorbed anti-avidin (1/1000 final dilution)
3) 10 µl J5 absorbed anti-avidin (1/1000 final dilution)
4) negative control
5) 2.5 µl PMB-Cys-Biotin stock (0.5 µl final concentration)+10 µl J5 absorbed anti-avidin (1/1000 final concentration)
6) 2.5 µl extravidin stock+10 µl J5 absorbed anti-avidin (1/1000 final concentration)

The bacteria were opsonized, and the phagocytosis assay performed as described above. Samples 1–4 were tested in duplicate independent experiments. The results are shown in Tables 56 and 57 below. (Note that the following key applies: 1) From 100 macrophage examined, 2) From 100 µl plating of a 10-3 dilution of macrophage in $dH_2O$)

TABLE 56

Opsonization With PMB-Cys-Biotin/Extravidin in a
Chase Format with Anti-Avidin Enhances Phagocytosis

| Test Conjugate | % Macrophage with phagocytosed bacteria[1] | Recovered bacterial colonies[2] |
|---|---|---|
| PMB-Cys-Biotin/extravidin (premixed) + anti-avidin | 60 | 178 |
| PMB-Cys-Biotin/extravidin premixed conjugate | 23 | 67 |
| anti-avidin | 14 | 46 |
| negative control | 14 | 72 |

TABLE 57

Opsonization with PMB-Cys-Biotin/Extravidin in a
Chase Format With Anti-Avidin Enhances Phagocytosis
Relative to PMB-Cys-Biotin or Extravidin Opsonized Cells

| Test Conjugate | % Macrophage with phagocytosed bacteria[1] | Recovered bacterial colonies[2] |
|---|---|---|
| PMB-Cys-Biotin/extravidin (premixed) + anti-avidin | 77 | 329 |
| PMB-Cys-Biotin/extravidin premixed conjugate | 16 | 72 |

TABLE 57-continued

Opsonization with PMB-Cys-Biotin/Extravidin in a
Chase Format With Anti-Avidin Enhances Phagocytosis
Relative to PMB-Cys-Biotin or Extravidin Opsonized Cells

| Test Conjugate | % Macrophage with phagocytosed bacteria[1] | Recovered bacterial colonies[2] |
|---|---|---|
| anti-avidin | 24 | 80 |
| negative control | 21 | 78 |
| PMB-Cys-Biotin + anti-avidin | 21 | 74 |
| Extravidin + anti-avidin | 22 | 57 |

The results demonstrate that opsonization with PMB-Cys-Biotin/Extravidin premixed conjugate followed by an anti-avidin chase targets cells for phagocytosis by the macrophage cell line; the control opsonization samples clearly demonstrate that this enhancement is antibody dependent. Therefore these results provides proof of principle for the use of Immunoadaptor™ compounds to target antibody effector functions, using avidin to link Immunoadaptor™ compounds as tetramers with anti-avidin in a chase format.

EXAMPLE 47

Phagocytosis of PMB-Cys-Biotin/Extravidin/Anti-Avidin Opsonized J5 cells: Premix and Chase Format As demonstrated in Example 46, opsonization of J5 bacteria utilizing a PMB-Cys-Biotin/extravidin premixed conjugate with an anti-avidin chase stimulated phagocytosis. Phagocytosis utilizing a PMB-Cys-Biotin/extravidin/antiavidin premix was assessed, to determine if a premix of the components can also target immune effector functions (phagocytosis). The example involved assessment of phagocytosis of PMB-Cys-Biotin/extravidin/anti-avidin opsonized J5 bacteria in a premix or chase format, relative to that of J5 cells opsonized with control reagents.

The phagocytosis assay was performed exactly as described in Example 46, using, where relevant, the same reagents as Example 46. Six opsonized bacterial samples were assayed for macrophage phagocytosis. Samples not described in Example 46 were prepared as follows.

A PMB-Cys-Biotin/Extravidin/antiavidin premixed conjugate (extravidin rather than avidin was utilized, since extravidin has lower background binding to bacteria than avidin) was prepared as follows. In a 1.5 ml microfuge tube, 10 µl Extravidin (Sigma; at 1 mg/ml) and 8 µl PMB-Cys-Biotin (4 µg) and 24 µl PBS were mixed and incubated 1 hr at room temperature, then 8 µl monoclonal anti-avidin added (Sigma) and the sample premixed overnight at 4 degrees. Final concentration of PMB-Cys-Biotin in sample is 80 µg/ml, extravidin concentration is 200 µg/ml.

To $1\times10^8$ J5 bacteria in HBSS in microfuge tubes (prepared as described above), the following test solutions (from above) were added:

1) 2.5 µl PMB-Cys-Biotin/extravidin premixed conjugate (Example 46; 0.5 µg/ml PMB-Cys-Biotin final concentration)
2) 2.5 µl PMB-Cys-Biotin/extravidin premixed conjugate (Example 46; 0.5 µg/ml PMB-Cys-Biotin final concentration)+10 µl J5 absorbed anti-avidin polyclonal (Example 46; 1/1000 final dilution)
3) 5 µl PMB-Cys-Biotin/extravidin/anti-avidin monoclonal premixed conjugate (0.4 µg/ml PMB-Cys-Biotin final concentration)

4) 2.5 µl PMB-Cys-Biotin/extravidin premixed conjugate (Example 6; 0.5 µg/ml PMB-Cys-Biotin final concentration), 2 min room temp,+1 µl anti-avidin monoclonal antibody (1/1000 final dilution)

5) 1 µl anti-avidin monoclonal (1/1000 final concentration)

6) negative control

The bacteria were opsonized, and the phagocytosis assay performed as described in Example 46 above. The results are shown in Table 58 below. (Note that for the following table the following key applies: 1) From 100 macrophage examined and 2) From 100 µl plating of a 10-3 dilution of macrophage in distilled $H_2O$)

TABLE 58

Opsonization With PMB-Cys-Biotin/Extravidin in a
Premix or Chase Format with Anti-Avidin Enhances Phagocytosis

| Test Conjugate | % Macrophage with phagocytosed bacteria[1] | Recovered bacterial colonies[2] |
|---|---|---|
| PMB-Cys-Biotin/extravidin premixed conjugate + anti-avidin polyclonal | 62 | 222 |
| PMB-Cys-Biotin/extravidin premixed conjugate | 25 | 54 |
| anti-avidin monoclonal | 22 | 30 |
| negative control | 23 | 76 |
| PMB-Cys-Biotin/extravidin + anti-avidin monoclonal (premix) | 63 | 154 |
| PMB-Cys-Biotin/ extravidin + anti-avidin monoclonal (chase) | 75 | 208 |

The results demonstrate that opsonization with PMB-Cys-Biotin/Extravidin premixed conjugate in a premix format with monoclonal anti-avidin or in a chase format with monoclonal or polyclonal anti-avidin targets cells for phagocytosis by the J774 macrophage cell line; the control opsonization samples clearly demonstrate that the observed enhancement of phagocytosis is dependant on the presence of both premixed conjugate and antibody. These results provides proof of principle for the use of Immunoadapter™ compounds to target antibody effector functions, using premix or chase formats with monoclonal or polyclonal antibodies.

EXAMPLE 48

Phagocytosis of PMB-Cys-Mal-FL/Antibody Opsonized J5 cells: Chase and Premix Format As demonstrated in Examples 46 and 47, opsonization of J5 bacteria utilizing a PMB-Cys-Biotin/extravidin premixed conjugate with an anti-avidin premix or chase stimulated phagocytosis. In Example 41, it was demonstrated that PMB-Cys-Mal-FL could recruit anti-fluorescein antibody to the bacterial surface. The phagocytosis assay was utilized, with PMB-Cys-Mal-FL and anti-fluorescein antibody, to determine if enhanced phagocytosis is also observed in premix and chase formats when an antibody reactive to the Immunoadapter™ compound hapten (rather than extravidin) is utilized. The example involved assessment of phagocytosis of PMB-Cys-Mal-FL/anti-fluorescein antibody opsonized J5 bacteria in a premix or chase format, relative to that of J5 cells opsonized with PMB-Cys-Mal-FL or anti-fluorescein antibody alone.

The phagocytosis assay was performed exactly as described in examples 46 and 47, using the PMB-Cys-Biotin/extravidin premixed conjugate and anti-avidin reagents described in Example 46. A PMB-Cys-Mal-FL/anti-fluorescein premixed conjugate was prepared as follows. In a 500 µl microfuge tube, 8.4 µl PMB-Cys-Mal-FL (1.0 µg) and 10 µl anti-fluorescein antibody (affinity purified 4-4-20 monoclonal, stock at 2 mg/ml) were mixed and incubated overnight at 4 degrees. Binding of anti-fluorescein antibody to the FL hapten was confirmed by the visible quenching of fluorescein in the sample (observed immediately after adding antiserum.

Six opsonized bacterial samples were assayed for macrophage phagocytosis. To $1\times10^8$ J5 bacteria in HBSS in microfuge tubes (prepared as described above), the following test solutions (from above) were added:

1) Negative control
2) 2.5 µl PMB-Cys-Biotin/extravidin premixed conjugate (made fresh as described in Example 46; 0.5 µg/ml PMB-Cys-Biotin final concentration)+10 µl J5 absorbed anti-avidin polyclonal (Example 46; 1/1000 final dilution)
3) 5 µl anti-fluorescein antibody (10 µg/ml final concentration).
4) 4.2 µl PMB-Cys-Mal-FL (0.5 µg/ml final concentration).
5) 9.2 µl PMB-Cys-Mal-FL/anti-fluorescein antibody premixed conjugate (0.5 µg/ml PMB-Cys-Mal-FL, 10 µg/ml anti-fluorescein antibody)
6) 4.2 µl PMB-Cys-Mal-FL, 2 min room temp, 5 µl antibody (0.5 µg/ml PMB-Cys-Mal-FL, 10 µg/ml anti-fluorescein antibody)

The bacteria were opsonized, and the phagocytosis assay performed as described above. The results are shown in Table 59 below. (Note that: 1=From 100 macrophage examined and 2=From 100 µl plating of a 10-3 dilution of macrophage in $dH_2O$)

TABLE 59

Opsonization with PMB-Cys-Biotin/Extravidin in a
Premix or Chase Format with Anti-Avidin Enhances Phagocytosis

| Test Conjugate | % Macrophage with phagocytosed bacteria[1] | Recovered bacterial colonies[2] |
|---|---|---|
| PMB-Cys-Biotin/extravidin premixed conjugate + anti-avidin polyclonal | 60 | 91 |
| Negative control | 13 | 21 |
| anti-fluorescein | 14 | 6 |
| PMB-Cys-Mal-FL | 15 | 29 |
| PMB-Cys-Mal-FL/anti-fluorescein antibody (premix) | 29 | 52 |
| PMB-Cys-Mal-FL anti-fluorescein antibody (chase) | 40 | 76 |

The results demonstrate that opsonization with PMB-Cys-Mal-FL in a premix or chase format with monoclonal anti-fluorescein antibody targets cells for phagocytosis by the J774 macrophage cell line; the control opsonization samples clearly demonstrate that the observed enhancement of phagocytosis is dependant on the presence of both premixed conjugate and antibody. These observations are duplicated in a second independent assay (Example 49). These results provides proof of principle for the use of Immunoadapter™ compounds to target antibody effector functions, using premix or chase formats with a monoclonal antibody directly reactive to the Immunoadapter™ compound hapten.

EXAMPLE 49

Phagocytosis of C90-99-Cys-Biotin/Extravidin/ Anti-Avidin Opsonized J5 Cells

As demonstrated in Examples 46–48, opsonization of J5 bacteria utilizing PMB containing conjugates in premix or chase formats stimulated phagocytosis. PMB is a member of a class of molecules that bind the bacterial cell surface through interactions with LPS. Conjugates of other LPS binding molecules (e.g., C90-99; Grey and Haseman, 1994, Infect. Immun. 62, 2732; and C19g; Darveau et al., 1992, J. Clin. Invest. 90, 447–455) were made to either Fl (C19g-Mal-Fl; described in Example 39) or biotin (C90-99-Cy-Biotin; described in Example 39). The phagocytosis assay was used to determine if enhanced phagocytosis is also observed in chase formats when Immunoadapter™ compounds utilizing these non-PMB targeting ligands are utilized. This will determine if the observed enhanced phagocytosis in Examples 46–48 is PMB specific or is a general feature of Immunoadapter™ compounds that utilize LPS binding molecules. The example involved assessment of phagocytosis utilizing Immunoadapter™ compounds containing various LPS binding peptides as ligand domain.

The phagocytosis assay was performed exactly as described in examples 46–48, except only % phagocytosed bacteria are described. The Example utilized the anti-avidin reagents described in Example 46, and the PMB-Cys-Mal-FL and anti-fluorescein described in Example 48. A C90-99-Cys-Biotin/Extravidin premixed conjugate (extravidin rather than avidin was utilized, since extravidin has lower background binding to bacteria than avidin) was prepared as follows. In a 1.5 ml microfuge tube, 100 µl Extravidin (Sigma; at 1 mg/ml) and 40 µl C90-99-Cys-Biotin (40 µg) and 20 µl PBS were mixed and incubated>1 hr at room temperature, then stored at 4 degrees. Final concentration of C90-99-Cys-Biotin in sample is 200 µg/ml, extravidin concentration is 500 µg/ml. The extravidin solution can bind approximately 18 µg biotin/mg extravidin. Biotin comprises approximately 10% of the C90-99-Cys-Biotin molecule. Thus the reaction contains 20 µg/ml biotin and 9 µg/ml biotin binding capacity (extravidin). Thus, the extravidin should be saturated with C90-99-Cys-Biotin, and thus be tetrameric for the ligand (C90-99).

Two independent phagocytosis assays were conducted, using independently opsonized bacterial samples. To $1\times10^8$ J5 bacteria in HBSS in microfuge tubes (prepared as described above), the following test solutions (from above) were added:

Experiment 1

1) Negative control
2) 5 µl C90-99-Cys-Biotin/extravidin premixed conjugate (0.5 µg/ml PMB-Cys-Biotin final concentration)+20 µl J5 absorbed anti-avidin polyclonal (Example 46; 1/500 final dilution)
3) 20 µl J5 absorbed anti-avidin polyclonal (Example 37; 1/500 final dilution)
4) 5 µl C90-99-Cys-Biotin/extravidin premixed conjugate (0.5 µg/ml PMB-Cys-Biotin final concentration)
5) 3.5 µl anti-fluorescein antibody (7 mg/ml stock, 25 µg/ml final concentration)
6) 4.2 µl PMB-Cys-Mal-FL (0.5 µg/ml final concentration)
7) 4.2 µml PMB-Cys-Mal-FL, 2 min room temp, 3.5 µl anti-fluorescein antibody (0.5 µg/ml PMB-Cys-Mal-FL, 25 µg/ml anti-fluorescein)(fluorescein chase)
8) 4.2 µl PMB-Cys-Mal-FL+3.5 µl anti-fluorescein antibody (0.5 µg/ml PMB-Cys-Mal-FL, 25 µg/ml anti-fluorescein antibody), premix 10 min room temperature (fluorescein premix)

The bacteria were opsonized, and the phagocytosis assay performed as described above. The results are shown in Table 60 below. (Note that 1=From 100 macrophage examined)

TABLE 60

Opsonization with C90-99-Cys-Biotin/Extravidin in a chase format with anti-avidin

| Test Conjugate | % macrophage with phagocytosed bacteria[1] |
|---|---|
| 1) Negative control | 2 |
| 2) C90-99 premixed conjugate + anti-avidin | 8 |
| 3) anti-avidin | 3 |
| 4) C90-99 premixed conjugate | 3 |
| 5) anti-fluorescein | 4 |
| 6) PMB-Cys-Mal-FL | 5 |
| 7) Fluorescein chase | 14 |
| 8) Fluorescein premix | 12 |

Clear elevation of phagocytosis was observed in the Fl chase and Fl premix samples (relative to controls) and a 2 fold increase with C90-99 premixed conjugate+anti-avidin was observed, relative to the C90-99 premixed conjugate or anti-avidin controls. The assay was repeated, to determine if the observed enhancement of phagocytosis is repeatable. As well, a C19g-Mal-FL conjugate was tested for enhancement of phagocytosis when incubated with anti-fluorescein antibody in a chase format.

To $1\times10^8$ J5 bacteria in HBSS in microfuge tubes (prepared as described above), the following test solutions (from above) were added:

Experiment 2

1) Negative control
2) 5 µl C90-99-Cys-Biotin/extravidin premixed conjugate (0.5 µg/ml PMB-Cys-Biotin final concentration)+25 µl J5 absorbed anti-avidin polyclonal (Example 46; 1/400 final dilution)
3) 25 µl J5 absorbed anti-avidin polyclonal (Example 46; 1/400 final dilution)
4) 5 µl C90-99-Cys-Biotin/extravidin premixed conjugate (0.5 µg/ml PMB-Cys-Biotin final concentration)
5) 2.0 µl anti-fluorescein antibody (7 mg/ml stock, 14 µg/ml final concentration)
6) 4.2 µl PMB-Cys-FL (0.5 µg/ml final concentration)
7) 4.2 µl PMB-Cys-FL, 2 min room temp, 2.0 µl antibody (0.5 µg/ml PMB-Cys-FL, 14 µg/ml anti-fluorescein antibody)(fluorescein chase)
8) 3.2 µl C19g-Cys-FL (0.5 µg/ml final concentration)
9) 3.2 µl C19g-Mal-FL, 2 min room temp, 2.0 µl antibody (0.5 µg/ml C19g-Mal-FL, 14 µg/ml anti-fluorescein antibody)(C19g chase)

The bacteria were opsonized, and the phagocytosis assay performed as described above. The results are shown in Table 61 below. (Note that 1=From 100 macrophage examined)

TABLE 61

Opsonization with C90-99-Cys-Biotin/Extravidin in a Chase Format with Anti-Avidin Enhances Phagocytosis

| Test Conjugate | % macrophage with phagocytosed bacteria[1] |
|---|---|
| 1) Negative control | 8 |
| 2) C90-99 premixed conjugate + anti-avidin | 19 |

TABLE 61-continued

Opsonization with C90-99-Cys-Biotin/Extravidin in a
Chase Format with Anti-Avidin Enhances Phagocytosis

| | Test Conjugate | % macrophage with phagocytosed bacteria[1] |
|---|---|---|
| 3) | anti-avidin | 4 |
| 4) | C90-99 premixed conjugate | 4 |
| 5) | anti-fluorescein | 13 |
| 6) | PMB-Cys-Mal-FL | 8 |
| 7) | Fluorescein chase | 43 |
| 8) | C19g-Mal-FL | 8 |
| 9) | C19g chase | 10 |

The assay demonstrates that the 2 fold enhancement of phagocytosis by C90-99 premixed conjugate+anti-avidin seen above is reproducible. This enhancement is considerably lower than that observed with the PMB-Cys-Mal-FL/anti-fluorescein antibody chase, which utilizes PMB as a targeting ligand. This is likely to be due to the reduced affinity of the C90-99 ligand for LPS relative to PMB. Indeed, this reduced affinity is reflected by reduced bacterial binding of the C90-99-Cys-Biotin conjugate relative to the PMB-Cys-Biotin conjugate (Example 45). C19g also has reduced affinity for LPS relative to PMB; it is probably that this reduced affinity prevents the C19g-Mal-FL conjugate from enhancing bacterial phagocytosis in the assay. These results provides proof of principle for the use of Immunoadapter™ compounds containing LPS binding ligands to target antibody effector functions; the affinity of the LPS binding ligand will be critical for maximal opsonization and subsequent phagocytosis.

EXAMPLE 50

Synthesis of a Depyrogenation Resin

Since monocysteinyl PMB was as active as PMB and had a free thiol group that can serve as an attachment point to an insoluble support, it should be possible to prepare a depyrogenation resin using this compound. The polymeric support should be hydrophilic so that the resin can be used for the removal of pyrogens from preparations. With these considerations in mind, we reacted Tentagel™—S—$NH_2$ (160 $\mu$mole $NH_2$/g) was reacted with N-hydroxysuccinimide ester of 3-maleimidobenzoic acid. After washing the resin, it was reacted with PMB-Cys to afford a PMB loaded resin. As expected, the resin was effective in removing pyrogen from an aqueous solution as determined by an Limulus Amebocyte Lysate assay (LAL; Associates of Cape Code).

EXAMPLE 51

Synthesis of a Fimbriae-Binding Compound

Several pathogenic bacteria have fimbriae or pili located on their surface. The present invention contemplates molecules that bind to the receptors on these pili may be used for targeting antibodies to these bacteria. Type 1 pili contain receptors for α-linked mannosides. Sharon has shown that the α-linked aromatic mannosides bind to the receptors on type 1 pili up to 700 times more strongly than methyl α-mannosides. (See N. Firon et al., Infect. Immunity 55:472 (1987)). The examples described by Sharon, however, have aromatic groups which do not permit any conjugation to other molecules.

An aromatic mannoside of the present invention is herein described that is amenable to a broad range of conjugation chemistries. The molecule has been found to have a high binding affinity for type 1 pili.

Starting with commercially available 4-aminophenyl-α-D-mannopyranoside, the N-benzoyl derivative was prepared (See Section I, below), which was found to be 1000-fold more active than methyl α-mannopyranoside in an assay that measures the inhibition of pili-induced yeast agglutination. Encouraged by these results, an N-phenylalanyl derivative of 4-aminophenyl-α-D-mannopyranoside was prepared. This molecule was also approximately 1000-fold more active than methyl mannoside in the same assay. This molecule bears an aliphatic primary amine which is amenable for a broad range of conjugation chemistries and thus, as one example of beneficial use, it can be utilized in an Immunoadaptor™ compound.

I. Preparation of 4-Benzamidophenyl-α-D-mannopyranoside

4-Aminophenyl-α-D-mannopyranoside (10 mg) (Sigma) was dissolved in pyridine and a few crystals of N,N-dimethylaminopyridine were added. The solution was cooled to 0° C. and benzoyl chloride (6 $\mu$l) was added. The mixture was stirred at 0° C. for 45 minutes and then at room temperature overnight. The solvent was evaporated in vacuo and chloroform (ca. 1.5 ml) was added to the residue followed by enough methanol to give a clear solution. Ether was then added to the cloud point and the material was allowed to crystallize. The solvent was removed by decanting and the crystals were washed with ether.

II. Preparation of 4-(N-phenylalanyl)-aminophenyl-α-D-mannopyranoside

To a solution of Boc-phenylalanine (353 mg) (Bachem) in anhydrous methylene chloride (12 ml) at 0° C. was added dropwise, under nitrogen, a solution of dicyclohexylcarbodiimide (DCC, 137 mg) in dichloromethane (12 ml). The mixture was stirred at 0° C. for 90 min and then at room temperature for 30 min. The resulting dicyclohexylurea (DCU) was removed by filtration and the cake was washed with a small amount of anhydrous dichloromethane. The combined organic solution was concentrated to ca. 5 ml under a stream of nitrogen gas. It was then added dropwise to a cold (0° C.) solution of 4-aminophenyl-α-D-mannopyranoside in anhydrous pyridine (18 ml). The mixture was then stirred under nitrogen at 0° C. for 1 hr and at room temperature overnight. The solvent was evaporated in vacuo. The residue was chromatographed on a flash chromatographic column using silica gel (230–400 mesh). The column was first eluted with 5% methanol in chloroform and after the non-polar impurities were eluted (TLC analysis), the eluent was changed to 10% methanol in chloroform. The fractions corresponding to the major product, 4-[N-(N-Boc-phenylalanyl)-α-D-mannopyranoside, (by TLC analysis, silica gel, 20% methanol in chloroform) were combined and evaporated to afford a white powder. The 300 MHz $^{1}H$-NMR spectrum in DMSO-$d_6$ showed all the expected signals.

The solid obtained above was dissolved in trifluoroacetic acid (TFA, 10 ml) containing 4% anisole at 0° C. and the mixture was stirred at 0° C. for 90 min. The solvent was evaporated in vacuo to afford a thick oil. Cold ether was added and the mixture was allowed to stand in an ice bath for 15 min and a solid was deposited on the walls of the container. The supernatant was separated, the residue was washed three times with cold ether and dried overnight under high vacuum (oil pump) to afford a white solid, i.e., 4-(N-phenylalanyl)-aminophenyl-α-D-mannopyranoside. The solid was easily soluble in water.

The 4-(N-phenylalanyl)-aminophenyl-α-D-mannopyranoside (the compound of Formula 1) was assayed for activity in an inhibition-of-yeast-agglutination assay, described below in Example 54 (Compound D in Table 62).

EXAMPLE 52

An Immunoadapter™ Compound Containing C1q or FcR Binding Peptides

Figure 16:
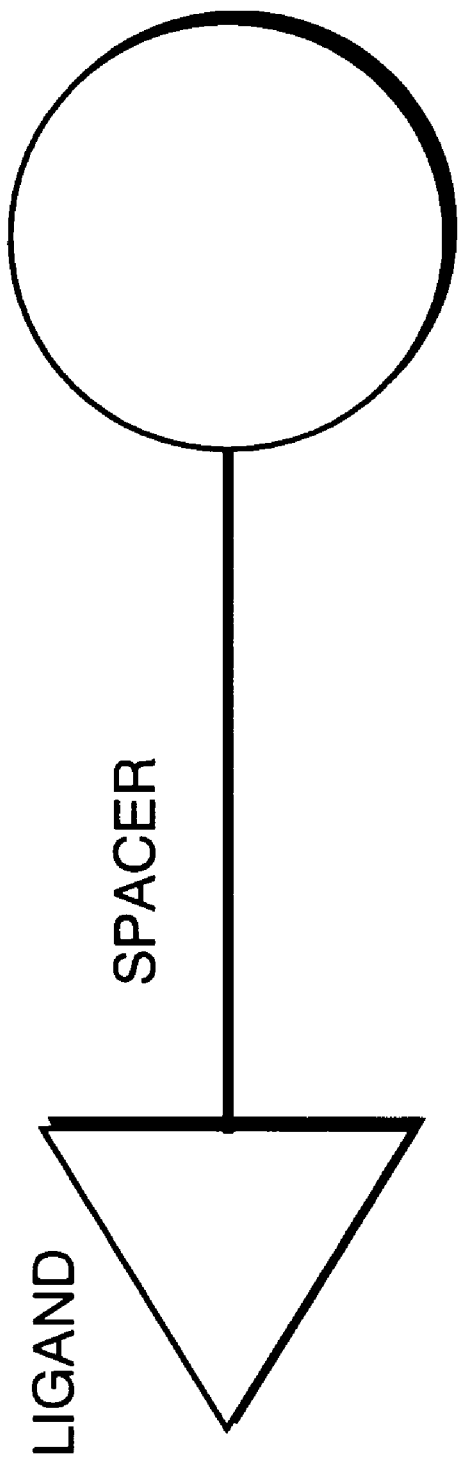
FIG. 16 shows a schematic illustrating the structure of a generic Immunoadapter™ compound.
Figure 17:
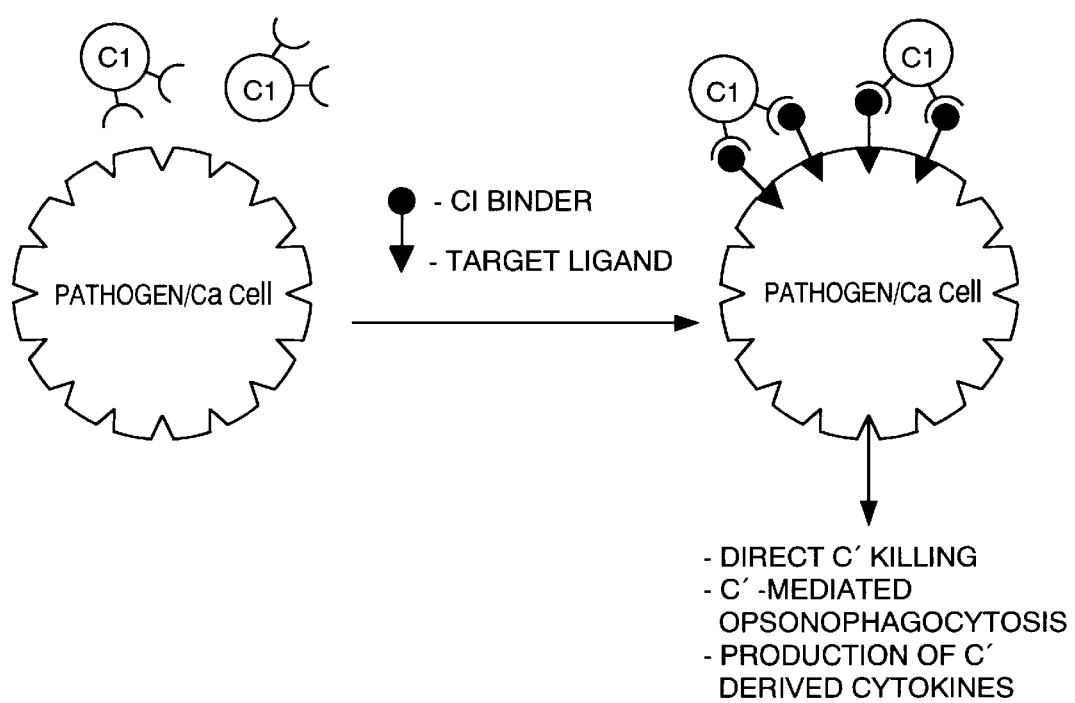
FIG. 17 shows a schematic illustrating the proposed functioning of the Immunoadaptor™ compound to combat disease.

An Immunoadapter™ molecule can be constructed incorporating the following three elements: 1) a binding ligand with specificity for the surfaces of microbes, cancer cells, or other targets of interest; 2) a molecule that binds to C1 (a peptide derived from amino acid sequence of immunoglobulin constant regions known to be the complement C1 binding domain) or the Fc receptor of phagocytic cells; and, 3) a suitable spacer between components 1 and 2 that would allow bridging between the target cell and C1 or Fc receptor. This molecule is shown schematically in FIG. 16. A proposed function in disease is illustrated in FIG. 17 (an analogous model could be constructed with a Fc receptor binder in place of C1 binder.)

The Immunoadapter™ ligand moiety has specificity for a target bacterium, cancer cell or other target. When the Immunoadaptor™ compound is administered to a diseased subject, via any number of possible routes (such as oral, parenteral, transdermal, aerosol, etc.), the ligand moiety will bind its target. A suitable ligand would have selective binding to the target of interest as compared to normal tissues which are devoid of the target. The subject's complement component C1 will then bind to the Immunoadaptor™ compound associated with the target, causing activation of C1 and initiation of the full complement cascade. The target is then subject to the destruction effects resulting from complement activation such as direct killing due to disruption of cellular membranes, opsonophagocytosis (phagocytic cells are known to have receptors for complement components that promote engulfment), or reactions due to the release of inflammatory cytokines.

It is not intended that the present invention be limited by any particular mechanism of action. Nonetheless it is believed the monomeric interaction of the C1 binding site on immunoglobulin (for example the human G isotype) with C1 is likely to be low, in the order of $10^4$ $M^{-1}$. This low affinity does not trigger the complement cascade when the immunoglobulin and complement molecules are free in plasma (or tissues). The Immunoadaptor™ molecule (which is monomeric at both ligand and complement binding sites) when free in solution should also be incapable of triggering complement activation. When the ligand attaches to the target site a multimeric presentation of the complement binding site will be created. The Immunoadaptor™ molecule would be designed to either mimic the orientation of complement binding sites of immunoglobulins at a target surface or to improve the orientation of complement binding sites. In either event, the orientation of complement binding sites would result in a high affinity association with the C1 protein, possibly by several orders of magnitude, resulting in triggering of the complement cascade. Conversely, it is possible that an increased avidity, due to multimeric association of ligand at a target surface, would result from association of the Immunoadaptor™ molecule to the C1 protein. In this mode, no target or hapten-specific immunoglobulin is needed to effect target attack. In some situations, an ill patient may need a supplement of normal plasma or complement components to promote optimum target attack. This concept can be generally applied to numerous therapeutic applications in infectious diseases, cancer or any other medical situations where target destruction is desired.

The following experiments clearly demonstrate proof of principle for these concepts. Toxin A of *C. difficile* is known to agglutinate rabbit erythrocytes at 4° C. but will not lyse the cells. If carefully removed from the 4° C. environment, the rabbit red blood cells will maintain the aggregated state when placed at room temperature and at 37° C. If toxin A protein is labeled with multimers of the peptide representing the C1q binding domain, then the complement cascade will be activated resulting in the lysis of the rabbit erythrocytes. The peptide representing the binding site for the C1q is represented by the following sequence:

```
     318 319 320 321   322
    -GLU-TYR-LYS-CYS-LYS- (SEQ ID NO:5)
```

Amino acids for positions #318, 320 and 322 (GLU, LYS and LYS cannot be substituted in the whole molecule without loss of C1q binding. A peptide represented by acetylated ALA-GLU-ALA-LYS-ALA-LYS-ALA (SEQ ID NO:6) amide (blocked N and C termini alanines) will inhibit the binding of C1q binding peptide to toxin A in two different orientations to delineate the proper conformation. This would necessitate the synthesis of the following peptides to be coupled to toxin A protein via sulfhydryl coupling: acetylated CYS-ALA-GLU-ALA-LYS-ALA-LYS-ALA (SEQ ID NO:7) amide and acetylated ALA-GLU-ALA-LYS-ALA-LYS-ALA-CYS (SEQ ID NO:8) amide.

Lipopolysaccharide (endotoxin) is sticky and could be used to coat red blood cells (human, rabbit, etc.). We have demonstrated in past experiments, along with other investigators, that polymyxin B has a high affinity in binding endotoxin. By chemically coupling PMB to C1q binding peptide, we could generate another conjugate which will bind to the endotoxin coated red blood cells resulting in a structure which will lyse in the presence of complement.

Erythrocytes are complex, differentiated cells having a mosaic structured membrane approximately 60 angstroms thick. Its chief components are stromatin, lipids, cerebrosides, gangliosides, unesterified cholesterol and glycoproteins. These components, especially the latter, are of interest because they would allow for the direct coupling of the C1q binding peptides to the erythrocyte itself. Once a critical density of peptide is achieved, the red cell will lyse in the presence of complement.

In addition to the accessibility of the Clq binding region on the IgG molecule, there appears to be another accessible peptide for the interaction with Fcγ receptors of phagocytic cells. Of the three groups of FCγRs, FCγRI has the distinctive property of high affinity for the IgG binding site. Even though monomeric IgG would occupy the receptor site on peripheral cells, large immune complexes would display a higher affinity and displace any monomeric IgG. Undoubtedly, it is the binding of the large multimeric complexes that generate cross-linking and signaling resulting in the triggering of the biological functions associated with these cell receptors. The IgG sequence which is implicated in binding to the FCγRI receptor resides in the lower hinge region of Cγ2 and consists of amino acids:

```
   234 235 236 237 238  239
   LEU-LEU-GLY-GLY-PRO-SER (SEQ ID NO:9)
```

Monoclonal antibodies to this epitope block ligand binding to the cells and bioengineering through amino acid switching disrupts the affinity of cell receptor interaction. Again, as in the previous examples for the demonstration of complement activation and lysis of erythrocytes, the receptor binding peptide will be substituted for the Clq binding peptide. The phagocytosis of red blood cells will be observed.

EXAMPLE 53

Synthesis of Other Fimbriae Binding Compounds

I. Preparation of 4-Benzamidophenyl-α-D-mannopyranoside (Compound C in Table 62)

4-Aminophenyl-α-D-mannopyranoside (10 mg) (Compound B in Table 62) was dissolved in anhydrous pyridine (1 ml) and a few crystals of 4-dimethylaminopyridine (DMAP) were added. The solution was cooled to 0° C. and benzoyl chloride (6 μl) was added. The mixture was stirred at 0° C. for 45 min and then at room temperature overnight. The solvent was evaporated in vacuo and the residue was suspended in chloroform (ca. 1.5 ml). Methanol was then added dropwise until a clear solution was obtained. Diethyl either was then added to a cloud point and the material was allowed to crystallize. The mother liquor was removed by decantation and the residue was washed with ether. The residue weighed 5 mg after drying in a vacuum dessicator.

II. Other Derivatives (A) Preparation of N-Boc, S-Acetamidomethyl-cysteinyl-[N-(phenylalanyl)]-4-aminophenyl-α-D-mannopyranoside N-(phenylalanyl)-4-aminophenyl-α-D-mannopyranoside (502 mg) was dissolved in anhydrous pyridine (7 ml) and the solution was cooled to −15° C. A solution of Boc-Cys-Acm-ONp (697 mg) in ca. 1 ml of anhydrous dichloromethane was then added dropwise. The mixture was allowed to stir under $N_2$ at 0° C. for 1 hr and at room temperature overnight. The solvent was then stripped in vacuo to afford 1.3 g. of crude product.

The crude product was loaded on a silica gel column (Merck, 230–400 mesh) and the column was eluted with 5→15% $CH_3OH$ in $CHCl_3$. The fractions were analyzed by TLC on silica gel plates (Merck, HPTLC, $F_{254}$) using 20% $CH_3OH$ in $CHCl_3$. The fractions containing the major product (i.e., N-Boc, S-acetamidomethyl-cysteinyl-[N-(phenylalanyl)]-4-aminophenyl-α-D-mannopyranoside) were combined and evaporated in vacuo to afford 210 mg of the purified product.

(B) Preparation of S-Acetamidomethyl-Cysteinyl-[N-(Phenylalanyl)]-4-Aminophenyl-α-D-Mannopyranoside (Compound E in Table 62)

200 mg of N-Boc, S-acetamidomethyl-cysteinyl-[N-(phenylalanyl)]-4-aminophenyl-α-D-mannopyranoside, prepared above, was cooled to −15° C. under $N_2$. A precooled (−15° C.) solution of 4% anisole in trifluoroacetic acid (20 ml) was then added through a double ended needle. The mixture was stirred at −15° C. under $N_2$ for 30 minutes. The solvent was stripped in vacuo and the residue was washed three times with ice cold anhydrous ether. The resulting white powder, i.e., S-acetamidomethyl-cysteinyl-[N-(phenylalanyl)]-4-aminophenyl-α-D-mannopyranoside, was extensively dried under an oil pump.

III. Preparation of a Biotinylated Compound (A) Preparation of Cysteinyl-[N-(Phenylalanyl)]-4-Aminophenyl-α-D-Mannopyranoside S-acetamidomethyl-cysteinyl-[N-(phenylalanyl)]-4-aminophenyl-α-D-mannopyranoside (75 mg) was dissolved in circa 10 ml of degassed 50% aqueous acetic acid. Solid mercury (II) acetate (318 mg) was added to the solution and the mixture was allowed to stir for 1 hr. Hydrogen sulfide gas was then bubbled through the solution for 10 min. The mixture was allowed to stir for a half hour and hydrogen sulfide was again bubbled through the solution for 10 min. The resulting black precipitate was removed by filtration over a pad of celite. The cake was washed with 50% aqueous acetic acid saturated with hydrogen sulfide and the filtrate and washings were combined and lyophilized to afford the final product, i.e., cysteinyl-[N-(phenylalanyl)]-4-aminophenyl-α-D-mannopyranoside.

(B) Preparation of Biotinylated Cysteinyl-[N-(phenylalanyl)]-4-aminophenyl-α-D-mannopyranoside (Compound F in Table 62)

Cysteinyl-[N-(phenylalanyl)]-4-aminophenyl-α-D-mannopyranoside, obtained above, was dissolved in 50 ml of degassed 1 mM EDTA. To this solution was added a solution of 200 mg of 1-biotinamido-4-[4'-maleimidomethyl)-cyclohexane-carboxamido]-butane (Biotin-BMCC) (Pierce) in 10 ml of DMSO. The mixture was stirred overnight and then lyophilysed. The crude material was purified over a CM 52 (weak cation exchange resin, Bio-Rad) using a 0→0.8 M salt gradient in 10 mM sodium phosphate, pH 6.67. The fractions were monitored by absorption at 254 nm and by ninhydrin assay. The peak that gave strongly positive ninhydrin reaction was considered as the material of interest, i.e., biotinylated cysteinyl-[N-(phenylalanyl)]-4-aminophenyl-α-D-mannopyranoside (Compound F).

IV. Additional Derivatives

Preparation of N-(S-acetylmercaptosuccinyl)-4-aminophenyl-α-D-mannopyranoside (Compound G in Table 62)

4-Aminophenyl-α-D-mannopyranoside (15 mg) was dissolved in anhydrous pyridine (4 ml) and the solution was cooled to 0° C. under $N_2$. To this solution was added dropwise a solution of S-acetylmercaptosuccinic anhydride (11.5 mg) in a mixture of methylene chloride (1 ml) and anhydrous pyridine (1 ml). The mixture was stirred under $N_2$ at 0° C. for 3 hr. The solvent was stripped in vacuo. No starting material could be detected by TLC on silica gel (Merck, HPTLC, $F_{254}$) using 7:2:1 $CHCl_3$-MeOH-AcOH as eluent. The material was purified on Macroprep High Q (Bio-Rad) strong anion exchange resin using a salt gradient in 20 mM sodium phosphate pH 6.9. The main peak (monitored at 254 nm) was isolated. The concentration of the material of interest, i.e., N-(S-acetylmercaptosuccinyl)-4-aminophenyl-α-D-mannopyranoside, was determined by deblocking the thiol group (hydroxylamine) followed by assay with Ellman's reagent.

EXAMPLE 54

Inhibition-of-Yeast-Agglutination Assay

Bacteria (HB101) bearing type 1 pili were grown overnight in LB broth at 37° C., pelletted by centrifugation and resuspended in PBS to an optical density of 0.5 at 530 nm. Commercial baker's yeast (Fleishmann) was suspended in PBS at 5 mg/ml. 10 μl of yeast suspension, 10 μl of test compound (or control) and 10 μl of bacterial suspension were added to depression wells and agglutination was observed visually after 1 minute. The minimum concentration of the sample that inhibited agglutination under these conditions is set forth in Table 62.

TABLE 62

| Entry | Compound[1] | Minimum Conc. Which Inhibited Agglutination | Activity[2] |
|---|---|---|---|
| 1 | A | 5 mg/ml | 1 |
| 2 | B | 100 μg/ml | 50 |
| 3 | C | 10 μg/ml | 500 |
| 4 | D | 5 μg/ml | 1000* |
| 6 | E | 50 μg/ml | 100 |
| 7 | F | 22.5 μg/ml | 222 |
| 8 | G | 50 μg/ml | 100 |

Figure 20A:
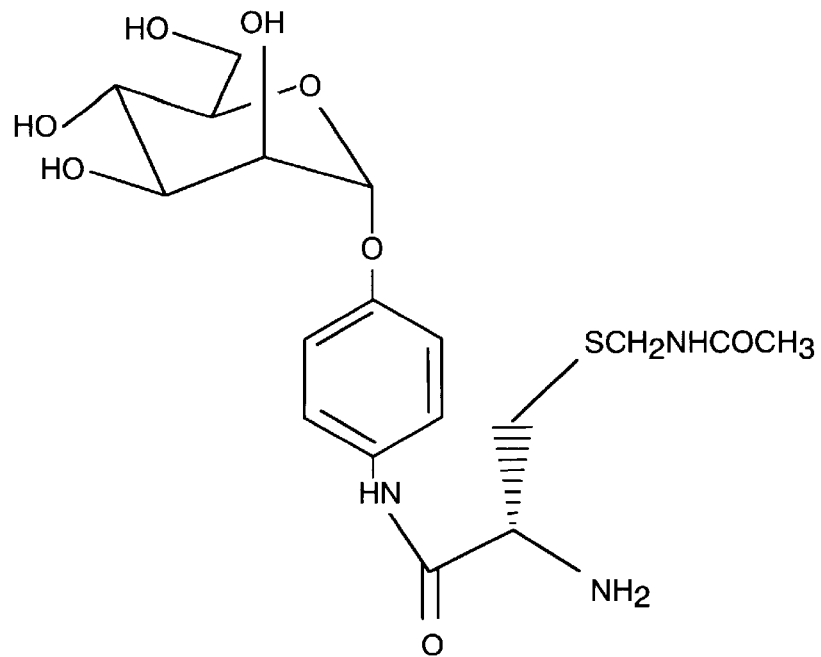
FIG. 20 shows fimbriae binding compounds E–G from Table 62.
Figure 20B:
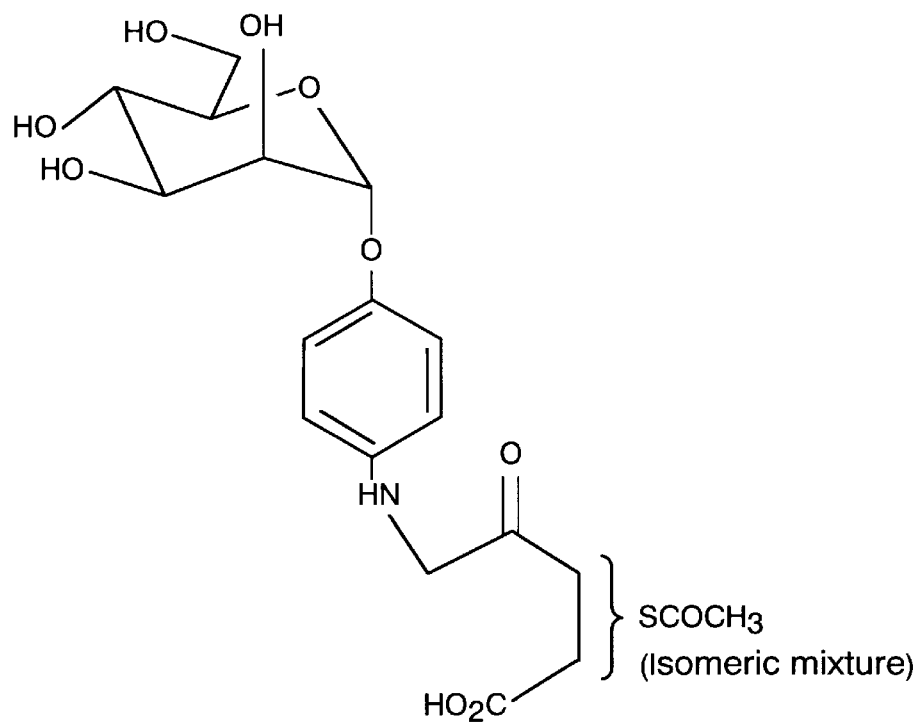
Figure 20C:
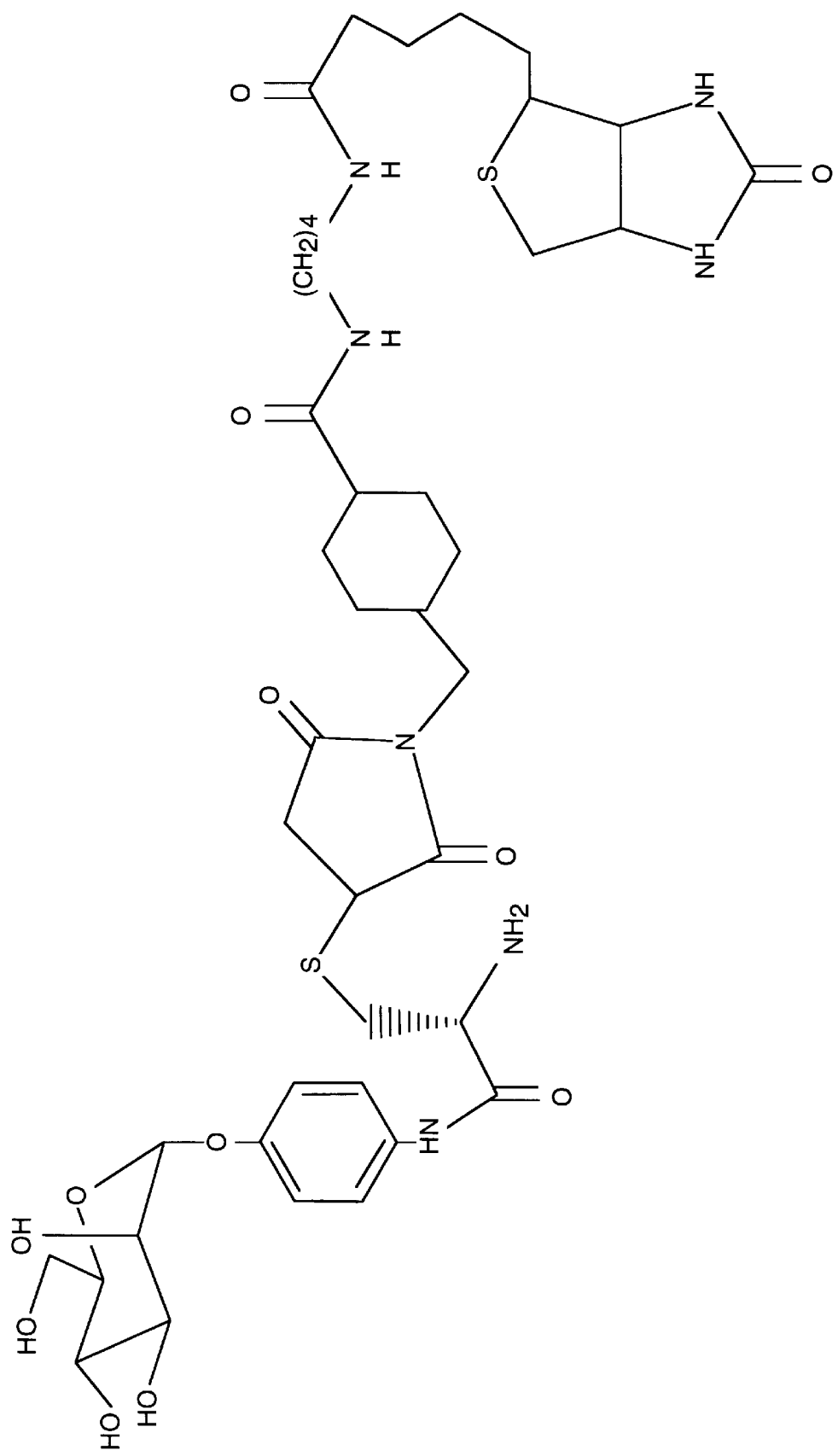

[1]Compounds A–G are illustrated in FIGS. 19 through 20.
[2]Activity [Minimum conc. of (A) which inhibited agglutination] ÷ [Minimum conc. of Compound which inhibited agglutination]
*When molar concentrations are compared (D) is 2156 times more active than (A). [Mol. Wt. of (A) = 194; Mol. Wt. of (D) = 418].

Compound A in the Table, methyl-1-α-D-mannopyranoside, served as the reference by which the activity of the other compounds was calculated. This allows for a comparison of relative activities (as opposed to absolute activities) under the particular conditions of the screening assay. Compound D, 4-(N-phenylalanyl)-aminophenyl-α-D-mannopyranoside, whose synthesis is described in Example 51, was a potent inhibitor of yeast agglutination. All the compounds tested showed inhibitory activity to varying extent.

It is to be understood that while the invention has been described in conjunction with the preferred embodiments thereof, the foregoing description as well as the examples which follow are intended to illustrate and not limit the scope of the invention. Other aspects, advantages and modifications within the scope of the invention will be apparent to those skilled in the art to which the invention pertains.

We claim:

1. A therapeutic formulation comprising N-(phenylalanyl)-4-aminophenyl-α-D-mannopyranoside.

2. A therapeutic formulation comprising cysteinyl-[N-(phenylalanyl)]-4-aminopheny-α-D-mannopyranoside.

3. A micellar formulation comprising N-(phenylalanyl)-4-aminophenyl-α-D-mannopyranoside.

4. A micellar formulation comprising cysteinyl-[N-(phenylalanyl)]-4-aminophenyl-α-D-mannopyranoside.

5. A method of treatment for bacterial disease comprising:
    a) providing i) a subject with symptoms of bacterial disease, ii) one or more fimbriae-binding compounds comprising a mannose of a anomeric configuration, an aromatic or heteroaromatic ring attached to said mannose by a glycosidic or pseudoglycosidic linkage, and a functional group, wherein said functional group provides a site for chemical modification remote from said mannose, and iii) a pharmaceutically carrier; and b) administering said fimbriae-binding compound to said subject.

6. The method of claim 5 wherein said glycosidic or pseudoglycosidic linkage consists of a carbon atom or hetero-atom substituted for a glycosidic oxygen atom.

7. The method of claim 5 wherein said functional group is a member of the group of functional groups consisting of hydroxyl, thiol, carboxylic acid, phenol, amine, halogen, amide, mesylate, tosylate, triflate or like groups, olefinic double bonds, and an acetylenic group.

8. The method of claim 5 wherein said compound is administered orally.

9. The method of claim 5 wherein said one or more compounds is administered as a micellar formulation.

10. The method of claim 9 wherein said one or more compounds is administered via a cleansing applicator.

11. The method of claim 9 wherein said one or more compounds is administered in a solution.

12. The method of claim 9 wherein said one or more compounds is administered in a suspension.

13. The method of claim 11 wherein said one or more compounds is administered as an irrigant.

14. The method of claim 11 wherein said one or more compounds is administered as a wash.

15. A method of treatment for bacterial disease comprising:

a) providing i) a subject at risk for bacterial disease, and ii) one or more fimbriae-binding compounds comprising a mannose of $\alpha$-anomeric configuration, an aromatic or heteroaromatic ring attached to said mannose by a glycosidic or pseudoglycosidic linkage, and a functional group, wherein said functional group provides a site for chemical modification remote from said mannose; and b) administering said fimbriae-binding compound to said subject.

16. The method of claim 15 wherein said glycosidic or pseudoglycosidic linkage consists of a carbon atom or hetero-atom substituted for a glycosidic oxygen atom.

17. The method of claim 15 wherein said functional group is a member of the group of functional groups consisting of hydroxyl, thiol, carboxylic acid, phenol, amine, halogen, amide, mesylate, tosylate, triflate or like groups, olefinic double bonds, and an acetylenic group.

18. The method of claim 15 wherein said compound is administered orally.

19. The method of claim 15 wherein said one or more compounds is administered as a micellar formulation.

20. The method of claim 15 wherein said one or more compounds is administered via a cleansing applicator.

21. The method of claim 15 wherein said one or more compounds is administered in a solution.

22. The method of claim 15 wherein said one or more compounds is administered in a suspension.

23. The method of claim 15 wherein said one or more compounds is administered as an irrigant.

24. The method of claim 15 wherein said one or more compounds is administered as a wash.

* * * * *

SEQUENCE LISTING

```
(1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 102 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Peptide
       (B) LOCATION: 36
       (D) OTHER INFORMATION: /note= "The amino acid at this
            location can be either Val or Ile."

(ix) FEATURE:
       (A) NAME/KEY: Peptide
       (B) LOCATION: 102
       (D) OTHER INFORMATION: /note= "The amino acid at this
            location can be either Gln or Glu."

(xi) SEQUENCE DESCRIPTION: SEQ ID NO:1:

Glu Gly Gly Ile Trp Thr Gln Leu Ala Leu Ala Leu Val Lys Asn Leu
1               5                   10                  15
```

```
Ala Thr Leu Trp Gln Ser Gly Asp Phe Gln Phe Leu Gly His Glu Cys
             20                  25                  30

His Tyr Arg Xaa Asn Pro Thr Val Lys Arg Leu Lys Trp Lys Tyr Lys
             35                  40                  45

Gly Lys Phe Trp Cys Pro Ser Trp Thr Ser Ile Thr Gly Arg Ala Thr
 50                          55                  60

Lys Ser Ser Arg Ser Gly Ala Val Glu His Ser Val Arg Asp Phe Val
 65                  70                  75                  80

Ser Gln Ala Lys Ser Ser Gly Leu Ile Thr Glu Lys Glu Ala Gln Thr
                 85                  90                  95

Phe Ile Ser Gln Tyr Xaa
            100
```

(2) INFORMATION FOR SEQ ID NO:2:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:2:

```
Ala Leu Tyr Lys Lys Leu Leu Lys Lys Leu Leu Lys Ser Ala Lys Lys
 1               5                  10                  15

Leu Gly
```

(2) INFORMATION FOR SEQ ID NO:3:

(i) SEQUENCE CHARACTERISTICS:
        (A) LENGTH: 19 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:3:

```
Ala Leu Tyr Lys Lys Leu Leu Lys Lys Leu Leu Lys Ser Ala Lys Lys
 1               5                  10                  15

Leu Gly Cys
```

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:4:

```
Cys Lys Trp Lys Ala Gln Lys Arg Phe Leu Lys
 1               5                  10
```

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:5:

Glu Tyr Lys Cys Lys
1               5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:6:

Ala Glu Ala Lys Ala Lys Ala
1               5

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:7:

Cys Ala Glu Ala Lys Ala Lys Ala
1               5

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:8:

Ala Glu Ala Lys Ala Lys Ala Cys
1               5

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:9:

Leu Leu Gly Gly Pro Ser
1               5